US008741291B2

(12) United States Patent
Bhat et al.

(10) Patent No.: US 8,741,291 B2
(45) Date of Patent: Jun. 3, 2014

(54) MULTIFUNCTIONAL ANTIBODY CONJUGATES

(75) Inventors: Abhijit Suresh Bhat, Encinitas, CA (US); Curt William Bradshaw, San Diego, CA (US); Olivier Alexandre Laurent, San Diego, CA (US); Alice Lee, Poway, CA (US); Richard Ryan Preston, Escondido, CA (US); David Tumelty, San Diego, CA (US); Lauren Diane Wood, San Diego, CA (US); Wei Hong Yu, San Diego, CA (US)

(73) Assignee: Covx Technologies Ireland, Limited, Dun Laoghaire County, Dublin (IE)

( * ) Notice: Subject to any disclaimer, the term of this patent is extended or adjusted under 35 U.S.C. 154(b) by 0 days.

(21) Appl. No.: 13/305,354

(22) Filed: Nov. 28, 2011

(65) Prior Publication Data

US 2012/0201809 A1 Aug. 9, 2012

Related U.S. Application Data

(63) Continuation of application No. PCT/IB2011/053092, filed on Jul. 11, 2011.

(60) Provisional application No. 61/363,507, filed on Jul. 12, 2010.

(51) Int. Cl.
*A61K 38/00* (2006.01)

(52) U.S. Cl.
USPC .................. 424/134.1; 424/178.1; 530/391.9

(58) Field of Classification Search
None
See application file for complete search history.

(56) References Cited

U.S. PATENT DOCUMENTS

| | | | |
|---|---|---|---|
| 6,309,881 B2 | 10/2001 | Barbas, III et al. | |
| 6,368,839 B1 | 4/2002 | Barbas, III et al. | |
| 7,037,498 B2 | 5/2006 | Cohen et al. | |
| 7,371,378 B2 | 5/2008 | Cohen et al. | |
| 7,521,425 B2 | 4/2009 | Bradshaw et al. | |
| 7,579,157 B2 | 8/2009 | Graus et al. | |
| 2003/0175921 A1 | 9/2003 | Barbas, III et al. | |
| 2004/0115165 A1* | 6/2004 | Rosen et al. | 424/78.38 |
| 2008/0166364 A1* | 7/2008 | Bradshaw et al. | 424/179.1 |
| 2009/0092614 A1 | 4/2009 | Demarest et al. | |
| 2009/0098130 A1 | 4/2009 | Bradshaw et al. | |
| 2010/0003267 A1 | 1/2010 | Doppalapudi et al. | |
| 2010/0111967 A1 | 5/2010 | Baehner et al. | |
| 2011/0189206 A1 | 8/2011 | Barbas, III | |

FOREIGN PATENT DOCUMENTS

WO WO02053596 7/2002
WO WO2005016967 2/2005

OTHER PUBLICATIONS

Junutula et al (Nature Biotech, 2008, 26:925-932).*
Wang et al (Protein Science, 2005, 14:2436-2446).*
Doppalapudi, V. R., et al., "Chemical Generation of Bispecific Antibodies," Proceedings of the National Academy of Sciences, 2010, 22611-22616, vol. 107, No. 52.
Herbst, R. S., et al., "Safety, Pharmacokinetics, and Antitumor Activity of AMG 386, a Selective Angiopoietin Inhibitor, in Adult Patients with Advanced Solid Tumors," Journal of Clinical Oncology, 2009, 3557-3565, vol. 27, No. 21.
Huang, H., et al., "Specifically Targeting Angiopoietin-2 Inhibits Angiogenesis, Tie-2-Expressing Monocyte Infiltration, and Tumor Growth," Journal of the American Association for Cancer Research, 2011, 1001-1011, vol. 17, No. 5.
Huang, H., et al., "Targeting the ANGPT-TIE2 Pathway in Malignancy," Nature Reviews, 2010, 575-585, vol. 10, No. 8.
Huang, H., et al., "Angiopoietin-2 Antagonist CovX-BodyTM Inhibits Tumor Growth and Reduces Microvessel Density," Proceedings of the Annual Meeting of the American Association for Cancer Research, 2007, 509, vol. 48.
Rosen, L. S., et al., "First-In-Human-Dose-Escalation Safety and PK Trial of a Novel Intravenous Humanized Monoclonal CovX Body Inhibiting Angiopoietin 2," Journal of Clinical Oncology, 2010, 2524, vol. 28, No. 15.
International Search Report.

* cited by examiner

*Primary Examiner* — Sean Aeder
*Assistant Examiner* — Julie Wu
(74) *Attorney, Agent, or Firm* — Wendy L. Hsu

(57) ABSTRACT

The present invention relates to Multifunctional Antibody Conjugates, comprising an antibody or antigen binding portion thereof, comprising at least a fragment of a light chain constant kappa region (CLκ) comprising $K^{188}$ according to Kabat numbering; a linker comprising the formula X-Y-Z, wherein Z is a group is covalently connected to the antibody through the side chain of $K^{188}$, Y is a linear or branched biologically compatible connecting chain, and X is a group covalently connected to at least one Effector Moiety.
The invention further provides specific MAC compounds and compositions of the invention.

42 Claims, 36 Drawing Sheets

FIG. 1A

Heavy chain

Figure 2B:
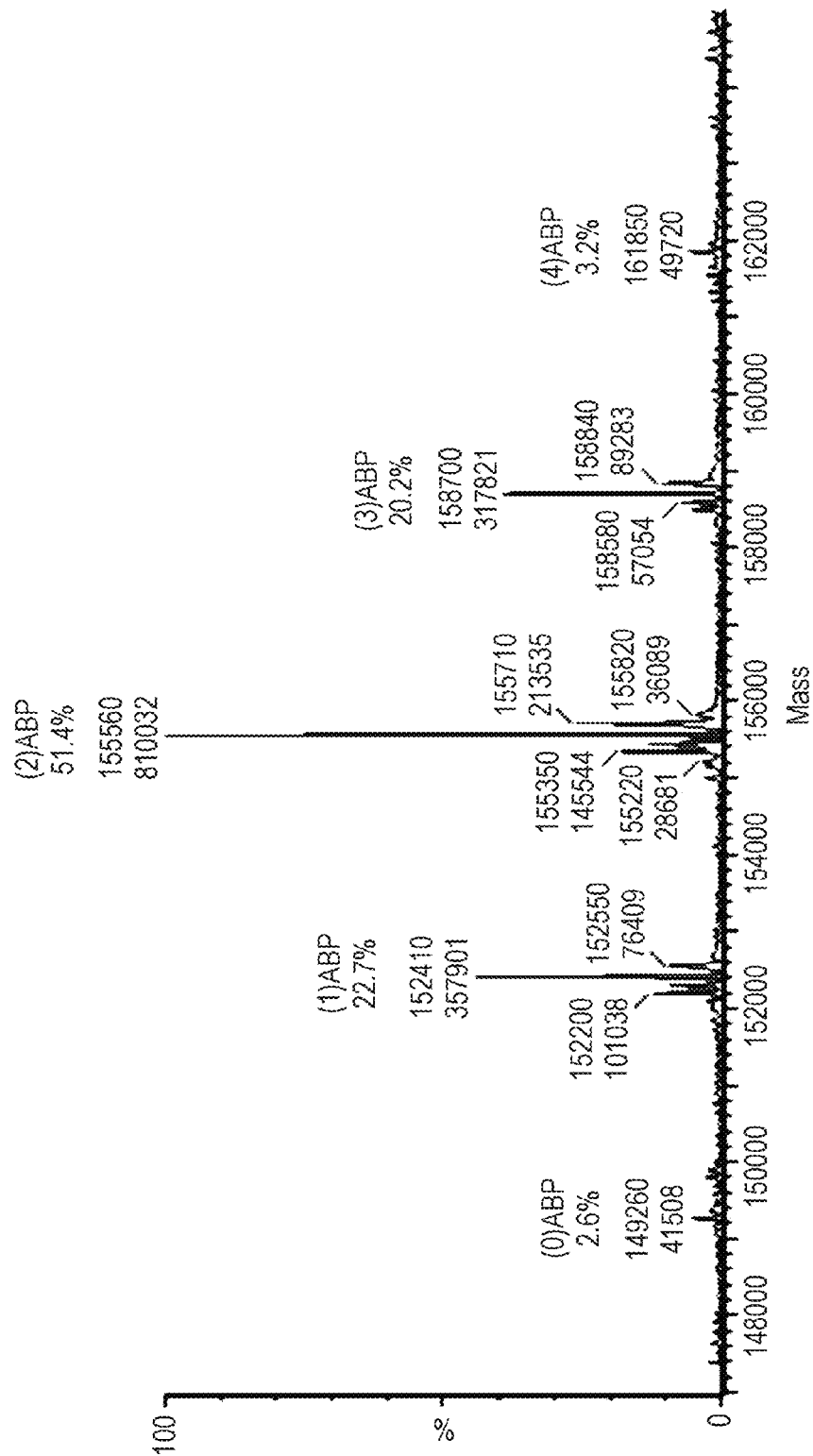

```
2.12.1      QAQLVESGGG LVKPGGSIRL SCAASGFTFS DYMSWIRQA PGKGLEWVSY ISSSGSTRDY ADSVKGRFTI      70
2.12.1.fx   QVQLVESGGG LVKPGGSIRL SCAASGFTFS DYMSWIRQA PGKGLEWVSY ISSSGSTRDY ADSVKGRFTI 2.12.1      SRDNAKNSLY LQMNSLRAED TAVYYCVRDG VETTFYYYY GMDVWGQGTT VTVSSASTKG PSVFPLAPCS     140
2.12.1.fx   SRDNAKNSLY LQMNSLRAED TAVYYCVRDG VETTFYYYY GMDVWGQGTT VTVSSASTKG PSVFPLAPCS 2.12.1      RSTSESTAAL GCLVKDYFPE PVTVSWNSGA LTSGVHTFPA VLQSSGLYSL SSVVTVPSSN FGTQTYTCNV     210
2.12.1.fx   RSTSESTAAL GCLVKDYFPE PVTVSWNSGA LTSGVHTFPA VLQSSGLYSL SSVVTVPSSN FGTQTYTCNV 2.12.1      DHKPSNTKVD KTVERKCCVE CPPCPAPPVA GPSVFLFPPK PKDTLMISRT PEVTCVVVDV SHEDPEVQFN     280
2.12.1.fx   DHKPSNTKVD KTVERKCCVE CPPCPAPPVA GPSVFLFPPK PKDTLMISRT PEVTCVVVDV SHEDPEVQFN 2.12.1      WYVDGVEVHN AKTKPREEQF NSTFRVVSVL TVVHQDWLNG KEYKCKVSNK GLPAPIEKTI SKTKGQPREP     350
2.12.1.fx   WYVDGVEVHN AKTKPREEQF NSTFRVVSVL TVVHQDWLNG KEYKCKVSNK GLPAPIEKTI SKTKGQPREP 2.12.1      QVYTLPPSRE EMTKNQVSLT CLVKGFYPSD IAVEWESNGQ PENNYKTTPP MLDSDGSFFL YSKLTVDKSR     420
2.12.1.fx   QVYTLPPSRE EMTKNQVSLT CLVKGFYPSD IAVEWESNGQ PENNYKTTPP MLDSDGSFFL YSKLTVDKSR 2.12.1      WQQGNVFSCS VMHEALHNHY TQKSLSLSPG K     451
2.12.1      WQQGNVFSCS VMHEALHNHY TQKSLSLSPG K
```

FIG. 1B

*Light chain*

```
2.12.1      DIQMTQSPSS LSASVGDRVT ITCRASQDIR RDLGWYQQKP GKAPKRLIYA ASRLQSGVPS RFSGSGSGTE
2.12.1.fx   DIQMTQSPSS LSASVGDRVT ITCRASQDIR RDLGWYQQKP GKAPKRLIYA ASRLQSGVPS RFSGSGSGTE 2.12.1      FTLTISSLQP EDFATYYCLQ HNNYPRTFGQ GTKVEIIRTV AAPSVFIFPP SDEQLKSGTA SVVCLLNNFY
2.12.1.fx   FTLTISSLQP EDFATYYCLQ HNNYPRTFGQ GTKLVIKRTV AAPSVFIFPP SDEQLKSGTA SVVCLLNNFY 2.12.1      PREAKVQWKV DNALQSGNSQ ESVTEQDSKD STYSLSSTLT LSKADYEKHK VYACEVTHQG LSSPVTKSFN
2.12.1.fx   PREAKVQWKV DNALQSGNSQ ESVTEQDSKD STYSLSSTLT LSKADYEKHK VYACEVTHQG LSSPVTKSFN 2.12.1      RGEC
2.12.1.fx   RGEC
```

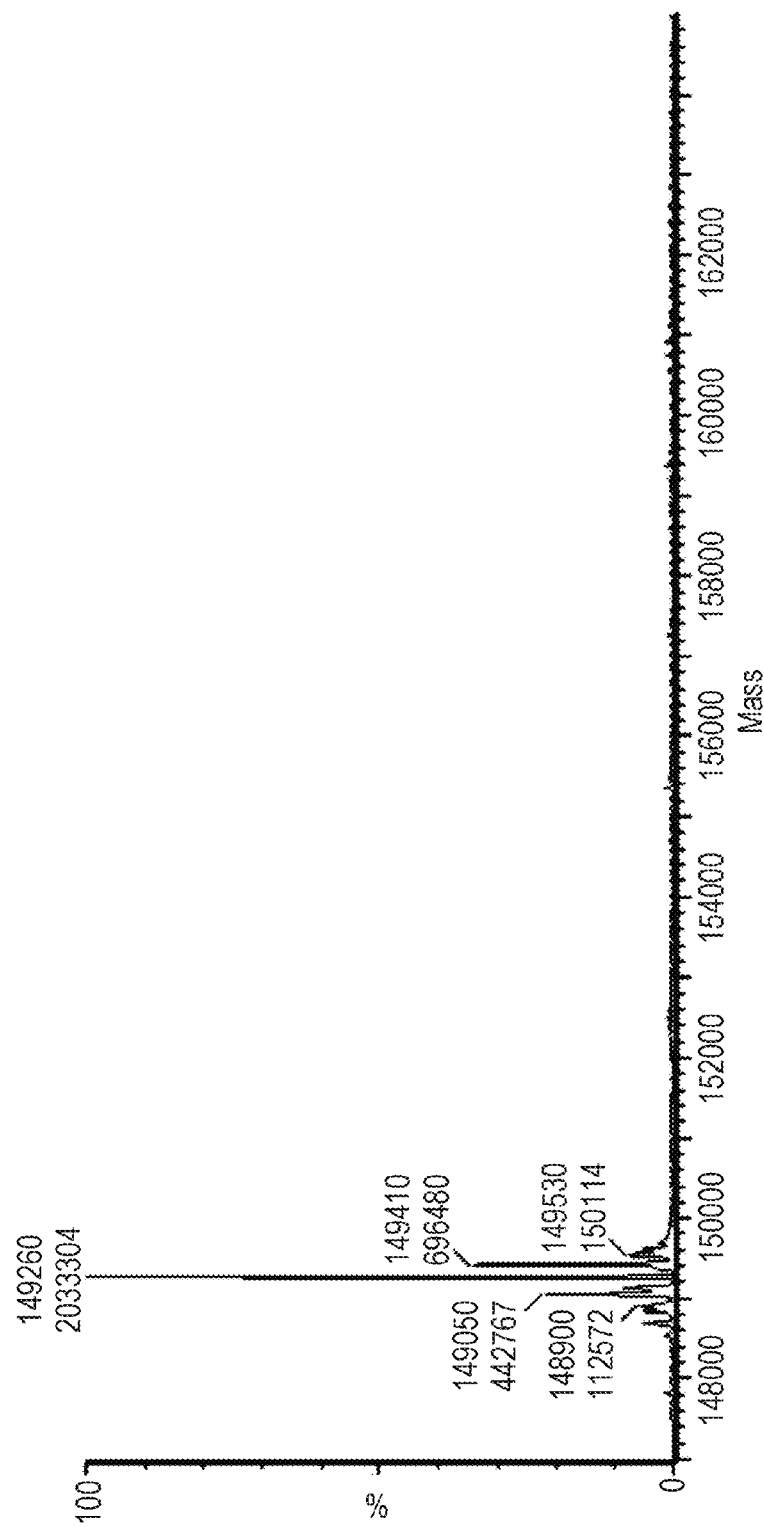

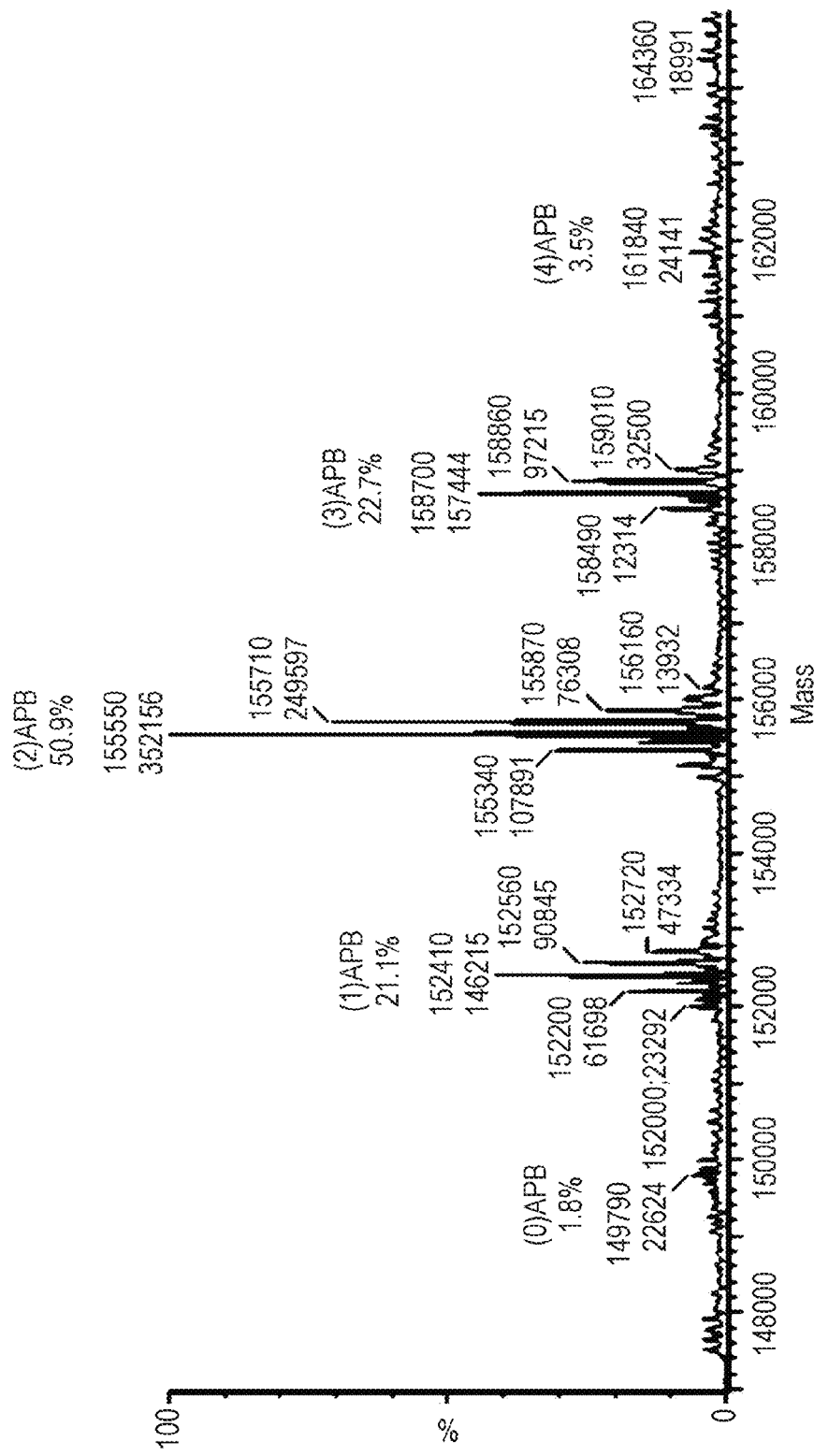

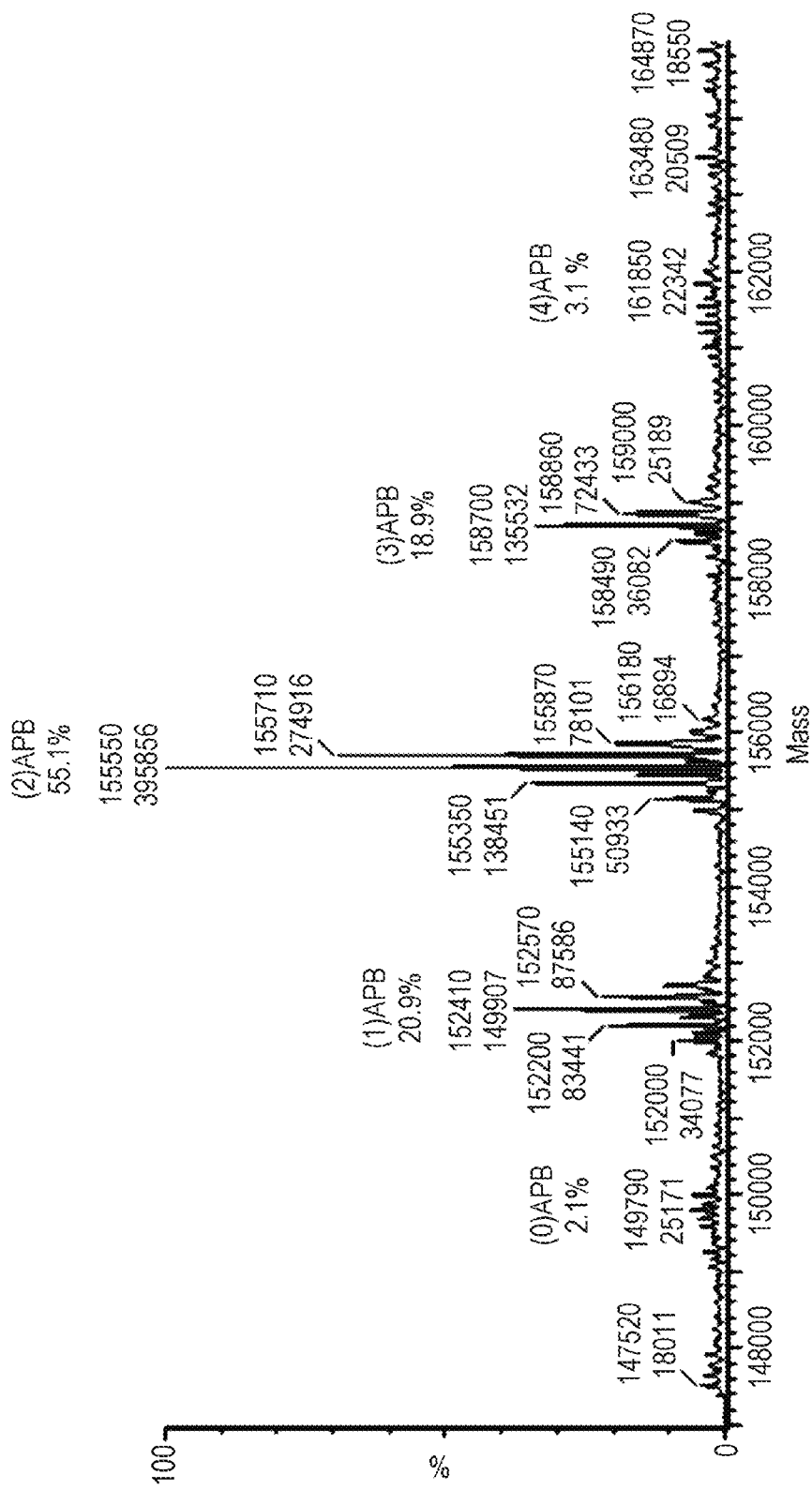

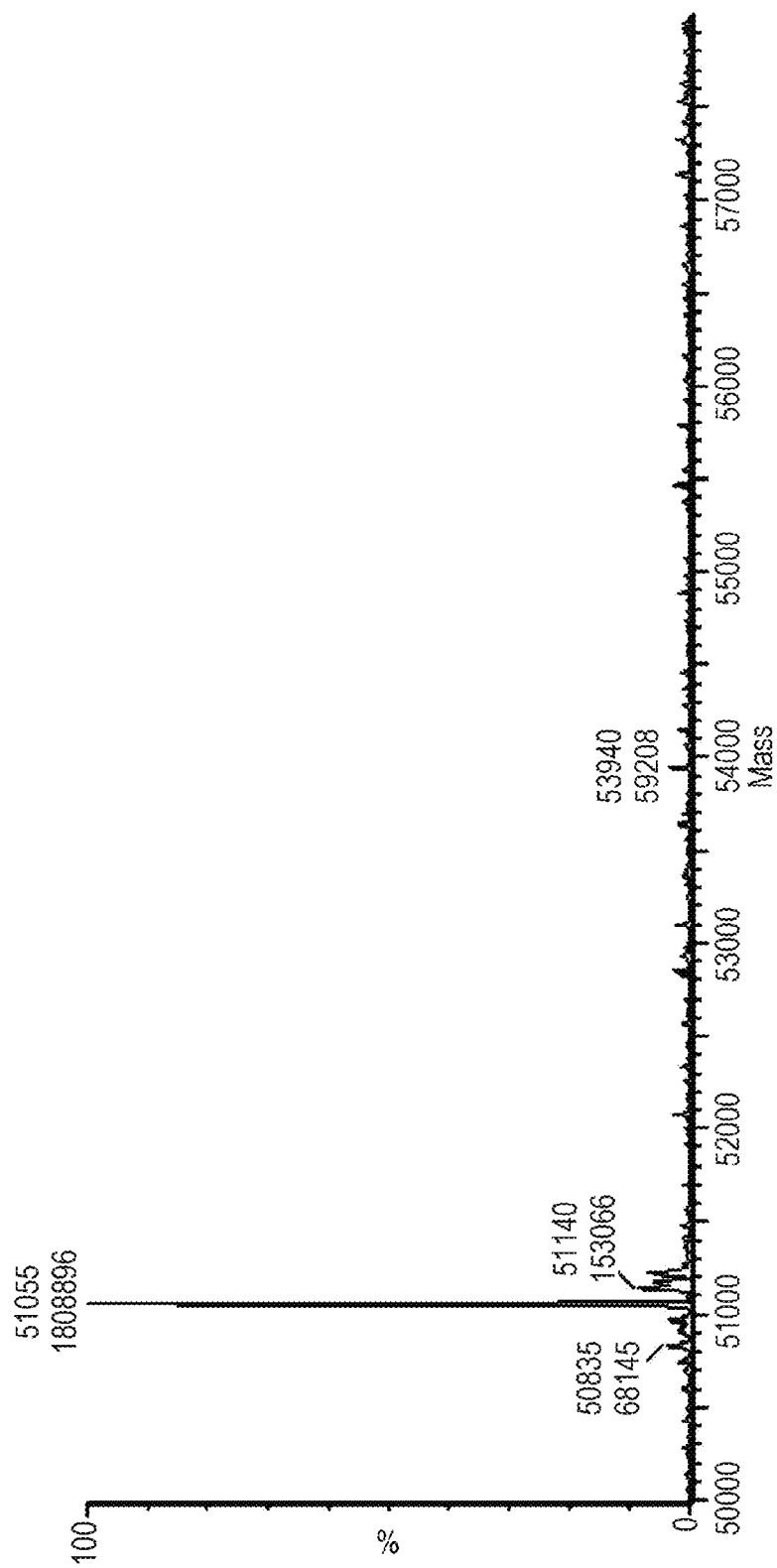

FIG. 4A

*LIGHT CHAIN*

DIQMTQSPSSLSASVGDRVTITCRASQDIRRDLGW・Y・*(Y3)*QQKPGKAPKRLIY・AASRLQSGVPSRF・
SGSGSGTEF・TLTISSLQPEDF・ATY・Y・CLQHNYPRTF・*(Y10)*GQGTKLVIKRTVAAPSVF・*(Y11)*
IFPPSDEQLKSGTASVVCLLNNF・Y・*(Y12)*PREAKVQW・*(Y13)*KVDNALQSGNSQESVTEQDSKDSTY
・*(Y14)*SLSSTLTLSKADY・*(Y15)*EKHKVY・*(Y16)*ACEVTHQGLSSPVTKSF・NRGEC

FIG. 4B

*HEAVY CHAIN*

*(Y1)*QVQLVESGGGLVKPGGSLRLSCAASGF・TF・SDY・Y・MSW・*(Y6)*IRQAPGKGLEW・VSY・ISSSGSTRDY・
*(Y9)*ADSVKGRF・*(Y10)*TISRDNAKNSLY・LQMNSLRAEDTAVY・Y・CVRDGVETTF・Y・Y・Y・Y・GMDVW・
*(Y20)*GQGTTVTVSSASTKGPSVFPLAPCSRSTSESTAALGCLVKDY・FPEPVTVSW・NSGALTSGVHTFPAVLQS
SGLY・SLSSVVTVPSSNF・GTQTY・*(Y25)*TCNVDHKPSNTKVDKTVERKCCVECPPCPAPPVAGPSVF・*(Y26)*L
FPPKPKDTLMISRTPEVTCVVVDVSHEDPEVQF・NW・Y・*(Y29)*VDGVEVHNAKTKPREEQF・NSTF・RVVSVLTV
VHQDW・*(Y32)*LNGKEY・*(Y33)*KCKVSNKGLPAPIEKTISKTKGQPREPQVY・*(Y34)*TLPPSREEMTKNQVSLT
CLVKGF・YPSDIAVEW・ESNGQPENNY・*(Y37)*KTTPPMLDSDGSF・F・LY・*(Y40)*SKLTVDKSRW・QQGNVF・
SCSVMHEALHNHY・*(Y43)*TQKSLSLSPG

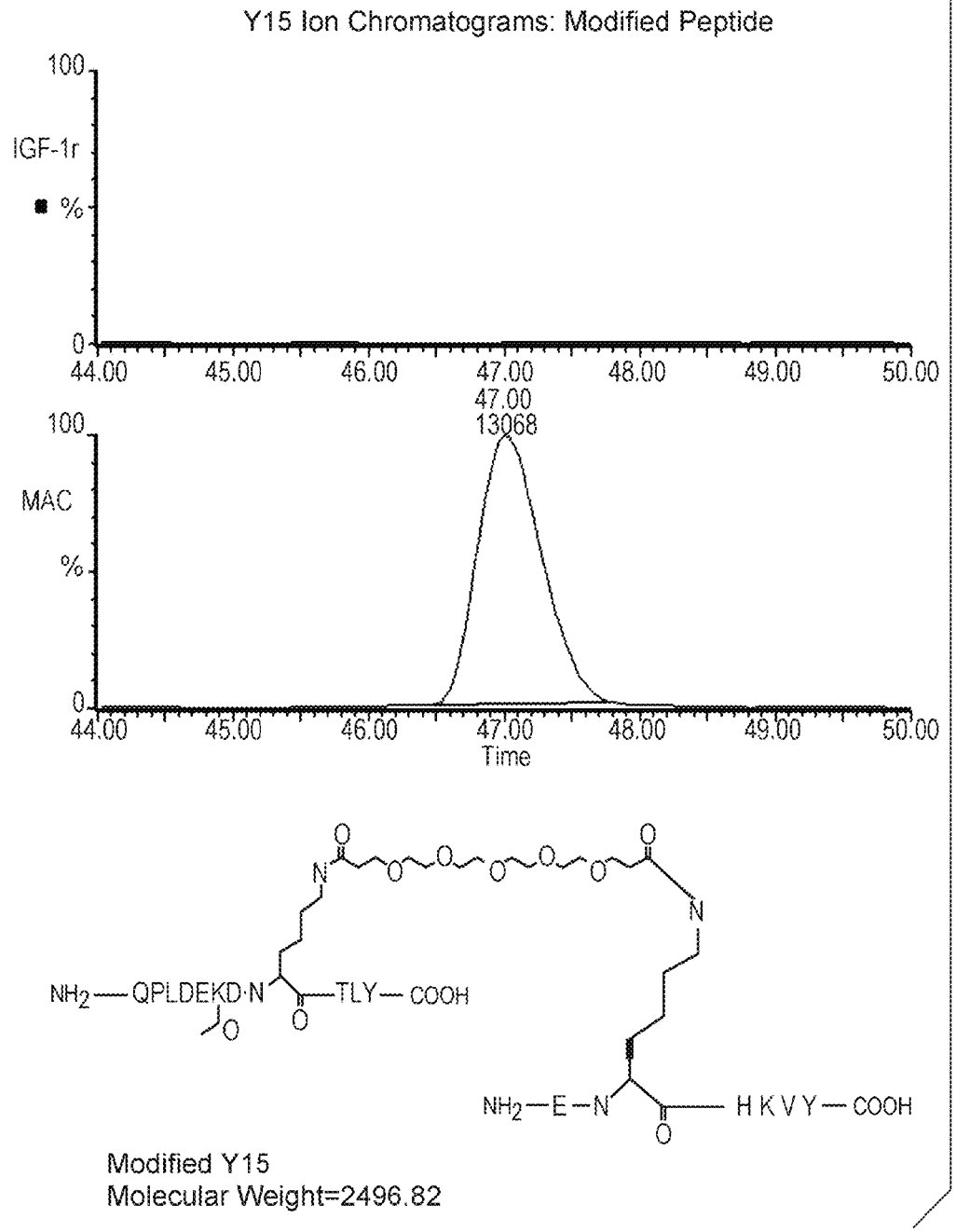

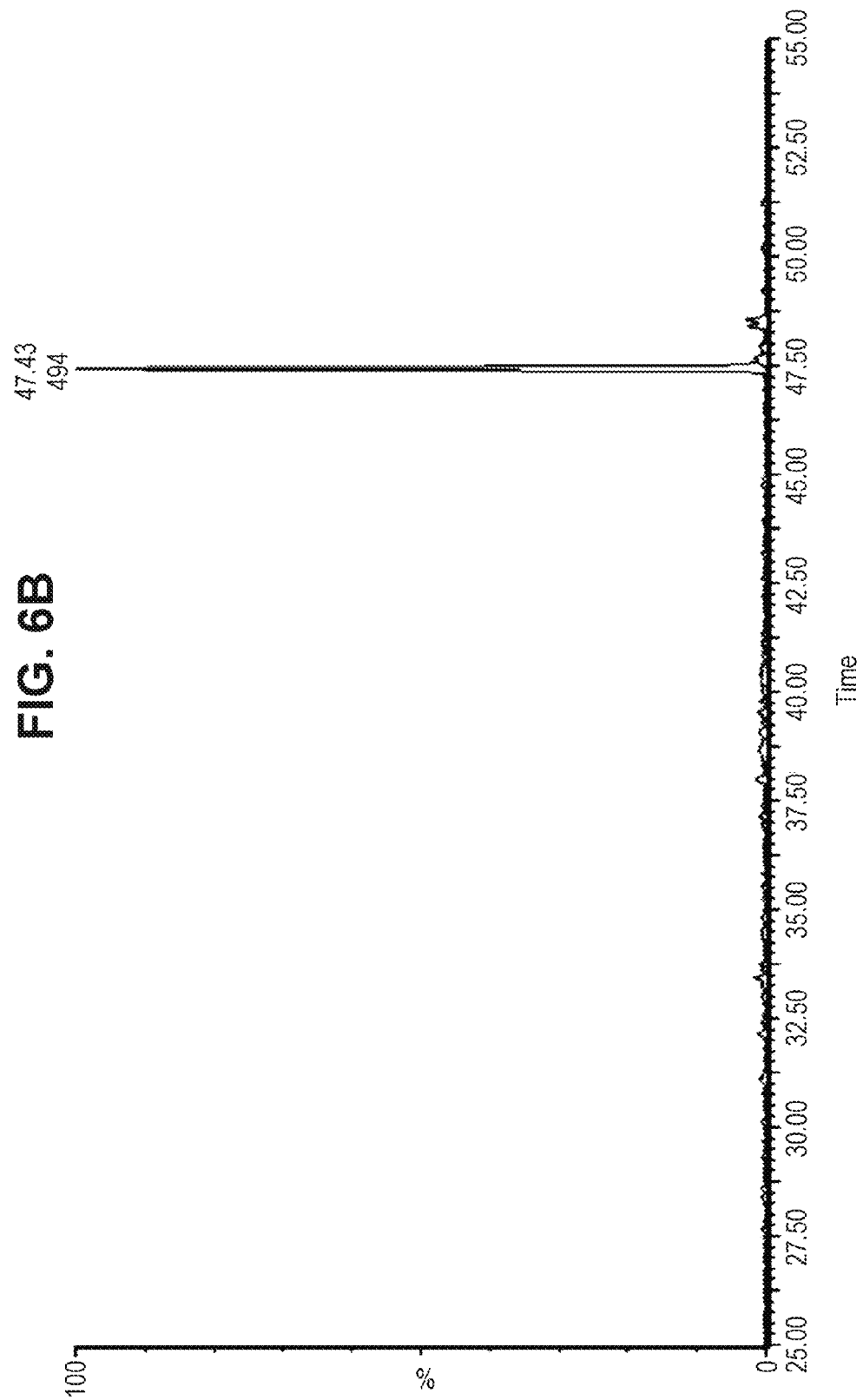

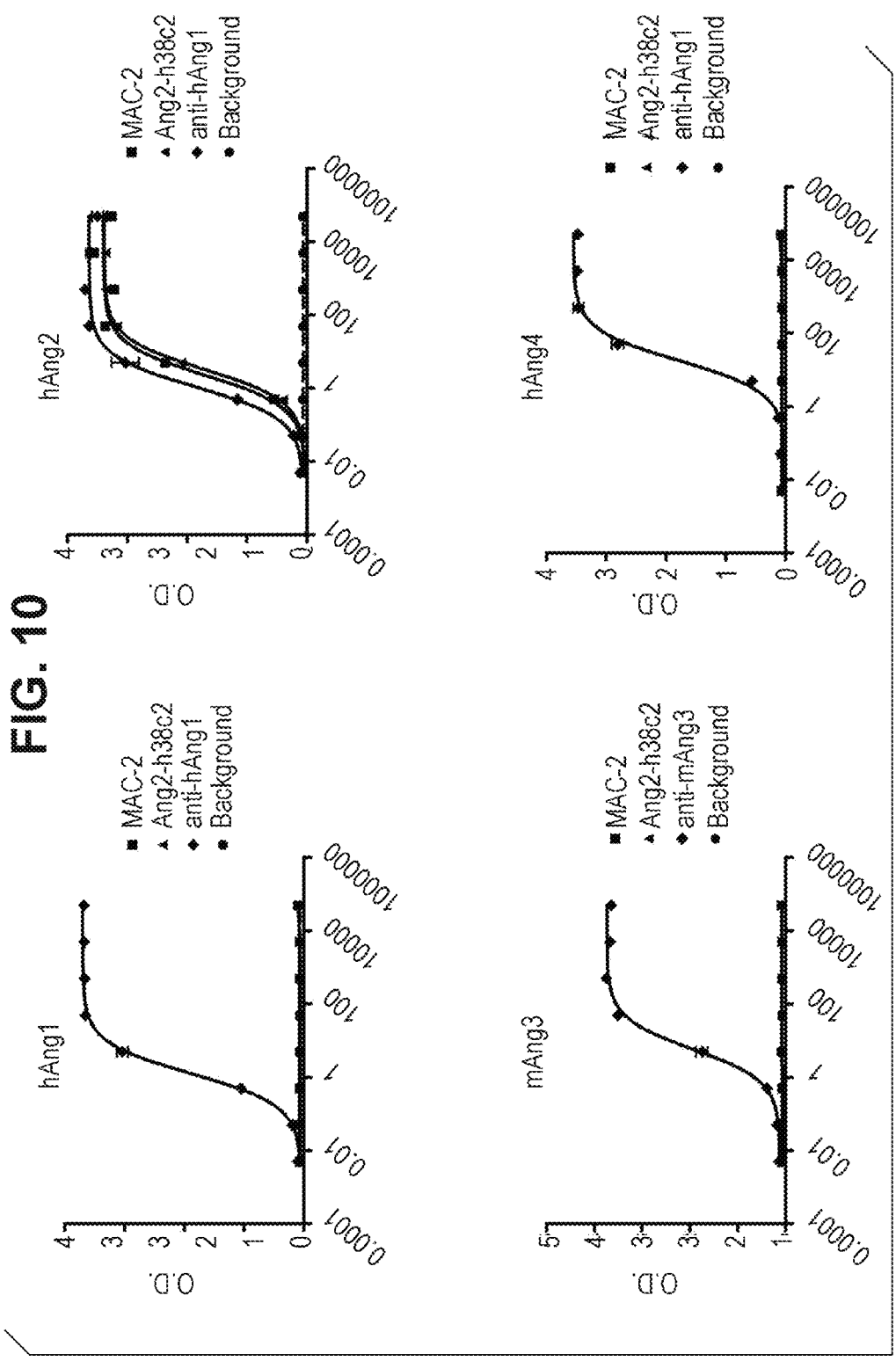

Newman-Keuls Multiple Comparison Test
*P<0.05, ***P<0.001

*P<0.05 vs. PBS, One-Way ANOVA, Dunnett's

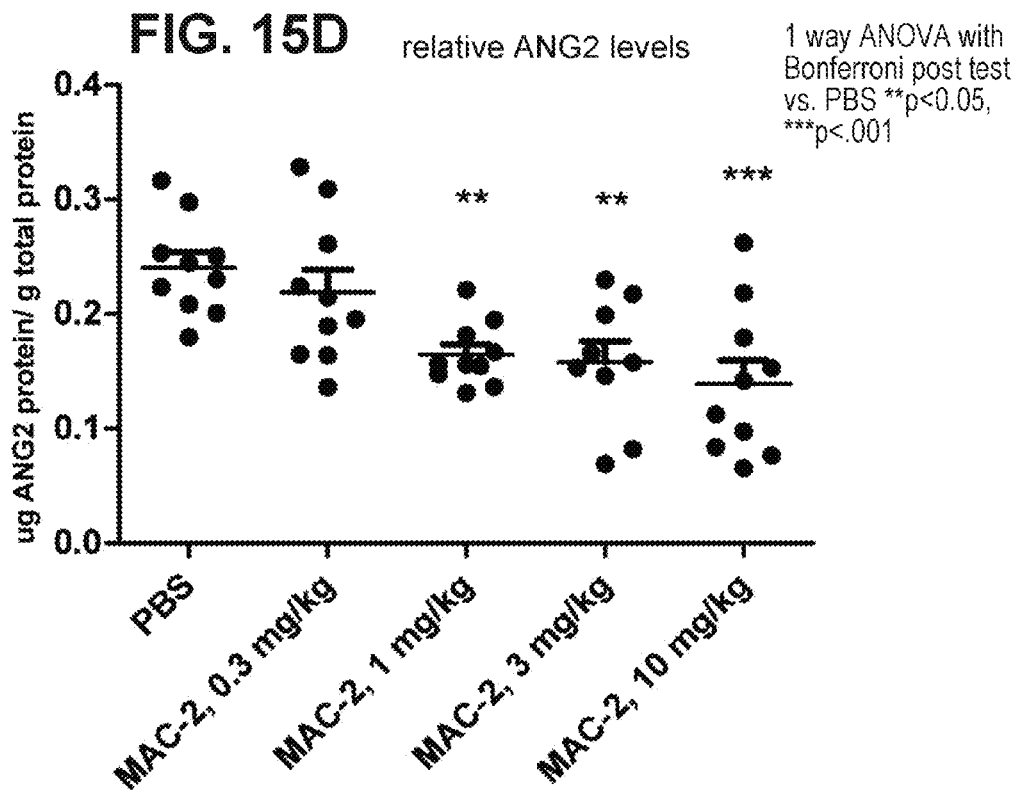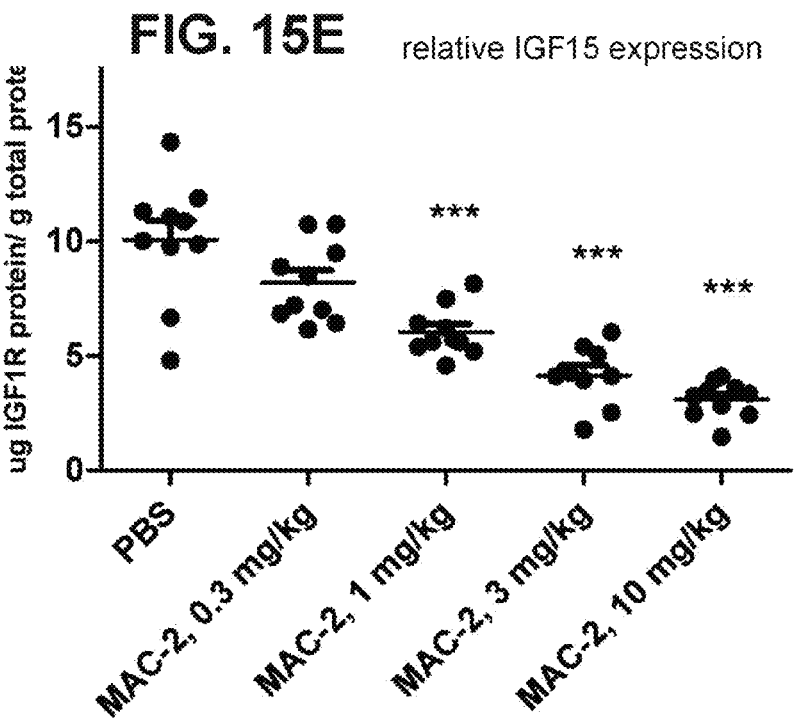

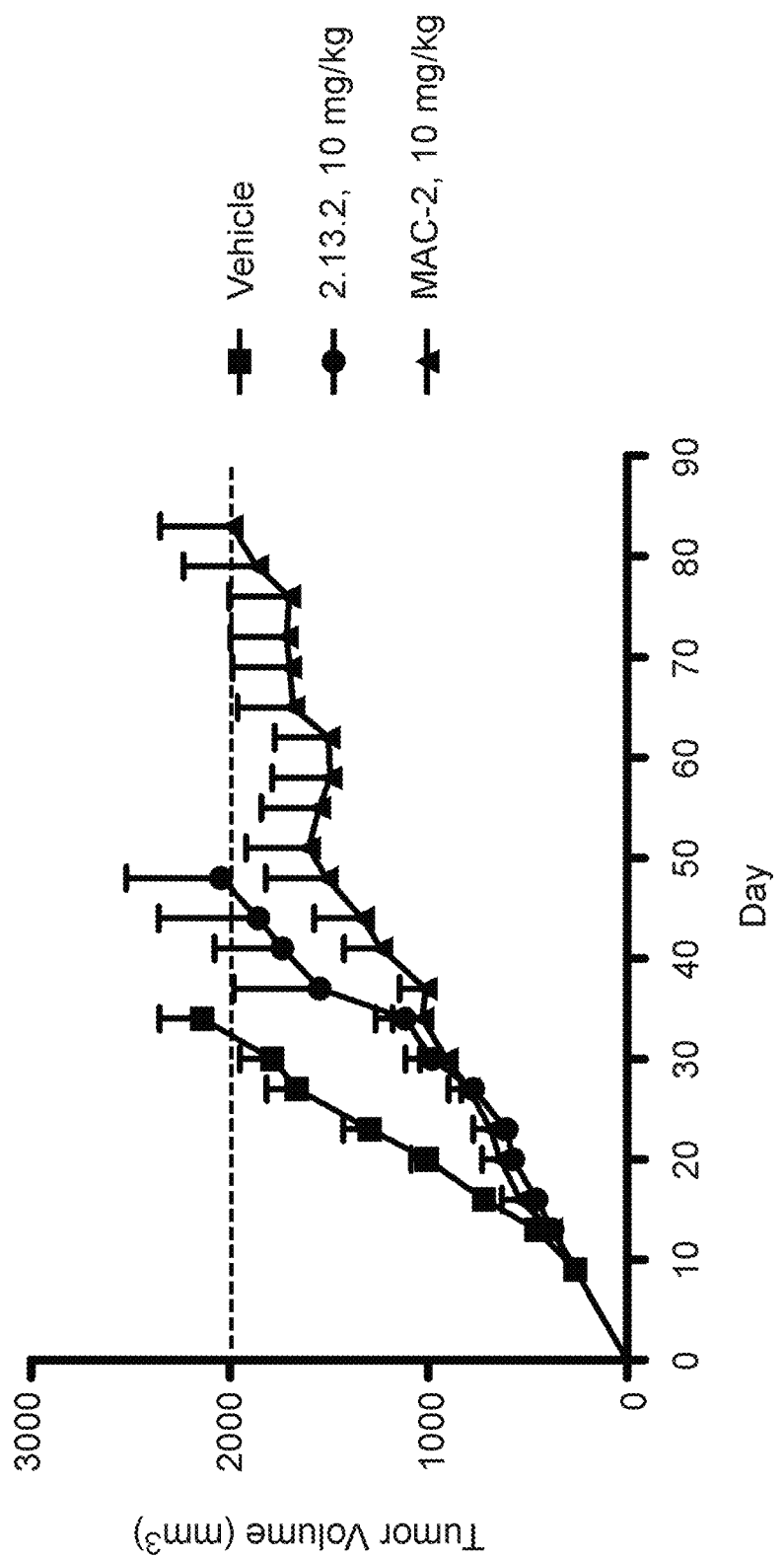

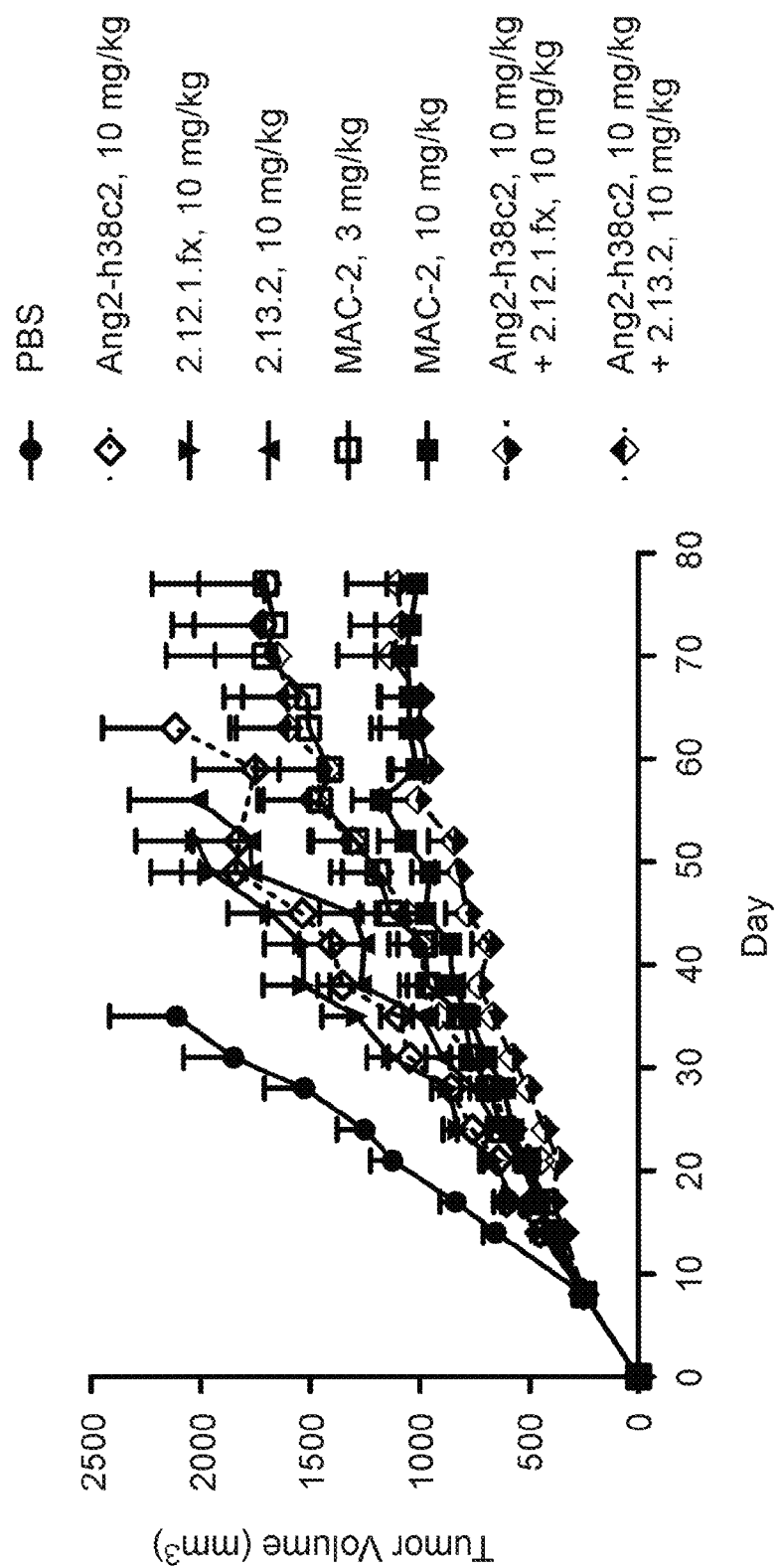

FIG. 18A

```
VL
              Fr1                            CDR1               FR2              CDR2             FR3                                      CDR3          FR4
              1         2                    3                  4                5         6           7         8                         9   1         1
              1234567890123                  45678901abcde234   567890123456789  0123456   789012345678901234567890123456789012345678      901234567    8901234567
m38c2    DVVMTQTPLSLPVRLGDQASISC             RSSQSLIHTYGSPYIN   WYLQKPGQSPKLLIY  KVSNRFS   GVPDRFSGSGSGTDFTLRISRVEAEDLGVYFC                SQGTHLPYT    FGGGTKLEIK
         ***  *  ****** ***                 *******            **               *                    *   *    *    ****  **                   *****    *
h38c2    ELQMTQSPSSLSASVGDRVTITC             RSSQSLIHTYGSPYIN   WYLQKPGQSPKLLIY  KVSNRFS   GVPSRFSGSGSGTDFTLTISSLQPEDFAVYFC                SQGTHLPYT    FGGGTKVEIK
          **                                 ********           * **             ** ***                                                      *****
DPK-9    DIQMTQSPSSLSASVGDRVTITC             RASQSISS----YLN    WYQQKPGKAPKLLIY  AASSLQS   GVPSRFSGSGSGTDFTLTISSLQPEDFATYYC                QQSYSTP
JK4                                                                                                                                              LT    FGGGTKVEIK VH
              FR1                           CDR1          FR2              CDR2                   FR3                                      CDR3               FR4
              1         2         3         1ab2345       6789012345678    5    6                 7         8         9   1                   1    1
              1234567890123456789012345678  1ab2345       67890123456789   012abc345678901234 5   6789012345678901234abc345678901234         56789012         34567890123
m38c2    EVKLVESGGGLVQPGGTMKLSCEISGLTFR     N--YMWS       WVRQSPEKGLEWVA    EIRLRSDNYATHYAESVKG   KFTISRDDSKSRLYLQMNSLRTEDTGIYYCKY           YFY-SFSY         WGQGTLVTVSA
                                                *        *                 *   *                       *                    *                                          *
h38c2    EVQLVESGGGLVQPGGSLRLSCAASGFTFS     N--YMWS       WVRQSPEKGLEWVS    EIRLRSDNYATHYAESVKG   RFTISRDNSKNTLYLQMNSLRAEDTGIYYCKT           YFY-SFSY         WGQGTLVTVSS
                *                               *         *                                                                 **  **
DP-47    EVQLLESGGGLVQPGGSLRLSCAASGFTFS     S--YAMS       WVRQAPGKGLEWVS    AISG--SGGSTYYADSVKG   RFTISRDNSKNTLYLQMNSLRAEDTAVYYCAK
JH4                                                                                                                                            YFDY         WGQGTLVTVSS
```

FIG. 18B

```
mCLκ  --ADAAPTVSIF PPSSEQLTSG GASVVCFLNN FYPRDINVKW KIDGSERQNG- VLNSWTDQDS
        **        +   ****  *         **       ***      +     * ** *  +
hCLκ  --TVAAPSVFIF PPSDEQLKSG TASVVCLLNN FYPREAKVQW KVDNA-LQSGN SQESVTEQDS    60
        * ++   *   ++   **   +*    +     +     *    +    *    +  ++   * *
hCLλ  GQPKAAPSVTLF PPSSEELQAN KATLVCLISD FYPGAVTVAW KADSSPVKAG- -VETTTPSKQ mCLκ  KDSTYSMSST LTLTKDEYER -HNSYTCEATH KTSTSPIVKS FNRNEC
         *    *    *   + +      *  *  *  +        +   *  *
hCLκ  KDSTYSLSST LTLSKADYEK -HKVYACEVTH QGLSSPVTKS FNRGEC               106
      *+  *+ **+ *  + +* *     *  +* *  +   ** + +  ++
hCLλ  SNNKYAASSY LSLTPEQW-K SHRSYSCQVTH EG-ST-VEKT VAPTEC
```

MULTIFUNCTIONAL ANTIBODY CONJUGATES

CROSS REFERENCE TO RELATED APPLICATIONS

This application is a Continuation of International Application No. PCT/IB2011/053092, filed Jul. 11, 2011, which claims the benefit of U.S. Provisional Application Ser. No. 61/363,507, filed Jul. 12, 2010, which are both incorporated by reference in their entirety.

REFERENCE TO SEQUENCE LISTING

This application is being filed electronically via EFS-Web and includes an electronically submitted sequence listing in .txt format. The .txt file contains a sequence listing entitled "PC34002B_Seq_List_ST25" created on Nov. 17, 2011 and having a size of 66.2 KB. The sequence listing contained in this .txt file is part of the specification and is herein incorporated by reference in its entirety.

BACKGROUND

The development of bifunctional therapeutics has great potential to augment combination therapy strategies. A bifunctional therapeutic can provide the benefit of a combination therapy by modulating 2 different pathways with one therapeutic entity. In addition, bifunctional therapeutics may also benefit from synergies between pathways and demonstrate increased activity compared to mono-functional agents. Furthermore, bifunctional therapeutics can provide benefits in terms of reduced manufacturing, storage, and shipping costs, as well as reducing the number of therapies given to the patient and simplifying dosage regimes.

IGF1 R is a transmembrane heterotetrameric protein, which has 2 extracellular chains and 2 membrane-spanning β-chains in a disulfide-linked (β-α-α-β) configuration. IGF1R binds IGF1 with high affinity. IGF1 is a 70 amino acid peptide that is mainly produced by the liver in response to growth hormone stimulation but can be synthesized by almost any tissue in the body and circulates in serum to concentrations of 100-200 ng/mL. IGF1R signalling may play a role in multiple tumour types and is specifically implicated in lung cancer. For instance, elevated plasma levels of IGF1 are associated with an increased risk of lung cancer. Additionally, IGF1, IGF2, and IGF1R are expressed by normal lung cells but over-expressed by lung cancer cells. IGF1R signalling has also been implicated in breast cancer, prostate cancer, colorectal cancer, sarcoma, multiple myeloma, and other malignancies. WO02053596, WO2005016967, WO2005005635, and WO2009032145 disclose IGF1R antibodies and antigen-binding portions thereof.

Angiopoietin-1 (Ang1) and Angiopoietin-2 (Ang2) mediate the angiogenesis process as ligands of the endothelial cell receptor Tie2, along with VEGF and other angiogenic regulators. Ang1 stimulates the phosphorylation of Tie2, recruits pericytes to newly-formed blood vessels, and promotes their maturation. Ang2 is known to be angiogenic and over-expressed in many cancers. Ang2 competes with Ang1 for binding of Tie2, promotes the dissociation of pericytes, and results in unstable blood vessels. In the presence of VEGF and other angiogenic factors, endothelial cells in these unstable vessels proliferate and migrate to form new blood vessels.

About 50% of patients with solid tumours have increased expression of Ang2 but the levels of Ang2 in cancer tissues are highly variable. Higher Ang2 expression is clearly correlated with poor survival, later stage disease and more invasive cancers. A lower ratio between Ang1 and Ang2 has also been correlated with a poor prognosis for ovarian cancer. Tie2 expression is reported to be up-regulated in hepatocellular carcinoma, astrocytoma, Kaposi's sarcoma, cutaneous angiosarcoma, and non-small cell lung carcinoma. Tie2 is over-expressed on the blood vessels of many tumours. Tie2 expressing monocytes contribute to the formation of tumour blood vessels. Newly published data demonstrate that specifically sequestering Ang2 can inhibit tumour growth and cause staged tumours to regress. WO2008056346 discloses Ang2-binding peptides.

Targeting both IGF1R and Ang2 in the same therapy may prove to be an effective tool for oncologists to use in multiple treatment settings. Such approaches have been postulated (for example, in WO2009088805 and WO2010040508), but none have been approved to date. There therefore exists a need to provide alternative oncology therapies targeting both IGR-1R and Ang2.

The reference to any art in this specification is not, and should not be taken as, an acknowledgement of any form or suggestion that the referenced art forms part of the common general knowledge.

SUMMARY OF THE INVENTION

The present invention provides a multifunctional antibody conjugate (MAC) comprising an antibody or antigen binding portion thereof, conjugated to at least one Effector Moiety, and pharmaceutically acceptable salts, stereoisomers, tautomers, solvates, and prodrugs thereof. The invention also provides for pharmaceutical compositions and samples comprising MACs of the invention.

The present invention also provides a multifunctional antibody conjugate (MAC) comprising an antibody or antigen binding portion thereof, conjugated to at least one Ang2-binding peptide.

The present invention provides a multifunctional antibody conjugate (MAC) comprising an anti-IGF1R antibody or antigen binding portion thereof, conjugated to at least one Ang2-binding peptide.

In some embodiments, the at least one Ang2-binding peptide is conjugated to the side chain of a conjugating residue of the antibody via a linker.

In some embodiments, the Effector Moiety is covalently attached to the side chain of a lysine residue in the Fab region of the antibody or antigen binding portion thereof. In some embodiments, the Effector Moiety is covalently attached to the side chain of a lysine residue in the constant heavy chain (CH) or constant light chain (CL) region. Reaction of the Effector Moiety with the CL domain of the antibody is particularly desirable to minimize, or prevent, any interference with binding of the Fc portion of the antibody to Fc receptors (such as FcγR and FcRn) or binding of the antibody to its respective target. Conversely, conjugation of the respective Effector Moiety to the Fc portion of the antibody is likely to decrease the antibody half-life in vivo and/or its capacity to interact with the immune system (effector function). Conjugation of the Effector Moiety in the variable heavy chain (VH) or variable light chain (VL) region of the antibody carry a risk of diminishing the binding of the antibody to its cognate.

In some embodiments, the Effector Moiety is covalently attached to the side chain of a lysine residue in the constant light chain kappa region (CLκ) domain. Preferential conjugation of the Effector Moiety to the CLκ domain simplifies the creation of MAC isotypes by allowing isotypic switches of the CH domains of the antibody without affecting the conjugation sites of the Effector Moiety to the antibody.

The Effector Moiety may be covalently attached to the side chain of $K^{80}$ of the light chain kappa domain constant region (CLκ), (SEQ ID NO:15, SEQ ID NO:45, SEQ ID NO:46, or SEQ ID NO:47) ($K^{188}$ according to Kabat numbering). In some embodiments, the Effector Moiety is covalently attached to $K^{80}$ of SEQ ID NO:15. $K^{80}$ of SEQ ID NO:15 is located away from key regions of the respective antibody, such as paratope region, FcRn binding domain, hinge, FcR binding domains; this provides the advantage that preferentially linking at these sites limits the amount of interference to antibody-antigen interaction when the MAC is conjugated to the Effector Moiety.

In some aspects, the Effector Moiety is covalently attached to K* of the motif K*HK. The K* of the K*HK motif may correspond to $K^{80}$ of SEQ ID NO:15. In some aspects, the Effector Moiety is covalently attached to $K^{188}$ of the motif $K^{188}H$ located on the CLκ region, according to the Kabat numbering system. In some aspect, the CLκ region comprises at least residues 62-103 of SEQ ID NO: 15, 45, 46 or 47. In some aspects, the CLκ region comprises SEQ ID NO: 15, 45, 46, or 47.

In some aspects, the CLκ region comprises at least residues 62-103 of SEQ ID NO:15. In some aspects, the CLκ region comprises SEQ ID NO:15. In some aspect, the CLκ region comprises at least residues 62-103 of SEQ ID NO:45. In some aspects, the CLκ region comprises SEQ ID NO:45. In some aspect, the CLκ region comprises at least residues 62-103 of SEQ ID NO:46. In some aspects, the CLκ region comprises SEQ ID NO:46. In some aspect, the CLκ region comprises at least residues 62-103 of SEQ ID NO:47. In some aspects, the CLκ region comprises SEQ ID NO:47.

In some aspects, the CLκ region comprises SEQ ID NO: 45 or 47. Where the CLκ region comprises SEQ ID NO:45 or 47 in part or entirely, $x^{82}$ may be selected from the group consisting of K, R, G, A, V, L, I, S, T, C, M, N, Q, D, E, H, F, W or Y. In some aspects, $x^{82}$ may be G, A, V, L, or I. In some aspects, $x^{82}$ may be K, R, N, or Q. In some aspects, $x^{82}$ may be D, or E. In some aspects, $x^{82}$ may be K, R, G, A, V, L, I, N, or Q. In some aspects, $x^{82}$ may be D, or E. In some aspects, $x^{82}$ may be K, R, G, A, V, L, I, N, Q, D or E. In some aspects, $x^{82}$ may be D, or E. In some aspects, $x^{82}$ may be H, F, W or Y. In some aspects $x^{82}$ is not proline. In some aspects, $x^{82}$ (of SEQ ID NOs:15, 45, 46, and/or 47) is R. In some aspects, $K^{190}$-CLκ is R.

SEQ ID NOs:45 and 47 comprise the polymorphisms identified in the CLκ; $V/A^{153}$ and $L/V^{191}$ (according to Kabat numbering). Thus, the three polymorphisms are: Km(1): $V^{153}/L^{191}$; Km(1,2): $A^{153}/L^{191}$; and Km(3) $A^{153}/V^{191}$. In some aspects of the invention comprising SEQ ID NO:45 and/or 47, $x^{45}$ is V, and $x^{83}$ is L (Km(1)). In some aspects of the invention comprising SEQ ID NO:45 and/or 47, $x^{45}$ is A, and $x^{83}$ is L (Km(1,2)). In some aspects of the invention comprising SEQ ID NO:45 and/or 47, $x^{45}$ is A, and $X^{83}$ is V (Km(3)).

In some aspects, the MAC comprises an Effector Moiety conjugated to CLκ $K^{188}$ on both light chains. In some aspects, the MAC comprises an Effector Moiety conjugated to CLκ $K^{188}$ on one light chain only. In some aspects, the Effector Moiety is only conjugated to the MAC at $K^{188}$ CLκ. In some aspects, the Effector Moiety is conjugated to the MAC at $K^{188}$ CLκ on one light chain and one other location on the antibody. In some aspects, the Effector Moiety is conjugated to the MAC at $K^{188}$ CLκ on one light chain and 2 other locations on the antibody. In some aspects, the Effector Moiety is conjugated to the MAC at $K^{188}$ CLκ on one light chain and 3 other locations on the antibody. In some aspects, the Effector Moiety is conjugated to the MAC at $K^{188}$ CLκ on both light chains, and at one other location. In some aspects, the Effector Moiety is conjugated to the MAC at $K^{188}$ CLκ on both light chains, and at 2 other locations. In some aspects, the Effector Moiety is conjugated to the MAC at $K^{188}$ CLκ on both light chains, and at 3 other locations.

Samples and Compositions of the Invention

In some aspects, the invention provides for a composition or sample of a MAC comprising an antibody (or antigen binding portion thereof) covalently conjugated to an Effector Moiety, wherein at least about 50% of the Effector Moiety in the composition or sample is conjugated to $K^{188}$-CLκ. In some aspects, the invention provides for a composition or sample of a MAC comprising an antibody (or antigen binding portion thereof) covalently conjugated to an Effector Moiety, wherein at least about 60% of the Effector Moiety in the composition or sample is conjugated to $K^{188}$-CLκ. In some aspects, the invention provides for a composition or sample of a MAC comprising an antibody (or antigen binding portion thereof) covalently conjugated to an Effector Moiety, wherein at least about 70% of the Effector Moiety in the composition or sample is conjugated to $K^{188}$-CLκ. In some aspects, the invention provides for a composition or sample of a MAC comprising an antibody (or antigen binding portion thereof) covalently conjugated to an Effector Moiety, wherein at least about 80% of the Effector Moiety in the composition or sample is conjugated to $K^{188}$-CLκ. In some aspects, the invention provides for a composition or sample of a MAC comprising an antibody (or antigen binding portion thereof) covalently conjugated to an Effector Moiety, wherein at least about 90% of the Effector Moiety in the composition or sample is conjugated to $K^{188}$-CLκ.

In some aspects, the invention provides for a composition (or sample) of a MAC comprising an antibody (or antigen binding portion thereof), wherein at least about 50% of the antibody comprises an Effector Moiety covalently attached to $K^{188}$-CLκ on at least one light chain. In some aspects, the invention provides for a composition (or sample) of a MAC comprising an antibody (or antigen binding portion thereof), wherein at least about 60% of the antibody comprises an Effector Moiety covalently attached to $K^{188}$-CLκ on at least one light chain. In some aspects, the invention provides for a composition (or sample) of a MAC comprising an antibody (or antigen binding portion thereof), wherein at least about 70% of the antibody comprises an Effector Moiety covalently attached to $K^{188}$-CLκ on at least one light chain. In some aspects, the invention provides for a composition (or sample) of a MAC comprising an antibody (or antigen binding portion thereof), wherein at least about 80% of the antibody comprises an Effector Moiety covalently attached to $K^{188}$-CLκ on at least one light chain. In some aspects, the invention provides for a composition (or sample) of a MAC comprising an antibody (or antigen binding portion thereof), wherein at least about 90% of the antibody comprises an Effector Moiety covalently attached to $K^{188}$-CLκ on at least one light chain. In some aspects, the Effector Moiety is covalently conjugated to both $K^{188}$-CLκ on both light chains.

In some aspects, the invention provides for a sample of MAC comprising an antibody or antigen binding portion thereof covalently conjugated to an Effector Moiety, wherein at least about 30% of the sample comprises Effector Moieties conjugated at about 2 locations per antibody, and wherein at least one Effector Moiety conjugation site is $K^{188}$-CLκ. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a sample of MAC comprising an antibody or antigen binding portion thereof covalently conjugated to an Effector Moiety, wherein at least about 30% of the sample comprises Effector Moieties conjugated at about 3 locations per antibody, and wherein at least 2 Effector Moiety conjugation sites are $K^{188}$-CLκ on each light chain. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a sample of MAC comprising an antibody or antigen binding portion thereof covalently conjugated to an Effector Moiety, wherein at least about 30% of the sample comprises Effector Moieties conjugated at about 4 locations per antibody, and wherein at least 2 Effector Moiety conjugation sites are $K^{188}$-CLκ on each light chain. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a sample of MAC comprising an antibody or antigen binding portion thereof covalently conjugated to an Effector Moiety, wherein at least about 30% of the sample comprises Effector Moieties conjugated at about 5 locations per antibody, and wherein at least 2 Effector Moiety conjugation sites are $K^{188}$-CLκ on each light chain. In some aspects, the amount is about 40%. In some aspects, the amount is about 50%. In some aspects, the amount is about 60%. In some aspects, the amount is about 70%. In some aspects, the amount is about 80%. In some aspects, the amount is about 90%. In some aspects, the amount is about 95%. In some aspects, the amount is about 99%.

In some aspects, the invention provides for a sample of MAC, wherein at least 50% of the light chain molecules are conjugated with at least one Effector Moiety. In some aspects, the invention provides for a sample of MAC, wherein at least about 60% of the light chain molecules are conjugated with at least one Effector Moiety. In some aspects, the invention provides for a sample of MAC, wherein at least about 65% of the light chain molecules are conjugated with at least one Effector Moiety. In some aspects, the invention provides for a sample of MAC, wherein at least about 70% of the light chain molecules are conjugated with at least one Effector Moiety. In some aspects, the invention provides for a sample of MAC, wherein at least about 75% of the light chain molecules are conjugated with at least one Effector Moiety. In some aspects, the invention provides for a sample of MAC, wherein at least about 80% of the light chain molecules are conjugated with at least one Effector Moiety. In some aspects, the invention provides for a sample of MAC, wherein at least about 85% of the light chain molecules are conjugated with at least one Effector Moiety. In some aspects, the invention provides for a sample of MAC, wherein at least about 90% of the light chain molecules are conjugated with at least one Effector Moiety. In some aspects, the invention provides for a sample of MAC, wherein at least about 95% of the light chain molecules are conjugated with at least one Effector Moiety.

In some aspects, the invention provides for a sample of MAC, wherein at least about 70% of the heavy chain molecules are unconjugated with the Effector Moiety. In some aspects, the amount is about 75%. In some aspects, the amount is about 80%. In some aspects, the amount is about 85%. In some aspects, the amount is about 90%. In some aspects, the amount is about 95%. In some aspects, the amount is about 99%. In some aspects, substantially all of the heavy chain molecules are unconjugated with the Effector Moiety.

In some aspects, the invention provides for a MAC comprising an antibody, or antigen binding portion thereof, covalently conjugated to an Effector Moiety via a linker, characterized in that the antibody or antigen binding portion thereof comprises the motif KHK, and the Effector Moiety is conjugated to the side chain of the $K^{188}$ residue (according to Kabat numbering).

In some aspects, the amount of individual light chain fragments that are unconjugated has a lower limit selected from the group consisting of about 1, 5, 10, 15, 20, 25, 30, 35, 40, 45, 50, and 55%, and an upper limit selected from the group consisting of about 5, 10, 15, 20, 25, 30, 35, 40, 45, 50, 55, and 60%. In some aspects, the amount of individual light chain fragments that are conjugated at one location has a lower limit selected from the group consisting of about 25, 30, 35, 40, 45, 50, and 55%, and an upper limit selected from the group consisting of about 30, 35, 40, 45, 50, 55, 60, 65, 70, 75, 80, 85, 90, and 95%. In some aspects, the amount of individual light chain fragments that are conjugated at 2 locations has a lower limit selected from the group consisting of about 1, 2, 3, 4, 5, 6, 7, 8, 9, 5, 10, 15, 20, and 25%, and an upper limit selected from the group consisting of about 5, 16, 7, 8, 9, 5, 10, 15, 20, 25, 30, 35, and 40%.

In some aspects, the amount of individual heavy chain fragments that are unconjugated has a lower limit selected from the group consisting of about 50, 55, 60, 65, 70, 75, and 80% and an upper limit selected from the group consisting of about 60, 65, 70, 75, 80, 85, 90, 95, and 99%. In some aspects, the amount of individual heavy chain fragments that are conjugated at one location has a lower limit selected from the group consisting of about 1, 2, 5, 10, 15, 20, and 25% and an upper limit selected from the group consisting of about 5, 10, 15, 20, 25, 30, 35, 40, and 50%. In some aspects, the amount of individual heavy chain fragments that are conjugated at 2 locations has a lower limit selected from the group consisting of about 0, 1, 2, 3, 4, 5, 10, and 15% and an upper limit selected from the group consisting of about 2, 3, 4, 5, 10, 15 and 20%.

In some aspects the number of conjugations per antibody in a sample or composition of the invention has a lower limit selected from the group consisting of about 0.5, 0.6, 0.7, 0.8, 0.9, 1, 1.1, 1.2, 1.3, 1.4, 1.5, 1.55, 1.6, 1.65, 1.7, 1.75, 1.8, 1.85, 1.9, 1.95 and 2, and an upper limit selected from the group consisting of about 1.6, 1.7, 1.75 1.8, 1.85, 1.9, 1.95, 2.0, 2.05, 2.1, 2.15, 2.2, 2.25, 2.3, 2.4, 2.5, 2.6, 2.7, 2.8, 2.9, 3.0, 3.5, 4.0, 4.5 and 5. In some aspects the number of conjugations per antibody in a sample or composition of the invention is between about 1.5 and about 2.5. In some aspects the number of conjugations per antibody in a sample or composition of the invention is between about 1.6 and about 2.4. In some aspects the number of conjugations per antibody in a sample or composition of the invention is between about 1.7 and about 2.3. In some aspects the number of conjugations per antibody in a sample or composition of the invention is between about 1.8 and about 2.2. In some aspects the number of conjugations per antibody in a sample or composition of the invention is an amount selected from the group consisting of about 1.5, about 1.55, about 1.6, about 1.65, about 1.7, about 1.75, about 1.8, about 1.85, about 1.9, about 1.95, about 2.0, about 2.05, about 2.1, about 2.15, about 2.2, about 2.25, about 2.3, about 2.4 and about 2.5. In some aspects, the amount is about 1.7. In some aspects, the amount is about 1.8. In some aspects, the amount is about 1.9. In some aspects, the amount is about 2. In some aspects, the amount is about 2.1. In some aspects, the amount is about 2.1. In some aspects, the amount is about 2.3.

In some aspects of the invention, the number of conjugations per antibody is less than 2, with at least 50% of the antibody population having only a single conjugation per antibody. These samples are advantageous as they allow additional conjugation reactions to be targeted at the remaining CLκ site. In some aspects the number of conjugations per antibody in a sample or composition of the invention is between about 0.5 and about 1.5. In some aspects the number of conjugations per antibody in a sample or composition of the invention is between about 0.6 and about 1.4. In some aspects the number of conjugations per antibody in a sample or composition of the invention is between about 0.7 and about 1.3. In some aspects the number of conjugations per antibody in a sample or composition of the invention is between about 0.8 and about 1.2. In some aspects the number of conjugations per antibody in a sample or composition of the invention is between about 0.9 and about 1.1.

One of the advantages of the invention is that depending on the reagents and reaction conditions (especially the leaving group ester and molar ratio of linker:antibody), compositions and samples of MACs can be generated with a defined number of Effector Moieties relative to a defined number of antibodies. This can be especially useful when balancing the relative reactivities and therapeutic windows of the Effector Moiety and antibody. Moreover, in some situations, increasing the number of peptides per antibody beyond a certain threshold may not result in increased target binding or therapeutic effect. It is useful, therefore, to be able to control the number of peptides conjugated per antibody, and in doing so, direct the location of conjugation so as to minimize Fc or combining site interference. In some situations, therefore, aspects of the invention that allow for reduced conjugation, preferentially decorating only a single $K^{188}$-CLκ can be advantageous.

In some aspects, a sample of MAC may be a pharmaceutical composition.

IGFR Antibody

In some embodiments, the at least one Ang2-binding peptide is conjugated via the side chain of a lysine residue on the anti-IGF1R antibody. In some embodiments, the at least one Ang2-binding peptide is covalently linked to the CL domain. In some embodiments, the at least one Ang2-binding peptide is covalently linked to the region of the anti-IGF1R antibody. In some embodiments, the at least one Ang2-binding peptide is covalently linked to the light chain constant region of the anti-IGR-1R antibody. In some embodiments, the anti-IGF1R antibody is covalently attached to the Ang2-binding peptide via a linker. In some embodiments, the Ang2-binding peptide is not fused to the C' or N' terminus of the anti-IGF1R antibody.

In some embodiments, the anti-IGF1R antibody is selected from those described in WO02053596 (U.S. Pat. No. 7,037, 498) and WO2005016967(U.S. Pat. No. 7,371,378) (each of whose contents is incorporated herein). In some embodiments the MAC comprises a heavy chain constant domain comprising SEQ ID NO:5.

In some embodiments, the MAC comprises a heavy chain variable domain selected from the group consisting of SEQ ID NO:6, residues 1-122 of SEQ ID NO:1, and residues 1-122 of SEQ ID NO:3. In some embodiments, the MAC comprises a heavy chain variable domain comprising residues 1-122 of SEQ ID NO:3.

In some embodiments, the heavy chain of the MAC comprises a VHCDR1 region comprising a sequence selected from the group consisting of SEQ ID NO:7, residues 26-35 of SEQ ID NO:1, and residues 26-35 of SEQ ID NO:3. In some embodiments, the MAC comprises a VHCDR1 region comprising SEQ ID NO:7. In some embodiments, the heavy chain of the MAC comprises a VHCDR2 region comprising a sequence selected from the group consisting of SEQ ID NO:8, residues 50-64 of SEQ ID NO:3, and residues 50-64 of SEQ ID NO:5. In some embodiments, the MAC comprises a VHCDR2 region comprising SEQ ID NO:8.

In some embodiments, the heavy chain of the MAC comprises a VHCDR3 region comprising a sequence selected from the group consisting of SEQ ID NO:9, residues 99-114 of SEQ ID NO:1, and residues 99-114 of SEQ ID NO:3. In some embodiments, the MAC comprises a VHCDR3 region comprising SEQ ID NO:9.

In some embodiments, the heavy chain of the MAC comprises a VHFR1 region comprising a sequence selected from the group consisting of SEQ ID NO:10, residues 1-25 of SEQ ID NO:1, residues 1-25 of SEQ ID NO:3, and SEQ ID NO:11. In some embodiments, the MAC comprises a VHFR1 region comprising SEQ ID NO:11.

In some embodiments, the heavy chain of the MAC comprises a VHFR2 region comprising a sequence selected from the group consisting of SEQ ID NO:12, residues 36-49 of SEQ ID NO:1, and residues 36-49 of SEQ ID NO:3. In some embodiments, the MAC comprises a VHFR2 region comprising SEQ ID NO:12.

In some embodiments, the heavy chain of the MAC comprises a VHFR3 region comprising a sequence selected from the group consisting of SEQ ID NO:13, residues 65-98 of SEQ ID NO:1, and residues 65-98 of SEQ ID NO:3. In some embodiments, the MAC comprises a VHFR3 region comprising SEQ ID NO: 13.

In some embodiments, the heavy chain of the MAC comprises a VHFR4 region comprising a sequence selected from the group consisting of SEQ ID NO:14, residues 115-122 of SEQ ID NO:1, and residues 115-122 of SEQ ID NO:3. In some embodiments, the MAC comprises a VHFR4 region comprising SEQ ID NO:14.

In some embodiments, the VHCDR1, VHCDR2 and VHCDR3 regions of the anti-IGF1R antibody comprise residues 26-35 of SEQ ID NO:3, residues 50-64 of SEQ ID NO:3, and residues 99-114 of SEQ ID NO:3 respectively.

In some embodiments, the VHFR1, VHFR2, VHFR3, and VHFR4 regions of the anti-IGF1R antibody comprise residues 1-25 of SEQ ID NO:3, residues 36-49 of SEQ ID NO:3, residues 65-98 of SEQ ID NO:3, and residues 115-122 of SEQ ID NO:3 respectively.

In some embodiments, the anti-IGF1R antibody comprises a heavy chain selected from the group consisting of SEQ ID NO:1 and SEQ ID NO:3. In some embodiments, the anti-IGF1R antibody comprises a heavy chain comprising SEQ ID NO:3.

In some embodiments the MAC comprises a light chain constant domain comprising SEQ ID NO:15. In some embodiments the MAC comprises a light chain constant domain comprising SEQ ID NO:45, 46 or 47.

In some embodiments, the MAC comprises a light chain variable domain selected from the group consisting of SEQ ID NO:16, residues 1-108 of SEQ ID NO:2, and residues 1-108 of SEQ ID NO:4. In some embodiments, the MAC comprises a light chain variable domain comprising residues 1-108 of SEQ ID NO:4.

In some embodiments, the light chain of the MAC comprises a VLCDR1 (variable light chain complimentary determining region-1) region comprising a sequence selected from the group consisting of SEQ ID NO:17, residues 24-34 of SEQ ID NO:2, and residues 24-34 of SEQ ID NO:4. In some embodiments, the MAC comprises a VLCDR1 region comprising SEQ ID NO:17.

In some embodiments, the light chain of the MAC comprises a VLCDR2 region comprising a sequence selected from the group consisting of SEQ ID NO:18, residues 48-54 of SEQ ID NO:2, and residues 48-54 of SEQ ID NO:4. In some embodiments, the MAC comprises a VLCDR2 region comprising SEQ ID NO:18.

In some embodiments, the light chain of the MAC comprises a VLCDR3 region comprising a sequence selected from the group consisting of SEQ ID NO:19, residues 89-97 of SEQ ID NO:2, and residues 89-97 of SEQ ID NO:4. In some embodiments, the MAC comprises a VLCDR3 region comprising SEQ ID NO:19.

In some embodiments, the light chain of the MAC comprises a VLFR1 region comprising a sequence selected from the group consisting of SEQ ID NO:20, SEQ ID NO:21, residues 1-23 of SEQ ID NO:2, and residues 1-23 of SEQ ID NO:4. In some embodiments, the MAC comprises a VLFR1 region comprising SEQ ID NO:21.

In some embodiments, the light chain of the MAC comprises a VLFR2 region comprising a sequence selected from the group consisting of SEQ ID NO:22, residues 35-47 of SEQ ID NO:2, and residues 35-47 of SEQ ID NO:4. In some embodiments, the MAC comprises a VLFR2 region comprising SEQ ID NO:22.

In some embodiments, the light chain of the MAC comprises a VLFR3 region comprising a sequence selected from the group consisting of SEQ ID NO:23, residues 55-88 of SEQ ID NO:2, and residues 55-88 of SEQ ID NO:4. In some embodiments, the MAC comprises a VLFR3 region comprising SEQ ID NO:23.

In some embodiments, the light chain of the MAC comprises a VLFR4 region comprising a sequence selected from the group consisting of SEQ ID NO:24, SEQ ID NO:25, residues 98-108 of SEQ ID NO:2, and residues 98-108 of SEQ ID NO:6. In some embodiments, the MAC comprises a VLFR4 region comprising SEQ ID NO:25.

In some embodiments, the VLCDR1, VLCDR2 and VLCDR3 regions of the anti-IGF1R antibody comprise residues 24-34 of SEQ ID NO:4, residues 48-54 of SEQ ID NO:4, and residues 89-96 of SEQ ID NO:4 respectively.

In some embodiments, the VLFR1, VLFR2, VLFR3, AND VLFR4 regions of the anti-IGF1R antibody comprise residues 1-24 of SEQ ID NO:4, residues 35-47 of SEQ ID NO:4, residues 55-88 of SEQ ID NO:4, and residues 97-108 of SEQ ID NO:4 respectively.

In some embodiments, the anti-IGF1R antibody comprises a light chain selected from the group consisting of SEQ ID NO:2 and SEQ ID NO:4. In some embodiments, the anti-IGF1R antibody comprises a light chain comprising SEQ ID NO:4.

In some embodiments, the anti-IGF1R antibody comprises a heavy chain comprising SEQ ID NO:1 and a light chain comprising SEQ ID NO:2.

In some embodiments, the anti-IGF1R antibody comprises a heavy chain comprising SEQ ID NO:3 and a light chain comprising SEQ ID NO:4.

The antibody 2.12.1 has been described in WO02053596. A hybridoma, 2.12.1, producing monoclonal antibodies specific for IGF1R was deposited in the American Type Culture Collection (ATCC), 10801 University Boulevard, Manassas, Va. 20110-2209, on Dec. 12, 2000 with the deposit number PTA-2792.

In some embodiments, the anti-IGF1R antibody comprises the motif $K^{188}H^{189}x^{190}$ in the CLκ region, wherein x is G, A, V, I, L, S, T, C, M, N, Q, D, E, F, Y, W, H, R or K, according to Kabat numbering. In some aspects, the anti-IGF1R antibody is one selected from WO2009032145 (US2009092614) or WO2005005635 (U.S. Pat. No. 7,579,157), both of whose contents are herein incorporated. In some embodiments, a MAC of the invention comprises an anti-IGF1R antibody or antigen binding portion thereof, conjugated to at least one Ang2-binding peptide in such a way so as not to abrogate the IGF1R binding affinity of the antibody.

In some aspects, the antibody targets a different target within the same pathway as the Effector Moiety. In some aspects, the antibody targets a different target to the Effector Moiety.

In some aspects, the antibody used for conjugation may be useful in the field of oncology. Suitable antibodies include; Rituximab, (Rituxan™), a chimeric, $IgG1_\kappa$, anti-CD20 antibody, used to treat cancer and in particular non Hodgkin's lymphoma and also rheumatoid arthritis; Cetuximab (Erbitux™) a chimeric, $IgG1_\kappa$, anti-EGF receptor antibody, used to treat cancer, and in particular colon, head & neck cancer.

In some aspects, the antibody used for conjugation may be useful in the field of auto-immune and other immunological disorders. Suitable antibodies include Infliximab (Remicade™) a chimeric, $IgG1_\kappa$, anti-TNFα antibody, used to treat rheumatoid arthritis, ulcerative colitis, Crohn's disease, psoriasis, psoriatic arthritis, and ankylosing spondylitis; Adalimumab (Humira™) a human, $IgG1_\kappa$, anti-TNFα antibody, used to treat rheumatoid arthritis, Crohn's disease, psoriasis, psoriatic arthritis, juvenile idiopathic arthritis and ankylosing spondylitis; Natalizumab (Tysabri™) a humanized, $IgG4_\kappa$, anti-α4-integrin antibody used to treat multiple sclerosis, rheumatoid arthritis, psoriasis, juvenile idiopathic arthritis, psoriatic arthritis, ankylosing spondylitis, Crohn's disease; Omalizumab (Xolair™) a humanized, $IgG1_\kappa$, anti-IgE antibody used to treat allergic asthma; Ranibizumab (Lucentis™) a humanized, $IgG1_\kappa$, anti-VEGF antibody, used to treat wet AMD; and Palivizumab (Synagis™) a humanized, $IgG1_\kappa$, anti-RSV antibody, used to treat infective diseases, including respiratory syncytical virus.

In some aspect, compounds and compositions of the invention may be used to treat the above mentioned conditions.

Effector Moieties

The Effector Moiety may be a therapeutic agent, protein, peptide, nucleic acid, aptamer, small molecule, protein agonist, protein antagonist, metabolic regulator, hormone, toxin, growth factor or other regulatory protein, or may be a diagnostic agent, such as an enzyme that may be easily detected or visualized, such as horseradish peroxidase.

In some aspects, the Effector Moiety may be a protein or peptide, and may be connected to the linker through a peptide-linking residue. The protein or peptide may comprise one or both of an amino-terminal capping group $R^1$ and a carboxyl-terminal capping group $R^2$. $R^1$ may be $CH_3$, $C(O)CH_3$, $C(O)CH_3$, $C(O)CH_2CH_3$, $C(O)CH_2CH_2CH_3$, $C(O)CH(CH_3)CH_3$, $C(O)CH_2CH_2CH_3$, $C(O)CH(CH_3)CH_2CH_3$, $C(O)C_6H_5$, $C(O)CH_2CH_2(CH_2CH_2O)_{1-5}Me$, dichlorobenzoyl (DCB), difluorobenzoyl (DFB), pyridinyl carboxlate (PyC) or amido-2-PEG, an amino protecting group, a lipid fatty acid group or a carbohydrate. $R^2$ may be OH, $NH_2$, $NH(CH_3)$, NHCH$_2$CH$_3$, NHCH$_2$CH$_2$CH$_3$, NHCH(CH$_3$)CH$_3$, NHCH$_2$CH$_2$CH$_2$CH$_3$, NHCH(CH$_3$)CH$_2$CH$_3$, NHC$_6$H$_5$, NHCH$_2$CH$_2$OCH$_3$, NHOCH$_3$, NHOCH$_2$CH$_3$, a carboxy protecting group, a lipid fatty acid group or a carbohydrate.

The protein or peptide linking residue may be K, K(SH), lysine homologs, Dap, Dab, Orn, R, C, thiol containing residues, S, T, Y, D, E, N or Q. The protein or peptide may be connected to the linker through the amino terminus of the N-terminal amino acid. The protein or peptide may be connected to the linker through the carboxyl terminus of the C-terminal amino acid. An additional amino acid residue may be added to the N- or C-terminus in order to function as a linking residue, whether by connection through the amino acid side chain, or the amino or carboxyl terminus.

Ang2-Binding Peptides

The Effector Moiety may be an Ang2-binding peptide. In some embodiments, the Ang2-binding peptide may comprise a sequence selected from those described in WO2008056346 (US2008166364) (whose content is incorporated herein). In some embodiments, the Ang2-binding peptide comprises the sequence:
Q$^1$ (AcK)$^2$ Y$^3$ Q$^4$ P$^5$ L$^6$ D$^7$ E$^8$X$^9$ D$^{10}$ K$^{11}$ T$^{12}$ L$^{13}$ Y$^{14}$ D$^{15}$ Q$^{16}$ F$^{17}$ M$^{18}$ L$^{19}$ Q$^{20}$ Q$^{21}$ G$^{22}$ (SEQ ID NO:26)
wherein X$^9$ of SEQ ID NO: 26 is acyl-lysine (AcK) or leucine, (hereinafter designated Ang2-X$^9$) and
wherein X$^9$, K$^{11}$, L$^{13}$, Q$^{16}$, M$^{18}$, or L$^{19}$ of the Ang2-binding peptide is substituted by an Ang2-linking residue comprising a nucleophilic side chain covalently attached to the linker, the linking residue being selected from the group consisting of K, Y, S, T, H, homologs of lysine, such as K(SH), homocysteine, homoserine, Dap, and Dab. In some embodiments, the Ang2-linking residue may be selected from the group consisting of K, K(SH), Y, S, T, H, Dap, and Dab. In some embodiments, the Ang2-linking residue is K. The Ang2-linking residue may be K$^{11}$. In some embodiments, the Ang2-linking residue may be K(SH). The Ang2-linking residue may be K(SH)$^{11}$.

In some embodiments, the Ang2-binding peptide comprises the sequence:
Q$^1$ (AcK)$^2$ Y$^3$ Q$^4$ P$^5$ L$^6$ D$^7$ E$^8$(AcK)$^9$ D$^{10}$ K$^{11}$ T$^{12}$ L$^{13}$ Y$^{14}$ D$^{15}$ Q$^{16}$ F$^{17}$ M$^{18}$ L$^{19}$ Q$^{20}$ Q$^{21}$ G$^{22}$ (SEQ ID NO:27)
wherein Ang2-K$^{11}$ is the Ang2-linking residue.

In some embodiments, the Ang2-binding peptide comprises the sequence:
Q$^1$ (AcK)$^2$ Y$^3$ Q$^4$ P$^5$ L$^6$ D$^7$ E$^8$L$^9$ D$^{10}$ K$^{11}$ T$^{12}$ L$^{13}$ Y$^{14}$ D$^{15}$ Q$^{16}$ F$^{17}$ M$^{18}$ L$^{19}$ Q$^{20}$ Q$^{21}$ G$^{22}$ (SEQ ID NO:28)
wherein Ang2-K$^{11}$ is the Ang2-linking residue.

In some embodiments, the Ang2-binding peptide comprises the sequence:
SEQ ID NO:29 Q$^1$ (AcK)$^2$ Y$^3$ Q$^4$ P$^5$ L$^6$ D$^7$ E$^8$ K$^9$ D$^{10}$ (AcK)$^{11}$ T$^{12}$ L$^{13}$ Y$^{14}$ D$^{15}$ Q$^{16}$ F$^{17}$ M$^{18}$ L$^{19}$ Q$^{20}$ Q$^{21}$ G$^{22}$
wherein Ang2-K$^9$ is the Ang2-linking residue.

In some embodiments, the Ang2-binding peptide comprises the sequence:
SEQ ID NO:30 Q$^1$ (AcK)$^2$ Y$^3$ Q$^4$ P$^5$ L$^6$ D$^7$ E$^8$L$^9$ D$^{10}$ (AcK)$^{11}$ T$^{12}$ L$^{13}$ Y$^{14}$ D$^{15}$ K$^{16}$ F$^{17}$ M$^{18}$ L$^{19}$ Q$^{20}$ Q$^{21}$ G$^{22}$
wherein Ang2-K$^{16}$ is the Ang2-linking residue.

In some embodiments, the Ang2-binding peptide comprises the sequence:
SEQ ID NO:31 Q$^1$ (AcK)$^2$ Y$^3$ Q$^4$ P$^5$ L$^6$ D$^7$ E$^8$L$^9$ D$^{10}$ (AcK)$^{11}$ T$^{12}$ L$^{13}$ Y$^{14}$ D$^{15}$ Q$^{16}$ F$^{17}$ K$^{18}$ L$^{19}$ Q$^{20}$ Q$^{21}$ G$^{22}$
wherein Ang2-K$^{18}$ is the Ang2-linking residue.

In some embodiments, the Ang2-binding peptide comprises the sequence:
SEQ ID NO:32 Q$^1$ (AcK)$^2$ Y$^3$ Q$^4$ P$^5$ L$^6$ D$^7$ E$^8$L$^9$ D$^{10}$ (AcK)$^{11}$ T$^{12}$ L$^{13}$ Y$^{14}$ D$^{15}$ Q$^{16}$ F$^{17}$ M$^{18}$ K$^{19}$ Q$^{20}$ Q$^{21}$ G$^{22}$
wherein Ang2-K$^{19}$ is the Ang2-linking residue.

In some embodiments, the Ang2-binding peptide further comprises a N-terminal capping group R$^1$— wherein R$^1$ is CH$_3$, C(O)CH$_3$, C(O)CH$_3$, C(O)CH$_2$CH$_3$, C(O)CH$_2$CH$_2$CH$_3$, C(O)CH(CH$_3$)CH$_3$, C(O)CH$_2$CH$_2$CH$_2$CH$_3$, C(O)CH(CH$_3$)CH$_2$CH$_3$, C(O)C$_6$H$_5$, C(O)CH$_2$(CH$_2$CH$_2$O)$_{1-5}$Me, dichlorobenzoyl (DCB), difluorobenzoyl (DFB), pyridinyl carboxylate (PyC) or amido-2-PEG, an amino protecting group, a lipid fatty acid group or a carbohydrate.

In some embodiments, the Ang2-binding peptide further comprises a C-terminal capping group —R$^2$ wherein R$^2$ is OH, NH$_2$, NH(CH$_3$), NHCH$_2$CH$_3$, NHCH$_2$CH$_2$CH$_3$, NHCH(CH$_3$)CH$_3$, NHCH$_2$CH$_2$CH$_2$CH$_3$, NHCH(CH$_3$)CH$_2$CH$_3$, NHC$_6$H$_5$, NHCH$_2$CH$_2$OCH$_3$, NHOCH$_3$, NHOCH$_2$CH$_3$, a carboxy protecting group, a lipid fatty acid group or a carbohydrate.

In some embodiments R$^1$ may be C(O)CH$_3$. In some embodiments R$^2$ may be NH$_2$.

The Ang2-binding peptide together with N-terminal and C-terminal capping groups may comprise the formula: [C(O)CH$_3$]-[SEQ ID NO:27]-[NH$_2$]: [C(O)CH$_3$]-Q$^1$ (A$_c$K)$^2$ Y$^3$ Q$^4$ P$^5$ L$^6$ D$^7$ E$^8$(A$_c$K)$^9$ D$^{10}$ K$^{11}$ T$^{12}$ L$^{13}$ Y$^{14}$ D$^{15}$ Q$^{16}$ F$^{17}$ M$^{18}$ L$^{19}$ Q$^{20}$ Q$^{21}$ G$^{22}$-[NH$_2$] wherein Ang2-K" is the Ang2-linking residue.

The Ang2 peptides described herein may be conjugated as described to numerous types of antibodies, in particular antibodies useful in the treatment of proliferative disorders such as cancer or increased angiogenesis, and may also be conjugated to catalytic antibodies such as h38C2, to form MACs.

Linkers

The Effector Moiety of the invention (such as a small molecule, aptamer, nucleic acid, protein, or peptide (e.g. Ang2-binding peptide)) may be covalently attached to the antibody or antigen binding portion thereof (e.g. anti-IGF1R antibody) by a linker. The linker may be covalently attached to the peptide by an amino group of the side chain of the peptide-linking residue. This may be a lysine residue. In some embodiments, the linking residue is a thiol bearing residue, such as Cys or K(SH) and the linker is covalently attached to the peptide via the terminal thiol group of the linking residue.

The linker may be linear or branched (to allow for conjugation to more than one Effector Moiety per Conjugation Addition), and optionally includes one or more carbocyclic or heterocyclic groups. Linker length may be viewed in terms of the number of linear atoms between the Effector Moiety and Antibody, with cyclic moieties such as aromatic rings and the like to be counted by taking the shortest route around the ring. In some embodiments, the linker has a linear stretch of between 5-15 atoms, in other embodiments 15-30 atoms, in still other embodiments 30-50 atoms, in still other embodiments 50-100 atoms, and in still other embodiments 100-200 atoms. In some embodiments, the length of the linker is a range with a lower limit selected from the group consisting of 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, and an upper limit selected from the group consisting of 7, 8, 9, 10, 11, 12, 13, 14, 15, 16, 17, 18, 19, 20, 25, 30, 35, 40, 45, 50, 55, 60, 65, 70, 75, 80, 85, 90, 95, 100, 105, 110, 120, 130, 140, 150, 160, 170, 180, 190, and 200.

Other linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, modulation of antibody binding, the ability to be incorporated into a micelle or liposome, and the like.

The linker may be a peptidyl linker. In some embodiments, the peptidyl linker may be between 3-20 amino acids long, such as repeats of a single amino acid residue (e.g. poly glycine) or combinations of amino acid residues to give a peptide linker which imparts favorable presentation of the Effector Moiety or pharmacokinetics. Peptidyl linkers that would be most compatible with the presence of activating groups may lack lysine and histidine residues. SEQ ID NO:59 is an exemplary peptidyl linker.

Alternatively, the linker may be a non-peptidyl linker. Typical examples of these types of linker would be those based on straight or branched chain hydrocarbons or polyethylene glycols of varying lengths. These may incorporate other groups to effect solubility, rigidity, isoelectric point, such as aromatic or non-aromatic rings, halogens, ketones, aldehydes, esters, sulfonyls, phosphate groups, and so on.

In some aspects of the invention, the linker may comprise the formula: -X-Y-Z-; wherein X is the attachment group to the Effector Moiety (for example, via a peptide-linking residue), Y is a spacer region, and Z is an attachment moiety to the side chain of a lysine or cysteine residue on an antibody (for example, an anti-IGF1R antibody). In some aspects, the linker may be of the formula XYZ* when unbound to the antibody, where Z* is a leaving group, such that when conjugated to the antibody, the leaving group Z* reacts with the conjugation site of the antibody to form the conjugated linker XYZ.

X may be selected so as to enable a specific directional covalent linking strategy to the Effector Moiety (for example, via the peptide-linking residue). In some aspects, X may be selected from the group consisting of COOH, isocyanate, isothiocyanate, acyl azide, sulfonic acid, sulfonyl halide, aldehyde, ketone, epoxide, carbonate, arylating reagent, imidoester, amine group, and a malemide group. For example, where the peptide-linking residue comprises a nucleophilic group, X may be an electrophilic group and vice versa. For example, if the peptide-linking residue side chain comprises an amine group, such as K, H, Ornithine, Dap, or Dab, X may be COOH, or other similarly reactive electrophile, for example, an isocyanate, isothiocyanate, acyl azide, sulfonic acid or sulfonyl halide, aldehyde or ketone, epoxide, carbonate, arylating reagent or imidoester. If the peptide-linking residue is D or E, X may comprise a nucleophilic group, such as an amine group. Either of these strategies permits a covalent bond to be formed between the X group and the peptide-linking residue by amide bond formation strategies. For example, when X is COOH, it may be activated as a pentafluorophenyl ester. In this case, reaction with an amine group on the peptide-linking peptide leads to amide bond formation, while the pentafluorophenol is a leaving group (which may be termed X*).

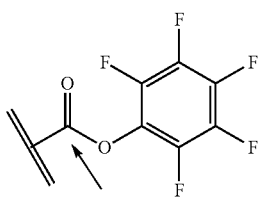

The arrow indicates the point of attachment to the peptide-linking residue and the parallel line represents the point of attachment to the Y group of the linker.

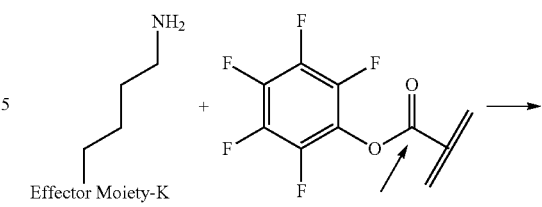

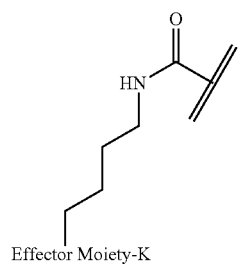

Where the peptide-linking group is C, homologs of C, or other thiol-group containing residues (such as K(SH)), X may comprise a malemide group, permitting a thiol-malemide addition reaction strategy to covalently link the X group to the peptide-linking residue. In some aspects, X may be maleimide:

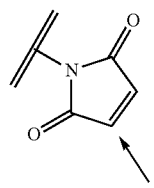

wherein the arrow indicates the point of attachment to the peptide linking residue and the parallel line represents to attachment to the Y group of the linker. For ease of nomenclature, linkers described herein that have been constructed using maleimide groups are described as maleimide-containing linkers, and may be titled MAL to indicate this, even though following construction of the linker, the maleimide group is generally converted to a succinimide ring.

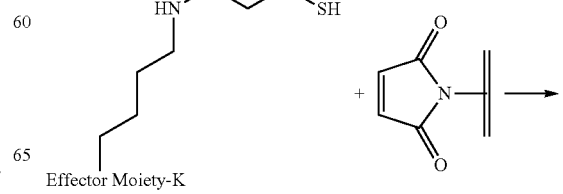

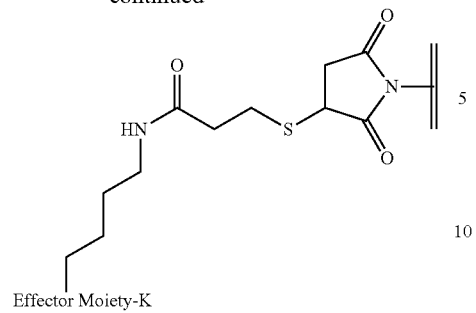

In some aspects, the linking residue is K(SH), and the X group is maleimide.

In some aspects, X may comprise a pentafluorophenyl ester activated carboxyl function which may form an amide with the lysine side chain on the peptide.

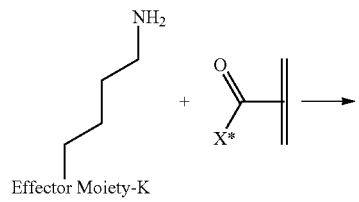

In some aspects, X may comprise a thiol group, allowing a disulphide bridge to be formed between the peptide-linking residue and X group.

In some embodiments, Y is a biologically compatible connecting chain including any atom selected from the group consisting of C, H, N, O, P, S, F, Cl, Br, and I, and may comprise one or more amino acids, polymer or block copolymer. Y may be selected so as to provide an overall length of the linker of between 2-100 atoms. Y may be selected so that the overall length of the linker is between 5 and 30 atoms. Y may be selected so that the overall length of linker is 15-25 atoms. Y may be selected so that the overall length of linker is between about 17 and about 19 atoms.

In some aspects, Y may be an amino polyethyleneglycol acid, such as:

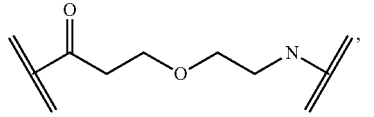

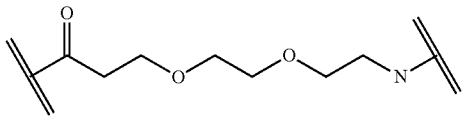

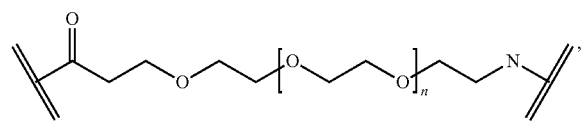

where n=0 to 10, in some aspects 1-10, in some aspects, 1-5, and in some aspects, 1.

In some aspects, Y may be a polyethylene glycol diacid, such as:

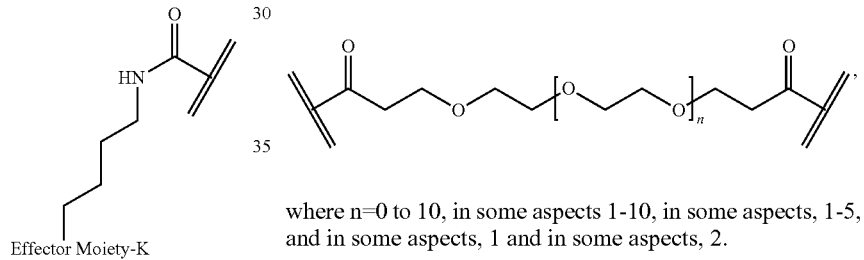

where n=0 to 10, in some aspects 1-10, in some aspects, 1-5, and in some aspects, 1 and in some aspects, 2.

In some aspects of the invention, the Y portion of the linker comprises the formula:

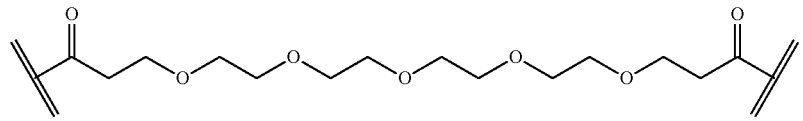

In some aspects, Y may be an amino alkanoic acid, such as:

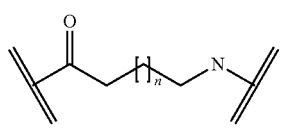

where n=0 to 20 in some aspects 1-10, in some aspects, 1-5, and in some aspects, 1 and in some aspects, 2.

In some aspects, Y may be an alkanoic diacid, such as:

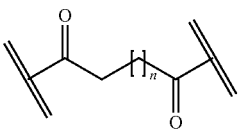

where n=0 to 20 in some aspects 1-10, in some aspects, 1-5, and in some aspects, 1 and in some aspects, 2.

In some aspects, Y may be a polyglycine, such as:

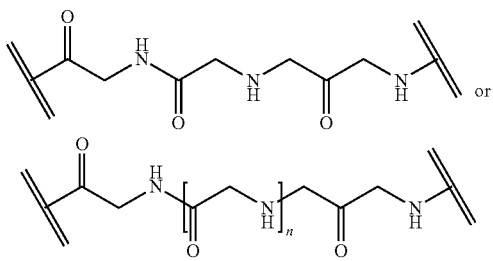

where n=0 to 10, in some aspects 1-10, in some aspects, 1-5, and in some aspects, 1 and in some aspects, 2.

In some aspects, Y, X-Y, Y-Z, and X-Y-Z may be selected from the group consisting of:

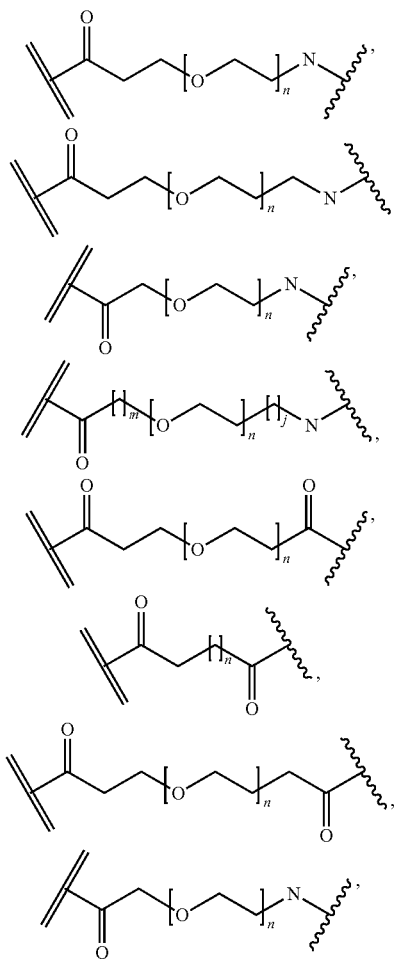

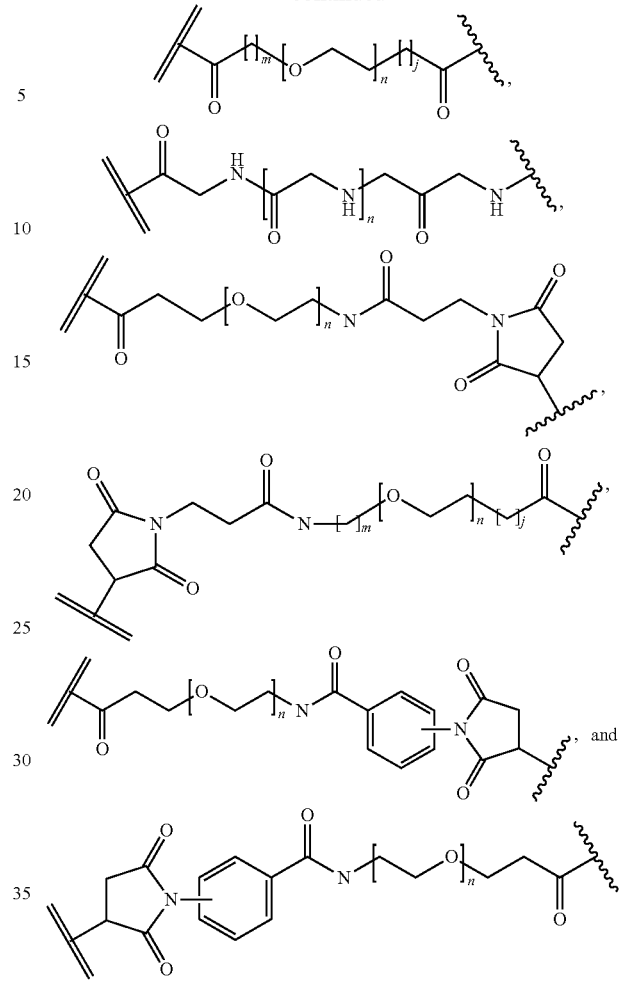

where m, n and j are each independently 0 to 30. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects, the overall length of Y does not exceed 200 atoms. In some aspects, the overall length of Y does not exceed 150 atoms. In some aspects, the overall length of Y does not exceed 100 atoms. In some aspects, the overall length of Y does not exceed 50 atoms. In some aspects, the range of overall chain length of Y in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100. In some aspects, the XYZ linker may be identical to the above Y groups. In some aspects, the wavy line connects to the X group. In some aspects, the parallel lines connect to the X group. In some aspects, the wavey line connects to the Z group. In some aspects, the parallel lines connect to the Z group. In some aspects, the wavy line connects to the side chain of $K^{188}$-CLκ. In some aspects, the parallel lines connect to the side chain of $K^{188}$-CLκ. In some aspects, the wavy line connects to the Effector Moiety. In some aspects, the parallel lines connect to Effector Moiety.

In some aspects, Y, Y-Z and/or X-Y may be a maleimide PEG acid, such as:

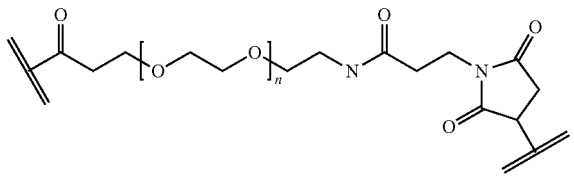

where n=1 to 12, in some aspects 1-10, in some aspects, 1-5, and in some aspects, 1 and in some aspects, 2.

In some aspects, Y, Y-Z and/or X-Y may be a maleimide PEG acid, such as:

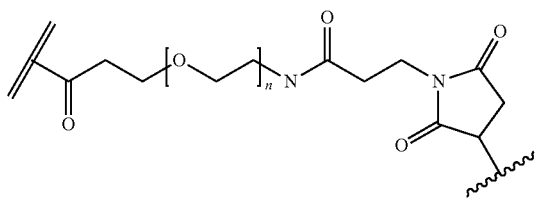

such that the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects, Y, Y-Z and/or X-Y comprises the formula:

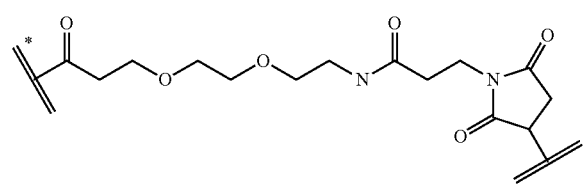

Z* may be selected so as to enable a specific directional covalent linking strategy to a lysine side chain on the antibody. For example, Z may be COOH, or another similarly reactive electrophile to react with the ε-amino of the surface lysine side chains using one of a number of possible amide bond formation strategies.

In some aspects, Z* may be used to form an active ester. Active esters connect to amines, and can thus conjugate to the ε-amino of a lysine side chain of the antibody. The Z carboxyl function to enable the formation of the active ester will be present at the terminus of Y group. The alcoholic or phenolic function of the active ester acts as a leaving group Z* during the conjugation reaction, enabling connection with the lysine side chain on the antibody via generation of an amide.

In some embodiments, the Z* group comprises a structure of the formula:

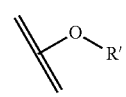

where R' is an aliphatic or aromatic group.
In some embodiments, the Z* group is of the formula:

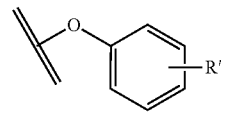

where R'=any of F, Cl, Br or I, nitro, cyano, trifluoromethyl, alone or in combination, and may be present in an amount of between 1 and 5. In some embodiments, $R^1$ may be a halogen, and 4 or 5 halogen atoms may be present. In some embodiments, there may be 4 $R^1$ atoms. In some embodiments, there may be 5 $R^1$ atoms. In some embodiments, Z* may be tetrafluorophenyl. In some embodiments, Z* may comprise the formula:

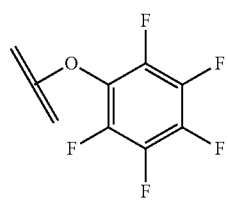

Pentafluorophenyl
wherein the parallel line represents the point of attachment to the Y portion of the linker.
In some aspects, the Z* group is of the formula:

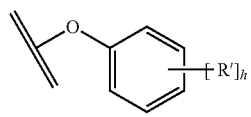

where R'=any of F, Cl, Br or I, nitro, cyano, trifluoromethyl, alone or in combination, and h=1, 2, 3, 4, or 5. In some embodiments, $R^1$ may be a halogen. In some embodiments, $R^1$ is F or Cl, and h=4 or 5. In some embodiments, $R^1$ is F or Cl, and h=5. In some embodiments, $R^1$ is F, and h=2, 3, 4 or 5. In some embodiments, $R^1$ is F, and h=3, 4 or 5. In some embodiments, $R^1$ is F, and h=4 or 5. In some embodiments, $R^1$ is F, and h=5. In some aspects, Z* may be selected from the group consisting of:

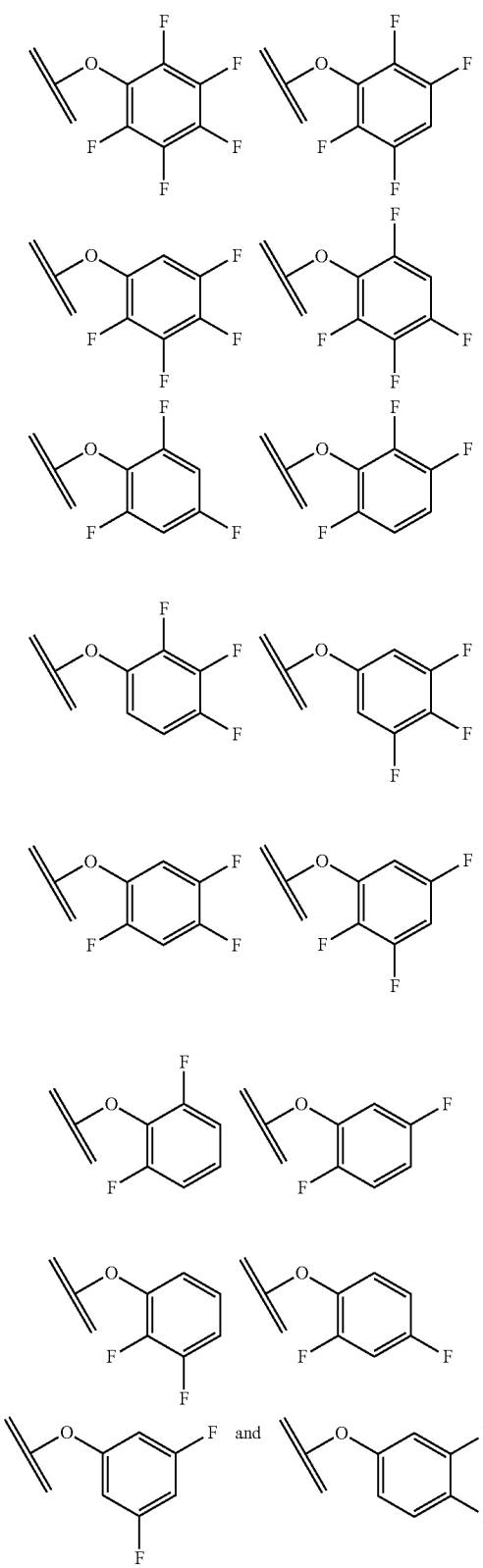

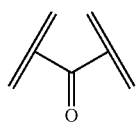

Z group

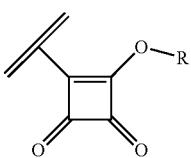

−PfpOH (Z*)

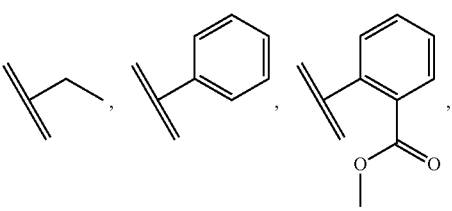

For such active esters, the leaving group is Z* and the Z group itself is the carbonyl attached to the Y group. When reacted with the antibody, the Z* group forms an amide, as shown below, In some embodiments, Z is In some embodiments, the Z* group comprises a squarate ester such as wherein R=aliphatic group or substituted aromatic and may be selected from the group consisting of:

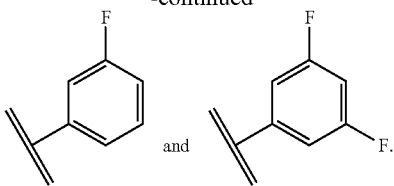

and

In some embodiments, the Z group comprises a Maleimide group:

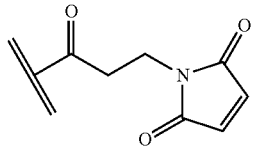

In some aspects, the X*YZ* linker comprises a Maleimide-PEG-PFP ester of the structure:

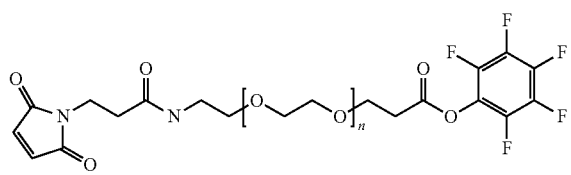

where n=1 to 12. In some aspects, n=1 to 5. In some aspects n=2. In some aspects n=1.

In some aspects, the MAC comprises a XYZ linker of the formula:

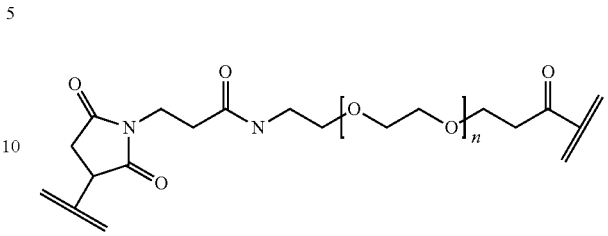

wherein n=1-12. In some aspects, n=1 to 5. In some aspects n=1 to 3. In some aspects n=2. In some aspects n=1.

In some aspects, the X*YZ* linker comprises a structure selected from the group consisting of:

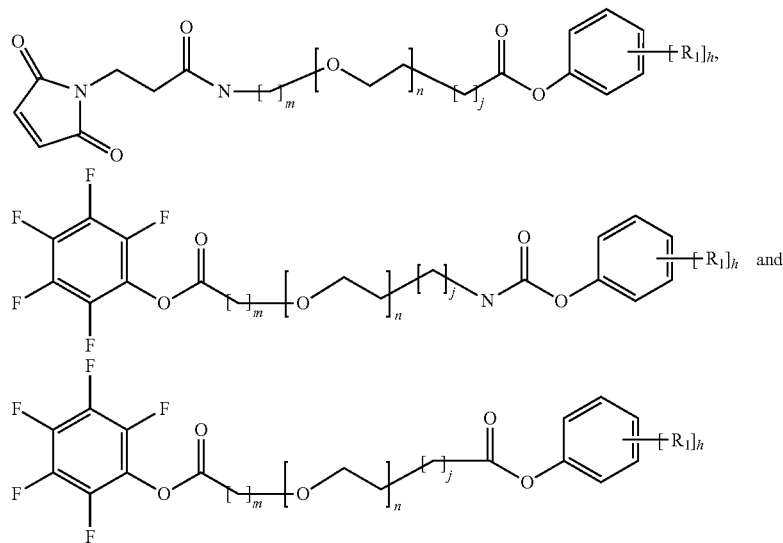

where m, n and j are each independently 0 to 30, R1 is F and h=2, 3, 4, or 5. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects, the overall length of Y does not exceed 200 atoms. In some aspects, the overall length of Y does not exceed 150 atoms. In some aspects, the overall length of Y does not exceed 100 atoms. In some aspects, the overall length of Y does not exceed 50 atoms. In some aspects, the range of overall chain length of Y in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100.

In some aspects the MAC comprises a XYZ linker of the formula:

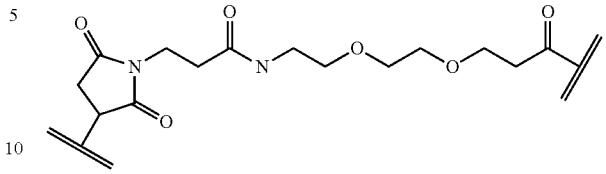

In some aspects, the X*YZ* linker comprises a PEG-bis-pentafluorophenyl ester of the formula:

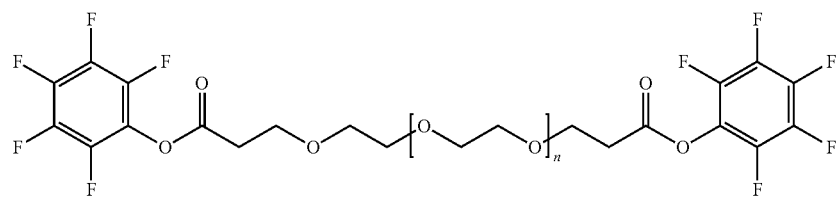

where n=1 to 12. In some aspects n=1 to 10. In some aspects n=1 to 5. In some aspects n=2. In some aspects n=1.

In some aspects, the MAC comprises a XYZ linker of the formula:

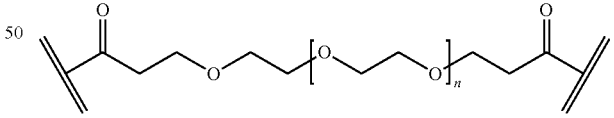

In some aspects, the MAC comprises a XYZ linker of the formula:

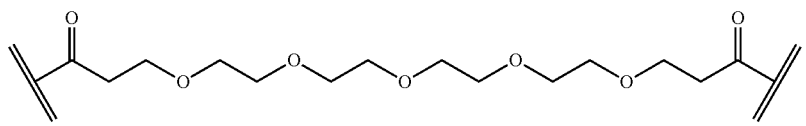

In some embodiments, the peptide when tethered to the XYZ*linker comprise the formula:
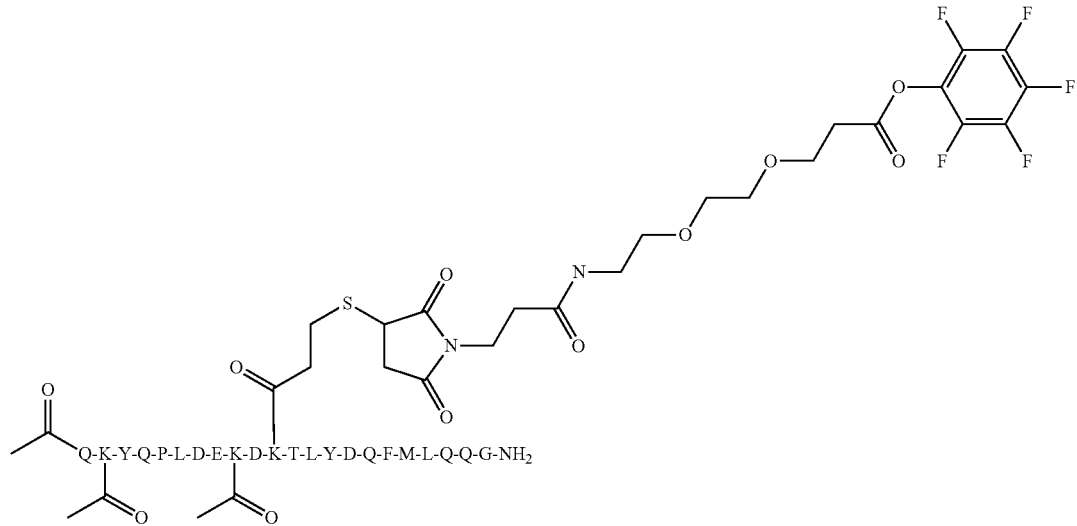
In some embodiments, the peptide tethered to the XYZ*linker comprise the formula:
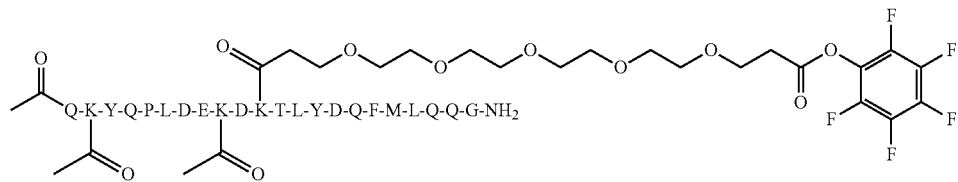
In some aspects, the MAC comprises a compound of the formula:
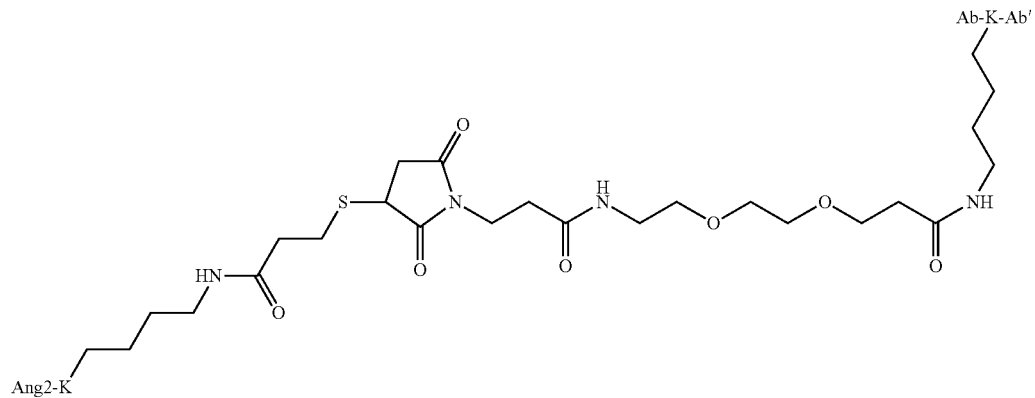
wherein Ang2-K is a lysine or modified lysine residue of an Ang2-binding peptide, and Ab-K-Ab' is a lysine residue on an anti-IGF1R antibody.

In some aspects, the MAC comprises a coupound of the formula:
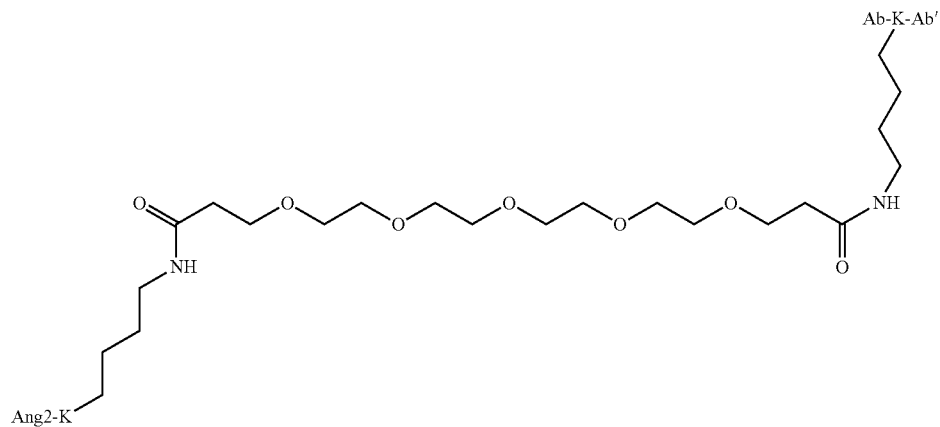
wherein Ang2-K is a lysine or modified lysine residue of an Ang2-binding peptide, and Ab-K-Ab is a lysine residue on an anti-IGF1R antibody.
In some aspects, the MAC comprises the formula:
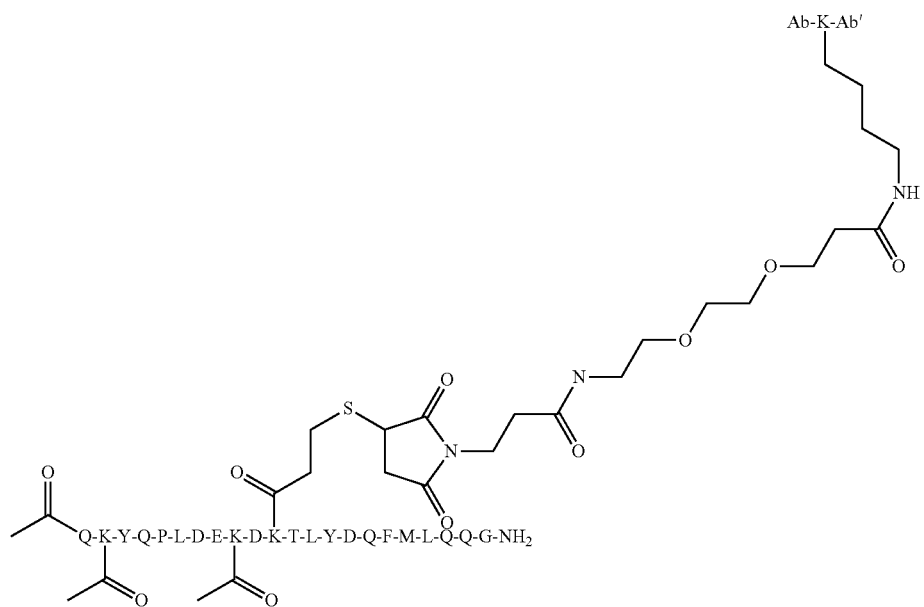
wherein Ab-K-Ab is $K^{188}$ of antibody 2.12.1.fx.

In some aspects, the MAC comprises the formula:

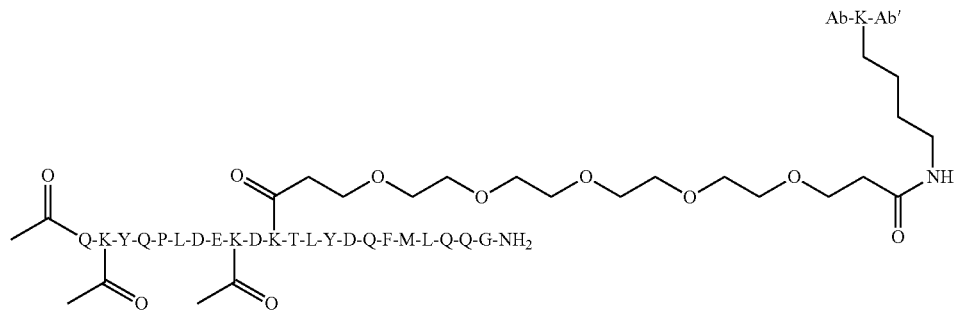

wherein Ab-K-Ab is $K^{188}$ of antibody 2.12.1.fx.

In some aspects the MAC comprises 2 peptides (which may be Ang2-binding peptides) conjugated per antibody (which may be an anti-IGF1R antibody). In some aspects, one peptide is conjugated at each of the 2 $K^{188}$ residues of the antibody or antigen binding fragment thereof (which may be antibody 2.12.1.fx).

In some aspects, the MAC comprises a formula selected from the group consisting of:

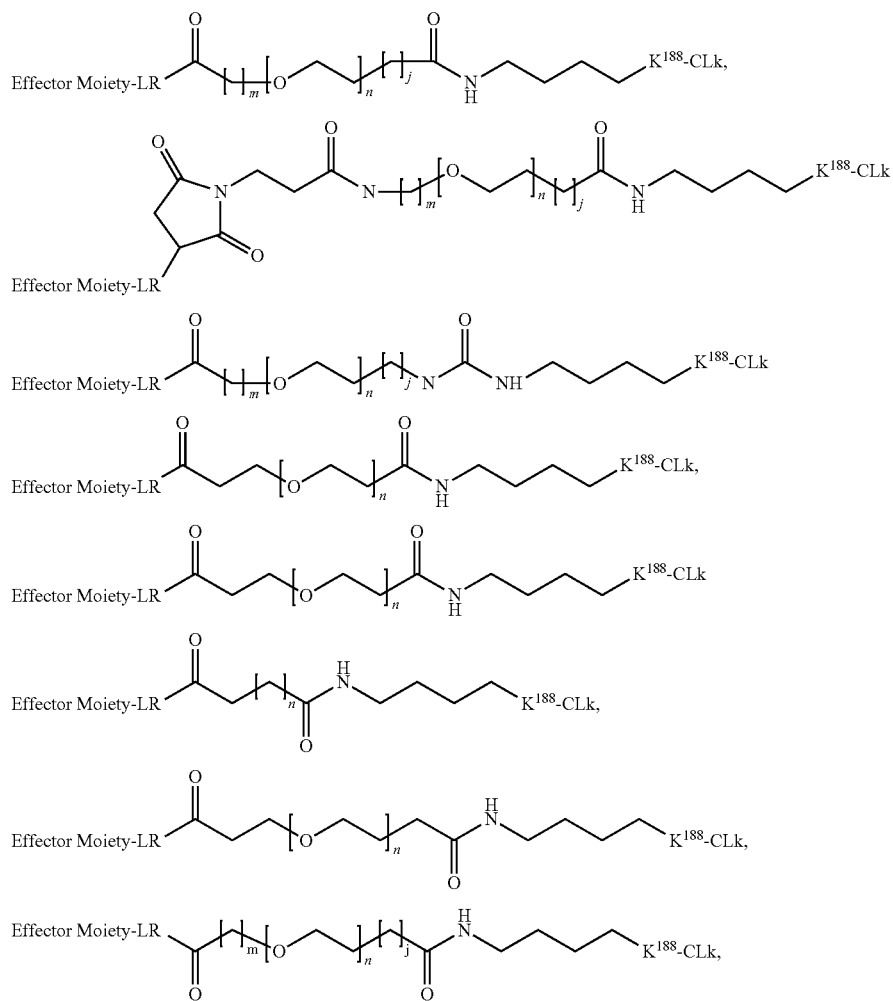

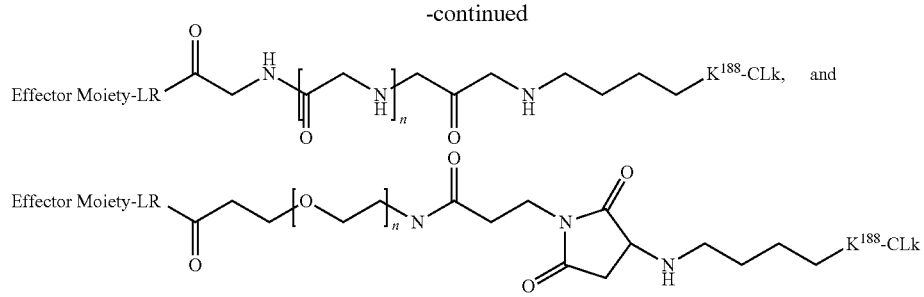

wherein $K^{188}$-CLκ is a covalent link to the side chain of said $K^{188}$-CLκ, Effector Moiety-LR is a covalent link to the Effector Moiety, and m, n and j are each independently 0-30. In some aspects n=1-10, in some aspects, n=1-5. In some aspects, the lower limit of the range of values for n is selected from the group consisting of 0, 1, 2, 3, 4, 5, 6, 7, 8, 9, 10, 11, 12, 13, 14, 15, 16, 17, 18, 19, and 20, and the upper limit for the range of values for n is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. N may be 1. N may be 2. N may be 3. N may be 4. N may be 5. N may be 6. In some aspects m=1-10, in some aspects, m=1-5. In some aspects, the lower limit of the range of values for m is selected form the group consisting of 0, 1, 2, 3, 4, 5, 6, 7, 8, 9, 10, 11, 12, 13, 14, 15, 16, 17, 18, 19, and 20, and the upper limit for the range of values for m is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. M may be 1. M may be 2. M may be 3. M may be 4. M may be 5. M may be 6. In some aspects j=1-10, in some aspects, j=1-5. In some aspects, the lower limit of the range of values for j is selected from the group consisting of 0, 1, 2, 3, 4, 5, 6, 7, 8, 9, 10, 11, 12, 13, 14, 15, 16, 17, 18, 19, and 20, and the upper limit for the range of values for j is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30. J may be 1. J may be 2. J may be 3. J may be 4. J may be 5. J may be 6. In some aspects, the overall length of Y does not exceed 200 atoms. In some aspects, the overall length of Y does not exceed 150 atoms. In some aspects, the overall length of Y does not exceed 100 atoms. In some aspects, the overall length of Y does not exceed 50 atoms. In some aspects, the range of overall chain length of Y in numbers of atoms may have a lower limit selected from the group consisting of 3, 4, 5, 6, 7, 8, 9, 10, 11, 12, 13, 14, 15, 20, 25, 30, 35, 40, 45, 50, 55, and 60, and an upper limit selected from the group consisting of 5, 10, 15, 20, 25, 30, 35, 40, 45, 50, 55, 60, 65, 70, 75, 80, 85, 90, 95, and 100.

Methods of Conjugation

In some aspects, the invention provides for a method of preparing a multifunctional antibody conjugate (MAC) comprising an antibody or antigen binding portion, the antibody being covalently conjugated to at least one Effector Moiety through a linker attached to a side chain of CLκ-$K^{188}$ (according to Kabat numbering) said method comprising: covalently attaching the Effector Moiety to a linker terminating in a leaving group Z* of the formula:

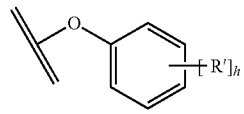

where $R^1$ is any of F, Cl, Br or I, nitro, cyano, trifluoromethyl, alone or in combination, and may be present in an amount of between 1 and 5, and reacting the Effector Moiety-linker-leaving group complex so formed with the antibody at a molar ratio of between about 3.5:1 to about 4.5:1 of Effector Moiety:antibody. In some aspects, the molar ratio is about 3.7:1 to about 4.3:1.

In some aspects, the Z* group is of the formula:

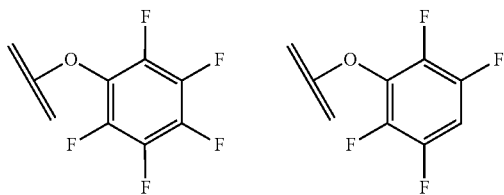

where $R^1$=any of F, Cl, Br or I, nitro, cyano, trifluoromethyl, alone or in combination, and h=1, 2, 3, 4, or 5. In some embodiments, $R^1$ may be a halogen. In some embodiments, $R^1$ is F or Cl, and h=4 or 5. In some embodiments, $R^1$ is F or Cl, and h=5. In some embodiments, $R^1$ is F, and h=2, 3, 4 or 5. In some embodiments, $R^1$ is F, and h=3, 4 or 5. In some embodiments, $R^1$ is F, and h=4 or 5. In some embodiments, $R^1$ is F, and h=5. In some aspects, Z* may be selected from the group consisting of:

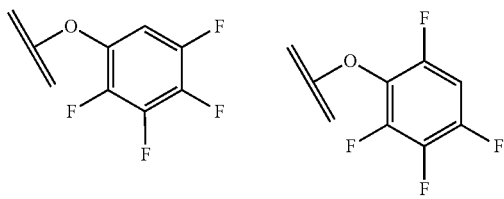

-continued

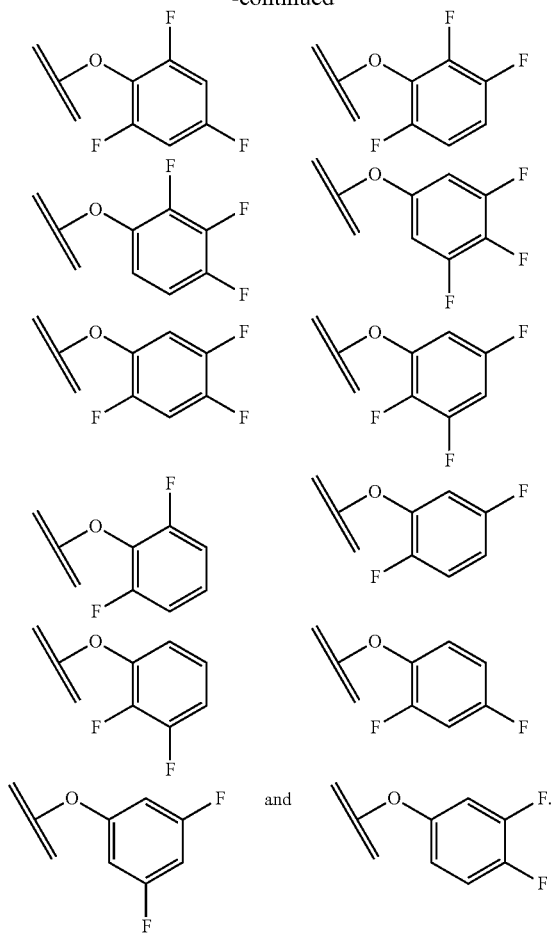

$R^1$ may be present in an amount of between 3 and 5. There may be 3 $R^1$ groups. $R^1$ may be present in an amount of between 4 and 5. There may be 4 $R^1$ groups. There may be 5 $R^1$ groups. $R^1$ may be fluorine. $R^1$ may be chlorine. $R^1$ may be bromine. The leaving group may comprise the formula:

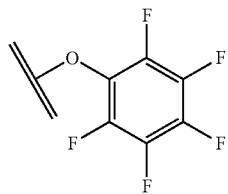

In some aspects, the invention provides for methods of producing a MAC, wherein the MAC comprises an antibody, or fragment thereof, covalently linked to at least one Effector Moiety that binds an additional target (such as peptide, small molecule, aptamer, nucleic acid molecule, or protein), characterised in that Effector Moiety comprises a linker with a PFP leaving group capable of reacting with the £-amino of surface lysine residues of the antibody. In some aspects, the invention provides for a process for conjugating an Effector Moiety (such as a peptide) to an antibody comprising a kappa light chain constant region comprising residues 62-103 SEQ ID NO:15, SEQ ID NO:45, SEQ ID NO:46 or SEQ ID NO:47, comprising conjugating the Effector Moiety with a linker comprising a leaving group of the formula:

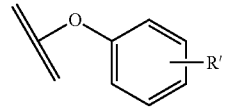

where $R^1$ is any of F, Cl, Br or I, nitro, cyano, trifluoromethyl, alone or in combination, and may be present in an amount of between 1 and 5 and reacting the leaving group with the side chain of $K^{80}$ of SEQ ID NO:15 so as to provide an antibody with an Effector Moiety conjugated to the constant light chain region.

The antibody may comprise a light chain constant region substantially homologous to residues 74-106 of SEQ ID NO:15. The antibody may comprise a light chain constant region substantially homologous to residues 62-103 of SEQ ID NO:15, SEQ ID NO:45, SEQ ID NO:46 or SEQ ID NO:47. In some aspects, the antibody may comprise a light chain region substantially homologous to residues 74-90 of SEQ ID NO:15. In some aspects, the Effector Moiety is conjugated at $K^{80}$ of SEQ ID NO:15. In some aspects, the Effector Moiety is conjugated at $K^{82}$. In some forms, an Ang2 binding peptide is conjugated to an anti-IGF1R antibody at CLκ-$K^{188}$ (according to Kabat numbering).

In some aspects, the method comprises combining an antibody or antigen binding portion thereof with an Effector Moiety, wherein the Effector Moiety is covalently attached to a linker comprising a PFP leaving group.

In some aspects, the invention provides for a method of conjugating an Effector Moiety to a protein, wherein the Effector Moiety is attached to a linker terminating in a leaving group Z* of the formula:

where R'=any of F, Cl, Br or I, nitro, cyano, trifluoromethyl, alone or in combination, and may be present in an amount of between 1 and 5, and the protein comprises residues 62-103 of SEQ ID NO:15, SEQ ID NO:45, SEQ ID NO:46 or SEQ ID NO:47 including $K^{80}$, such that the Effector Moiety is conjugated to the ε-amino group of the $K^{80}$ residue, comprising reacting the Effector Moiety and attached linker with the protein at a molar ratio of between about 3.7:1 and about 4.3:1 of Effector Moiety:protein.

In some aspects, the Effector Moiety, linker and leaving group may be as herein described. In some aspects, the protein may comprise an antibody light chain constant region. In some aspects, the protein may comprise SEQ ID NO:15, and the site of conjugation is $K^{80}$.

In some aspects, the molar ratio of Effector Moiety:antibody (for example, ABP:anti-IGF1R antibody) is between about 2.5 and about 4.6:1. In some aspects of the invention, the molar ratio is about 3.7:1, and about 4.3:1. In some aspects of the invention, the molar ratio of Effector Moiety:antibody is about 4:1. In some aspects, the molar ratio is between about 2:1 and about 7:1. In some aspects, the molar ratio is between about 3:1 and about 6:1. In some aspects, the molar ratio is between about 3:1 and about 7:1. In some aspects, the molar ratio is between about 3:1 and about 5:1.

In aspects of the invention where it is desirable to have less than 1.5 conjugations per antibody (such as where a single Effector Moiety is required) the molar ratio may be between about 1:1 and about 6:1, wherein the buffer comprises HEPES at a concentration of at least 0.1M. The concentration of HEPES may be between about 0.1M and about 1M. The concentration of HEPES may between about 0.1M and about 0.5M. In aspects of the invention where it is desirable to have less than 1.5 conjugations per antibody (such as where a single Effector Moiety is required) the molar ratio may be between about 1:1 and about 3:1.

In some aspects, the preferred molar ratio is a range with a lower limit selected from the group consisting of about 1, about 1.2, about 1.4, about 1.5, about 1.6, about 1.8, about 2, about 2.2, about 2.4, about 2.5, about 2.6, about 2.8, about 3, about 3.2, about 3.3, about 3.4, about 3.5, about 3.6, about 3.7, about 3.8, about 3.9, about 4.0, about 4.1, about 4.2, about 4.3, about 4.4. about 4.5, about 4.6, about 4.7, about 4.8, about 4.9, about 5, about 5.2, about 5.4, about 5.5, about 5.6, about 5.8, about 6, about 6.2, about 6.4, about 6.5, about 6.6, about 6.8, about 7, about 7.3, about 7.5, about 7.7, about 8, about 8.5, about 9, about 9.5, and about 10 to 1, and an upper limit selected from the group consisting of about 1.5, about 1.6, about 1.8, about 2, about 2.2, about 2.4, about 2.5, about 2.6, about 2.8, about 3, about 3.2, about 3.3, about 3.4, about 3.5, about 3.6, about 3.7, about 3.8, about 3.9, about 4.0, about 4.1, about 4.2, about 4.3, about 4.4. about 4.5, about 4.6, about 4.7, about 4.8, about 4.9, about 5, about 5.2, about 5.4, about 5.5, about 5.6, about 5.8, about 6, about 6.2, about 6.4, about 6.5, about 6.6, about 6.8, about 7, about 7.3, about 7.5, about 7.7, about 8, about 8.5, about 9, about 9.5, about 10, and about 15 to 1.

In some aspects, the invention further comprises conjugating the Effector Moiety and protein together for at least about 30 minutes. In some aspects, the duration is at least about 60 minutes. In some aspects, the duration is at least about 2 hrs. In some aspect, the invention further comprises conjugating the Effector Moiety and antibody at between about 4° C. and about 40° C. In some aspect, the invention further comprises conjugating the Effector Moiety and antibody at between about 10° C. and about 30° C. In some aspect, the invention further comprises conjugating the Effector Moiety and antibody at between about 15° C. and about 30° C. In some aspects, the reaction is conducted at about 18° C. to about 25° C. In some aspects, the reaction is conducted at about 22° C. In some aspects, the reaction is conducted at about room temperature.

In some aspects, the conjugation reaction takes place at between about pH 6.5 and about pH 8.0. In some aspects, the conjugation reaction takes place at between about pH 6.75 and about pH 8.0. In some aspects, the conjugation reaction takes place at about pH 7.7. In some aspects, the conjugation reaction takes place at about pH 7. In some aspects, the conjugation reaction takes place at about pH 7.2. In some aspects, the conjugation reaction takes place at about pH 7.5. In some aspects, the conjugation reaction takes place at between a range of pH values, whose lower limit is selected from the group consisting of 5.5, 6, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 and 8, and whose upper limit is selected from the group consisting of 6.5, 6.6, 6.7, 6.8, 6.9, 7.0, 7.1, 7.2, 7.3, 7.4, 7.5, 7.6, 7.7, 7.8, 7.9, 8.0, 8.5, and 9.

In some aspects, the pH may be below 6.5; this may be particularly useful in applications were less than about 1.5 conjugations per antibody are required. In some aspects, the pH is between about 5.5 and about 6.5.

In some aspects, the salt concentration may be below about 0.2M. The salt may be a halide salt (F, Cl, Br, I) and may comprise a metal such as Li, Na, K, Be, Mg, Ca. The salt may be NaCl. The salt may be KCl. Salt concentrations of above about 0.1M may be used to limit the rate and/or number of conjugations per antibody. The salt concentration may be between about 0 and about 0.1M. The salt concentration may be between about 0 and about 0.5M. The salt concentration may be between about 0 and about 0.3M.

In some aspects, the method of the invention comprises formulating the antibody or antigen binding portion thereof in a formulation buffer at about pH 5.5. The formulation buffer may be sodium acetate and trehalose buffer. This buffer has the advantage of not containing any primary amines, and lends itself well to pH adjustment. The antibody may be present in an amount of about 15 to about 25 mg·ml$^{-1}$. In some aspects, the antibody may be present at an amount of 20 mg·ml$^{-1}$.

The pH of the formulation buffer may be adjusted to about pH 7.2 to about pH 8.0; in some embodiments, the formulation buffer may be adjusted to pH 7.7. The pH of the formulation buffer may be adjusted with a phosphate buffer. The phosphate buffer may be at a concentration of between about 40 mM and about 80 mM. The phosphate buffer may be at a concentration of between about 10 mM and about 200 mM.

In some aspects, the concentration of antibody during the conjugation reaction with the Effector Moiety/linker and leaving group Z* may be in a range where the lower limit of the range is selected from about 5, about 6, about 7, about 8, about 9, about 10, about 15, about 20, about 30, and about 40 mg·ml$^{-1}$, and the upper limit of the range is selected form the group consisting of about 7, about 8, about 9, about 10, about 15, about 20, about 30, about 40, about 50, about 60, about 70, about 80, about 90, about 100, about 150, about 200, about 500 mg·ml$^{-1}$.

The Effector Moiety (such as peptide or ABP) may be reconstituted at a concentration of about 5 to about 20 mg·ml$^{-1}$ in diluted propylene glycol prior to use and, in some embodiments, may be at a concentration of 10 mg·ml$^{-1}$.

The conjugation reaction may be performed by combining the antibody or antigen binding portion thereof and the Effector Moiety at a molar ratio of 4 moles Effector Moiety to 1 mole of antibody and incubated at about 18° C. to about 25° C. for about 2 to about 24 hrs. In some embodiments, the conjugation reaction between antibody and Effector Moiety is at room temperature for 2 hrs. In some embodiments, the conjugation reaction is for at least about 2 hrs. In some embodiments, the conjugation reaction is for at least about 30 minutes.

The reaction may be quenched and adjusted to about pH 5.0 to about pH 6.0. In some embodiments, the quenched reaction may be adjusted to pH 5.5. This may be accomplished using a succinate and glycine buffer at, for example, about pH 4.0. This buffer has advantages over other more common buffers such as TRIS, or other amino-acid buffers. The succinate assists in limiting aggregation and precipitation during diafiltration, which can be stressful on the conjugated molecule, and glycine contains an additional primary amine, (particularly in the cases of MAC-1 and MAC-2).

The reaction may be concentrated and unreacted Effector Moiety (e.g. peptide or ABP), related species (such as peptide where the linker was hydrolyzed by reaction with water solvent) and other unreacted elements of the reaction mixture (such as PFP) may be removed by diafiltration, for example, using a 50 kDa membrane or size exclusion chromatography into a succinate, glycine, sodium chloride, and trehalose buffer, pH 5.5 at 30 mg·ml$^{-1}$.

In some aspects, the method may comprise conjugating an Effector Moiety to CLκ-K$^{188}$ (according to Kabat numbering). In some aspects, the invention comprises conjugating a peptide to a light chain λ domain of an antibody or antigen binding portion thereof, comprising substituting a portion of the CLλ region with a corresponding portion of a CLκ region, attaching to the peptide a linker comprising a leaving group Z* as herein defined, and reacting said peptide-linker-leaving group complex with the antibody, characterised in that the CLκ region substituted into the antibody comprises at least residues 62-103 of SEQ ID NOs:15, 45, 46, or 47. In some aspects, the CLκ region comprises at least residues 62-106 of SEQ ID NOs:15, 45, 46, or 47. In some aspects, the CLκ region comprises at least residues 1-103 of SEQ ID NOs:15, 45, 46, or 47. In some aspects, the CLκ region comprises at least residues 1-106 of SEQ ID NOs:15, 45, 46, or 47.

In some aspects, the invention comprises conjugating a peptide to a light chain domain of murine antibody or antigen binding portion thereof, comprising substituting a portion of the murine CL region with a corresponding portion of a human CLκ region, attaching to the peptide a linker comprising a leaving group Z* as herein defined, and reacting said peptide-linker-leaving group complex with the antibody, characterised in that the human CLκ region substituted into the antibody comprises at least residues 62-103 of SEQ ID NOs:15, 45, 46, or 47. In some aspects, the human CLκ region comprises at least residues 62-106 of SEQ ID NOs:15, 45, 46, or 47. In some aspects, the human CLκ region comprises at least residues 1-103 of SEQ ID NOs:15, 45, 46, or 47. In some aspects, the human CLκ region comprises at least residues 1-106 of SEQ ID NOs:15, 45, 46, or 47. These aspects of the invention can be advantageous, as murine CLκ regions do not comprise $K^{188}$ (the corresponding sequence in murine CLκ is RHN; see residues 79-81 of SEQ ID NO:49).

Pharmaceutical Compositions of the Invention

The invention provides a pharmaceutical composition comprising the MAC and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof, and may include isotonic agents, for example, sugars, polyalcohols such as mannitol, sorbitol, or sodium chloride in the composition. Pharmaceutically acceptable substances such as wetting or minor amounts of auxiliary substances such as wetting or emulsifying agents, preservatives or buffers, which enhance the shelf life or effectiveness of the antibody or antibody portion.

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with antibodies in general. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

The pharmaceutical composition may further comprise another component, such as an anti-tumour agent or an imaging reagent. Another aspect of the present invention provides kits comprising MACs of the invention and pharmaceutical compositions comprising these antibodies. A kit may include, in addition to the MAC or pharmaceutical composition, diagnostic or therapeutic agents. A kit may also include instructions for use in a diagnostic or therapeutic method. In some embodiments, the kit includes the antibody or a pharmaceutical composition thereof and a diagnostic agent. In other embodiments, the kit includes the antibody or a pharmaceutical composition thereof and one or more therapeutic agents, such as an additional antineoplastic agent, anti-tumour agent or chemotherapeutic agent.

These agents and compounds of the invention can be combined with pharmaceutically acceptable vehicles such as saline, Ringer's solution, dextrose solution, and the like. The particular dosage regimen, i.e., dose, timing and repetition, will depend on the particular individual and that individual's medical history.

Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

Liposomes containing compounds of the invention are prepared by methods known in the art, such as described in U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy, 20th Ed., Mack Publishing (2000).

Sustained-release preparations may be prepared. Suitable examples of sustained-release preparations include semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic compounds of the invention are generally placed into a container having a sterile access port, for example, an intravenous solution bag or vial having a stopper pierceable by a hypodermic injection needle.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g., soybean oil, safflower oil, cottonseed oil, sesame oil, corn oil or almond oil) and an emulsion formed upon mixing with a phospholipid (e.g., egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a compound of the invention with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Compounds and compositions of the invention may be used in conjunction with established treatments for the relevant indication. Examples include 5-Fluorouracil, irinotecan, oxilaplatin, cetuximab, sunitinib, and rituximab for the treatment of angiogenic disorders in particular, especially cancer. Other examples include ranibizumab, infliximab, adalimumab, natalizumab, omalizumab, and palivizumab.

Therapeutic Methods of the Invention

Therapeutic methods are also provided by the invention. A therapeutic method comprises administering a compound or composition of the invention to a subject in need thereof.

The invention provides for the use of compounds of the invention or pharmaceutical compositions of the invention in a method of inhibiting or reducing angiogenesis or for treating or preventing a disease or symptom associated with an angiogenic disorder. The invention provides methods of inhibiting or reducing angiogenesis or treating or preventing a disease or symptom associated with an angiogenic disorder comprising administering to a patient a therapeutically effective dose of compounds and compositions of the invention. Also provided are methods of delivering or administering compounds and compositions of the invention and methods of treatment using compounds and compositions of the invention. Also provided are methods of treating cancer comprising administering to the subject a therapeutically effective amount of a compound or pharmaceutical composition according to the invention. As used herein, an angiogenesis-mediated condition is a condition that is caused by abnormal angiogenesis activity or one in which compounds that modulate angiogenesis activity have therapeutic use. Diseases and conditions that may be treated and/or diagnosed with compounds and compositions of the invention include cancer, arthritis, hypertension, kidney disease, psoriasis, angiogenesis of the eye associated with ocular disorder, infection or surgical intervention, macular degeneration, diabetic retinopathy, and the like.

More specifically, examples of "cancer" when used herein in connection with the present invention include cancers of the lung (NSCLC and SCLC), the head or neck, the ovary, the colon, the rectum, the prostate, the anal region, the stomach, the breast, the kidney or ureter, the renal pelvis, the thyroid gland, the bladder, the brain, renal cell carcinoma, carcinoma of, neoplasms of the central nervous system (CNS), primary CNS lymphoma, non-Hodgkins's lymphoma, spinal axis tumours, carcinomas of the oropharynx, hypopharynx, esophagus, pancreas, liver, gallbladder and bile ducts, small intestine, urinary tract; or lymphoma or a combination of one or more of the foregoing cancers. Still more specifically, examples of "cancer" when used herein in connection with the present invention include cancer selected from lung cancer (NSCLC and SCLC), breast cancer, ovarian cancer, colon cancer, rectal cancer, prostate cancer, cancer of the anal region, or a combination of one or more of the foregoing cancers.

In other embodiments, pharmaceutical compositions of the invention relate to non-cancerous hyperproliferative disorders such as, without limitation, age-related macular degeneration, restenosis after angioplasty and psoriasis. In another embodiment, the invention relates to pharmaceutical compositions for the treatment of a mammal that requires activation of IGF1R and/or Ang2, wherein the pharmaceutical composition comprises a therapeutically effective amount of an activating antibody of the invention and a pharmaceutically acceptable carrier. Pharmaceutical compositions of the invention may be used to treat osteoporosis, frailty or disorders in which the mammal secretes too little active growth hormone or is unable to respond to growth hormone.

As used herein, an "effective dosage" or "effective amount" of drug, compound, or pharmaceutical composition is an amount sufficient to effect any one or more beneficial or desired results. For prophylactic use, beneficial or desired results include eliminating or reducing the risk, lessening the severity, or delaying the outset of the disease, including biochemical, histological and/or behavioural symptoms of the disease, its complications and intermediate pathological phenotypes presenting during development of the disease. For therapeutic use, beneficial or desired results include clinical results such as reducing tumour size, spread, vasculature of tumours, or one or more symptoms of cancer or other diseases associated with increased angiogenesis, decreasing the dose of other medications required to treat the disease, enhancing the effect of another medication, and/or delaying the progression of the disease of patients. An effective dosage can be administered in one or more administrations. For purposes of this invention, an effective dosage of drug, compound, or pharmaceutical composition is an amount sufficient to accomplish prophylactic or therapeutic treatment either directly or indirectly. As is understood in the clinical context, an effective dosage of a drug, compound, or pharmaceutical composition may or may not be achieved in conjunction with another drug, compound, or pharmaceutical composition. Thus, an "effective dosage" may be considered in the context of administering one or more therapeutic agents, and a single agent may be considered to be given in an effective amount if, in conjunction with one or more other agents, a desirable result may be or is achieved.

An "individual" or a "subject" is a mammal, more preferably, a human. Mammals also include, but are not limited to, farm animals, sport animals, pets, primates, and horses.

Advantageously, therapeutic administration of compounds of the invention results in decrease in angiogenesis and/or in the case of cancers, stabilized or reduced tumour volume. Preferably, tumour volume is at least about 10% or about 15% lower than before administration of a MAC of the invention. More preferably, tumour volume is at least about 20% lower than before administration of the MAC. Yet more preferably, tumour volume is at least 30% lower than before administration of the MAC. Advantageously, tumour volume is at least 40% lower than before administration of the MAC. More advantageously, tumour volume is at least 50% lower than before administration of the MAC. Very preferably, tumour volume is at least 60% lower than before administration of the MAC. Most preferably, tumour volume is at least 70% lower than before administration of the MAC.

Administration of compounds of the invention in accordance with the method in the present invention can be continuous or intermittent, depending, for example, upon the recipient's physiological condition, whether the purpose of the administration is therapeutic or prophylactic, and other factors known to skilled practitioners. The administration of a compound of the invention may be essentially continuous over a preselected period of time or may be in a series of spaced doses.

Antibodies

An "immunoglobulin" is a tetrameric molecule. In a naturally occurring immunoglobulin, each tetramer is composed of 2 identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as κ and λ light chains. Heavy chains are classified as α, δ, ε, γ, and μ, and define the antibody's isotype as IgA, IgD, IgE, IgG, IgM, respectively. Within light and heavy chains, the variable and constant regions are joined by a "J" region of about 12 or more amino acids, with the heavy chain also including a "D" region of about 10 more amino acids. The variable regions of each light/heavy chain pair form the antibody binding site such that an intact immunoglobulin has 2 binding sites.

Immunoglobulin chains exhibit the same general structure of relatively conserved framework regions (FR) joined by 3 hypervariable regions, also called complementarity determining regions or CDRs. The CDRs from the 2 chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)).

The identity of the amino acid residues in a particular antibody that make up a CDR can be determined using methods well known in the art. For example, antibody CDRs may be identified as the hypervariable regions originally defined by Kabat et al (Kabat et al., 1992, Sequences of Proteins of Immunological Interest, 5th ed., Public Health Service, NIH, Washington D.C.). The positions of the CDRs may also be identified as the structural loop structures originally described by Chothia and others (Chothia et al., 1989, Nature 342:877-883). Other approaches to CDR identification include the "AbM definition," which is a compromise between Kabat and Chothia and is derived using Oxford Molecular's AbM antibody modeling software (now Accelrys®), or the "contact definition" of CDRs based on observed antigen contacts, set forth in MacCallum et al., 1996, J. Mol. Biol., 262:732-745. In another approach, referred to herein as the "conformational definition" of CDRs, the positions of the CDRs may be identified as the residues that make enthalpic contributions to antigen binding (Makabe et al., 2008, Journal of Biological Chemistry, 283:1156-1166). Still other CDR boundary definitions may not strictly follow one of the above approaches, but will nonetheless overlap with at least a portion of the Kabat CDRs, although they may be shortened or lengthened in light of prediction or experimental findings that particular residues or groups of residues or even entire CDRs do not significantly impact antigen binding. As used herein, a CDR may refer to CDRs defined by any approach known in the art, including combinations of approaches. The methods used herein may utilize CDRs defined according to any of these approaches. For any given embodiment containing more than one CDR, the CDRs (or other residue of the antibody) may be defined in accordance with any of Kabat, Chothia, extended, AbM, contact, and/or conformational definitions.

As used herein, certain residues have been accorded their Kabat numbering; thus, $K^{188}$-CLκ refers to residue 188 of the kappa light chain according to Kabat numbering, counting from the beginning of the kappa light chain. It is appreciated that the numbering of the residue may alter depending on the specific numbering convention applied.

An "antibody" refers to an intact immunoglobulin or to an antigen binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F(ab')2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. A Fab fragment is a monovalent fragment consisting of the VL, VH, CL and CH I domains; a F(ab')2 fragment is a bivalent fragment comprising two Fab fragments linked by a disulfide bridge at the hinge region; a Fd fragment consists of the VH and CH1 domains; an Fv fragment consists of the VL and VH domains of a single arm of an antibody; and a dAb fragment consists of a VH domain or a VL domain (e.g., human, camelid, or shark).

In general, references to antibodies are to be construed as also referring to antigen binding portions thereof, and in particular, antigen binding portions thereof that comprise at least $K^{188}$ of CLκ.

A single-chain antibody (scFv) is an antibody in which a VL and VH regions are paired to form a monovalent molecules via a synthetic linker that enables them to be made as a single protein chain. Diabodies are bivalent, bispecific antibodies in which VH and VL domains are expressed on a single polypeptide chain, but using a linker that is too short to allow for pairing between the 2 domains on the same chain, thereby forcing the domains to pair with complementary domains of another chain and creating 2 antigen binding sites. One or more CDRs may be incorporated into a molecule either covalently or noncovalently to make it an immunoadhesin. An immunoadhesin may incorporate the CDR (s) as part of a larger polypeptide chain, may covalently link the CDR (s) to another polypeptide chain, or may incorporate the CDR(s) noncovalently. The CDRs permit the immunoadhesin to specifically bind to a particular antigen of interest.

An antibody may have one or more binding sites. If there is more than one binding site, the binding sites may be identical to one another or may be different. For instance, a naturally-occurring immunoglobulin has 2 identical binding sites, a single-chain antibody or Fab fragment has one binding site, while a "bispecific" or "bifunctional" antibody has 2 different binding sites.

An "isolated antibody" is an antibody that (1) is not associated with naturally-associated components, including other naturally-associated antibodies, that accompany it in its native state, (2) is free of other proteins from the same species, (3) is expressed by a cell that does not naturally express the antibody, or is expressed by a cell from a different species, or (4) does not occur in nature.

The term "human antibody" includes all antibodies that have one or more variable and constant regions derived from human immunoglobulin sequences. In some embodiments of the present invention, all of the variable and constant domains of the anti-IGF1R antibody are derived from human immunoglobulin sequences (a fully human antibody). A humanized antibody is an antibody that is derived from a non-human species, in which certain amino acids in the framework and constant domains of the heavy and light chains have been mutated so as to avoid or abrogate an immune response in humans. Alternatively, a humanized antibody may be produced by fusing the constant domains from a human antibody to the variable domains of a non-human species.

The term "chimeric antibody" refers to an antibody that contains one or more regions from one antibody and one or more regions from one or more other antibodies.

The term "epitope" includes any protein determinant capable of specific binding to an immunoglobulin or T-cell receptor. Epitopic determinants usually consist of chemically active surface groupings of molecules such as amino acids or sugar side chains and usually have specific 3 dimensional structural characteristics, as well as specific charge characteristics. An antibody is said to specifically bind an antigen when the dissociation constant is <1 uM, preferably <100 nM and more preferably: <10 nM.

The term multifunctional antibody conjugate, or MAC, refers to an antibody as defined herein, or antigen binding portion thereof, covalently conjugated to at least one Effector Moiety that binds to a target. The Effector Moiety may be a peptide, small molecule, protein, nucleic acid molecule, toxin, aptamer, or antigen binding antibody or fragment thereof. References to conjugation of peptides and the like referred to throughout the specification generally applies to conjugation to proteins and (antigen binding) antibodies or fragments thereof. The attachment between Effector Moiety and antibody (or fragment thereof) may be a covalent linkage. In some embodiments where the Effector Moiety is a protein or peptide, the Effector Moiety may be fused to the N- or C-terminus of one of the antibody chains. By fused, it is understood that the Effector Moiety and antibody are fused by means of a peptide bond between their respective peptide backbones. In some aspects, the Effector Moiety is covalently conjugated to the antibody via a linker and is not fused through peptide bonds connecting the 2 the peptide backbones.

In some embodiments, MACs of the invention comprise humanized anti-IGF1R antibodies. MACs of the invention may comprise fully human anti-IGF1R antibodies by introducing human immunoglobulin genes into a rodent so that the rodent produces fully human antibodies. Also provided are fully human anti-IGF1R antibodies. Fully human anti-IGF1R antibodies are expected to minimize the immunogenic and allergic responses intrinsic to mouse or mouse-derivatized monoclonal antibodies (Mabs) and thus to increase the efficacy and safety of the administered antibodies. The use of fully human antibodies can be expected to provide a substantial advantage in the treatment of chronic and recurring human diseases, such as inflammation and cancer, which may require repeated antibody administrations. In another embodiment, the invention provides a MAC comprising an anti-IGF1R antibody that does not bind complement.

Methods of producing anti-IGF1R antibodies for use in the invention are described in WO02053596 and WO2005016967, both of which are incorporated herein by reference.

In some embodiments, there are no greater than 10 amino acid changes in either the VH or VL regions of the mutated anti-IGF1R antibody compared to the anti-IGF1R antibody prior to mutation. In some embodiments, there are no more than 5 amino acid changes in either the VH or VL regions of the mutated anti-IGF1R antibody. There may be no more than 3 amino acid changes. In other embodiments, there are no more than 15 amino acid changes in the constant domains. There may be no more than 10 amino acid changes in the constant domains. There may be no more than 5 amino acid changes in the constant domains.

In addition, fusion antibodies can be created in which 2 (or more) single-chain antibodies are linked to one another. This is useful if one wants to create a divalent or polyvalent antibody on a single polypeptide chain, or if one wants to create a bispecific antibody.

One type of derivatized antibody is produced by crosslinking 2 or more antibodies (of the same type or of different types; e.g. to create bispecific antibodies). Suitable crosslinkers include those that are heterobifunctional, having 2 distinctly reactive groups separated by an appropriate spacer (e.g., m-maleimidobenzoyl-N-hydroxysuccinimide ester) or homobifunctional (e.g., disuccinimidyl suberate).

Another type of derivatized antibody is a labelled antibody. Useful detection agents with which an antibody or antibody portion of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An antibody may also be labelled with enzymes that are useful for detection, such as horseradish peroxidase, galactosidase, luciferase, alkaline phosphatase, glucose oxidase and the like. When an antibody is labelled with a detectable enzyme, it is detected by adding additional reagents that the enzyme uses to produce a reaction product that can be discerned. For example, when the agent horseradish peroxidase is present, the addition of hydrogen peroxide and diaminobenzidine leads to a colored reaction product, which is detectable. An antibody may also be labelled with biotin, and detected through indirect measurement of avidin or streptavidin binding. An antibody may be labelled with a magnetic agent, such as gadolinium. An antibody may also be labelled with a predetermined polypeptide epitope recognized by a secondary reporter (e.g., leucine zipper pair sequences, binding sites for secondary antibodies, metal binding domains, epitope tags). In some embodiments, labels are attached by spacer arms of various lengths to reduce potential steric hindrance.

The antibody may also be derivatized with a chemical group such as polyethylene glycol (PEG), a methyl or ethyl group, or a carbohydrate group. These groups may be useful to improve the biological characteristics of the antibody, e.g. to increase serum half-life or to increase tissue binding.

Catalytic Antibodies

In some aspects of the invention, the MAC comprises a catalytic antibody, or antigen binding portion thereof. In some aspects, the antibody may be an aldolase antibody.

The contents of US2006205670 are incorporated herein by reference—in particular paragraphs [0153]-[0233], describing antibodies, useful fragments and variants and modifications thereof, combining sites and CDRs, antibody preparation, expression, humanization, amino acid modification, glycosylation, ADCC, CDC, increasing serum half life of antibodies, expression vectors, mammalian host systems, and folding, amongst other elements of antibody technology.

"Combining site", as used herein, (also known as the antibody binding site) refers to the region of the immunoglobulin or Ig domains that combine (or can combine) with the determinant of an appropriate antigen (or a structurally similar protein). The term generally includes the CDRs and the adjacent framework residues that are involved in antigen binding.

"Aldolase antibodies" as used herein, refers to antibodies containing combining site portions that, when unencumbered (for example by conjugation), catalyze an aldol addition reaction between an aliphatic ketone donor and an aldehyde acceptor. Aldolase antibodies are capable of being generated by immunization of an immune-responsive animal with an immunogen that includes a 1,3 diketone hapten of the formula:

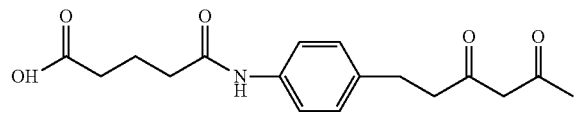 [SMILES: CC(=O)CC(=O)CCc1ccc(NC(=O)CCCC(=O)O)cc1]

coupled to a carrier protein, and further characterized by having a lysine with a reactive ε-amino group in the combining site of the antibody. Aldolase antibodies are further characterized by their catalytic activity being subject to inhibition with the 1,3-diketone hapten by formation of a complex between the 1,3-diketone hapten and the ε-amino group of the lysine of the catalytic antibody.

As discussed, in certain embodiments, certain antibodies that can be used to make MACS, compositions and samples of the invention may comprise a reactive side chain in the antibody combining site. A reactive side chain may be present naturally or may be placed in an antibody by mutation. The reactive residue of the antibody combining site may be associated with the antibody, such as when the residue is encoded by nucleic acid present in the lymphoid cell first identified to make the antibody. Alternatively, the amino acid residue may arise by purposely mutating the DNA so as to encode the particular residue. The reactive residue may be a non-natural residue arising, for example, by biosynthetic incorporation using a unique codon, tRNA, and aminoacyl-tRNA as discussed herein. In another approach, the amino acid residue or its reactive functional groups (e.g., a nucleophilic amino group or sulfhydryl group) may be attached to an amino acid residue in the antibody combining site. Thus, covalent linkage with the antibody occurring "through an amino acid residue in a combining site of an antibody" as used herein means that linkage can be directly to an amino acid residue of an antibody combining site or through a chemical moiety that is linked to a side chain of an amino acid residue of an antibody combining site. In some embodiments, the amino acid is cysteine, and the reactive group of the side chain is a sulfhydryl group. In other embodiments, the amino acid residue is lysine, and the reactive group of the side chain is the ε-amino group. In some embodiments, the amino acid is $K^{93}$ on the heavy chain according to Kabat numbering. In some embodiments, the amino acid is $K^{99}$ on HC h38C2 according to the numbering of SEQ ID NOs: 52 and 54.

Catalytic antibodies are one source of antibodies with suitable combining sites that comprise one or more reactive amino acid side chains. Such antibodies include aldolase antibodies, beta lactamase antibodies, esterase antibodies, and amidase antibodies.

One embodiment comprises an aldolase antibody such as the mouse monoclonal antibodies mAb 33F12 and mAb 38C2 (whose VL and VH comprise SEQ ID NO:56 and 57), as well as suitably chimeric and humanized versions of such antibodies (e.g., h38C2IgG1: SEQ ID NOs:51 and 52 and h38C2-IgG2: SEQ ID NOs:53 and 54). Mouse mAb 38C2 (and h38C2) has a reactive lysine near to but outside HCDR3, and is the prototype of a new class of catalytic antibodies that were generated by reactive immunization and mechanistically mimic natural aldolase enzymes. Other aldolase catalytic antibodies that may be used include the antibodies produced by the hybridoma 85A2, having ATCC accession number PTA-1015; hybridoma 85C7, having ATCC accession number PTA-1014; hybridoma 92F9, having ATCC accession number PTA-1017; hybridoma 93F3, having ATCC accession number PTA-823; hybridoma 84G3, having ATCC accession number PTA-824; hybridoma 84G11, having ATCC accession number PTA-1018; hybridoma 84H9, having ATCC accession number PTA-1019; hybridoma 85H6, having ATCC accession number PTA-825; hybridoma 90G8, having ATCC accession number PTA-1016. Through a reactive lysine, these antibodies catalyze aldol and retro-aldol reactions using the enamine mechanism of natural aldolases.

Compounds of the invention may also be formed by linking a targeting agent to a reactive cysteine, such as those found in the combining sites of thioesterase and esterase catalytic antibodies. Reactive amino acid-containing antibodies may be prepared by means well known in the art, including mutating an antibody combining site residue to encode for the reactive amino acid or chemically derivatizing an amino acid side chain in an antibody combining site with a linker that contains the reactive group.

The antibody may be a humanized antibody. Where compounds of the invention are covalently linked to the combining site of an antibody, and such antibodies are humanized, it is important that such antibodies be humanized with retention of high linking affinity for the W group. Various forms of humanized murine aldolase antibodies are contemplated. One embodiment uses the humanized aldolase catalytic antibody h38c2 IgG1 or h38c2 Fab with human constant domains $C_\kappa$ and $C_{\gamma1}1$. C Human germline $V_k$ gene DPK-9 and human $J_k$ gene JK4 were used as frameworks for the humanization of the kappa light chain variable domain of m38c2, and human germline gene DP-47 and human $J_H$ gene JH4 were used as frameworks for the humanization of the heavy chain variable domain of m38c2. FIG. 18C illustrates a sequence alignment between the variable light and heavy chains in m38c2, h38c2, and human germlines. h38c2 may utilize IgG1, IgG2, IgG3, or IgG4 constant domains, including any of the allotypes thereof. Another embodiment uses a chimeric antibody comprising the variable domains ($V_L$ and $V_H$) of h38c2 (SEQ ID NOS: 55 and 56) and the constant domains from an IgG1, IgG2, IgG3, or IgG4 antibody that comprises $K^{188}$-CLκ. The antibody may be a full-length antibody, Fab, Fab', F(ab')$_2$, F$_v$, dsF$_v$, scF$_v$, V$_H$, V$_L$, diabody, or minibody comprising V$_H$ and V$_L$ domains from h38c2. The antibody may be an antibody comprising the V$_L$ and V$_H$ domains from h38c2 and a constant domain selected from the group consisting of IgG1, IgG2, IgG3, and IgG4. The antibody may be h38C2 IgG1 (SEQ ID NOS: 51 and 52). The antibody may be h38C2 IgG2 (SEQ ID NOS: 53 and 54). The antibody may be a humanized version of a murine aldolase antibody comprising a constant region from a human IgG, IgA, IgM, IgD, or IgE antibody. In another embodiment, the antibody is a chimeric antibody comprising the V$_L$ and V$_H$ region from a murine aldolase antibody (e.g. SEQ ID NO:57 and 58) and a constant region from a human IgG, IgA, IgM, IgD, or IgE antibody. In further embodiments, the antibody is a fully human version of a murine aldolase antibody comprising a polypeptide sequence from natural or native human IgG, IgA, IgM, IgD, or IgE antibody.

Various forms of humanized aldolase antibody fragments are also contemplated. One embodiment uses h38c2 F(ab')$_2$. h38c2 F(ab')$_2$ may be produced by the proteolytic digestion of h38c2 IgG1. Another embodiment uses an h38c2 scFv comprising the V$_L$ and V$_H$ domains from h38c2 which are optionally connected by the intervening linker (Gly$_4$Ser)$_3$ (SEQ ID NO: 59). As an alternative to humanization, human antibodies can be generated. For example, it is now possible to produce transgenic animals (e.g., mice) that are capable, upon immunization (or reactive immunization in the case of catalytic antibodies) of producing a full repertoire of human antibodies in the absence of endogenous immunoglobulin production.

As used herein, "pharmacokinetics" refers to the concentration of an administered compound in the serum over time. Pharmacodynamics refers to the concentration of an administered compound in target and nontarget tissues over time and the effects on the target tissue (e.g., efficacy) and the non-target tissue (e.g., toxicity). Improvements in, for example, pharmacokinetics or pharmacodynamics can be designed for a particular targeting agent or biological agent, such as by using labile linkages or by modifying the chemical nature of any linker (e.g., changing solubility, charge, and the like). The term "$K_{off}$" refers to the off rate constant for dissociation of an antibody from the antibody/antigen complex. The term "$K_d$" refers to the dissociation constant of a particular antibody-antigen interaction.

In some embodiments, the anti-IGF1R antibody portion of the MAC has a selectivity for IGF1R that is at least 50 times greater than its selectivity for insulin receptor. In some embodiments, the selectivity of the anti-IGF1R antibody portion of the MAC is more than 100 times greater than its selectivity for insulin receptor. In some embodiments, the anti-IGF1R antibody portion of the MAC does not exhibit any appreciable specific binding to any other protein other than IGF1R.

In some aspects of the invention, the MAC binds to IGF1R with high affinity. In some embodiments, the MAC binds to IGF1R with a $K_d$ of $1 \times 10^{-8}$ M or less. In some embodiments, the MAC binds to IGF1R with a $K_d$ or $1 \times 10^{-9}$ M or less. In some embodiments, the MAC binds to IGF1R with a $K_d$ or $5 \times 10^{-1}$ M or less. In some embodiments, the MAC binds to IGF1R with a $K_d$ or $1 \times 10^{-1}$ M or less.

In some aspects of the invention, the MAC has a low dissociation rate from IGF1R. In one embodiment, the MAC has a $K_{off}$ of $1 \times 10^4$ s$^{-1}$ or lower. In some embodiments, the $K_{off}$ is $5 \times 10^{-5}$ s$^{-1}$ or lower.

In some aspects, the invention provides for pharmaceutically acceptable salts, stereoisomers, tautomers, solvates, and prodrugs of compounds, samples, compositions and pharmaceutical compositions of the invention.

Catalytic Antibody Linkers

Certain linkers suitable for connecting targeting agents to the combining site of catalytic antibodies (Catalytic Antibody Linkers: CA-linkers) are disclosed in US2009098130, the contents of which are incorporated herein by reference. The term "targeting agents" is used herein to distinguish from the term "Effector Moiety" but it is apparent that the types of molecules attached at the end of a CA-linker or MAC-linker may be interchangable. In particular, aspects of US2009098130 pertaining to the general formulae describing (CA-)linkers, specific (CA-)linker structure, synthesis of (CA-)linkers and combinations of different elements of P, Q and W, and (therein classified as X, Y and Z groups respectively) as specifically and generally described therein are herein included.

The CA-linker may be CA-linear or branched, and optionally includes one or more carbocyclic or heterocyclic groups. CA-linker length may be viewed in terms of the number of linear atoms, with cyclic moieties such as aromatic rings and the like to be counted by taking the shortest route around the ring. In some embodiments, the CA-linker has a linear stretch of between 5-15 atoms, in other embodiments 15-30 atoms, in still other embodiments 30-50 atoms, in still other embodiments 50-100 atoms, and in still other embodiments 100-200 atoms. Other CA-linker considerations include the effect on physical or pharmacokinetic properties of the resulting compound, such as solubility, lipophilicity, hydrophilicity, hydrophobicity, stability (more or less stable as well as planned degradation), rigidity, flexibility, immunogenicity, and modulation of antibody binding, the ability to be incorporated into a micelle or liposome, and the like.

In some aspects the CA-linker may be covalently linked to the side chain of the TA-linking residue. The linker may comprise the formula: P-Q-W; wherein P is a biologically compatible connecting chain including any atom selected from the group consisting of C, H, N, O, P, S, F, Cl, Br, and I, and may comprise a polymer or block co-polymer, and is covalently linked to the linking residue (through side chain, amino terminus, or carboxyl terminus as appropriate) where the linker is linear, Q is an optionally present recognition group comprising at least a ring structure; and W is an attachment moiety comprising a covalent link to an amino acid side chain in a combining site of an antibody.

When present, Q may have the optionally substituted structure:

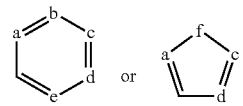

wherein a, b, c, d, and e are independently carbon or nitrogen; f is carbon, nitrogen, oxygen, or sulfur; Q is attached to P and W independently at any 2 ring positions of sufficient valence; and no more than 4 of a, b, c, d, e, or f are simultaneously nitrogen and preferably a, b, c, d, and e in the ring structure are each carbon. In some aspects, Q may be phenyl. Although not wishing to be bound by any theory, it is believed that the Q group can assist in positioning the reactive group into a suitable antibody combining site so that the W group can react with a reactive amino acid side chain.

The CA-linker may be designed such that it contains a reactive group capable of covalently or non-covalently forming a bond with a macromolecule, such as an antibody, protein, or fragment thereof. The reactive group is chosen for use with a reactive residue in a particular combining site. For example, a chemical moiety for modification by an aldolase antibody may be a ketone, diketone, beta lactam, active ester haloketone, lactone, anhydride, maleimide, alpha-haloacetamide, cyclohexyl diketone, epoxide, aldehyde, amidine, guanidine, imine, enamine, phosphate, phosphonate, epoxide, aziridine, thioepoxide, masked or protected diketone (ketal for example), lactam, haloketone, aldehyde, and the like.

In some embodiments, W, prior to conjugation with the side-chain of a residue in the combining site of an antibody, includes one or more C=O groups arranged to form an azetidinone, diketone, an acyl beta-lactam, an active ester, a haloketone, a cyclohexyl diketone group, an aldehyde, a maleimide, an activated alkene, an activated alkyne or, in general, a molecule comprising a leaving group susceptible to nucleophilic or electrophilic displacement. Other groups may include a lactone, an anhydride, an alpha-haloacetamide, an imine, a hydrazide, or an epoxide. Exemplary linker electrophilic reactive groups that can covalently bond to a reactive nucleophilic group (e.g., a lysine or cysteine side chain) in a combining site of antibody include acyl beta-lactam, simple diketone, succinimide active ester, maleimide, haloacetamide with linker, haloketone, cyclohexyl diketone, aldehyde, amidine, guanidine, imine, enamine, phosphate, phosphonate, epoxide, aziridine, thioepoxide, a masked or protected diketone (a ketal for example), lactam, sulfonate, and the like, masked C=O groups such as imines, ketals, acetals, and any other known electrophilic group. In certain embodiments, the reactive group includes one or more C=O groups arranged to form an acyl beta-lactam, simple diketone, succinimide active ester, maleimide, haloacetamide with linker, haloketone, cyclohexyl diketone, or aldehyde. W may be a substituted alkyl, substituted cycloalkyl, substituted aryl, substituted arylalkyl, substituted heterocyclyl, or substituted heterocyclylalkyl, wherein at least one substituent is a 1,3-diketone moiety, an acyl beta-lactam, an active ester, an alpha-haloketone, an aldehyde, a maleimide, a lactone, an anhydride, an alpha-haloacetamide, an amine, a hydrazide, or an epoxide. In some aspects, the W group is covalently linked to a macromolecule scaffold that can provide increased half-life to the peptides of the invention. In some aspects, the W group if present is covalently linked to the combining site of an antibody.

In some aspects, prior to conjugation (for example, with the combining site of an antibody), W has the structure:

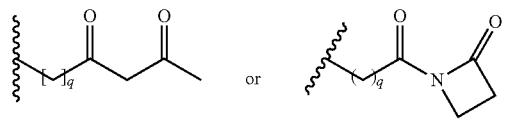

wherein q=0-5. q may be 1 or 2. q may be 1. In other aspects, q may be 2. In some aspects, following conjugation with the antibody combining site, W has the structure:

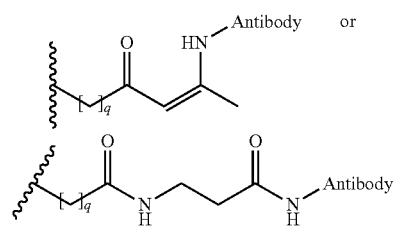

wherein q=0-5 and Antibody-N— is a covalent bond to a side chain in a combining site of an antibody. q may be 1 or 2. q may be 1. In other aspects, q may be 2.

P may be a group comprising three components; Pp-Ps-Py, wherein Pp is a group specifically adapted to be combinable with the targeting agent, Ps is a spacer region of the P group, and Py is a group adapted to bind to the W group. In some aspects, Py is selected from an amide bond, an enamine bond, or a guanidinium bond. Py may be selected so as to provide a hydrogen molecule adjacent (within two atoms) to the Q group. While not wishing to be bound by theory, it is believed that the H atom can assist the Q group recognition of a hydrophobic pocket through H-bond interaction, particularly in respect of the hydrophobic pocket of the binding cleft of a catalytic antibody, such as h38C2. Thus the amide bond, for example, may be orientated such that the NH group is directly bonded to the Q group, providing the H of the NH group for hydrogen bonding. Alternatively, the C=O group of an amide may be bonded to the Q group, with the H of the NH group about 2 atoms adjacent to the Q group, but still available for H-bonding. In some embodiments, Py is absent. In some embodiments the Py group has the formula:

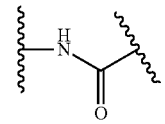 [SMILES: *NC(*)=O]

In some aspects, Ps is selected such that Ps does not provide any overly reactive groups. Ps may be selected so as to provide an overall length of the P groups of between 2-15 atoms. Ps may be selected so that the overall length of the P group is between 2 and 10 atoms. Xs may be selected so that the overall length of P group is 4-8 atoms. Ps may be selected so that the overall length of P group is 5 atoms. Ps may be selected so that the overall length of P group is 6 atoms. In some aspects, Ps may comprise one of the following formulae:

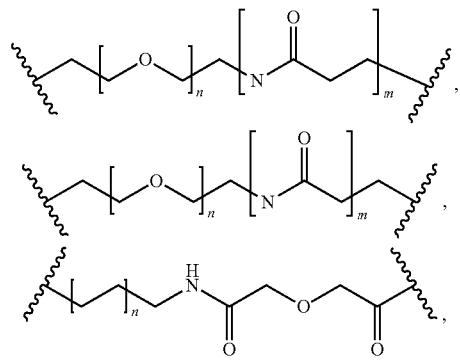

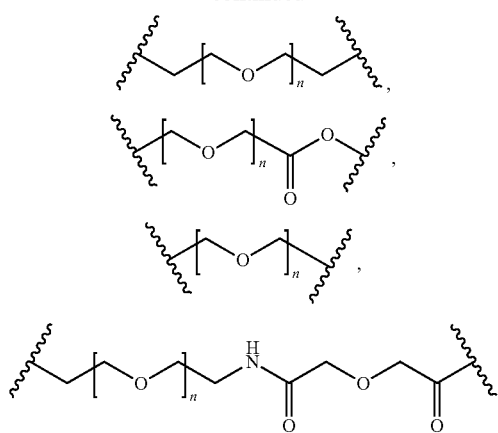

where n=1, 2, 3, 4, 5, 6, 7, 8, 9, or 10, and m is present or absent; n may be 1, 2, 3, 4, 5, or 6; n may be 1, 2, 3, or 4; n may be 1; n may be 2; n may be 3; n may be 4.

In some aspects, Ps comprises one of the following formulae:

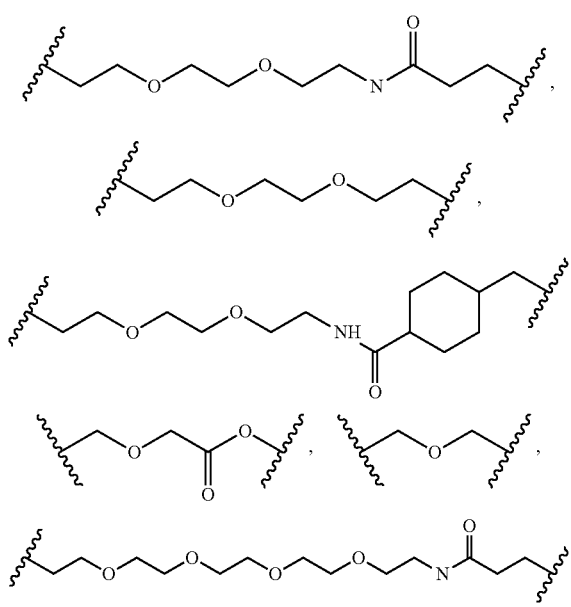

Pp ideally is selected so as to enable a specific directional covalent linking strategy to the linking residue of a targeting molecule (TA-linking residue), such as a peptide, protein, small molecule, nucleic acid or aptamer. For example, where the TA-linking residue comprises a nucleophilic group, Pp may be an electrophilic group and vice versa. For example, if the TA-linking residue side chain comprises an amine group, such as K, H, Y, orthinine, Dap, or Dab, Xp may be COOH, or other similarly reactive electrophile. If the TA-linking residue is D or E, Pp may comprise a nucleophilic group, such as an amine group. Either of these strategies permits a covalent bond to be formed between the Pp group and the TA-linking residue by amide bond formation strategies. Where the TA-linking group is an amine group, Pp may comprise the formula:

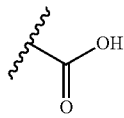

P may be an optionally present biologically compatible polymer or block copolymer. P may be of the structure:

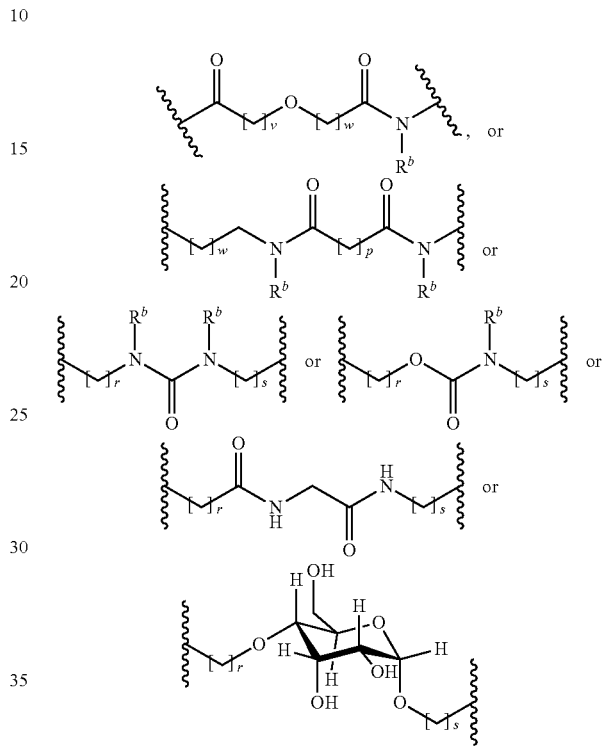

wherein p is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 32, 43, 44, or 45; w, r, and s are each independently 0, 1, 2, 3, 4, 5, 6, 7, 8, 9, 10, 11, 12, 13, 14, 15, 16, 17, 18, 19 or 20; and Rb at each occurrence is independently hydrogen, substituted or unsubstituted $C_{1-10}$ alkyl, substituted or unsubstituted $C_{3-7}$ cycloalkyl-$C_{0-6}$ alkyl, or substituted or unsubstituted aryl-$C_{0-6}$ alkyl.

Where the TA-linking residue is C, homologs of C, or other thiol-group containing residues, Pp may comprise a maleimide group (or similar) permitting a thiol-maleimide addition reaction strategy to covalently link the Pp group to the TA-linking residue. In some aspects, Pp may also comprise a thiol group, allowing a disulphide bridge to be formed between the TA-linking residue and Pp group. In some aspects, Pp may be be maleimide:

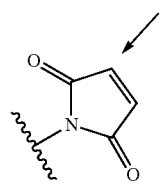 [SMILES: *N1C(=O)C=CC1=O]

wherein the arrow indicates the point of attachment to the targeting molecule and the parallel line represents to attachment to the Q group of the linker. Where the point of attachment to the targeting molecule comprises a cysteine residue, or other thiol bearing side chain, the mechanism of conjugation may be as follows:

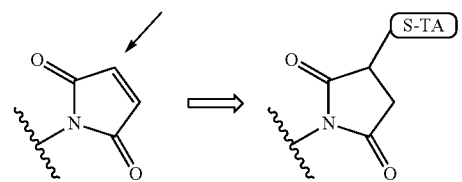

In some aspects, the Pp group comprises a substituted maleimide:

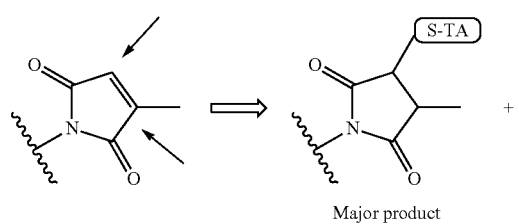

Major product

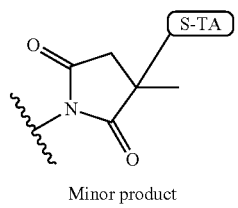

Minor product

In some aspects, P is

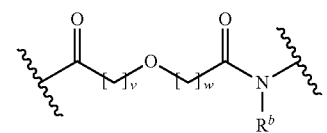

wherein v and w are selected such that the backbone length of X is 6-12 atoms;

In some aspects, the TA-linker is of the formula:

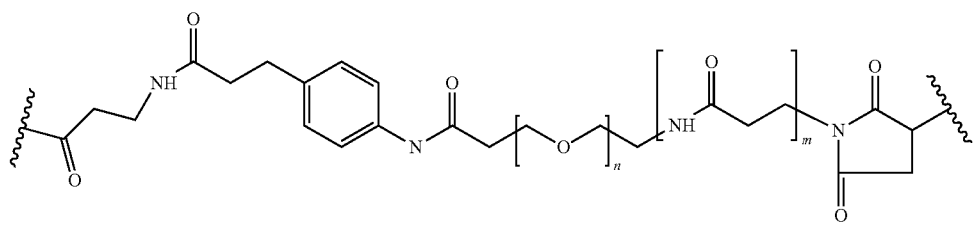

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some aspects, TA-linker is of the formula:

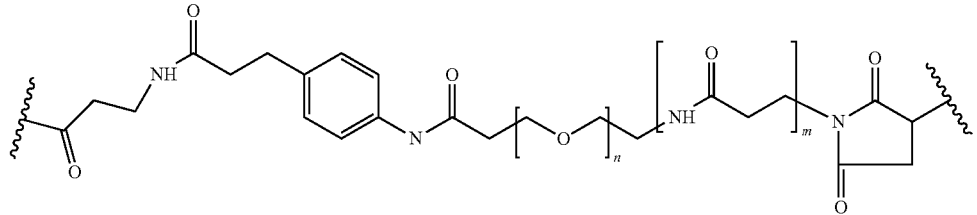

wherein n=1, or 2, or 3, or 4, 5, 6, 7, 8, 9, or 10; n may be 1, 2, 3, 4, 5, or 6; n may be 1; n may be 2; n may be 3; n may be 4. M may be absent. M may be present.

In some aspects, the P portion of CA-linkers may be used as the Y, X-Y, Y-Z and X-Y-Z, portion of linkers for a MAC of the invention.

Peptides and Proteins

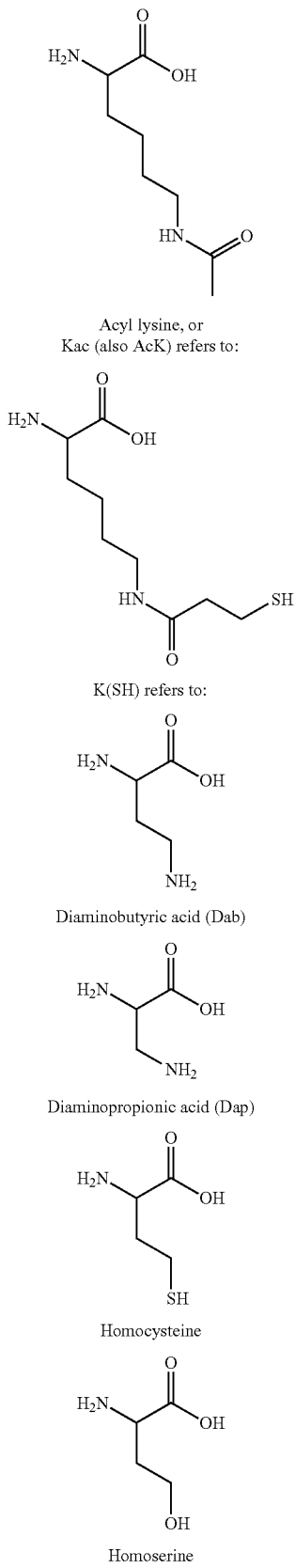

Acyl lysine, or
Kac (also AcK) refers to:

K(SH) refers to:

Diaminobutyric acid (Dab)

Diaminopropionic acid (Dap)

Homocysteine

Homoserine

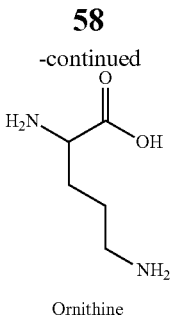

Ornithine

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. As used herein, the 20 conventional amino acids and their abbreviations follow conventional usage. "Polypeptide," "peptide," and "protein" are used interchangeably to refer to a polymer of amino acid residues. As used herein, these terms apply to amino acid polymers in which one or more amino acid residues is an artificial chemical analog of a corresponding naturally occurring amino acid. These terms also apply to naturally occurring amino acid polymers. Amino acids can be in the L or D form as long as the binding and other desired characteristics of the peptide are maintained. A polypeptide may be monomeric or polymeric.

Unless indicated otherwise by a "D" prefix, e.g., D-Ala or N-Me-D-Ile, or written in lower case format, e.g., a, i, I, (D versions of Ala, Ile, Leu), the stereochemistry of the alpha-carbon of the amino acids and aminoacyl residues in peptides described in this specification and the appended claims is the natural or "L" configuration.

All peptide sequences are written according to the generally accepted convention whereby the α-N-terminal amino acid residue is on the left and the α-C-terminal amino acid residue is on the right. As used herein, the term "N-terminus" refers to the free α-amino group of an amino acid in a peptide, and the term "C-terminus" refers to the free α-carboxylic acid terminus of an amino acid in a peptide. A peptide which is N-terminated with a group refers to a peptide bearing a group on the alpha-amino nitrogen of the N-terminal amino acid residue. An amino acid which is N-terminated with a group refers to an amino acid bearing a group on the α-amino nitrogen.

As used herein, "halo," "halogen" or "halide" refers to F, Cl, Br or I.

As used herein, "biological activity" refers to the in vivo activities of a compound, composition, or other mixture, or physiological responses that result upon in vivo administration of a compound, composition or other mixture. Biological activity thus encompasses therapeutic effects, diagnostic effects and pharmaceutical activity of such compounds, compositions, and mixtures. The term "biologically active" or "functional" refers to a polypeptide that exhibits at least one activity that is characteristic of or similar to an AA targeting agent.

The term "biologically compatible" as used herein means something that is biologically inert or non reactive with intracellular and extra cellular biological molecules, and non toxic.

The phrase "substituted alkyl" refers to an alkyl group in which one or more bonds to a carbon(s) or hydrogen(s) are replaced by a bond to non-hydrogen and non-carbon atoms such as, but not limited to, a halogen atom in halides such as F, Cl, Br, and I; an oxygen atom in groups such as hydroxyl groups, alkoxy groups, aryloxy groups, and ester groups; a sulfur atom in groups such as thiol groups, alkyl and aryl sulfide groups, sulfone groups, sulfonyl groups, and sulfoxide groups; a nitrogen atom in groups such as amines, amides, alkylamines, dialkylamines, arylamines, alkylarylamines, diarylamines, N-oxides, imides, and enamines; a silicon atom in groups such as in trialkylsilyl groups, dialkylarylsilyl groups, alkyldiarylsilyl groups, and triarylsilyl groups; and other heteroatoms in various other groups. Substituted alkyl groups also include groups in which one or more bonds to a carbon(s) or hydrogen(s) atom is replaced by a bond to a heteroatom such as oxygen in carbonyl, carboxyl, and ester groups; nitrogen in groups such as imines, oximes, hydrazones, and nitriles. Substituted alkyl groups include, among others, alkyl groups in which one or more bonds to a carbon or hydrogen atom is/are replaced by one or more bonds to fluorine atoms. One example of a substituted alkyl group is the trifluoromethyl group and other alkyl groups that contain the trifluoromethyl group. Other alkyl groups include those in which one or more bonds to a carbon or hydrogen atom is replaced by a bond to an oxygen atom such that the substituted alkyl group contains a hydroxyl, alkoxy, aryloxy group, or heterocyclyloxy group. Still other alkyl groups include alkyl groups that have an amine, alkylamine, dialkylamine, arylamine, (alkyl)(aryl)amine, diarylamine, heterocyclylamine, (alkyl)(heterocyclyl)amine, (aryl)(heterocyclyl)amine, or diheterocyclylamine group.

The phrase "unsubstituted alkyl" refers to a divalent unsubstituted alkyl group as defined above. Thus methylene, ethylene, and propylene are each examples of unsubstituted alkylenes. The phrase "substituted alkyl" refers to a divalent substituted alkyl group as defined above. Substituted or unsubstituted lower alkylene groups have from 1 to about 6 carbons.

The phrase "unsubstituted cycloalkyl" refers to cyclic alkyl groups such as cyclopropyl, cyclobutyl, cyclopentyl, cyclohexyl, cycloheptyl, and cyclooctyl and such rings substituted with straight and branched chain alkyl groups as defined above. The phrase also includes polycyclic alkyl groups such as, but not limited to, adamantyl norbornyl, and bicyclo[2.2.2]octyl and the like, as well as such rings substituted with straight and branched chain alkyl groups as defined above. Thus, the phrase would include methylcyclohexyl groups among others. The phrase does not include cyclic alkyl groups containing heteroatoms. Unsubstituted cycloalkyl groups may be bonded to one or more carbon atom(s), oxygen atom(s), nitrogen atom(s), and/or sulfur atom(s) in the parent compound. In some embodiments unsubstituted cycloalkyl groups have from 3 to 20 carbon atoms. In other embodiments, such unsubstituted alkyl groups have from 3 to 8 carbon atoms while in others, such groups have from 3 to 7 carbon atoms.

The phrase "substituted cycloalkyl" has the same meaning with respect to unsubstituted cycloalkyl groups that substituted alkyl groups have with respect to unsubstituted alkyl groups. Thus, the phrase includes, but is not limited to, oxocyclohexyl, chlorocyclohexyl, hydroxycyclopentyl, and chloromethylcyclohexyl groups.

DETAILED DESCRIPTION OF FIGURES

FIG. 1A: Alignments of amino acid sequences from the heavy chains of antibodies 2.12.1 and 2.12.1.fx, with the consensus sequence for the variable region shown. FIG. 1B: Alignments of amino acid sequences from the light chains of antibodies 2.12.1 and 2.12.1.fx, with the consensus sequence for the variable region shown. CDRs are underlined, and constant regions are shown in italics. Sequences of antibodies 2.12.1 and 2.12.1.fx as disclosed in WO2005016967 and WO2005016967.

FIG. 2: Intact molecular weight analysis of MAC by mass spectrometry demonstrates that multiple peptides are attached to the anti-IGF1R antibody 2.12.1.fx. FIG. 2A: mass spectrometry data of anti-IGF1R antibody 2.12.1.fx. FIG. 2B-2D: mass spectrometry data of MAC-2, showing replicate experiments of 3 individual lots.

FIG. 3: Mass spectrometry data of 2.12.1.fx (IGF1R) and 3 lots of MAC-2 (MAC) where the disulfide bonds have been reduced. FIG. 3A: Mass spectrometry data of 2.12.1.fx (IGF1R), light chain. FIG. 3B: Mass spectrometry data of 2.12.1.fx
(IGF1R), heavy chain. FIG. 3C: mass spectrometry data of light chain of MAC-2, lot-1.

Figure 3A:
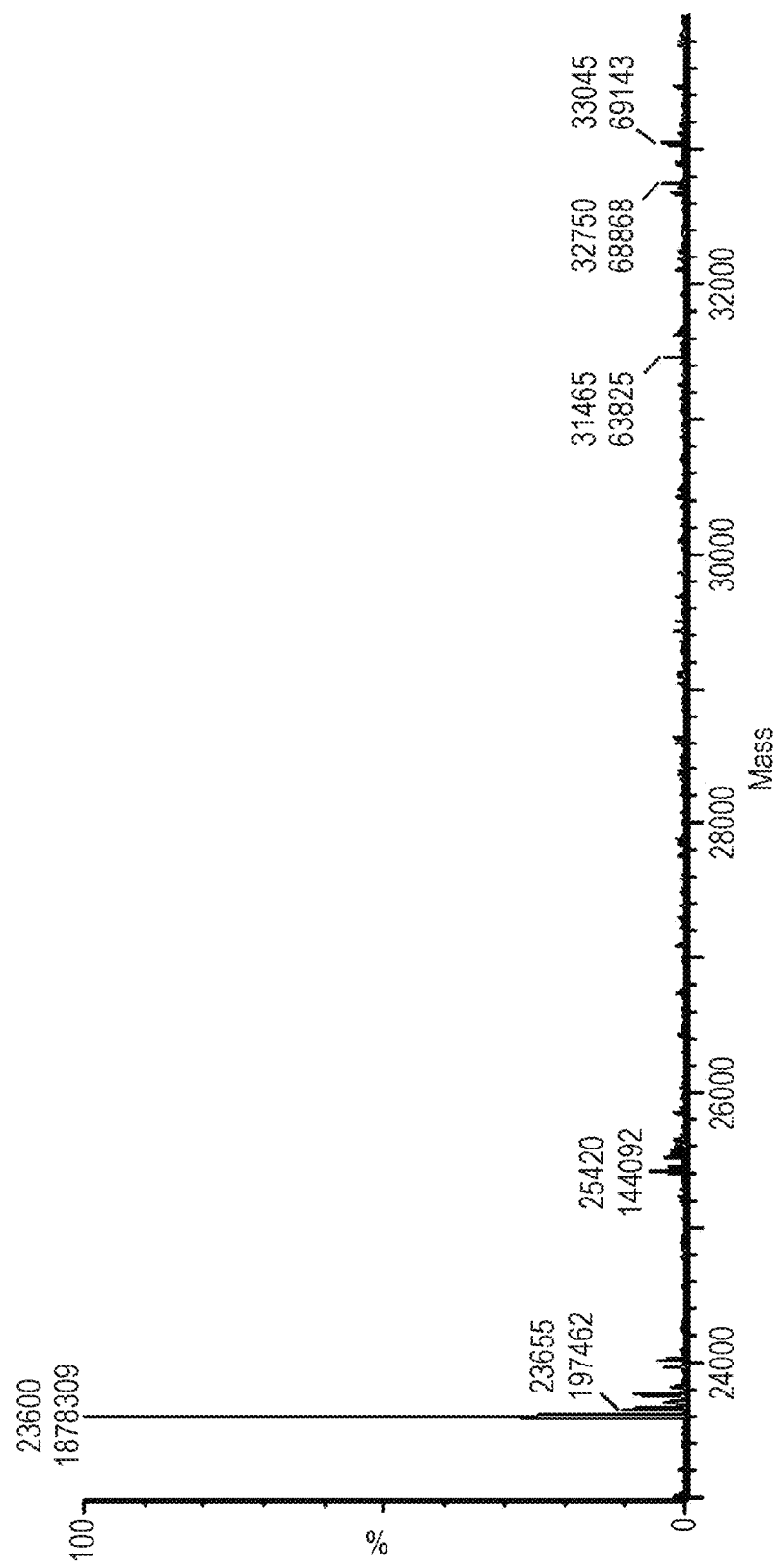
Figure 3C:
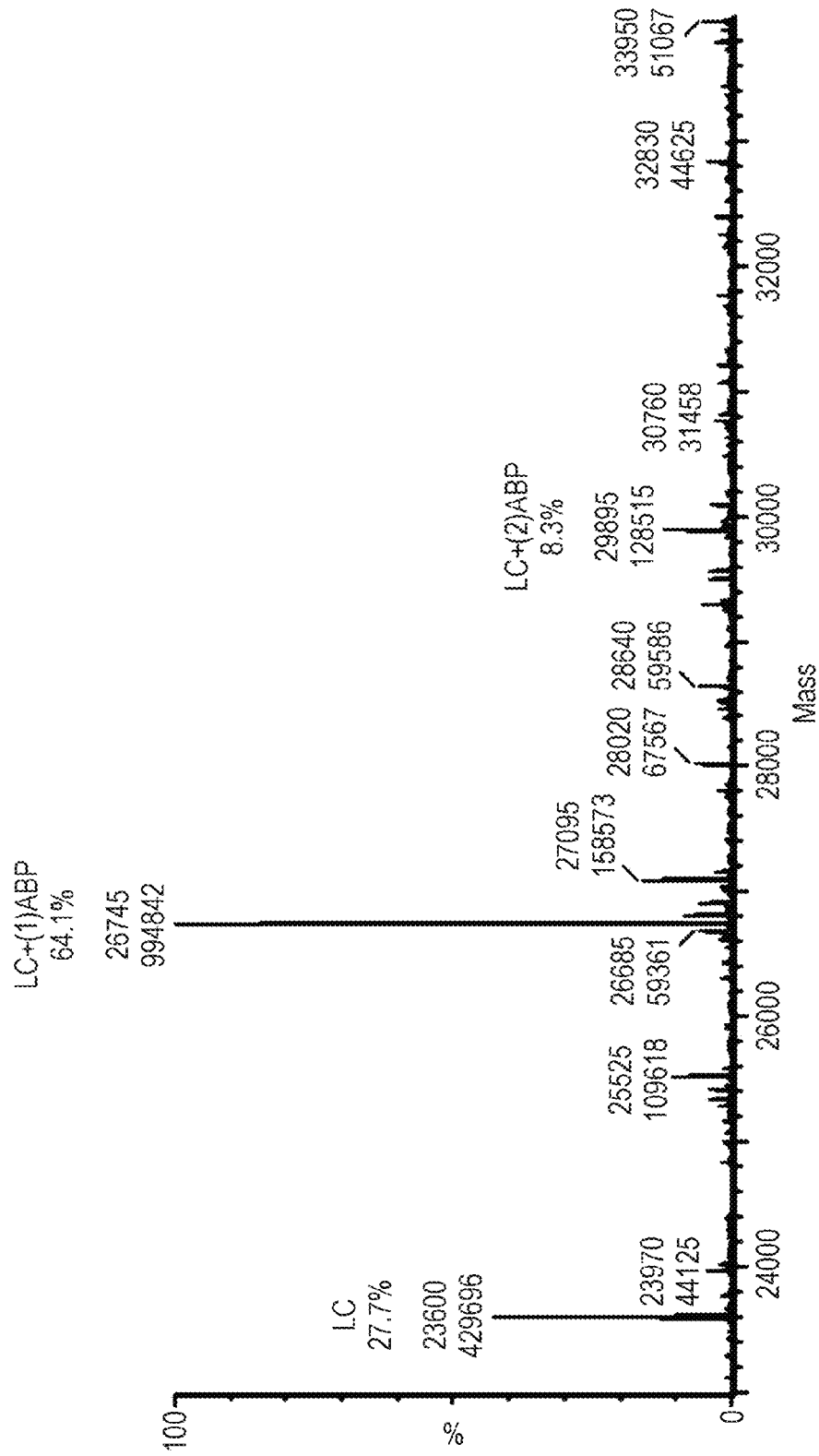
Figure 3E:
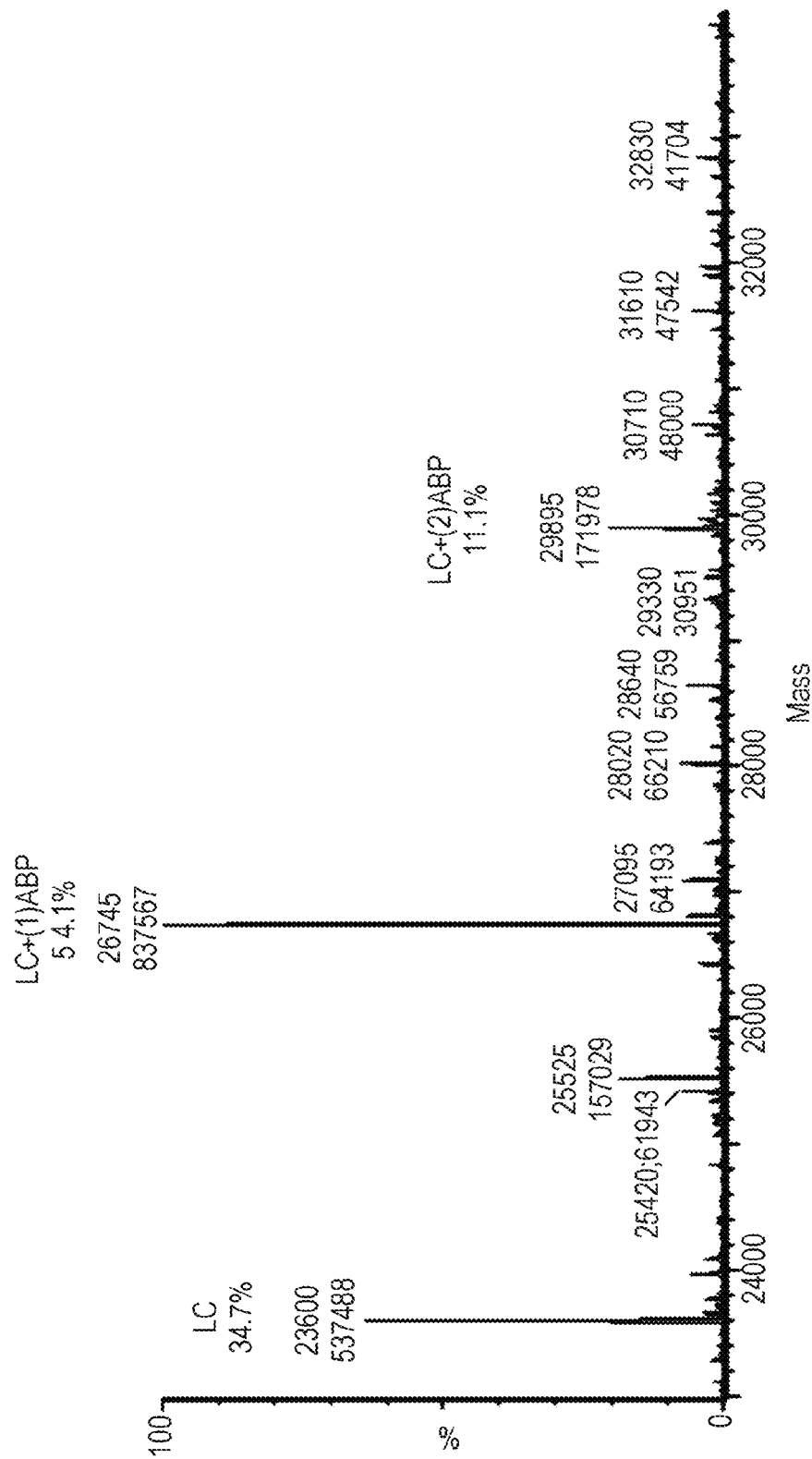
Figure 3F:
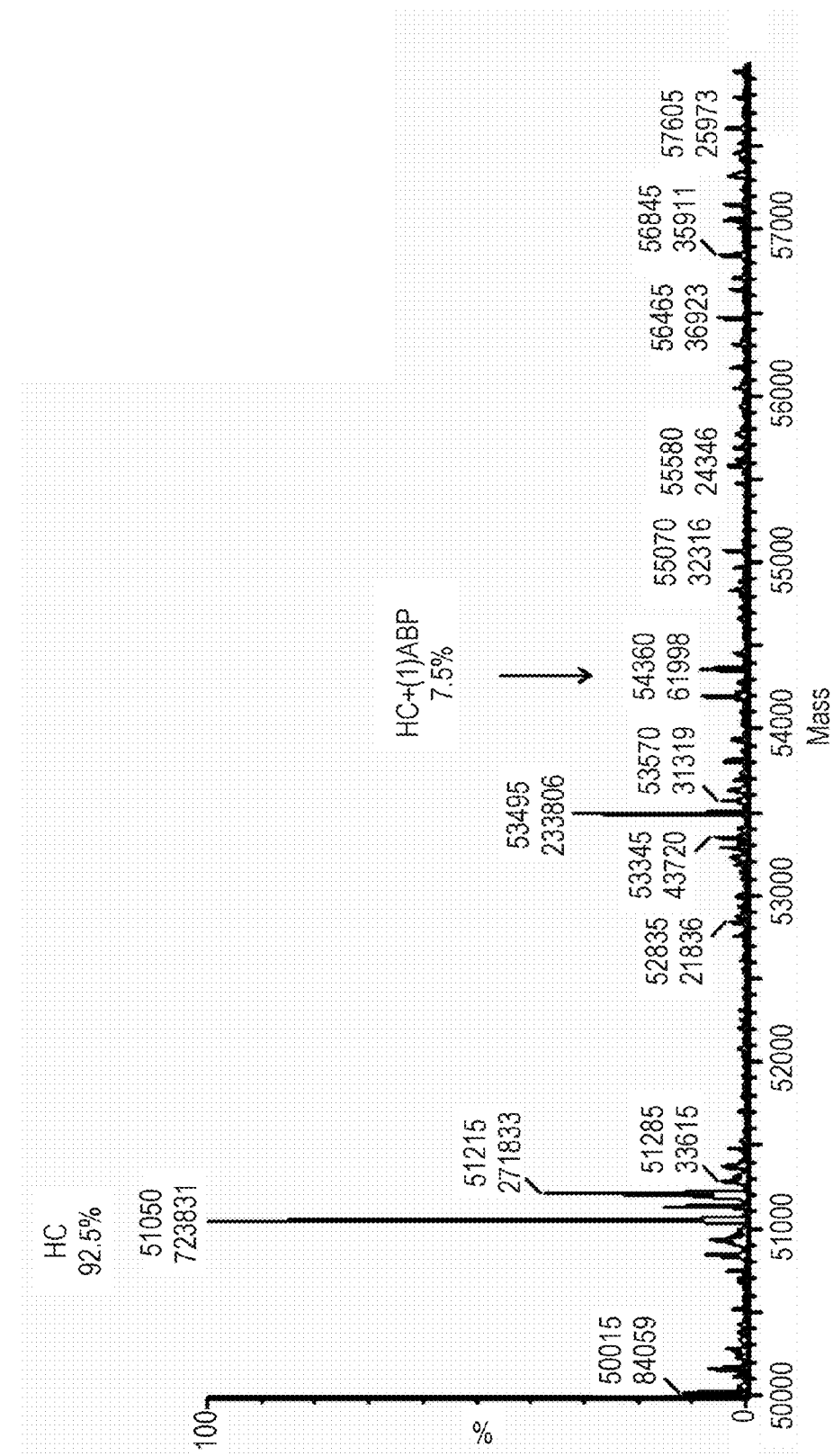
Figure 3G:
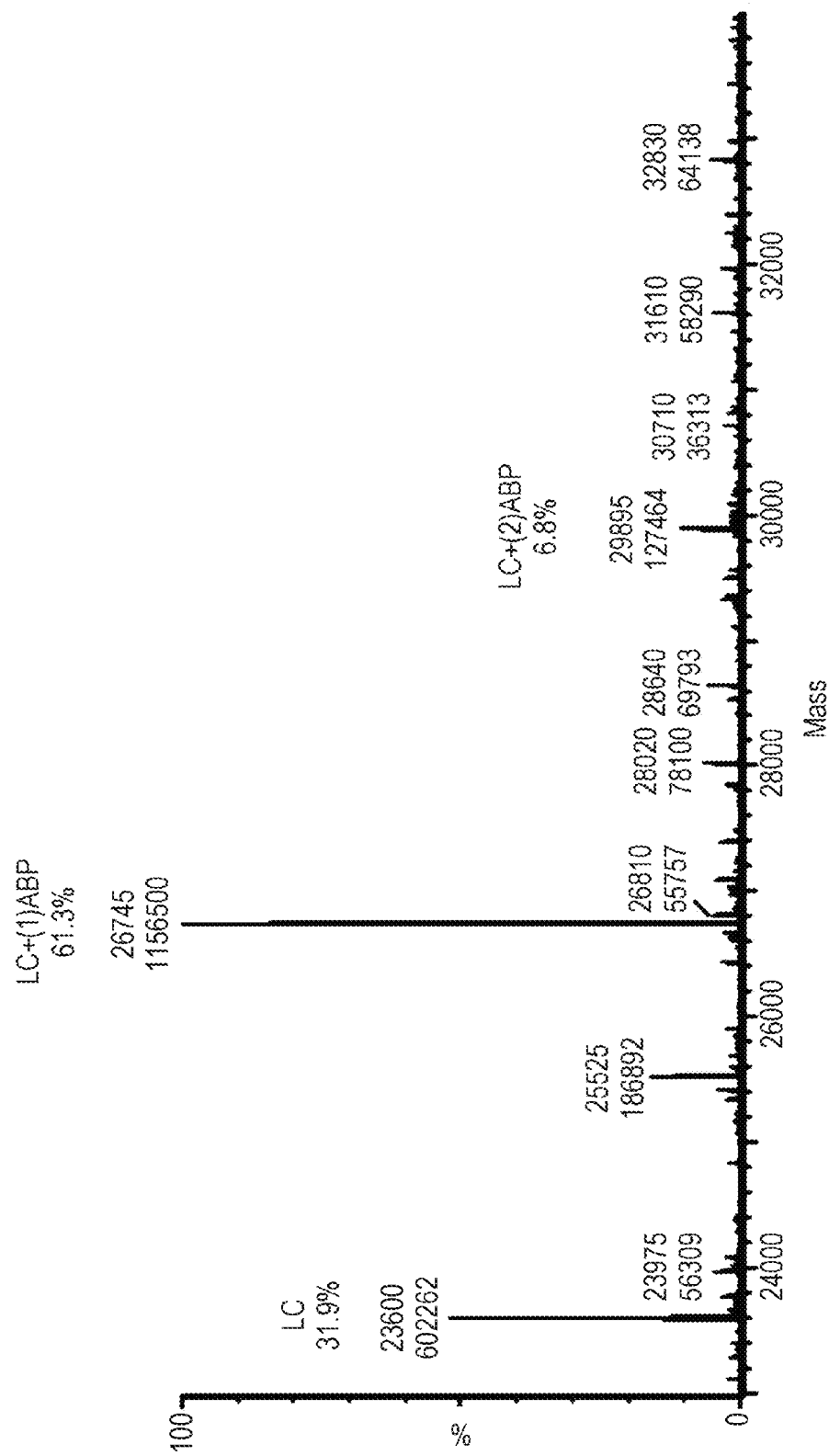
Figure 3H:

FIG. 3D: mass spectrometry data of heavy chain of MAC-2, lot-1. FIG. 3E: mass spectrometry data of light chain of MAC-2, lot-2. FIG. 3F: mass spectrometry data of heavy chain of MAC-2, lot-2. FIG. 3G: mass spectrometry data of light chain of MAC-2, lot-3. FIG. 3H: mass spectrometry data of heavy chain of MAC-2, lot-3.

FIG. 4A: Amino acid sequence of light chain of antibody 2.12.1.fx with chymotrypsin cleavage sites noted with bullets. Chymotryptic fragments that contain a Lys residue (site of potential conjugation) are labeled by number from the N-terminus. The Y15 fragment of the light chain is underlined. FIG. 4B: Amino acid sequence of heavy chain of antibody 2.12.1.fx with chymotrypsin cleavage sites noted with bullets. Chymotryptic fragments that contain a Lys residue (site of potential conjugation) are labeled by number from the N-terminus.

FIG. 5A: Mass spectrometry data of a conjugated lysine-containing peptide: light chain Y15, showing mass spectrometry data for unconjugated anti-IGF1R antibody 2.12.1.fx (IGF1r) and MAC-2 (MAC), as well as a representation of the Y15 fragment.

Figure 5B:
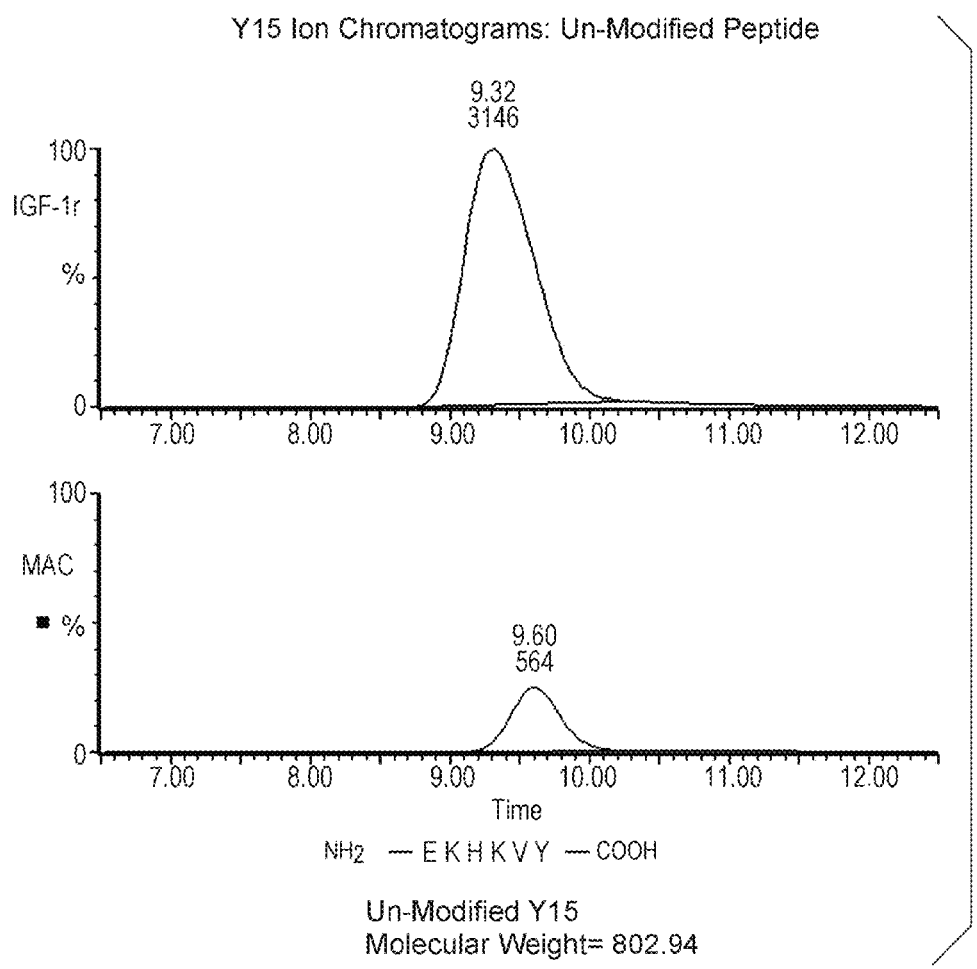

FIG. 5B: Mass spectrometry data of un-conjugated light chain Y15 fragment, showing mass spectrometry data for unconjugated anti-IGF1R antibody 2.12.1.fx (IGF1 r) and MAC-2 (MAC), as well as a representation of the Y15 fragment.

Figure 6A:
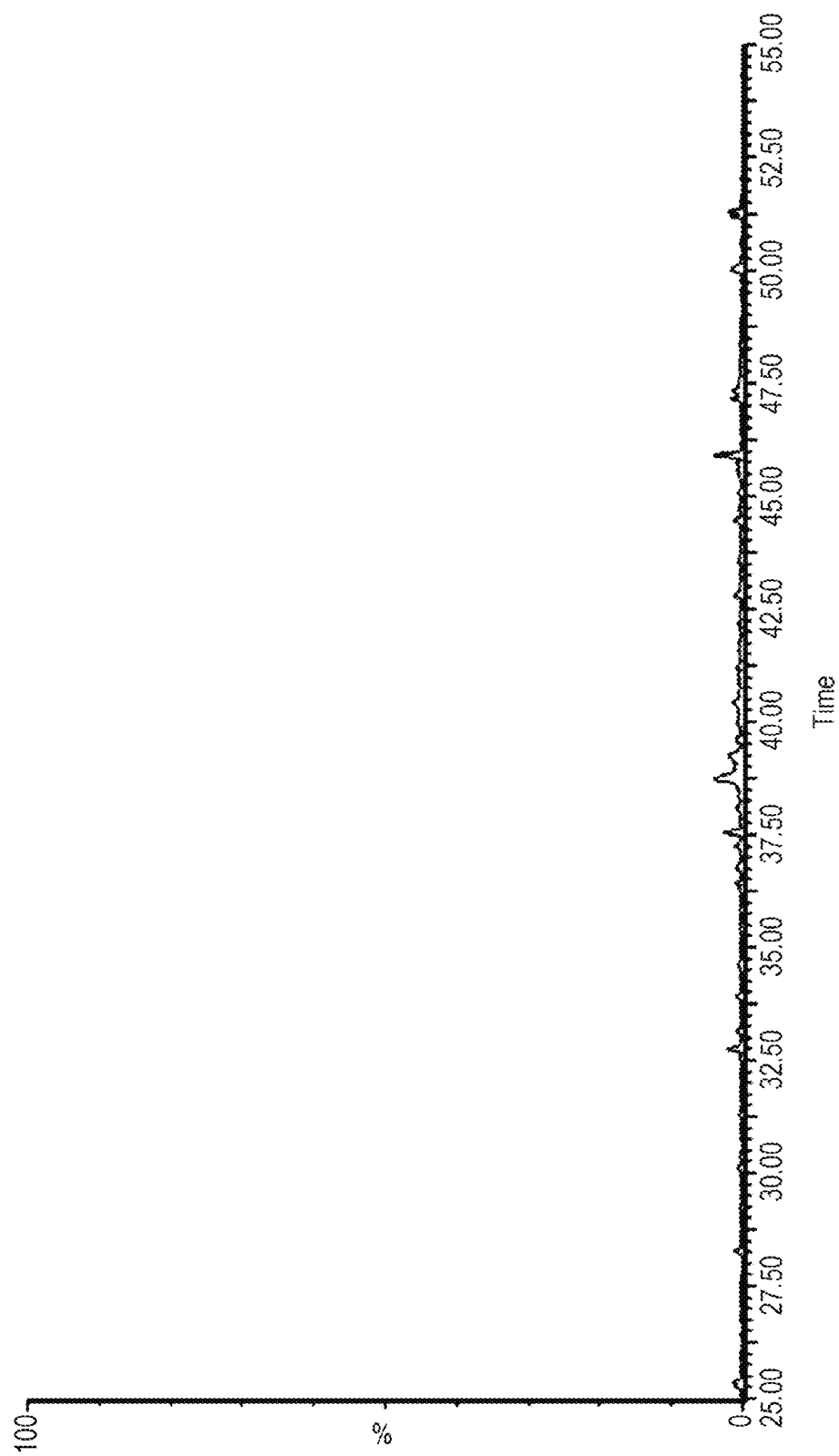

FIG. 6A: The selected ion LCMS chromatogram data for the tryptic fragment of 2.12.1.fx. FIG. 6B: The selected ion LCMS chromatogram data for the tryptic fragment when $Lys^{188}$ is modified with ABP of MAC-2.

Figure 7A:
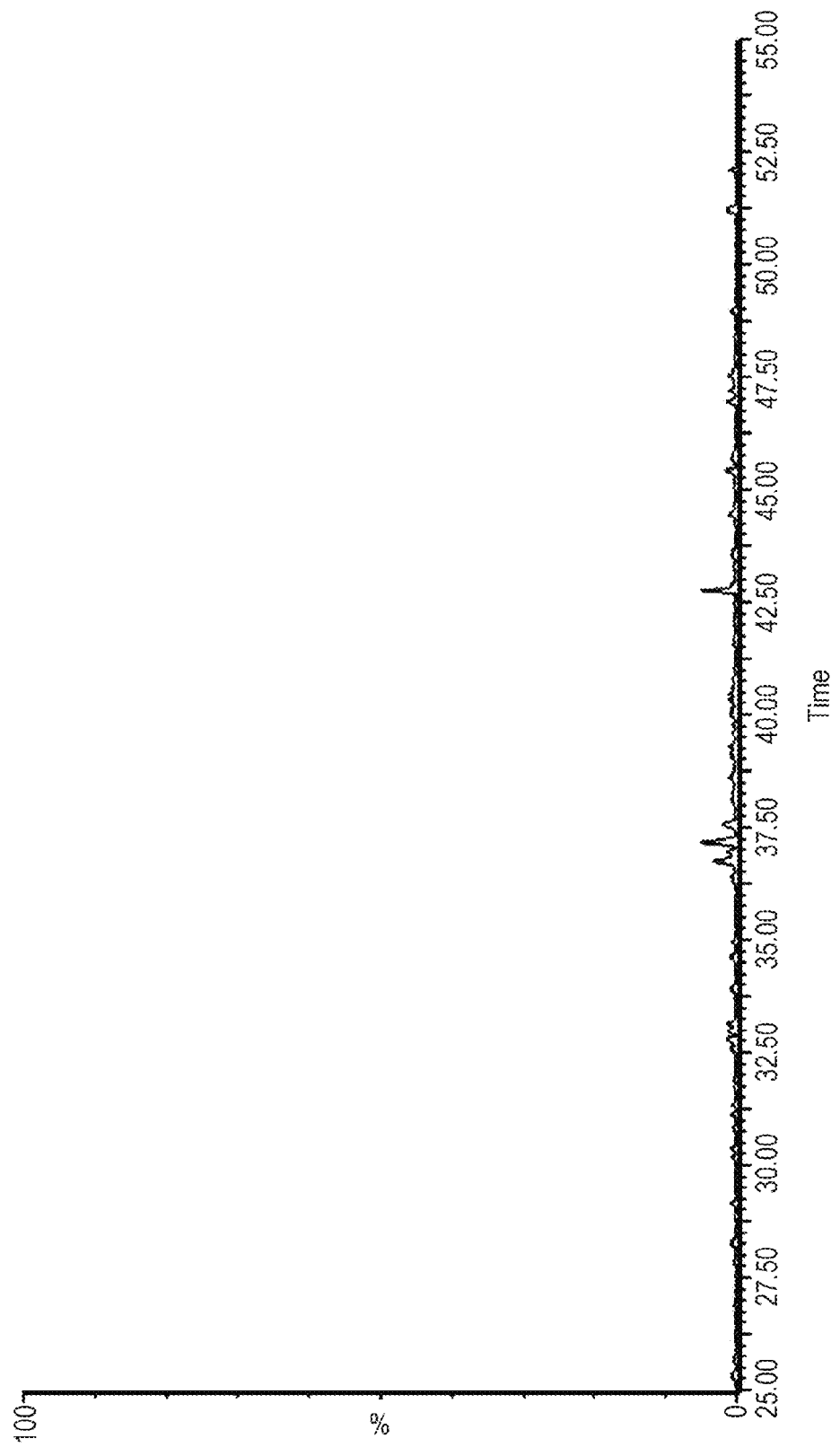
Figure 7B:
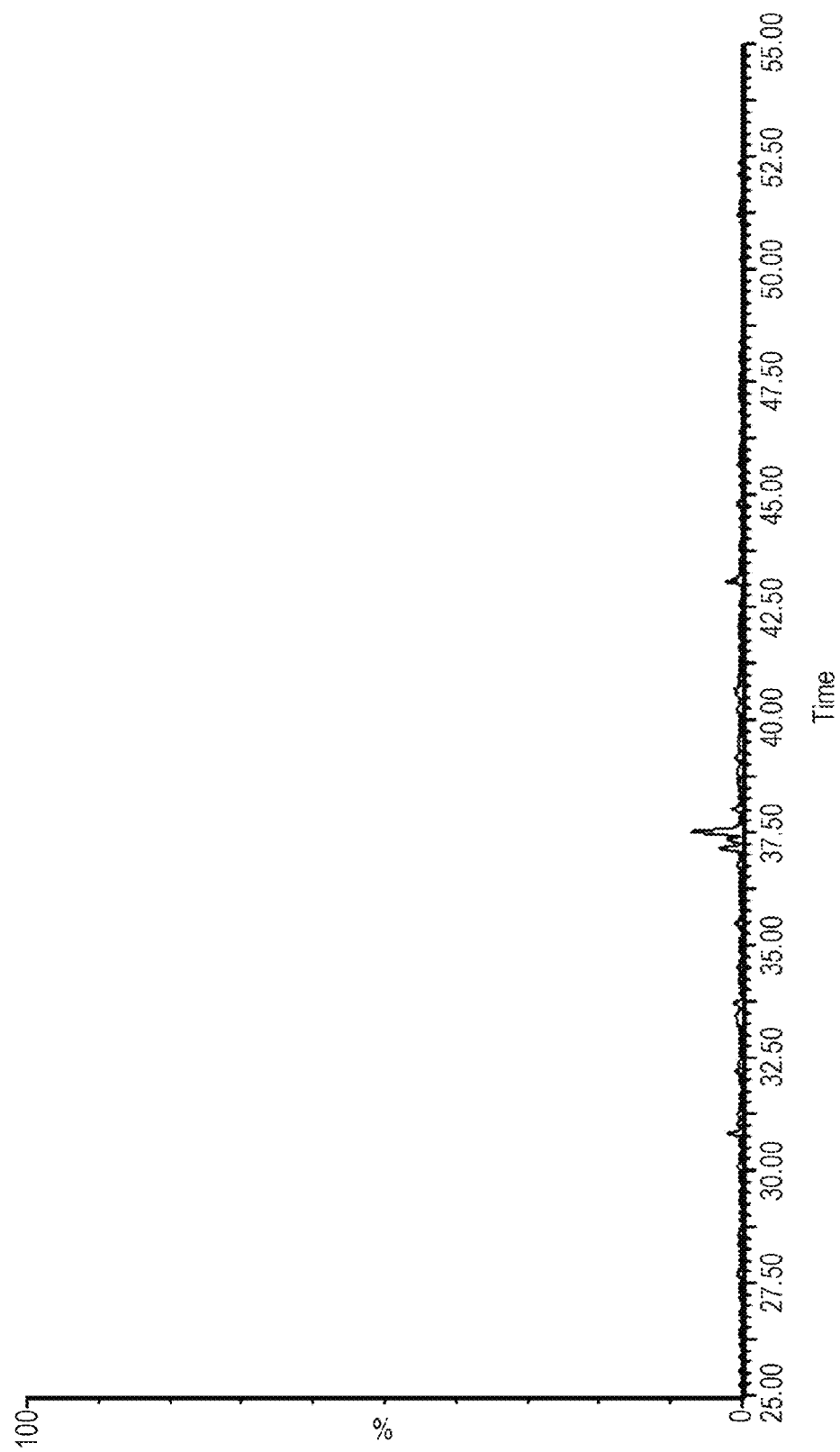

FIG. 7A: The selected ion LCMS chromatogram data for the tryptic fragment of 2.12.1.fx. FIG. 7B: The selected ion LCMS chromatogram data for the tryptic peptide when $Lys^{190}$ is modified with ABP of MAC-2.

Figure 8:
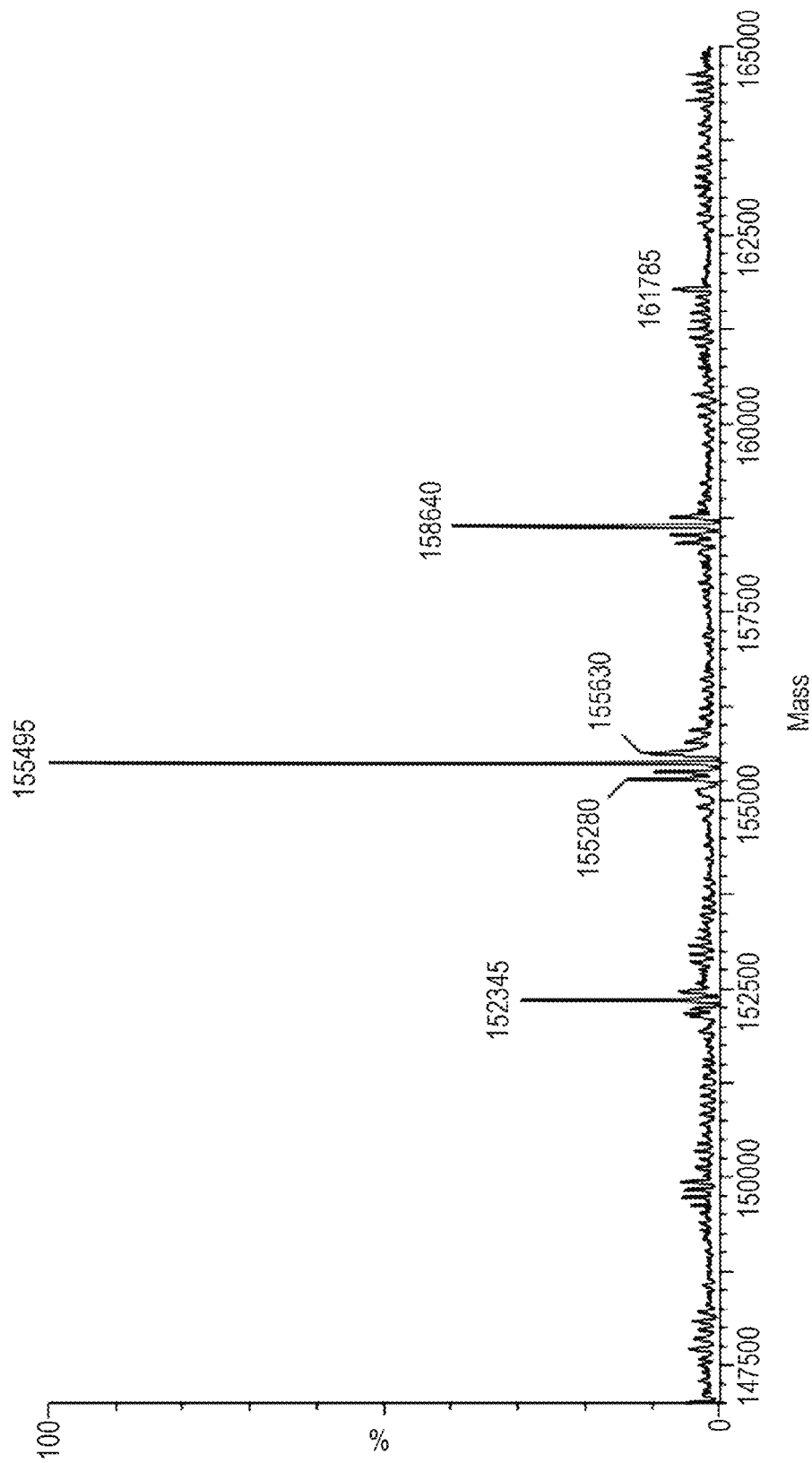
Figure 9A:
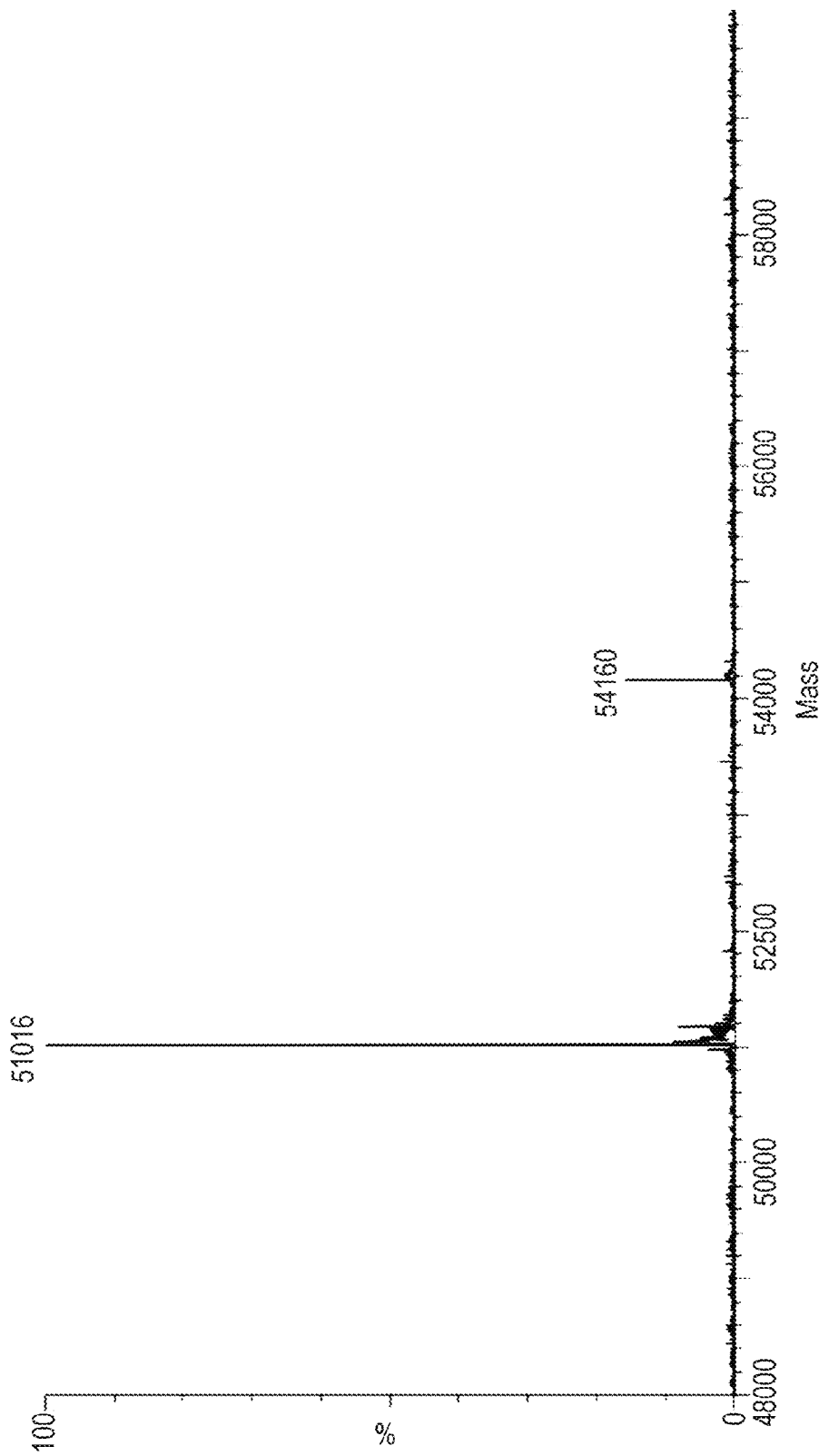
Figure 9B:
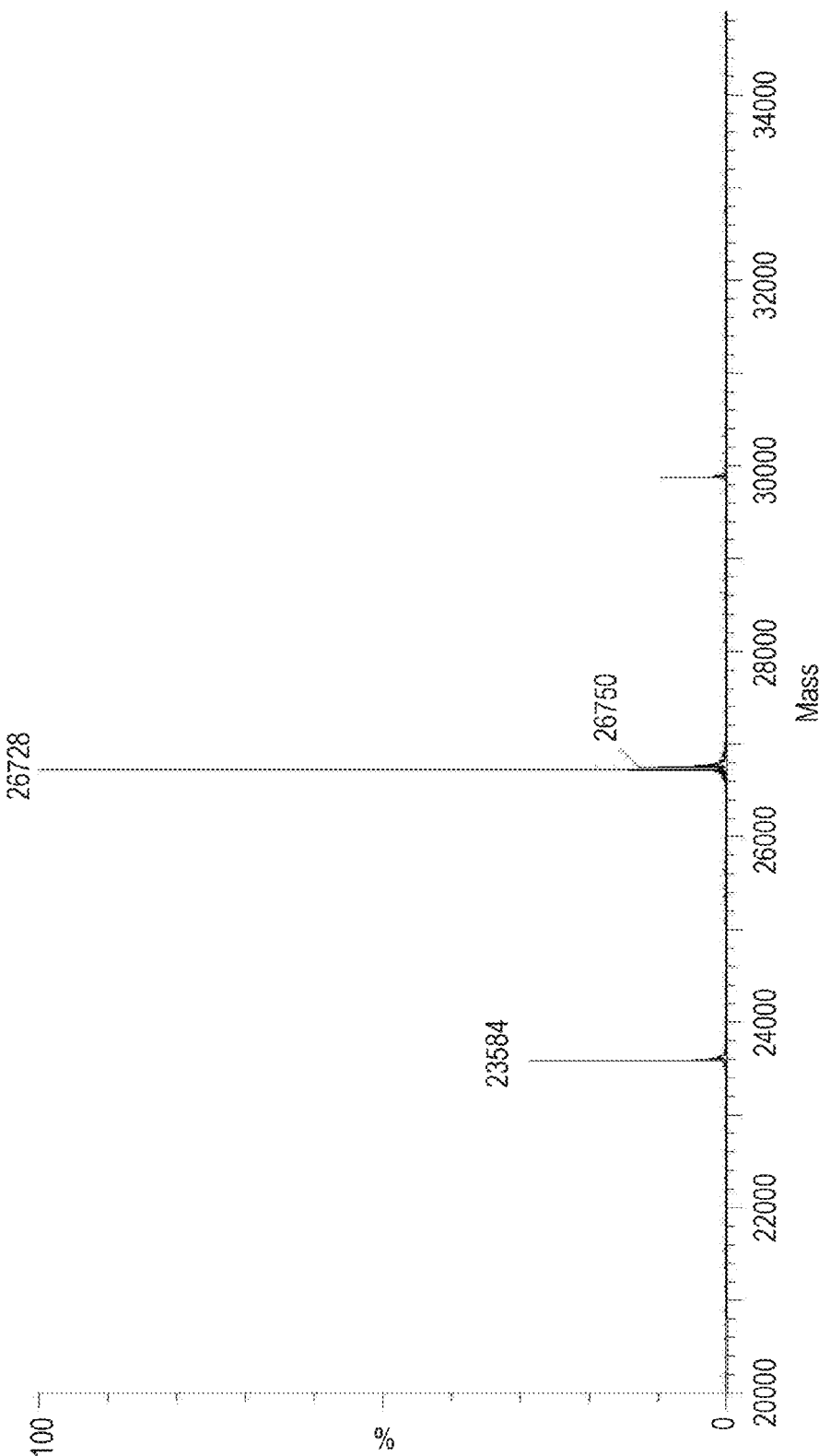

FIG. 8: Mass spectra of intact MAC-2. FIG. 9A: Mass spectra of reduced heavy chain for MAC-2. FIG. 9B: Mass spectra of reduced light chain for MAC-2.

FIG. 10: Ang1-4 binding ELISA. Representative graph of MAC binding to Ang family members (Ang1-4).

Figure 11:
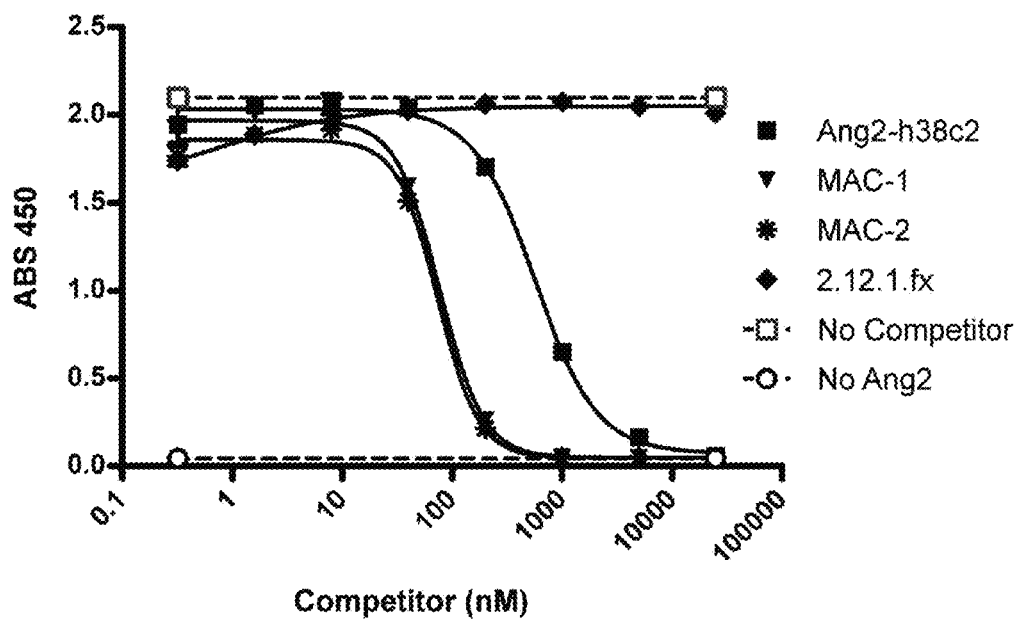

FIG. 11: Ang2 competition ELISA. Representative graph of competition with Ang2 binding to Tie2 receptor for MACs.

Figure 12:
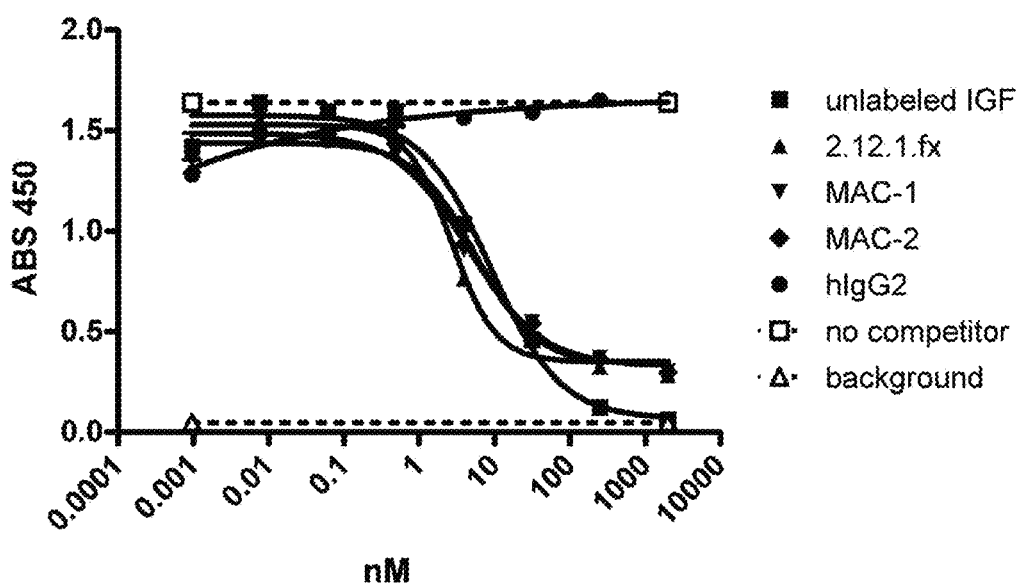

FIG. 12: IGF1R competition ELISA. Representative graph of competition with IGF1 binding to IGF1R for MACs.

Figure 13:
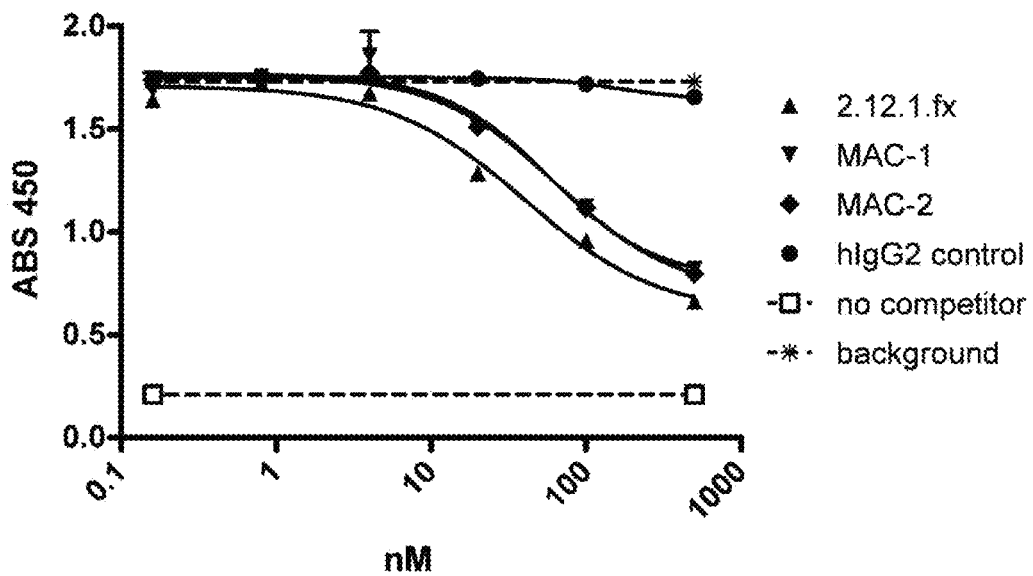

FIG. 13: Inhibition of IGF1 induced IGF1R autophosphorylation by MACs on 3T3-hIGF1R cells.

Figure 14A:
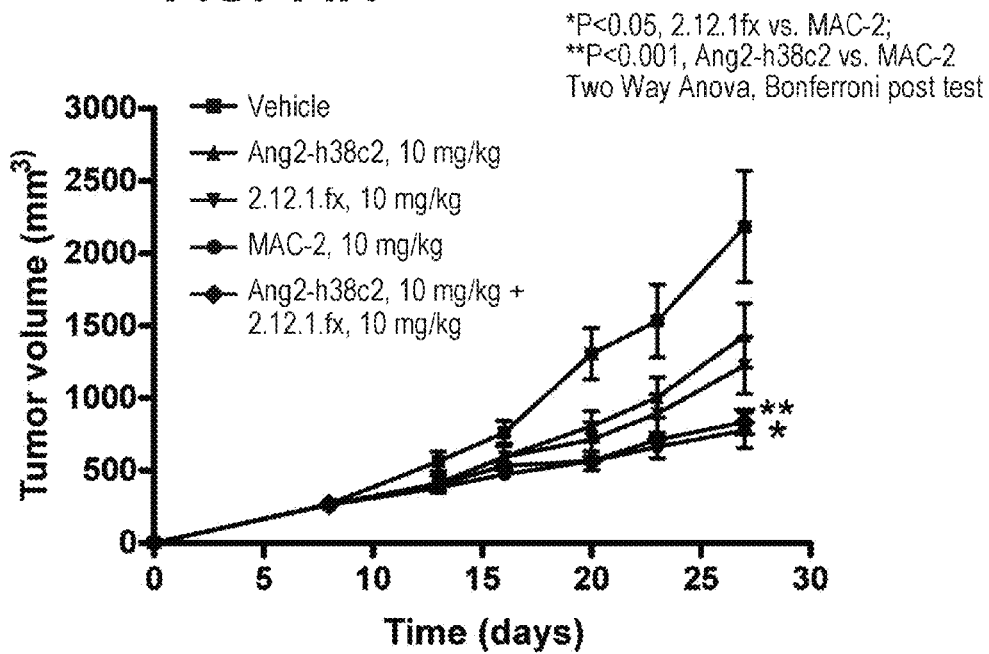
Figure 14B:
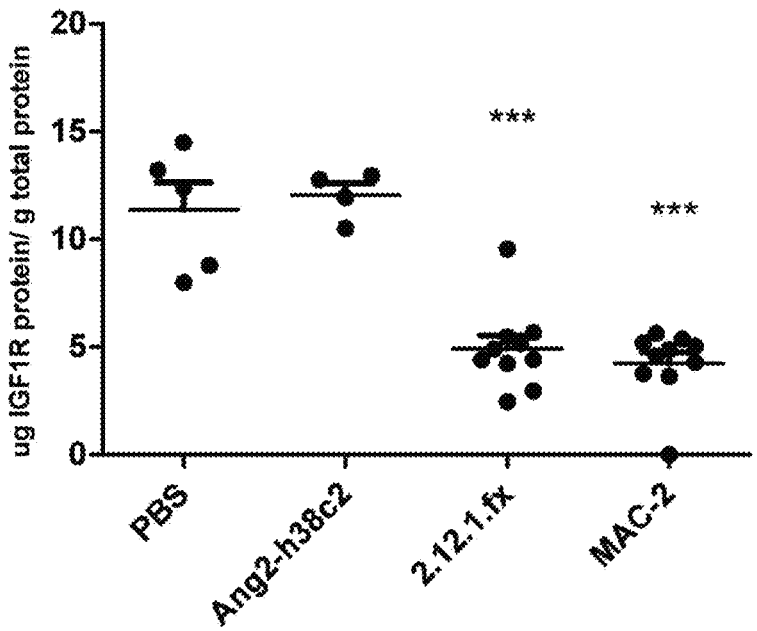

FIG. 14A: Tumour volume of Colo205 colon adenocarcinoma xenografts after treatment with vehicle, Ang2-h38c2, IGF1R antibody (2.12.1.fx) or MAC-2 (IP, 1×/wk). Data are depicted as the mean and SE of n=10/group for days 0-28 (n=10 for all groups beyond day 28). *: P<0.05, IGF1R antibody (2.12.1.fx) 10 mg/kg vs. MAC-2 10 mg/kg; : P<0.01, Ang2-h38C2 vs. MAC-2; Two Way Anova, Bonferroni posttest. FIG. 14B**: Relative IGF1R expression levels in lysates prepared from excised and frozen tumours.

Figure 15A:
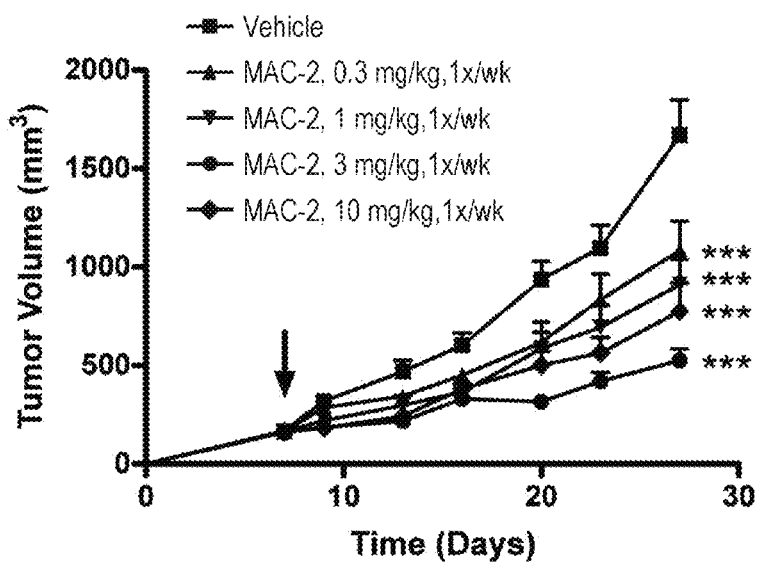
Figure 15B:
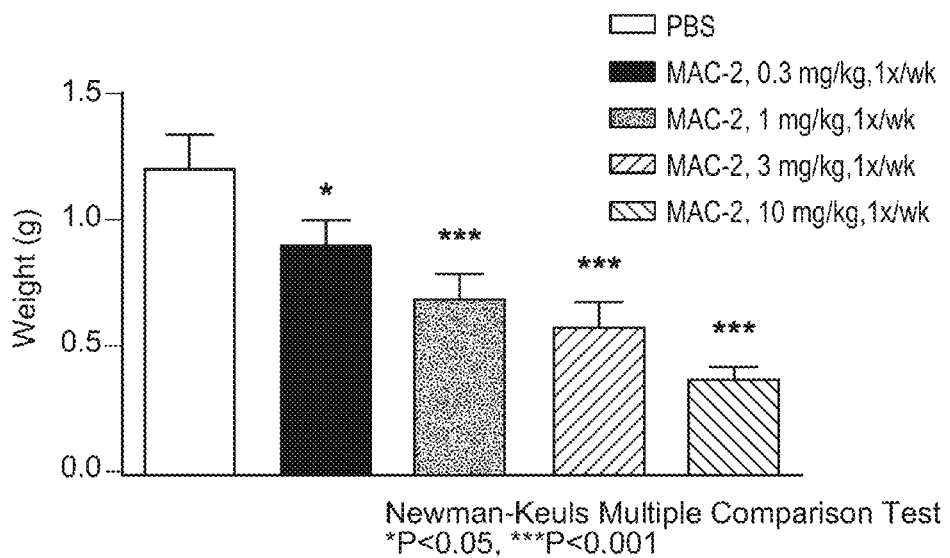
Figure 15C:
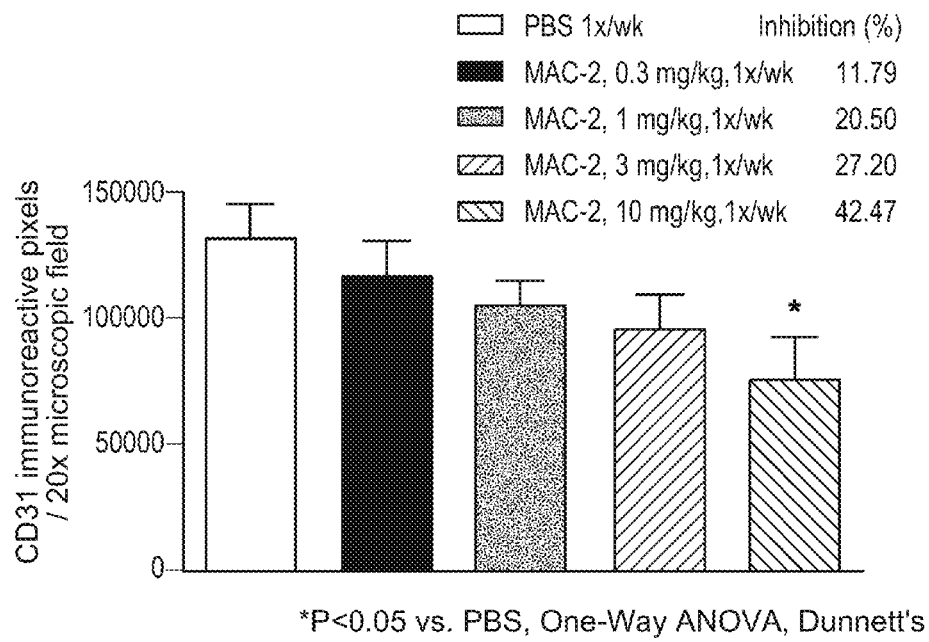

FIG. 15A: Tumour volume of Colo205 colon adenocarcinoma xenografts after weekly IP treatment with Vehicle or MAC-2 (IP, 1×/wk, 0.3-10 mg/kg). Data are depicted as the mean and SE of n=10/group. *: P<0.001, PBS vs. MAC-2 (all doses); Two Way Anova, Bonferroni posttest. FIG. 15B: Final tumour weights at Day 28. FIG. 15C: Tumour microvessel density of Colo205 colon adenocarcinoma xenografts after treatment with vehicle or MAC-2 (IP, once weekly). FIG. 15D: Relative Ang2 expression levels in lysates prepared from excised and frozen tumours. FIG. 15E**: Relative IGF1R expression levels in lysates prepared from excised and frozen tumours.

Figure 16A:
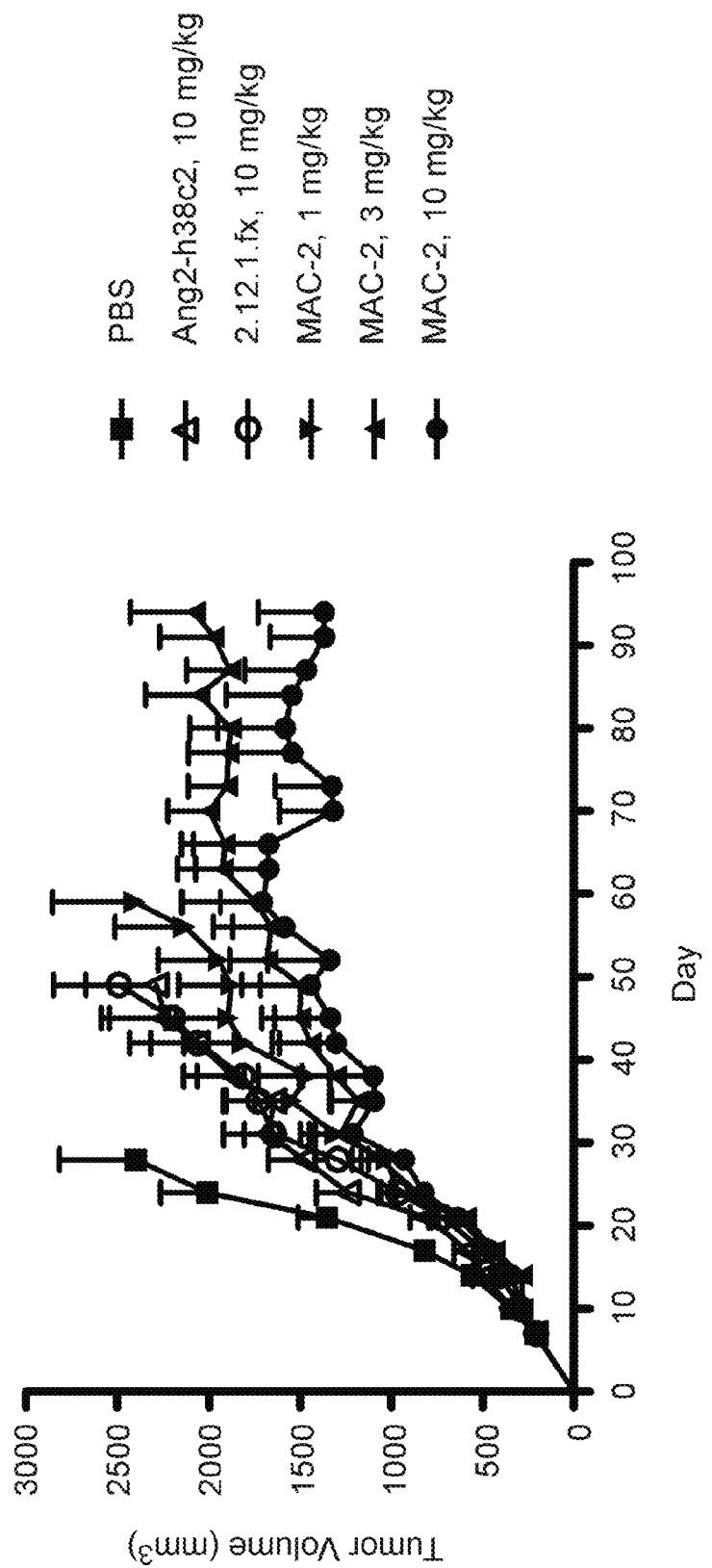

FIG. 16A: Tumour volume of Colo205 colon adenocarcinoma xenografts after once weekly IP treatment with vehicle, Ang2-h38c2 (10 mg/kg), IGF1R antibody (2.12.1.fx) (10 mg/kg) or MAC-2 (1, 3 or 10 mg/kg). FIG. 16B: Tumour volume of Colo205 colon adenocarcinoma xenografts after once weekly IP treatment with vehicle, IGF1R antibody (2.13.2) (10 mg/kg) or MAC-2 (10 mg/kg). FIG. 16C: Tumour volume of Colo205 colon adenocarcinoma xenografts after once weekly IP treatment with vehicle, Ang2-h38c2 (10 mg/kg), IGF1R antibodies (2.12.1.fx and 2.13.2) (10 mg/kg), MAC-2 (1, 3 or 10 mg/kg) or Ang2-h38c2 (10 mg/kg) in combination with either 2.12.2.fx or 2.13.2 (10 mg/kg). All data are depicted as the mean and SE of n=10/group.

Figure 17:
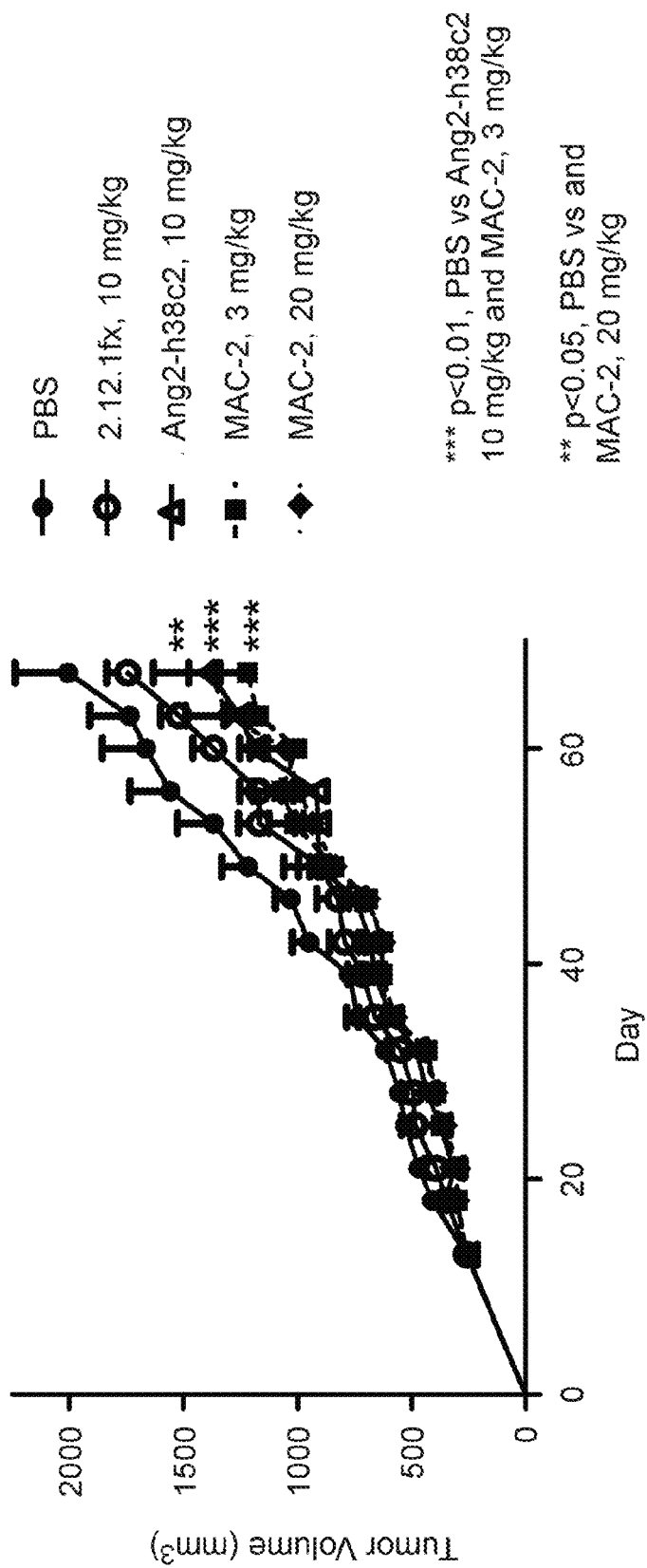

FIG. 17: Tumour volume of MDA-MB-435 melanoma after weekly treatment with vehicle or MAC-2 (IP, once weekly). : P<0.05, PBS vs. MAC-2, 20 mg/kg; *: P<0.01 PBS vs Ang2-h38c2, 10 mg/kg or MAC-2, 3 mg/kg: Two Way Anova, Bonferroni posttest. Data are depicted as the mean and SE of n=10/group.

FIG. 18A: Amino acid sequence alignment of the variable domains of m38c2, h38c2, and human germlines. Framework regions (FR) and complementarity determining regions (CDR) are defined according to Kabat et al. Asterisks mark differences between m38c2 and h38c2 or between h38c2 and the human germlines.

FIG. 18B: Amino acid sequence alignment of murine constant light chain kappa region (mCLκ), human constant light chain kappa region (hCLκ), and human constant light chain lambda region (hCLλ). Differences between mCLκ and hCLκ; and between hCLκ and hCLλ; are shown as asterisks, and conserved substations are shown as crosses.

In order that this invention may be better understood, the following examples are set forth. These examples are for purposes of illustration only and are not to be construed as limiting the scope of the invention in any manner.

EXAMPLES

Example 1

Synthesis of Peptides Used in the Invention

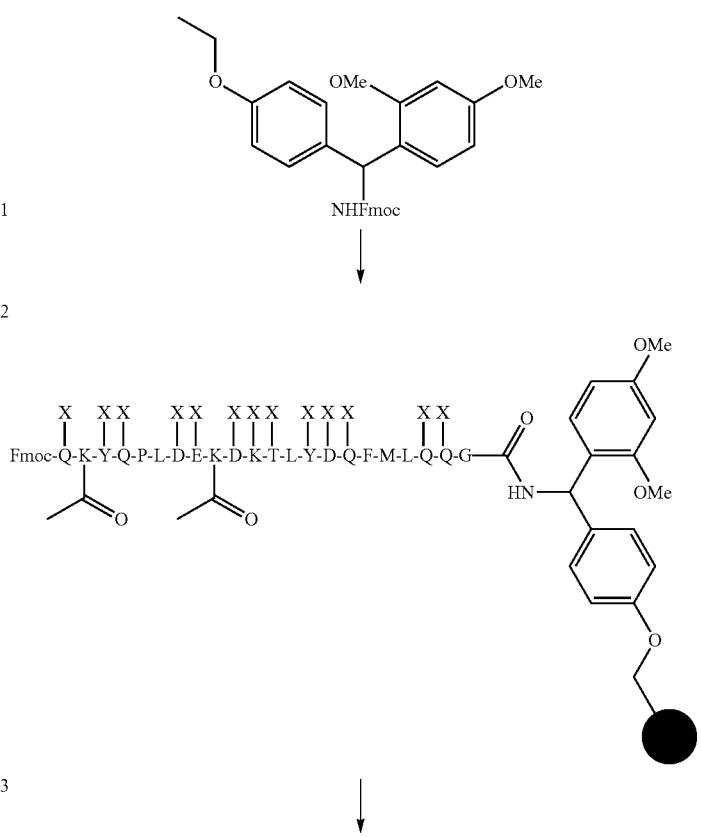

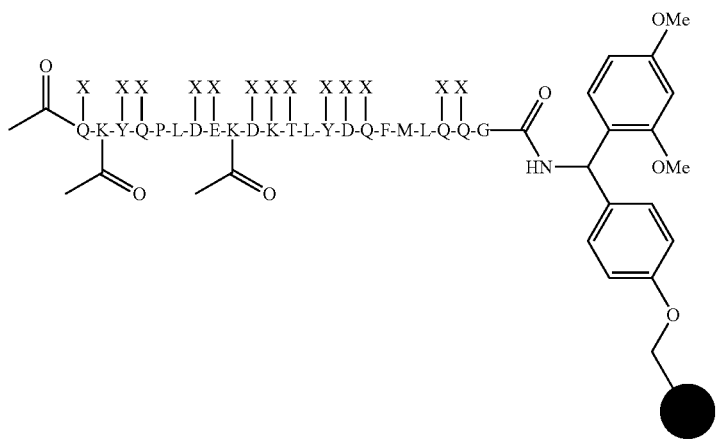

4

5

Rink Amide Resin

Steps for SPPS using Fmoc chemistry: (i) Fmoc removal with 20% piperidine/DMF, (ii) Amino acid coupling; HBTU: Amino acid:HOBt:NMM ratio relative to resin amine loading is 5:5:5:20. Solvent used was NMP, (iii) Repeat steps for each amino acid coupling. X=acid-labile side chain protecting group.

Completed assembly of fully-protected, resin-bound peptide:
(i) Fmoc removal with 20% piperidine/DMF, (ii) Acetylation: acetic anhydride/NMM/NMP. Completed assembly of N-acetylated, protected, resin-bound peptide.

Scheme 1. Solid phase synthesis of a peptide chain using Fmoc chemistry (exemplified with a typical Ang2-binding peptide (ABP) SEQ ID NO:27)

Example 2

Cleavage from Resin of the Peptide Prepared as in Example 1

Scheme 2: Cleavage of ABP (SEQ ID NO: 27) from resin

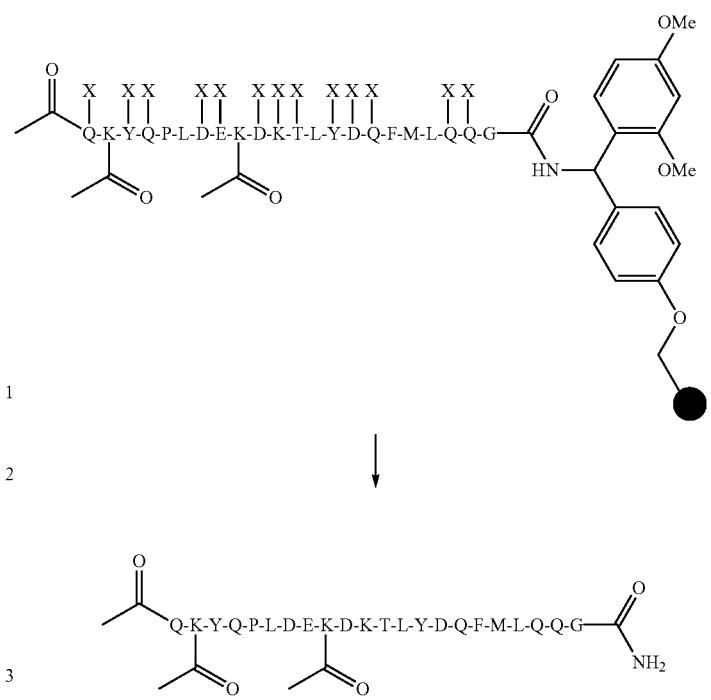

1
2
3

1. Completed assembly of N-acetylated, protected, resin-bound peptide.
2. TFA/water/phenol/triisopropylsilane (90:4:4:2).

Example 3

Synthesis of ABP-Thiol-Linker Compounds

Scheme 3: Synthesis of ABP-1-ti (3.3) (SEQ ID NO: 27 with $K^{11}$ substituted with linking residue K(SH))

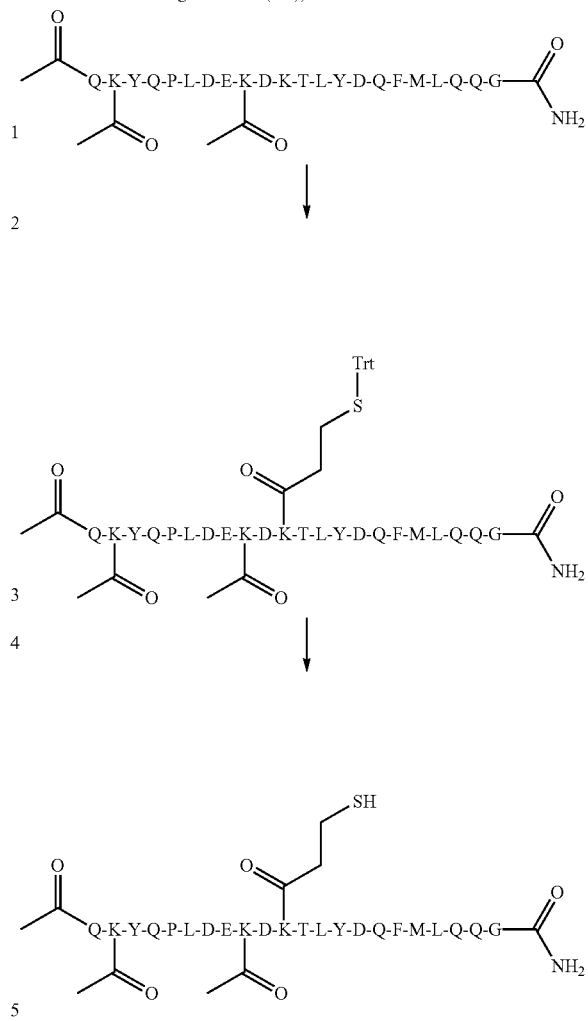

1. Ang2 binding peptide.
2. S-Trityl-mercaptopropionic acid/HBTU/NMM (5:5:10 ratio with respect to the Ang2 peptide).
3. Trityl-protected thiol Ang2 peptide intermediate.
4. TFA/DCM/TIPS (5:93:2 ratio).
5 Thiol bearing Ang2 modified peptide.

Analogs of an Ang-2-binding peptide (ABP) with different tether points were synthesized (see Examples 1 and 2). Initially the free thiol ABP intermediate was synthesized and purified, and then a maleimide-PEG$_2$-PFP linker added, followed by a final purification step to obtain a pure, PFP-activated ABP. The peptide chain assembly and cleavage were carried out as outlined in Schemes 1 & 2 to generate the pure ABP.

ABP (284 mg, 0.1 mmol) was dissolved in dimethylformamide (0.5 ml) with stirring. Separately, S-Trityl-mercaptopropionic acid (MPA, 62 mg, approx 0.125 mmol), HBTU (48 mg, 0.125 mmol) and N-methylmorpholine (0.025 ml, 0.25 mmol) were stirred in DMF (0.5 ml) for 5 min until dissolved. The ABP solution and activated MPA solutions were mixed together for 2 hrs. Progress of the reaction was monitored by LCMS. After 2 hrs, the solution was slowly added to ice-cold ether (40 ml) to precipitate the ABP-S-trityl-MPA product. The white precipitate was collected by filtration then dried. The solid residue was then dissolved in a solution of trifluoroacetic acid in dichloromethane (1:10, ml), with triisopropylsilane (TIPS) added (0.050 ml) and stirred for 1 hr. The solution was evaporated under reduced pressure to a light-yellow oil then the crude thiol peptide precipitated by the addition of ice-cold ether. The product was collected by centrifugation and dried in vacuo. The residue was dissolved in 50% aqueous acetonitrile then lyophilized to yield the crude thiol peptide (approx 80% pure by HPLC analysis). The crude thiol peptide was purified by semi-preparative HPLC to yield 145 mg of SEQ ID NO:27.

Synthesis of SEQ ID NO:27-K(SH)$^{11}$-MAL-2PEG-PFP

Scheme 4
Synthesis of SEQ ID NO: 27-K(SH)$^{11}$-MAL-2PEG-PFP

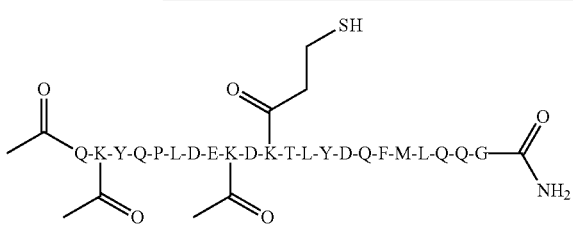

4.1 SEQ ID NO: 27-K(SH)$^{11}$

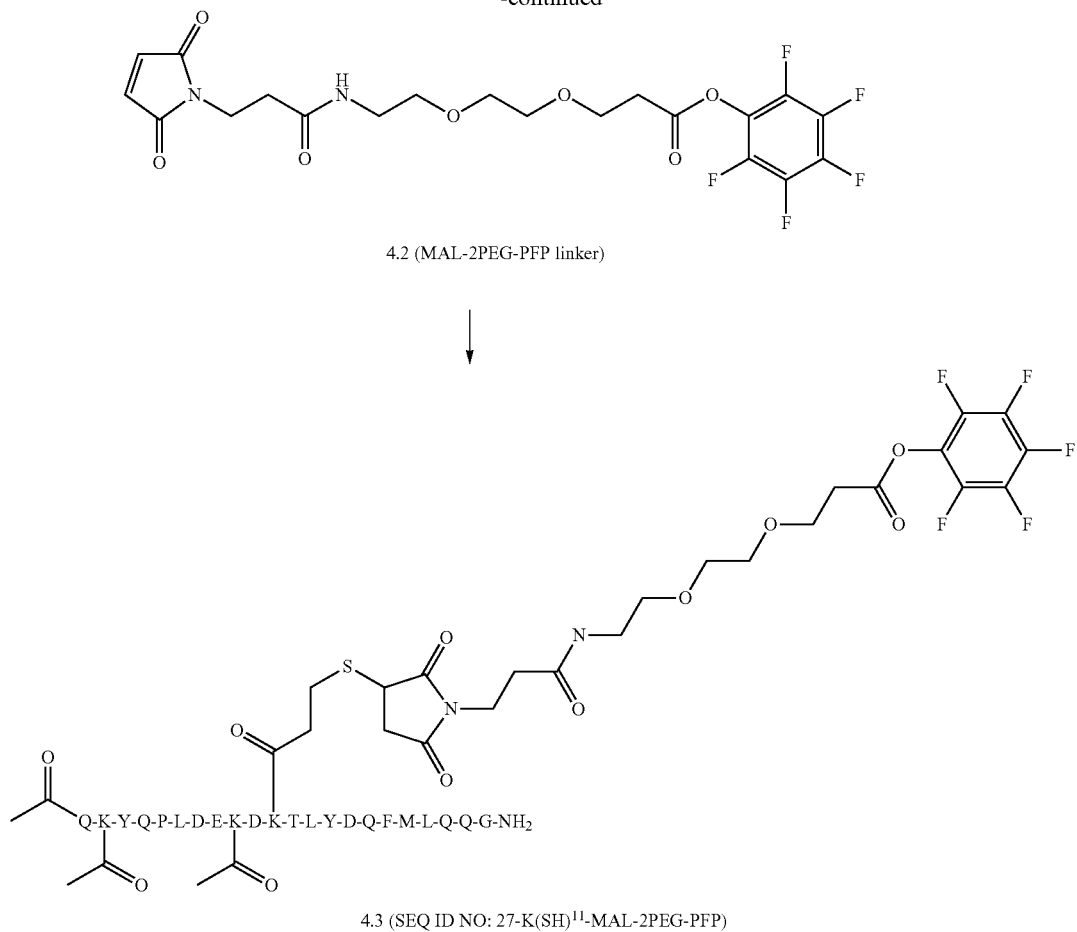

4.2 (MAL-2PEG-PFP linker)

4.3 (SEQ ID NO: 27-K(SH)[11]-MAL-2PEG-PFP)

Example 4

Generation of Ang-2-Binding-Peptide-Thiol Intermediates (ABP-ti)

Peptide chain assembly was conducted on a 0.1 millimole scale. The resin used was Fmoc-Rink-PL resin (150 mg, 0.67 mmol/g substitution). Standard Fmoc chemistry protocols were used to assemble the peptide. Fmoc removal was with 20% piperidine/DMF for 3×5 min. and all resin washing steps used DMF. To incorporate the amino acids, a single coupling step was employed for each residue, using HBTU/HOBt/NMM activation, for a 2 hr period. The Linking Residue (K(SH)) was incorporated as Fmoc-Lys(N$^\epsilon$-mercaptopropionate-S-Trt)-OH. Upon chain assembly, the N-terminal Fmoc group was removed and the peptidoresin capped by acetylation. The final resin was washed with DCM and dried overnight in vacuo. The final resin weights obtained were as follows: SEQ ID NO: 29-K(SH)$^9$: 627 mg, SEQ ID NO:30-K(SH)$^{16}$: 573 mg, SEQ ID NO:31-K(SH)$^{18}$: 642 mg, and SEQ ID NO:32-K(SH)$^{19}$: 641 mg.

Acidolytic removal of protecting groups and cleavage of the peptide from the resin was achieved using a cocktail of TFA/water/dithiothreitol/triisopropylsilane (ratio 90:4:4:2, 5 ml) for 2 hrs. The solution was filtered from the resin and the resin washed with another 5 ml of neat TFA. The combined filtrates were evaporated to a syrup then addition of ice-cold ether precipitated a white powder. The powder was collected by centrifugation then dissolved in 50% aqueous acetonitrile (20 ml), frozen and lyophilized overnight.

Results:

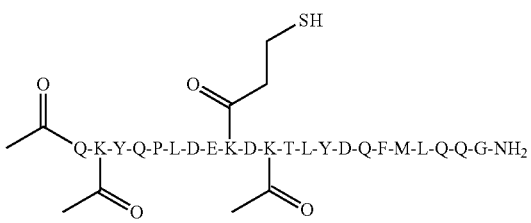

SEQ ID NO: 29-K(SH)$^9$

The amount of crude SEQ ID NO:29-K(SH)$^9$ obtained was 252 mg. Analysis of the crude SEQ ID NO:29-K(SH)$^9$ by HPLC showed a clean major peak; 5-95% B/30 min, C18, Rt=18.3 min. Further LCMS analysis of the crude SEQ ID NO:29-K(SH)$^9$ showed that the major peak was desired product; [M+H]$^+$=2930, +2=1465, +3=977 observed.

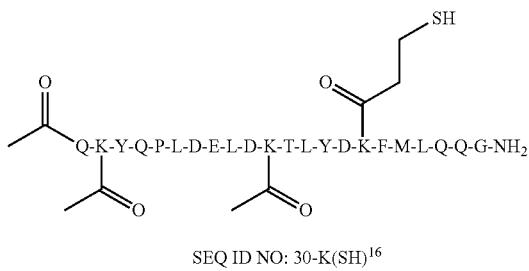

SEQ ID NO: 30-K(SH)¹⁶

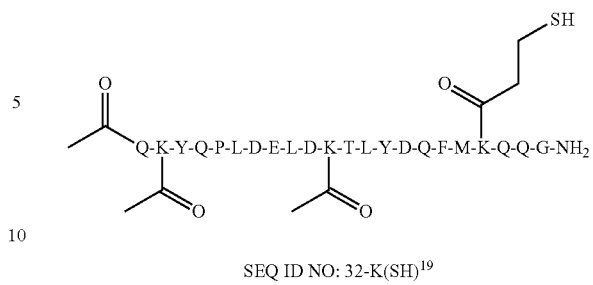

SEQ ID NO: 32-K(SH)¹⁹

The amount of crude SEQ ID NO:30-K(SH)¹⁶ obtained was 229 mg. Analysis of the crude SEQ ID NO:30-K(SH)¹⁶ by HPLC showed a clean major peak; 5-95% B/30 min, C18, Rt=22.0 min. Further LCMS analysis of the crude SEQ ID NO:30-K(SH)¹⁶ showed that the major peak was desired product; [M+H]+=2915, +2=1458, +3=972 observed.

The amount of crude SEQ ID NO:32-K(SH)¹⁹ obtained was 261 mg. Analysis of the crude SEQ ID NO:32-K(SH)¹⁹ by HPLC showed a clean major peak; 5-95% B/30 min, C18, Rt=20.0 min. Further LCMS analysis of the crude SEQ ID NO:32-K(SH)¹⁹ showed that the major peak was desired product; [M+H]⁺=2930, +2=1465, +3=977 observed.

Purification:

A preparative HPLC column was pre-equilibrated with dilute aqueous TFA and acetonitrile. The crude ABP-thiol intermediates (i.e., ABP with K(SH) as linking residue) was dissolved in DMF (3 ml), then adsorbed onto the column and eluted by applying a gradient of acetonitrile in dilute TFA. Fractions were collected automatically by mass (M=1465). Elution from the column was monitored by UV, the fractions obtained were analyzed by analytical RP-HPLC. The purest fractions (>95% by analytical HPLC) were combined and lyophilized to give the following quantities: 87 mg of pure SEQ ID NO:29-K(SH)⁹, 50 mg of pure SEQ ID NO:30-K(SH)¹⁶, 59 mg of pure SEQ ID NO:31-K(SH)¹⁸, and 39 mg of pure SEQ ID NO:32-K(SH)¹⁹.

Linker Synthesis 5 different activation strategies were considered for conjugating an ABP to anti-IGF1R antibodies of the invention, (Examples 5-9) (exemplary structures are shown using SEQ ID NO:27-K(SH)¹¹):

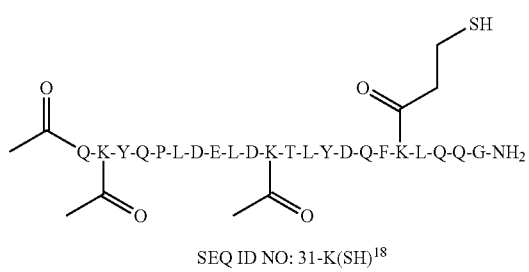

SEQ ID NO: 31-K(SH)¹⁸

The amount of crude SEQ ID NO:31-K(SH)¹⁸ obtained was 252 mg. Analysis of the crude SEQ ID NO:31-K(SH)¹⁸ by HPLC showed a clean major peak; 5-95% B/30 min, C18, Rt=21.1 min. Further LCMS analysis of the crude SEQ ID NO:31-K(SH)¹⁸ showed that the major peak was desired product; [M+H]+=2912, +2=1456, +3=971 observed.

Example 5

N-hydroxysuccinimide Esters (NHS) (SEQ ID NO:27-K¹¹-NHS)

Scheme 5
Synthesis of SEQ ID NO: 27-K¹¹-5PEG-NHS

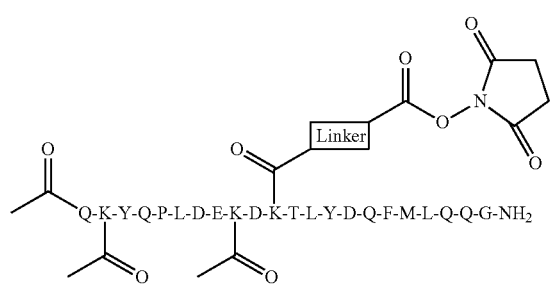

N-hydroxysuccinimide esters (NHS) (SEQ ID NO: 27-K¹¹-NHS)

-continued

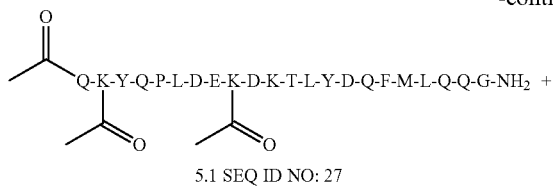

5.1 SEQ ID NO: 27

5.2 Bis-PEG$_5$-NHS ester

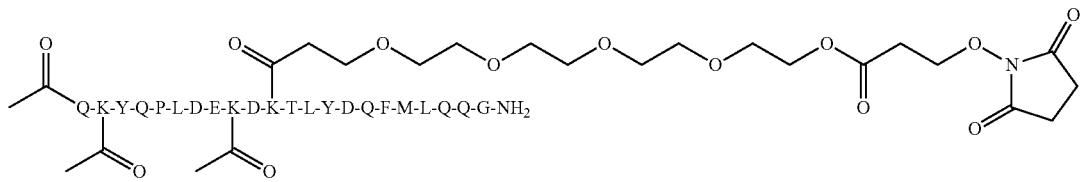

5.3 SEQ ID NO: 27-K$^{11}$-5PEG-NHS

Synthesis of SEQ ID NO:27-K$^{11}$-5PEG-NHS

SEQ ID NO:27 (5.1) was reacted with a Bis-NHS, PEG$_x$-linker (5.2), such that the NHS-activated carboxyl group remained on the final activated peptide product (5.3) and remained available for subsequent conjugation. This was necessitated by the presence of 4 other free carboxyl groups on the ABP. These precluded a simple in situ activation strategy, as the position of the activated group could not have been easily controlled and it would be likely that multiple carboxyl side chains would have been activated.

The reaction between the bis-PEG$_5$-NHS ester and the ABP (SEQ ID NO:27) was examined. Using a 10-fold excess of the linker in DMSO, a solution of the ABP and N-methylmorpholine (as base) in DMSO was slowly titrated into a well-stirred solution. Samples were taken and examined by HPLC and LCMS at various time-points. After about 2 hrs, there was substantial product formation (around 80% conversion from 5.1 to form 5.3) and this was easily separated from the bis-NHS linker reagent. However, even in DMSO, the product 5.3 slowly converted over time to the free acid form (where the NHS-ester group converted to the inactive free carboxyl). Also, when the crude reaction mixture was fractionated to isolate the desired product 5.3, this was also subject to hydrolysis during the purification and subsequent lyophilization steps. Although the procedure was successful at synthesizing some product, it was thought that the aqueous lability of the resulting NHS-ester would limit its application in subsequent conjugation reactions. Further tests of MAL-PEG2-NHS are shown in Example 30 (comprising Z* group Z13).

Example 6

Maleimide (Mal) (SEQ ID NO:27-K$^{11}$-Mal)

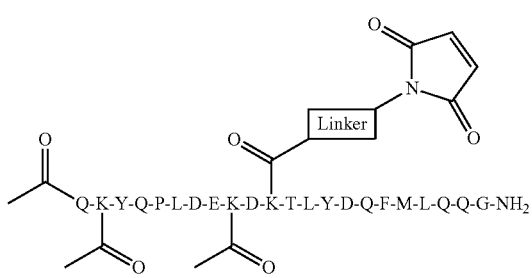

Maleimide activation is generally used in concert with a free thiol conjugation partner. Although no free thiol residues are present in antibody 2.12.1.fx, there are several chemical procedures that can be used to introduce free thiols into proteins and thus provide linkage sites for maleimide-based conjugation.

Mal-containing peptides are in general relatively straightforward to synthesize using simple maleimide/acid containing linkers. Several SEQ ID NO:27-MAL compounds were synthesized, as shown below. In general, the maleimide-activated peptides did not conjugate well to proteins or antibodies which lack either an endogenous thiol (derived from a free cysteine side chain) or a thiol introduced by other chemical means, e.g. via Traut's reagent.

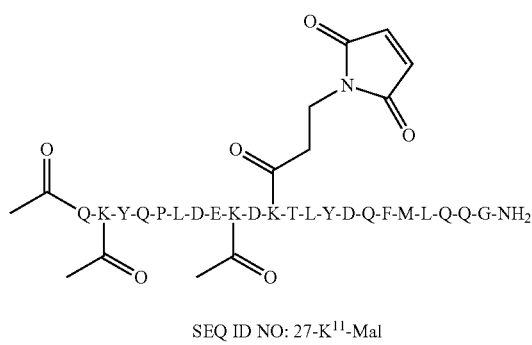

SEQ ID NO: 27-K[11]-Mal

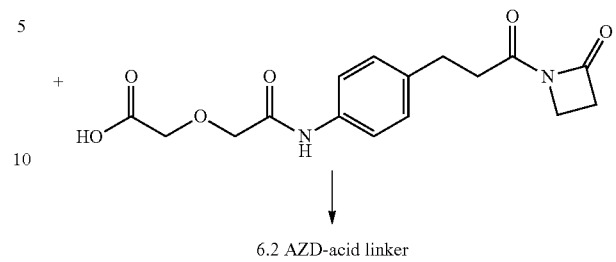

6.2 AZD-acid linker

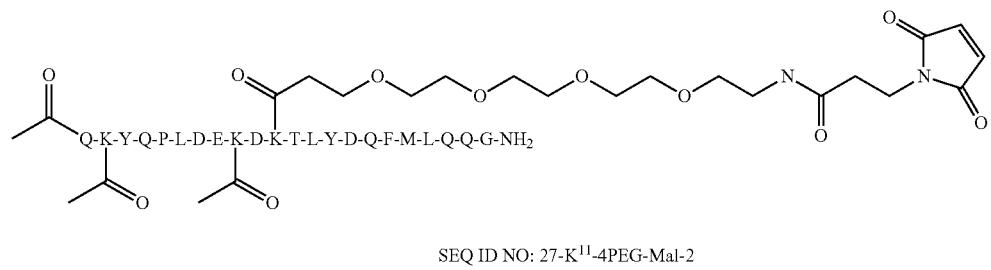

SEQ ID NO: 27-K[11]-4PEG-Mal-2

Example 7

Azetidinone (AZD) (SEQ ID NO:27-K[11]-AZD)

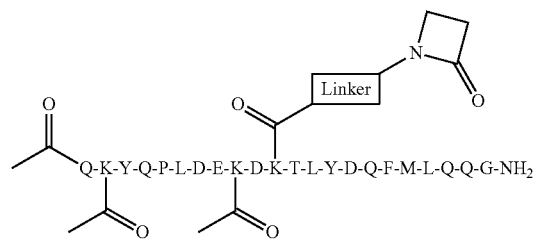

SEQ ID NO: 27-AZD

AZD-activated ABP was synthesized by attaching an AZD-acid linker to the ABP in solution.

AZD Activation:

Scheme 6: Synthesis of SEQ ID NO: 27-K[11]AZD (6.3)

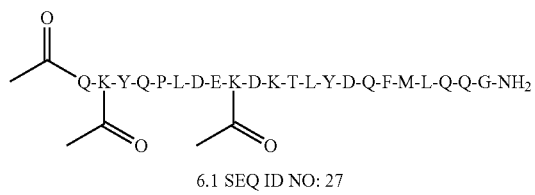

6.1 SEQ ID NO: 27

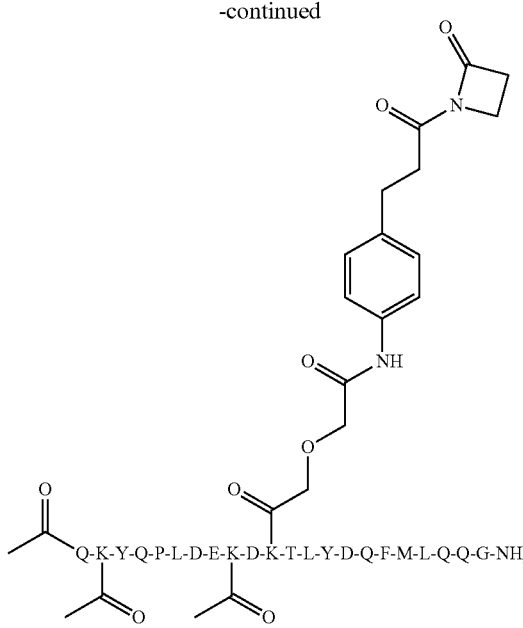

6.3 SEQ ID NO: 27-K[11]-AZD

The AZD-activated ABP reacted very slowly with lysine side chain amino groups. Conjugation was attempted at pH 7 to 9 in phosphate buffer to increase the nucleophile tendency of the antibody surface lysines by decreasing their charge (the pKa of lysines on the surface proteins is about 9.1 to 11.2). Issues with antibody stability and AZD hydrolysis precluded the use of pH above 9. 15 moles of AZD-activated ABP was added per 1 mole of antibody) over 3 days of reaction time, yielding low levels of conjugation (an average of 2 AZD-activated ABP per antibody). At basic pH, AZD hydrolysis occurs rapidly (50% after 24 hrs) contributing to the decreased levels of conjugation.

Example 8

Esters of Squaric Acid (Squarates). (SEQ ID NO:27-Squarate)

Scheme 7:
Scheme 7: Squaric acid derivatives SEQ ID NO: 27-$K^{11}$-Squarate linker-1 -> ABP-1-Squarate-1

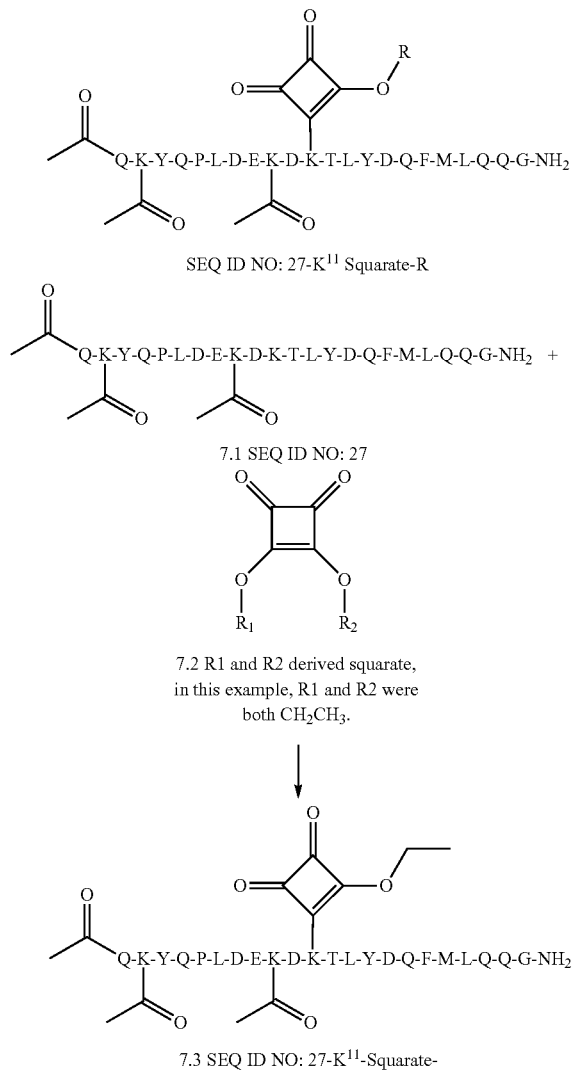

Alkyl esters made from squaric acid are known to react selectively with thiols at neutral pH, while at higher pHs (around 8.5 and above), they can also react with amines but more slowly. The reactivity of squarates can be significantly enhanced by replacement of alkyl with aryl groups. The present invention provides for several squarate derivatives of the ABP, where the nature of the 'R' is varied (R is selected from the group consisting of ethyl, phenyl, 2-methoxycarbonylphenyl, 3-fluorophenyl and 3,5-difluorophenyl), and other derivatives where the linker position has been varied. The ethyl squarates conjugate well to free thiols but poorly to free amines on proteins and antibodies unless the pH is above 9. The aryl squarates demonstrated better efficiency when conjugated to free lysines on the antibodies of the invention at neutral pH.

Example 9

Pentafluorophenyl esters (PFP) (SEQ ID NO:27-PFP)

The present invention also provides for the use of pentafluorophenyl (PFP) esters to form relatively stable activated peptides. This method has several advantages over other approaches in that the PFP group can be introduced in solution easily from a stable activated peptide product, which itself can be purified using standard HPLC methods with little PFP ester hydrolysis observed. The challenge in synthesizing an ABP covalently connected to a linker with a reactive group capable of conjugation to an antibody is the presence of four acidic side chains (3 aspartic acids and one glutamic acid) in the ABP sequence. These preclude a simple activation strategy using the peptide and an activating agent since there are no known simple methods to ensure site-specific activation on one particular acid side chain.

To solve this problem, the present invention provides a synthetic route whereby an activated ester group, such as PFP, can be coupled directly to a side chain lysine on the peptide by either a chemoselective reaction (using thiol/maleimide chemistry) or by using a bis-active ester reagent, which forms an amide with the peptide side chain but leaves the other end as the active ester.

In some embodiments, the strategy may be a bis-acid PEG with each acid activated as a PFP ester. In organic solutions, with some base present, the end of the bis-PFP linker reacted with the N-ε-amino side chain of lysine in the required tether position to form a stable amide linkage, while the other end maintained the other PFP group. One potential problem with this strategy is the possibility of forming peptide dimers, where a peptide would add to each of the PFP moieties present at each end of the linker. In some aspects, the present invention overcomes this additional problem by altering the stoichiometry and addition of the respective peptide and bis-PEG-PFP linker. One solution provided by the invention is to have an excess of the bis-Pfp linker in solution and slowly add the peptide in solution, such that an excess of linker over peptide is always present. By having a ratio of between about 3.7:1 to about 4.3:1, or in some embodiments, a ratio of about 4:1, of linker over peptide, the required PFP-activated peptide can be synthesized with no dimer present. The synthesis scheme for SEQ ID NO:27-$K^{11}$-5PEG-PFP is shown below in Scheme 8:

Scheme 8 SEQ ID NO: 27-K[11]-5PEG-PFP

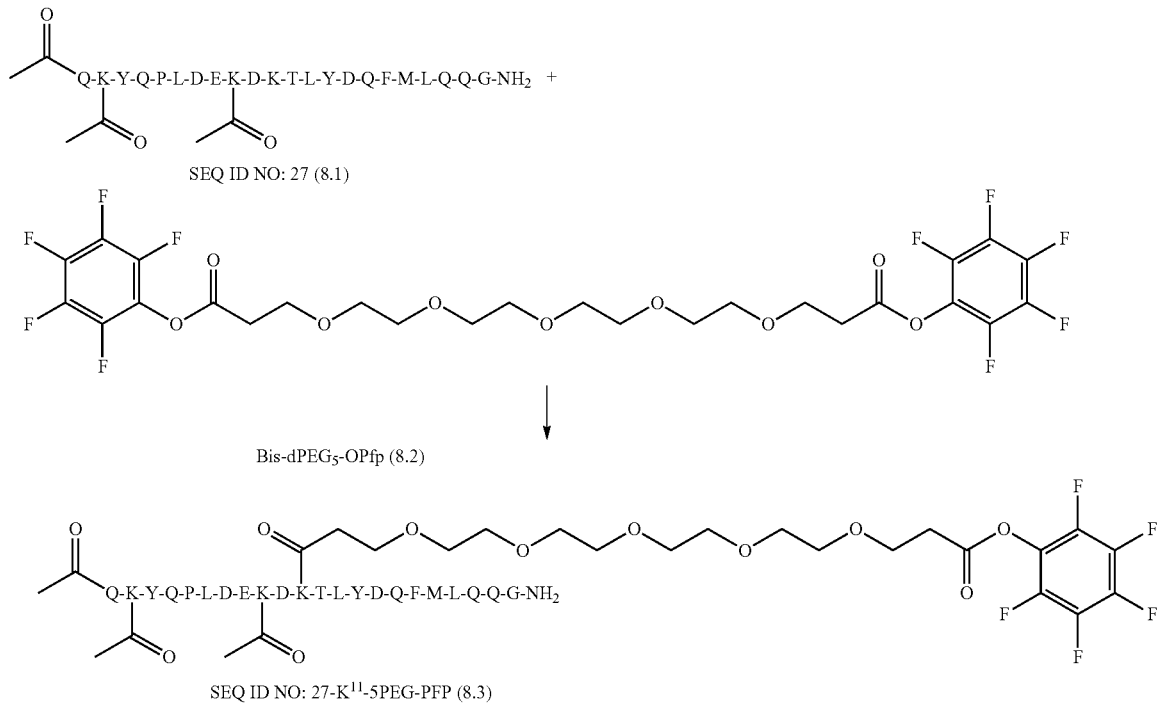

SEQ ID NO: 27 (8.1)

Bis-dPEG$_5$-OPfp (8.2)

SEQ ID NO: 27-K[11]-5PEG-PFP (8.3)

Synthesis of Bis-dPEG$_5$-OPfp Linker (8.2)

Bis-dPEG$_5$-acid (1 mmol, 338 mg) was dissolved in anhydrous dichloromethane (5 ml) then pentafluorophenol (2 mmol, 368 mg) was added, along with dicyclohexycarbodiimide (1 mmol, 208 mg). The solution was stirred overnight at RT. After this time, the fine white dicyclohexylurea side-product was filtered off and the filtrate evaporated to dryness to give a pale yellow light oil. Analysis by TLC and HPLC indicated a pure product with correct MS=670. The product was used in the next step without further purification. The product is stable for several months at −20° C.

Synthesis of SEQ ID NO:27-K[11]-5PEG-PFP (8.3)

SEQ ID NO:27 (8.1) (730 mg) was dissolved in anhydrous dimethylformamide (8 ml) and N-methylmorpholine (0.05 ml) added. An aliquot of neat bis-dPEG$_5$-OPfp reagent (8.2) (0.5 ml) was placed in a glass vial (20 ml). With vigorous stirring, the SEQ ID NO:27/NMM solution was added in 4×2 ml aliquots to the bis-dPEG$_5$-OPfp reagent over 2 hr, then the final mixture stirred for a further 1 hr. Progress of the conversion to SEQ ID NO:27-K[11]-5PEG-PFP product was monitored by analytical HPLC. At the end of the reaction, the solution was filtered and directly purified by semi-preparative HPLC on a 1" C8 column. The purest fractions (>95% by analytical HPLC) were combined and lyophilized to give 400 mg (48% yield) of final ABP-1-5PEG-PFP peptide-linker-2 product. A similar mechanism can be used to generate SEQ ID NO:27-K(SH)[11]-Maleimide-2PEG-PFP (see Scheme 4).

Synthesis of Maleimide-2PEG-PFP Linker

Scheme 9 Maleimide-dPEG2-acid (9.1) → Maleimide-2PEG-PFP (9.2)

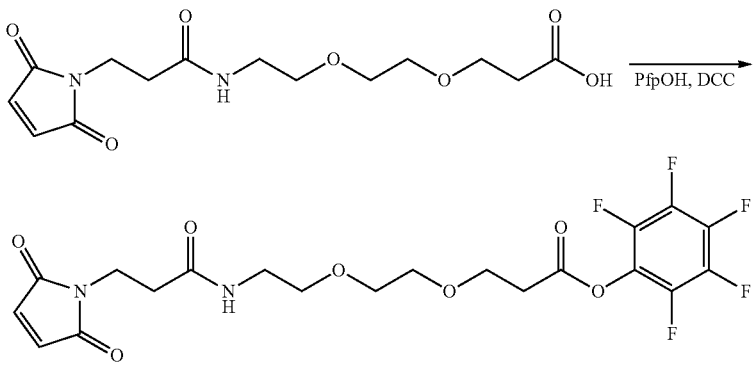

Maleimide-dPEG$_2$-acid (328 mg, 1 mmol, Quanta Biodesign), pentafluorophenol (0.103 ml, 1 mmol, PFP) and dicyclohexylcarbodiimide (206 mg, 1 mmol, DCC) were dissolved in dry DCM (10 ml) and stirred for 1 hr at RT. The fine white precipitate (DCU side-product) that formed was removed by filtration and the filtrate evaporated to dryness in vacuo. The product was obtained as a fine white powder in high yield (490 mg, quantitative). Purity was >95% by analytical HPLC; MS showed [M+H]$^+$=495.

Synthesis of PFP-Activated ABP Analogs

A sample (30-40 mg) of each of the purified ABP-thiol-intermediates (i.e. ABP with K(SH) as linking residue) was dissolved in anhydrous DMF (2 ml). Mal-PEG$_2$-PFP (20 mg) was added along with N-methylmorpholine (5 mL). The reaction was stirred and monitored at RT by HPLC to follow the time-course of product formation. The complete conversion of starting peptide to PFP-activated ABP product was observed within the first 2 hrs. The solution was filtered and the product peak directly isolated by semi-preparative HPLC. In each case, the product was isolated in approximately 40% yield after lyophilization.

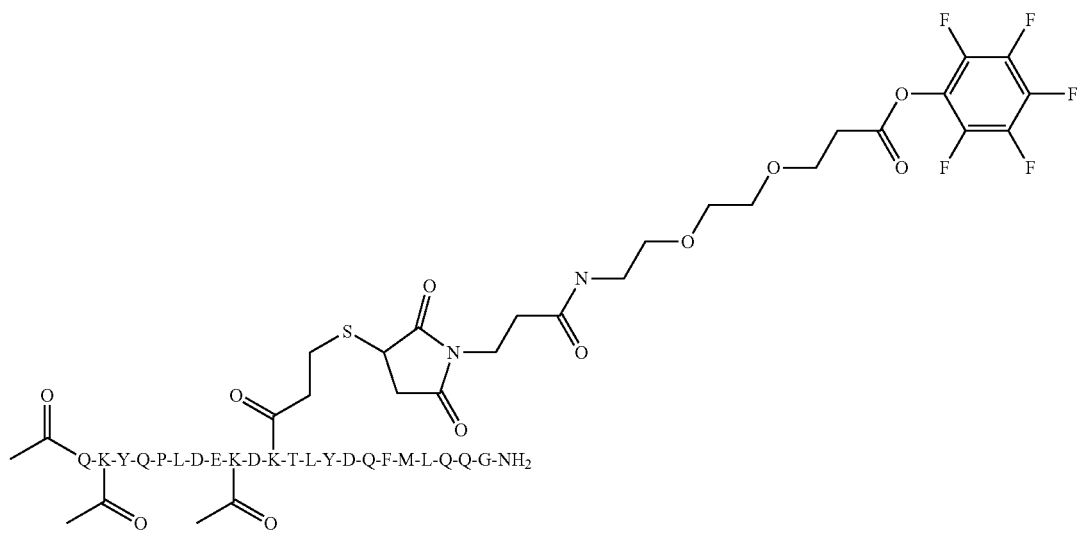

SEQ ID NO: 27-K(SH)$^{11}$-MAL-2PEG-PFP: 21 mg

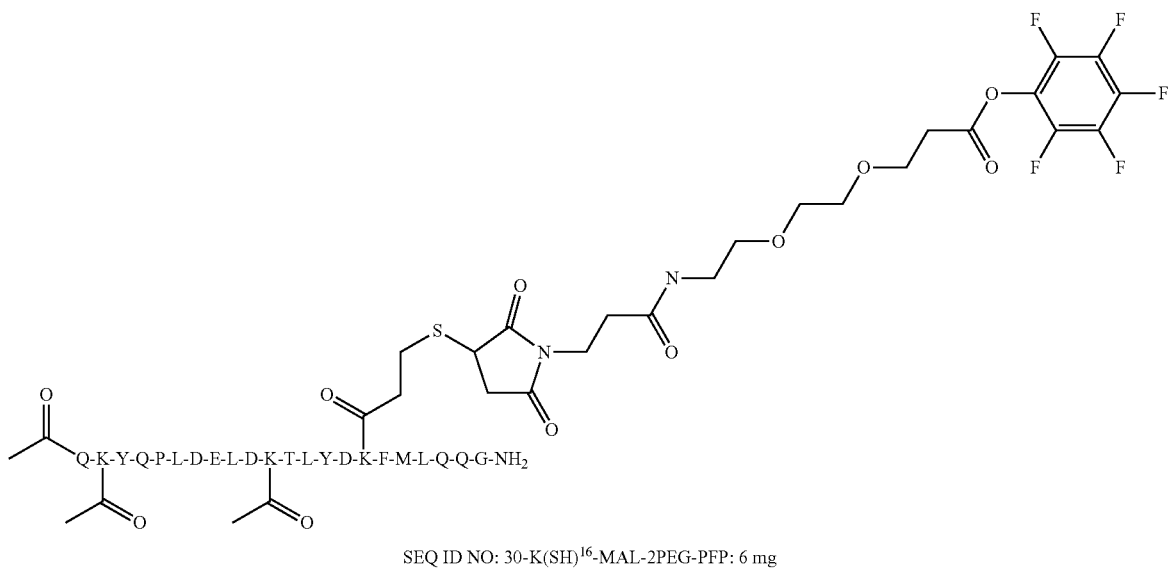

SEQ ID NO: 30-K(SH)$^{16}$-MAL-2PEG-PFP: 6 mg

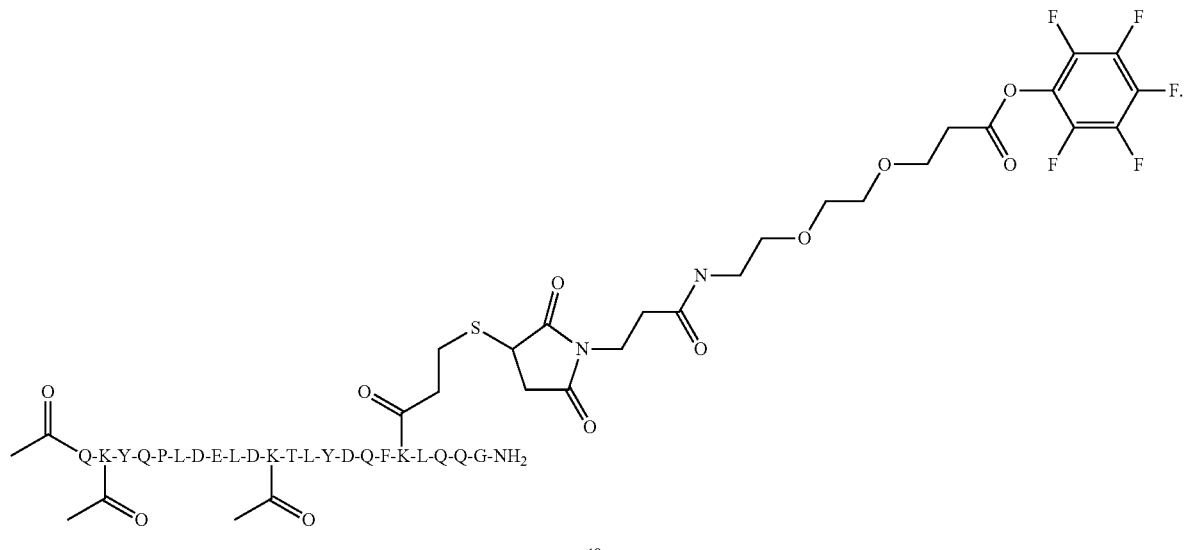

SEQ ID NO: 31-K(SH)$^{18}$-MAL-2PEG-PFP: 9 mg

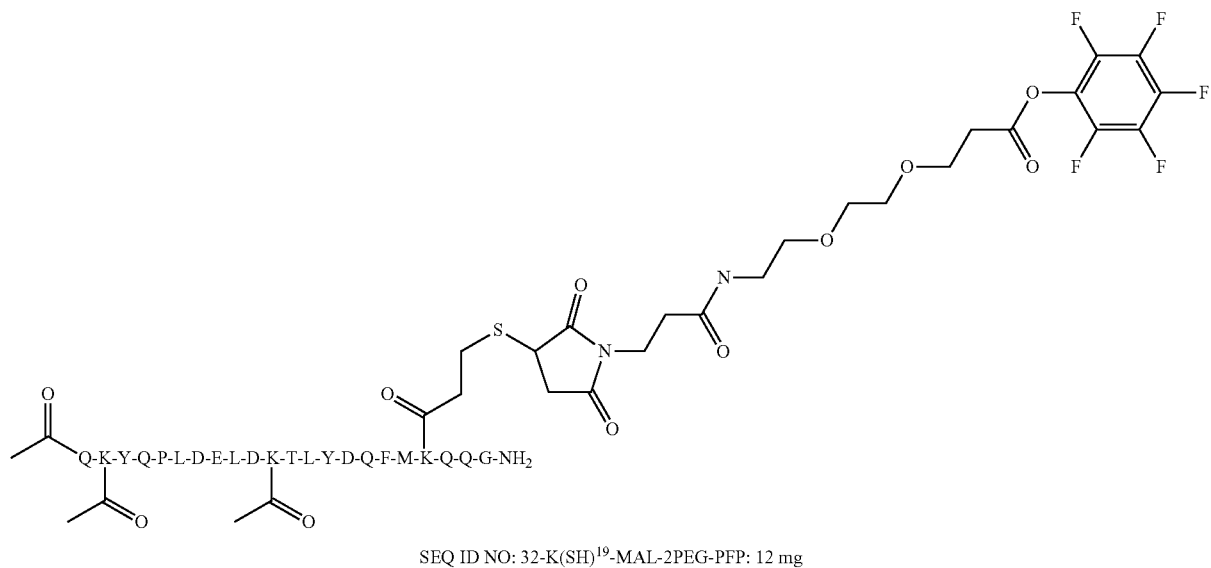

SEQ ID NO: 32-K(SH)$^{19}$-MAL-2PEG-PFP: 12 mg

Example 10

Antibody Conjugation

The MAC-1 and MAC-2 drug products were made by conjugating 2.12.1.fx with an Ang2 binding peptide. MAC-1 comprises of 2.12.1.fx with SEQ ID NO:27-K(SH)$^{11}$-MAL-2PEG-PFP and MAC-2 comprises of 2.12.1.fx with SEQ ID NO:27-K$^{11}$-5PEG-PFP. Number of peptide conjugations per 2.12.1.fx molecule in a sample of each MAC was calculated (see Table 1).

TABLE 1 conjugation profile of MAC-1 and MAC-2

|  | Conjugation Additions (CA) (%) | | | | | Avg |
|---|---|---|---|---|---|---|
|  | 0 | 1 | 2 | 3 | 4 | CA |
| MAC-2 | 2 | 20 | 47 | 26 | 5 | 2.12 |
| MAC-1 | 3 | 26 | 42 | 25 | 3 | 1.97 |

Generation of MAC-1
Scheme 10: Reaction of SEQ ID NO: 27-K(SH)[11]-MAL-2PEG-PFP with a lysine side chain of an antibody (Ab-K-Ab):
Where the antibody is 2.12.1.fx, the MAC is MAC-1
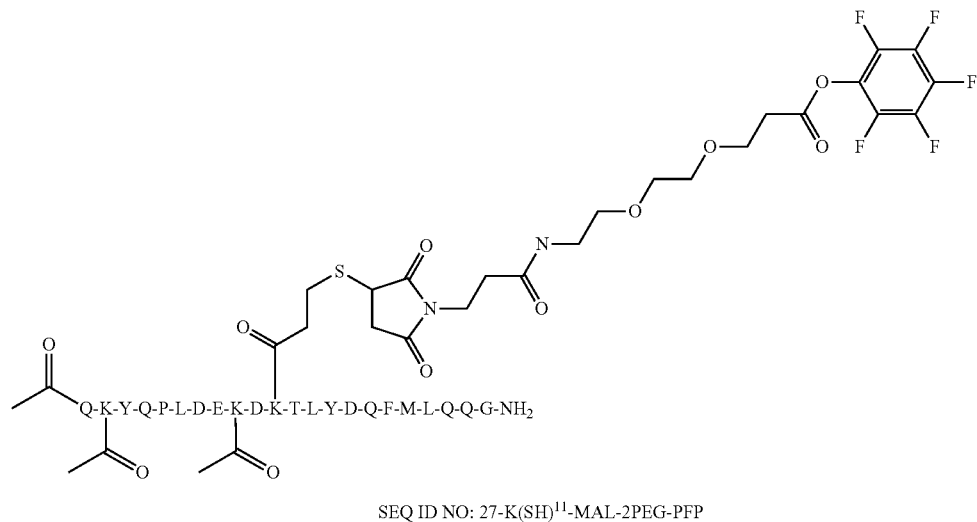
SEQ ID NO: 27-K(SH)[11]-MAL-2PEG-PFP
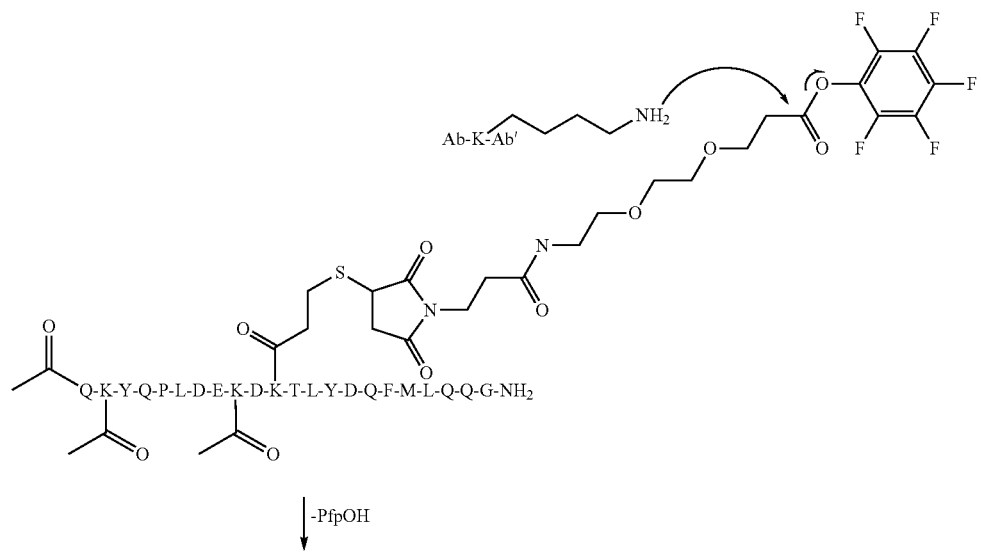
-PfpOH

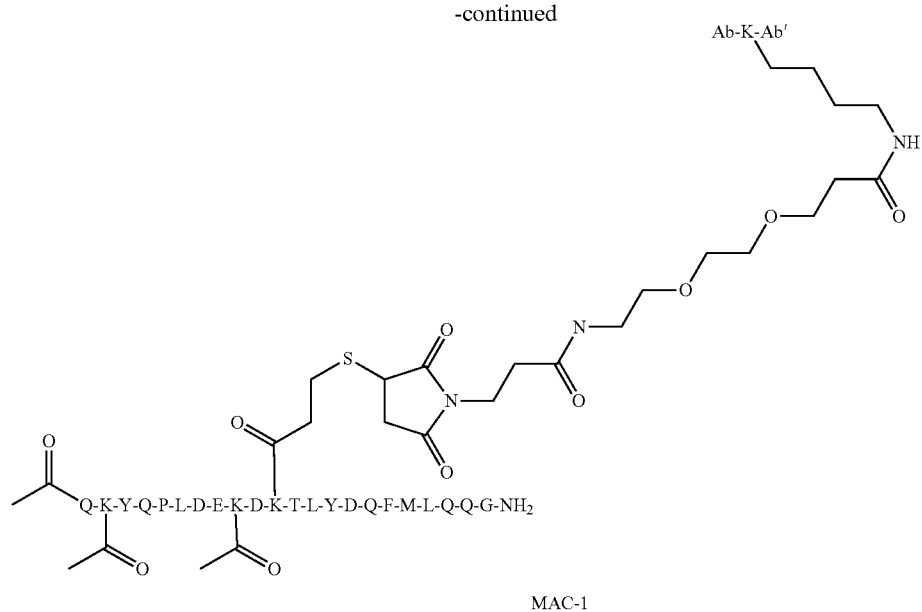
MAC-1
Generation of MAC-2
Scheme 11: Reaction of SEQ ID NO: 27-K[11]-5PEG-PFP with a lysine side chain of an antibody (Ab-K-Ab): Where the antibody is 2.12.1.fx, the MAC is MAC-2
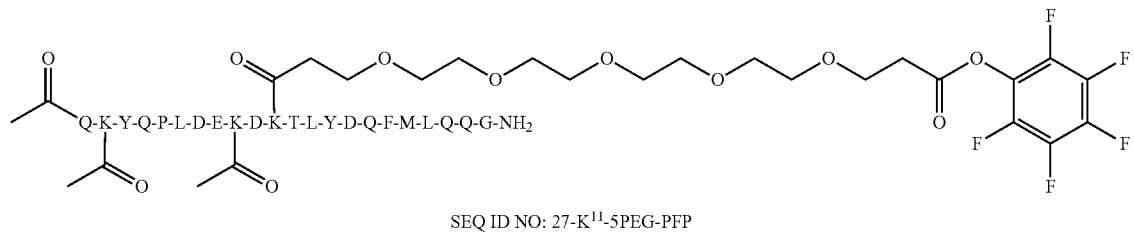
SEQ ID NO: 27-K[11]-5PEG-PFP
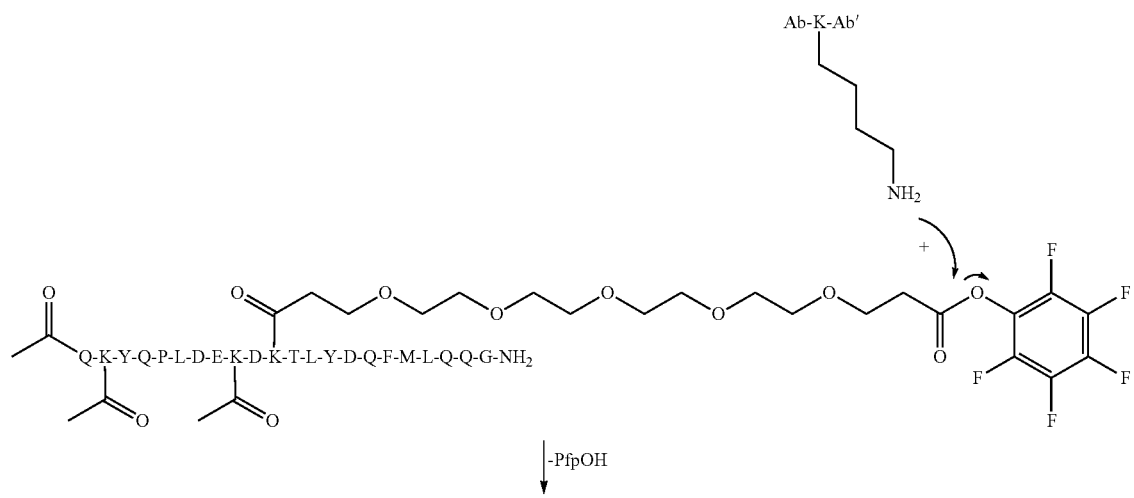
-PfpOH

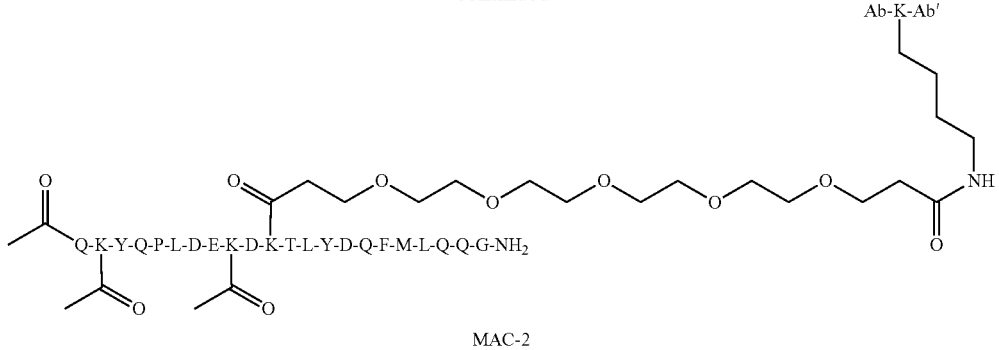

MAC-2

Example 11

Optimizing Conditions for PFP-Based Conjugation

A series of assays were run to establish optimal reaction conditions for directed conjugation. At the end of each reaction conjugation, the reaction was quenched with a succinate and glycine buffer, lowering the pH to approximately 5.5 and quenching any free peptide or peptide/linker. MAC-2 analysis was conducted by measuring the intact molecular weight (MW) of the MAC using electrospray time-of-flight mass spectrometry detection following protein separation from salts and excipients through a size exclusion chromatography column.

Temperature 2.12.1.fx antibody was adjusted to 18 mg·ml$^{-1}$ at pH 7.7 with a phosphate buffer to a final concentration of 0.06M sodium phosphate. The peptide/linker (SEQ ID NO:27-K$^{11}$ 5PEG-PFP) was reconstituted in a propylene glycol solution to 10 mg·ml$^{-1}$. The peptide/linker was added to 2.12.1.fx antibody at a molar ratio of 4.3:1 and allowed to react for 2 hrs at 18, 22, or 25° C. Results are presented in Table 2.

TABLE 2

Reaction temperature in 0.06M phosphate at 4.3:1 peptide:antibody
Reaction pH

| Temp | CA (%) | | | | | Avg CA |
|---|---|---|---|---|---|---|
| | 0 | 1 | 2 | 3 | 4 | |
| 18 C. | 1 | 16 | 51 | 23 | 8 | 2.21 |
| 22 C. | 3 | 15 | 57 | 21 | 5 | 2.11 |
| 25 C. | 2 | 12 | 53 | 25 | 7 | 2.24 |

2.12.1.fx antibody was adjusted to 18 mg·ml$^{-1}$ at pH 6.5, 6.75, 7.0, 7.25, 7.5, 7.75, or 8.0 with a phosphate buffer to a final concentration of 0.06M sodium phosphate. SEQ ID NO:27-K$^{11}$ 5PEG-PFP (L2) was reconstituted in a propylene glycol solution to 10 mg·ml$^{-1}$. The peptide/linker was added to 2.12.1.fx antibody at a molar ratio of 4.3:1 and allowed to react for 2 hrs at room temperature. The results are presented in Table 3.

TABLE 3 pH in 0.06M sodium phosphate buffer at 4.3:1 peptide:antibody

| pH | CA (%) | | | | | Avg CA |
|---|---|---|---|---|---|---|
| | 0 | 1 | 2 | 3 | 4 | |
| 6.5 | 7 | 42 | 41 | 9 | 0 | 1.51 |
| 6.75 | 3 | 31 | 52 | 12 | 3 | 1.83 |
| 7.0 | 3 | 24 | 53 | 16 | 4 | 1.94 |
| 7.25 | 2 | 18 | 54 | 22 | 5 | 2.12 |
| 7.5 | 2 | 12 | 57 | 23 | 7 | 2.23 |
| 7.75 | 3 | 15 | 55 | 22 | 6 | 2.15 |
| 8.0 | 1 | 14 | 52 | 29 | 4 | 2.21 |

2.12.1.fx antibody was adjusted to 2 mg·ml$^{-1}$ at pH 7.0, 7.5. and 8.0 with a HEPES buffer to a final concentration of 0.02M. SEQ ID NO:27-K$^{11}$ 5PEG-PFP was reconstituted in DMSO to 10 mg·ml$^{-1}$. The peptide/linker was added to 2.12.1.fx antibody at a molar ratio of 5:1 and allowed to react overnight at room temperature. The results are presented in Table 4. The level of conjugation decreased above pH 8.0

TABLE 4 pH in 0.02M HEPES Buffer at 5:1 peptide:antibody

| pH | ABP Additions (%) | | | | | Avg CA |
|---|---|---|---|---|---|---|
| | 0 | 1 | 2 | 3 | 4 | |
| 7 | 2 | 21 | 41 | 28 | 4 | 2.03 |
| 7.5 | 3 | 22 | 44 | 26 | 5 | 2.08 |
| 8 | 9 | 30 | 42 | 17 | 2 | 1.73 |

Duration of Conjugation Reaction 2.12.1.fx antibody was adjusted to 18 mg·ml$^{-1}$ at pH 7.7 with a phosphate buffer to a final concentration of 0.06M sodium phosphate. SEQ ID NO:27/5PEG-PFP was reconstituted in a propylene glycol solution to 10 mg·ml$^{-1}$. The peptide/linker was added to 2.12.1.fx antibody at a molar ratio of 4.3:1 and allowed react for 30, 60, 120, 180, 240, 300, or 2400 mins at room temperature (Table 5).

TABLE 5

Duration of conjugation reaction in 0.06M sodium phosphate at 4.3:1 peptide:antibody

| Time (mins) | CA (%) | | | | | Avg CA |
|---|---|---|---|---|---|---|
| | 0 | 1 | 2 | 3 | 4 | |
| 30 | 6 | 38 | 44 | 13 | 0 | 1.64 |
| 60 | 1 | 22 | 52 | 21 | 3 | 2.02 |

TABLE 5-continued

Duration of conjugation reaction in 0.06M sodium phosphate at 4.3:1 peptide:antibody

| Time (mins) | CA (%) 0 | 1 | 2 | 3 | 4 | Avg CA |
|---|---|---|---|---|---|---|
| 120 | 0 | 15 | 50 | 29 | 6 | 2.24 |
| 180 | 1 | 12 | 51 | 31 | 5 | 2.28 |
| 240 | 1 | 9 | 51 | 33 | 5 | 2.33 |
| 300 | 1 | 9 | 50 | 35 | 5 | 2.35 |
| 2400 | 1 | 10 | 48 | 35 | 6 | 2.35 |

Molar Ratio of Peptide to Protein 2.12.1.fx antibody was adjusted 18 mg·ml$^{-1}$ to pH 7.5 with a HEPES buffer to a final concentration of 0.2M HEPES. SEQ ID NO:27-K$^{11}$ 5PEG-PFP was reconstituted in a propylene glycol solution to 10 mg·ml$^{-1}$. The peptide/linker was added to 2.12.1.fx antibody at a molar ratio of 1, 2, 3, 4, and 5:1 (Table 6), and allowed to react for at least 2 hrs at room temperature, but the high concentration of HEPES buffer resulted in a decreased level of conjugation.

TABLE 6

Molar ratio of peptide to protein 1:1-5:1 in 0.2M HEPES

| Peptide:2.12.1.fx | CA (%) 0 | 1 | 2 | 3 | 4 | 5 | 6 | 7 | Avg CA |
|---|---|---|---|---|---|---|---|---|---|
| 1:1 | 80 | 20 | 0 | 0 | 0 | | | | 0.20 |
| 2:1 | 60 | 35 | 5 | 0 | 0 | | | | 0.45 |
| 3:1 | 39 | 49 | 12 | 0 | 0 | | | | 0.73 |
| 4:1 | 27 | 51 | 19 | 3 | 0 | | | | 0.98 |
| 5:1 | 11 | 47 | 37 | 5 | 0 | | | | 1.36 |

2.12.1.fx antibody was adjusted 18 mg·ml$^{-1}$ to pH 7.7 with a phosphate buffer to a final concentration of 0.06M sodium phosphate. SEQ ID NO:27-K$^{11}$ 5PEG-PFP was reconstituted in a propylene glycol solution to 10 mg·ml$^{-1}$. The peptide/linker was added to 2.12.1.fx antibody at a molar ratio of 5, 7, 10, 12, and 15:1 (Table 7) and allowed to react for 2 hrs at room temperature to generate a MAC with a higher level of conjugation.

TABLE 7

Molar ratio of peptide to protein 7:1-15:1 in 0.06M sodium phosphate

| Peptide:2.12.1.fx | CA (%) 0 | 1 | 2 | 3 | 4 | 5 | 6 | 7 | Avg CA |
|---|---|---|---|---|---|---|---|---|---|
| 7:1 | 1 | 1 | 29 | 39 | 17 | 10 | 2 | 0 | 3.06 |
| 10:1 | 1 | 1 | 18 | 33 | 25 | 19 | 3 | 0 | 3.49 |
| 12:1 | 3 | 1 | 11 | 22 | 26 | 26 | 8 | 3 | 3.92 |
| 15:1 | 1 | 2 | 9 | 19 | 23 | 32 | 12 | 3 | 4.22 |

To further optimize the molar ratio of 2.12.1.fx antibody and SEQ ID NO:27-K$^{11}$ 5PEG-PFP, 2.12.1.fx antibody was adjusted 18 mg·ml$^{-1}$ to pH 7.7 with a phosphate buffer to a final concentration of 0.06M sodium phosphate. The peptide/linker was reconstituted in a propylene glycol solution to 10 mg·ml$^{-1}$. The peptide/linker was added to 2.12.1.fx antibody at a molar ratio of 2.5, 2.8, 3.1, 3.4, 3.7, 4.0, 4.3, or 4.6:1 (Table 8) and allowed to react for 2 hrs at room temperature.

TABLE 8

Molar ratio of peptide to protein 2.5:1-4.6:1 in 0.06M sodium phosphate

| Peptide:2.12.1.fx | CA (%) 0 | 1 | 2 | 3 | 4 | 5 | 6 | 7 | Avg CA |
|---|---|---|---|---|---|---|---|---|---|
| 2.5:1 | 14 | 53 | 30 | 4 | 0 | | | | 1.25 |
| 2.8:1 | 10 | 45 | 37 | 8 | 0 | | | | 1.43 |
| 3.1:1 | 7 | 39 | 45 | 8 | 0 | | | | 1.53 |
| 3.4:1 | 5 | 40 | 44 | 11 | 0 | | | | 1.61 |
| 3.7:1 | 4 | 25 | 51 | 15 | 5 | | | | 1.92 |
| 4.0:1 | 2 | 26 | 55 | 15 | 2 | | | | 1.89 |
| 4.3:1 | 1 | 24 | 55 | 16 | 4 | | | | 1.98 |
| 4.6:1 | 2 | 19 | 56 | 19 | 5 | | | | 2.08 |

2.12.1.fx antibody was adjusted to 2 mg·ml$^{-1}$ at pH 7.0 with a HEPES buffer to a final concentration of 0.02M. CVX-4176 was reconstituted in DMSO to 10 mg·ml$^{-1}$. The peptide/linker was added to 2.12.1.fx antibody at a molar ratio of 5, 6, 7, 8, 10:1 and allowed to react overnight at room temperature. The results are presented in Table 9.

TABLE 9

Molar ratio of peptide to protein 5:1-10:1 in 0.02M HEPES

| Peptide:2.12.1.fx | CA (%) 0 | 1 | 2 | 3 | 4 | 5 | 6 | 7 | Avg CA |
|---|---|---|---|---|---|---|---|---|---|
| 5:1 | 2 | 21 | 49 | 24 | 4 | 0 | 0 | 0 | 2.07 |
| 6:1 | 2 | 15 | 42 | 32 | 9 | 0 | 0 | 0 | 2.31 |
| 7:1 | 1 | 11 | 34 | 42 | 13 | 0 | 0 | 0 | 2.57 |
| 8:1 | 0 | 9 | 32 | 42 | 16 | 1 | 0 | 0 | 2.68 |
| 10:1 | 0 | 4 | 21 | 47 | 25 | 4 | 0 | 0 | 3.07 |

Conjugation Profile of 2.12.1.fx at Various Protein Concentrations

The conjugation profiles of 2.12.1.fx with SEQ ID NO:27-K$^{11}$-5PEG-PFP at various concentrations were analyzed. 2.12.1.fx was concentrated to >50 mg/mL, diluted to the desired concentration with 20 mM sodium acetate, 20 mM trehalose pH 5.5, and spiked with 60 mM sodium phosphate pH 7.7 SEQ ID NO:27-K$^{11}$-5PEG-PFP was resuspended with 50% propylene glycol and mixed with the antibody at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a peptide. Relative quantitation of multiple conjugation species is performed by measuring the signal magnitude. Table 10 shows the conjugation profile of 2.12.1.fx with peptide at various concentrations of antibody. At antibody concentrations 10 mg/mL to 50 mg/mL, the conjugation occurs at a distribution between 0-5 addition with an average of 1.8 or greater additions. At antibody concentrations 0.5 to 5 mg/mL, the conjugation occurs at a distribution between 0-3 additions with an average of 1.5 or less additions.

TABLE 10

Effect of antibody concentration

| Antibody Concentration (mg/ml) | CA (%) | | | | | | Avg CA |
|---|---|---|---|---|---|---|---|
| | 0 | 1 | 2 | 3 | 4 | 5 | |
| 0.5 | 65 | 32 | 3 | — | — | — | 0.37 |
| 1 | 44 | 44 | 12 | — | — | — | 0.67 |
| 5 | 10 | 41 | 40 | 8 | — | — | 1.45 |
| 10 | 3 | 30 | 47 | 17 | 2 | 1 | 1.87 |
| 15 | 1 | 24 | 51 | 20 | 3 | 1 | 2.02 |
| 20 | 1 | 16 | 57 | 22 | 2 | 1 | 2.11 |
| 30 | 2 | 20 | 55 | 20 | 3 | 1 | 2.04 |
| 40 | 2 | 21 | 53 | 22 | 2 | 0 | 2.04 |
| 50 | 2 | 19 | 50 | 24 | 4 | 1 | 2.11 |

Reaction Buffer Selection 2.12.1.fx antibody was adjusted to 18 mg·ml$^{-1}$ at pH 7.7 with a sodium carbonate, sodium borate, or sodium phosphate buffer to a final concentration of 0.05M sodium phosphate. SEQ ID NO:27-K$^{11}$-5PEG-PFP was reconstituted in a propylene glycol solution to 10 mg·ml$^{-1}$. The peptide/linker was added to 2.12.1.fx antibody at a molar ratio of 1, 2, 3, 4, or 5:1 and allowed to react for 2 hrs at room temperature. The low reaction pH resulted in the reduced level of conjugation (Table 11).

TABLE 11

Buffer and pH alterations

| Buffer | CA (%) | | | | | Avg CA |
|---|---|---|---|---|---|---|
| | 0 | 1 | 2 | 3 | 4 | |
| 50 mM sodium carbonate pH 7.4 | 2 | 24 | 48 | 26 | 0 | 1.98 |
| 50 mM sodium borate pH 7.0 | 1 | 17 | 45 | 31 | 5 | 2.20 |
| 50 mM sodium phosphate pH 7.0 | 10 | 48 | 38 | 4 | 0 | 1.36 |

2.12.1.fx antibody was adjusted to 18 mg·ml$^{-1}$ at pH 7.5, 7.7 and 8.0 with a sodium borate and sodium phosphate buffer to a final concentration of 0.04M. SEQ ID NO:27-K$^{11}$-5PEG-PFP was reconstituted in a propylene glycol solution to 10 mg·ml$^{-1}$. The peptide/linker was added to 2.12.1.fx antibody at a molar ratio of 4.3:1 and allowed to react for 2 hrs at room temperature (Table 12).

TABLE 12

Buffer and pH alterations

| Buffer | CA (%) | | | | | Avg CA |
|---|---|---|---|---|---|---|
| | 0 | 1 | 2 | 3 | 4 | |
| Phosphate, pH 7.5 | 1 | 21 | 53 | 21 | 3 | 2.02 |
| Phosphate, pH 7.7 | 0 | 15 | 50 | 29 | 6 | 2.26 |
| Phosphate, pH 8.0 | 1 | 14 | 52 | 29 | 4 | 2.21 |
| Borate, pH 7.5 | 46 | 44 | 10 | 0 | 0 | 0.64 |
| Borate, pH 7.7 | 22 | 51 | 23 | 4 | 0 | 1.09 |
| Borate, pH 8.0 | 1 | 17 | 48 | 30 | 4 | 2.19 |

2.12.1.fx antibody was adjusted to 18 mg·ml$^{-1}$ at pH 7.7 with a phosphate buffer to a final concentration of 0.04M, 0.06M, or 0.08M sodium phosphate. The peptide/linker (SEQ ID NO:27-K$^{11}$ 5PEG-PFP) was reconstituted in a propylene glycol solution to 10 mg·ml$^{-1}$. The peptide/linker was added to 2.12.1.fx antibody at a molar ratio of 4.3:1 and allowed to react for 2 hrs at room temperature. The results are presented in Table 13.

TABLE 13

Concentration of phosphate

| Concentration (mM) of phosphate at pH 7.7 | CA (%) | | | | | Avg CA |
|---|---|---|---|---|---|---|
| | 0 | 1 | 2 | 3 | 4 | |
| 40 | 2 | 23 | 54 | 16 | 4 | 1.95 |
| 60 | 2 | 28 | 51 | 15 | 4 | 1.91 |
| 80 | 2 | 29 | 51 | 13 | 4 | 1.86 |

Effect of Buffer Constituents on Conjugation

Propylene Glycol:

2.12.1.fx antibody was adjusted to 18 mg·ml$^{-1}$ at pH 7.7 with a phosphate buffer to a final concentration of 0.06M sodium phosphate. The peptide/linker (SEQ ID NO:27-K$^{11}$ 5PEG-PFP) was reconstituted in a propylene glycol solution to 20 mg·ml$^{-1}$ (5% propylene glycol in the conjugation reaction). The peptide/linker was added to 2.12.1.fx antibody at a molar ratio of 4.3:1 and spiked with an additional 0 to 15% propylene glycol (final propylene glycol percentage of 5, 10, 15, and 20%) and allowed to react for 2 hrs at room temperature. The results are presented in Table 14.

TABLE 14

Percent of propylene glycol in 0.06M sodium phosphate

| Percent (%) Propylene Glycol | CA (%) | | | | | Avg CA |
|---|---|---|---|---|---|---|
| | 0 | 1 | 2 | 3 | 4 | |
| 5 | 2 | 18 | 55 | 20 | 5 | 2.08 |
| 10 | 2 | 20 | 53 | 21 | 5 | 2.09 |
| 15 | 2 | 23 | 49 | 20 | 5 | 2.01 |
| 20 | 4 | 23 | 50 | 19 | 4 | 1.96 |

Sodium Chloride:

2.12.1.fx antibody was adjusted to 2 mg·ml$^{-1}$ at pH 7.0 with a HEPES buffer to a final concentration of 0.02M in the presence and absence of 0.14M sodium chloride. CVX-4176 was reconstituted in DMSO to 10 mg·ml$^{-1}$. The peptide/linker was added to 2.12.1.fx antibody at a molar ratio of 5:1 and allowed to react overnight at room temperature. The results are presented in Table 15. The level of conjugation decreases in the presence of sodium chloride

TABLE 15

Concentration of sodium chloride in 0.02M HEPES

| Concentration of sodium chloride (mM) | ABP Additions (%) | | | | | Avg CA |
|---|---|---|---|---|---|---|
| | 0 | 1 | 2 | 3 | 4 | |
| 0 | 2 | 21 | 41 | 28 | 4 | 2.03 |
| 0.14 | 9 | 34 | 42 | 14 | 1 | 1.64 |

HEPES:

2.12.1.fx antibody was adjusted to 2 mg·ml$^{-1}$ at pH 7.0 with a HEPES buffer to a final concentration of 0.2M and 0.02M. SEQ ID NO:27-K$^{11}$-5PEG-PFP was reconstituted in 50% propylene glycol to 10 mg·ml$^{-1}$. The peptide/linker was added to 2.12.1.fx antibody at a molar ratio of 5:1 and allowed to react 2 hrs at room temperature. The results are presented in Table 16. The level of conjugation is reduced at 0.2M HEPES Buffer

TABLE 16

| Concentration of HEPES (mM) | HEPES concentration ABP Additions (%) | | | | | Avg CA |
|---|---|---|---|---|---|---|
| | 0 | 1 | 2 | 3 | 4 | |
| 0.02 | 2. | 35 | 47 | 16 | 0 | 1.77 |
| 0.2 | 21 | 49 | 26 | 4 | 0 | 1.13 |

DMSO:

2.12.1.fx antibody was adjusted to 15 mg·ml$^{-1}$ at pH 7.7 with sodium phosphate buffer to a final concentration of 0.06M and DMSO was added to a final concentration of 30%. SEQ ID NO:27 K$^{11}$-5PEG-PFP was reconstituted in a propylene glycol solution to 10 mg·ml$^{-1}$. The peptide/linker was added to 2.12.1.fx antibody at a molar ratio of 4:1 and allowed to react for 2 hrs at room temperature. The results are presented in Table 17.

TABLE 17

| Percent of DMSO | DMSO in 0.06M sodium phosphate ABP Additions (%) | | | | | Avg CA |
|---|---|---|---|---|---|---|
| | 0 | 1 | 2 | 3 | 4 | |
| 0 | 3 | 28 | 49 | 14 | 6 | 1.92 |
| 30 | 8 | 28 | 32 | 22 | 10 | 1.98 |

Discussion of Conjugation Reaction Parameters

When the molar ratio of Effector Moiety (in this example, a peptide) to antibody is reduced below about 3.5:1, the level of conjugation is decreased, as seen in Table 8. Alternatively, Table 9 shows that increasing the molar ratio results in an increased level of conjugation. Increasing the number of peptides per antibody generally decreases the binding efficiency of the antibody (in this case 2.12.1 fx) to its antigen (in this case the IGF1R receptor), therefore the molar ratio of peptide to antibody was optimized to maximise both antibody-antigen, and peptide-cognate binding.

It was also found that varying the conjugation buffer can alter the conjugation pattern. Amine-containing excipients are less preferable in general as they can react with the PFP group. Buffers such as carbonate and borate can be used for conjugation but were avoided as their pKa (boric acid with a pKa ~9 and carbonate with two pKa of ~6 and ~11) were far from the conjugation pH of 7.7 that was identified as optimal for MAC-1 and MAC-2 (Table 11). The level of conjugation is not only dependent on the chemical conditions of the reaction but also based on time. After 2 hrs, most of the PFP-activated peptide had reacted with the antibody or the PFP Z* has hydrolyzed (Table 5).

The PFP-activated peptide/linker reacted quickly with lysine side chain amino groups. Conjugation was performed at pH 6.5 to 8 in phosphate buffer to increase the nucleophile tendency of the antibody surface lysines by decreasing their charge (the pKa of lysines on the surface proteins is about 9.1 to 11.2) as shown in Table 3 and 4.

Optimal conditions for conjugation of MAC-1 and MAC-2 are described as follows: 2.12.1.fx antibody was adjusted to pH 7.7 with a phosphate buffer to a final concentration of 0.06M sodium phosphate. The peptide/linker (SEQ ID NO:27-K$^{11}$-5PEG-PFP) was reconstituted in a propylene glycol solution to 10 mg·ml$^{-1}$ (final propylene glycol concentration in reaction is 10%). The peptide/linker was added to 2.12.1.fx antibody at a molar ratio of 4.3:1 and allowed to react for 2 hrs at ambient room temperature. The reaction was quenched with a succinate and glycine buffer, lowering the pH to approximately 6.0 and quenching any free peptide. In some aspects, the reaction may be concentrated and peptide-related species (such as peptides where the linker was hydrolyzed by reaction with water solvent) and other elements of the reaction mixture (such as PFP) may be removed by diafiltration, for example, using a 50 kDa membrane or size exclusion chromatography into a succinate, glycine, sodium chloride, and trehalose buffer, pH 5.5 at 30 mg·ml$^{-1}$.

The conjugation conditions listed above were varied to determine the range of each process parameter. Parameter ranges were set based on variability that may occur during the conjugation and/or were expanded until greater than 10% change in species population was observed. Table 18 summarizes the parameters that result in similar conjugation profiles for MAC-2.

TABLE 18

| Process parameters optimized for MAC-2 | | | |
|---|---|---|---|
| Parameters tested | Parameter range tested | Desirable range of parameters | Optimum reaction condition |
| Temperature | 18-25° C. | 18-25° C. | RT |
| Reaction pH | 6.5 to 8.0 | pH 7.25-8.0 | 7.7 |
| Reaction duration | 30-2400 mins | 180-2400 mins | >about 2 hrs |
| Molar ratio of Peptide to Antibody | 2.5 to 4.6 | 3.7:1 to 4.3:1 | 4.3:1 |
| 2.12.1.fx concentration added to the conjugation reaction | 0.5 to 50 mg/mL | 10 to 50 mg/mL | 20 mg/mL |
| Concentration of phosphate in the reaction buffer | 40 to 80 mM | 40-80 mM | 60 mM |
| Final propylene glycol concentration | 5 to 20% | 5-20% | 10% |

Example 12

Linker Site on Antibody

In general, only Z* leaving groups comprising halogen phenyl esters demonstrated consistent levels of directional conjugation, although squarates and NHS esters showed some potential for use in certain circumstances.

Only 2 of the 5 proposed linkers (PFP esters and squarates) were successful in preparing MACs. Although it is postulated that electrophilic linkers will generally allow the conjugation of peptides (such as Ang2 peptides (ABP)) to an antibody, (such as the IGF1R antibody), azetidinone linkers did not allow the conjugation of peptides to antibodies at acceptable rates (the reactions required significant excesses of azetidinone linkers and were extremely slow). Table 19 presents some considerations of each of the linkers used to prepare MACs.

TABLE 19

Activation methods via PFP esters and squarates.

| | PFP | Squarate |
|---|---|---|
| Ease of synthesis | Easy using thiol/maleimide chemistry, harder with direct addition to peptides | Easy, reacts with amines |
| Stability of peptide reagent in conditions conducive of linker reaction with antibody surface lysines. | Hydrolyses to free acid, half-life around 4 hrs | Little hydrolysis |
| Bond formed | Amide | Squaramide |
| Speed of conjugation | Rapid | Fairly slow |
| Ease of altering reactivity | Easy by addition of other alcohols, e.g NHS, HOBt. Related compounds, e.g. tetrafluorophenol ester are less active. Increased reactivity results in concomitant increase in hydrolysis rate | Fairly easy by altering pattern of substitution on phenol; as with PFPs, more reactive forms may be subject to side-reactions, including reacting with antibody side chains other than Lys |

Example 13

Location of Conjugated Peptides on Antibody

The MAC-2 drug product molecule consists of a distribution of 1-4 attached SEQ ID NO:27 molecules to the 2.12.1.fx antibody (α-IGF1R-1), using the 5PEG-PFP linker as described in Scheme 11. This was determined by measuring the intact molecular weight (MW) of the MAC-2 using electrospray, time-of-flight mass spectrometry detection following protein separation from salts and excipients through a size exclusion chromatography column. Mass spectrometry data that demonstrated the intact molecular weight (MW) of the 2.12.1.fx antibody and 3 lots of the MAC-2 are shown in FIG. 3. FIG. 2A shows 2.12.1.fx before conjugation. This is a uniform molecule that displays a single MW. The MAC-2 lots display a distribution of conjugated peptides to 2.12.1.fx; between 1-4 conjugation additions (CA) are observed. The relative amount of each form is consistent between lots and the most common form in each lot has 2 peptides (SEQ ID NO:27) attached to each individual 2.12.1.fx antibody.

By reducing disulfide bonds in the 2.12.1.fx antibody, light and heavy chains are observed separately. Disulfide reduction is performed by treating the intact 2.12.1.fx antibody with 20 mM tris(2-carboxyethyl) phosphine (TCEP). The resulting mixture of heavy and light chains is analyzed for intact molecular weight as described above. The data shown in FIG. 3 provides evidence toward the location of the ABP on 2.12.1.fx. The majority of light chain (>65%) in the MAC-2 lots are conjugated. Most of the conjugated light chain contains 1 CA. 2CA is also observed at a lower level. Almost all observed heavy chain (>90%) is unmodified, which suggests that very few of the conjugated peptides are located on the heavy chain.

Peptide mapping was used to determine the precise location of conjugation. The procedure was as follows: an aliquot of MAC-2 was denatured with 8M Guanidine-hydrochloride, disulfide bonds were reduced with TCEP, and the resulting cysteine sulfhydryls were alkylated with Iodoacetamide. This treated protein sample was then digested with the protease chymotrypsin (1:125 protease:MAC ratio by weight). The resulting chymotryptic peptides were then detected individually by mass spectrometry after separation through a C8 liquid chromatography column. With this technique, MAC-2 was digested by chymotrypsin on the heavy and light chains into fragments at the locations noted in the sequence (with bullets) in FIG. 4. Liquid chromatography-mass spectrometry (LC-MS) detection of the MW of each peptide was then used to determine which Lysine residues are modified by a conjugated peptide. If a fragment was modified by attachment of conjugated peptide, its MW was shifted accordingly.

Fragments Y1, Y6, Y9, Y10, Y20, Y25, Y26, Y29, Y32, Y33, Y34, Y37, Y40 and Y43 of the heavy chain contain Lys residues. Of these, peptide conjugation was detected at Y6, Y10, Y25, Y33, and Y37. Fragments Y3, Y10, Y11, Y12, Y13, Y14, Y15, and Y16 of the light chain contain Lys residues. Of these, conjugation was detected at Y3, Y13, and Y15.

The light chain fragment referred to as Y15 (the $15^{th}$ chymotryptic fragment on the light chain from the N-terminus) was found to be conjugated based on the data shown in FIG. 5. The MW of the modified Y15 fragment in MAC was clearly detected. In the un-conjugated 2.12.1.fx sample, there was no evidence of modified Y15 fragment. The unmodified Y15 fragment was observed in both MAC and 2.12.1.fx. The magnitude of this fragment is higher in the 2.12.1.fx sample because all of this fragment is present in the un-modified form. As this fragment is conjugated in MAC-2, the observed level of un-modified Y15 decreases, which is seen in FIG. 5 as a peak with a smaller area.

The amount of conjugation of SEQ ID NO:27-5PEG observed on light chain fragment Y15 in MAC-2 is estimated by measuring the decreased peak area of un-modified Y15. After normalizing the signal intensity such that unconjugated 2.12.1.fx showed 100%, 3 independent lots of MAC-2 showed 17%, 27% and 22% unconjugated Y15 fragments respectively.

The observed magnitude of Y15 in the MAC samples was normalized to the magnitude of Y15 in the 2.12.1.fx sample. Between 75-85% of the Y15 fragments are determined as modified in MAC-2. Considering that MAC-2 contains mostly 1-2 conjugation additions, this suggests that most of the conjugation in MAC-2 is located at one of the 2 K residues of light chain fragment Y15 ($K^{188}$ or $K^{190}$). The location of fragment Y15 in relation to the sequence of 2.12.1.fx is shown in FIG. 4.

Trypsin enzymatic digestion was used to discriminate between $K^{188}$ and $K^{190}$ (trypsin has specificity for the C-terminus of K and R). As trypsin does not digest conjugated K residues, the enzymatic digestion generates different peptide lengths, depending on which K residue is conjugated. Examination of LCMS data from MAC-2 that was digested with trypsin provides evidence that the peptide attaches specifically to $K^{188}$. No evidence of modified $K^{190}$ was observed.

MAC-2 was reduced with TCEP and denatured with guanidine hydrochloride as described above. The protein concentration was adjusted to 2 mg/ml and the pH to 7.8 with Tris digestion buffer. Purified trypsin was added at a 1:125 protease:MAC ratio by weight and incubated at 30° C. for 4 hrs. Samples were stored at −20° C. until analysed by LCMS. Fragment samples were separated on a C18 reversed phase column using water/acetonitrile+0.1% TFA mobile phases. Detection of fragments was monitored both by UV 214 nm and ESI-TOF mass spectrometry. All data analysis was performed using MassLynx software.

The formation of fragments upon trypsin digestion of MAC-2 depends on the site of peptide conjugation. Lysines are the targeted residue for conjugation. Data shown in FIGS. 2-5 indicates that the predominant site of peptide binding is either $K^{188}$ or $K^{190}$. The scheme below shows the trypsin digestion reactions that occur upon conjugation at $K_{188}$ or $K^{190}$.

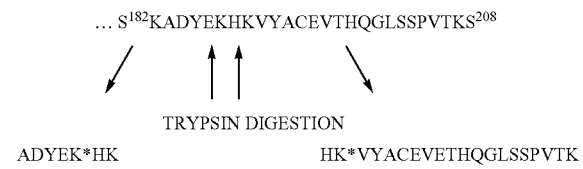

... S$^{182}$KADYEKHKVYACEVTHQGLSSPVTKS$^{208}$

TRYPSIN DIGESTION

ADYEK*HK      HK*VYACEVETHQGLSSPVTK

The chemical structures of the two potential digestion fragments in question are as follows:

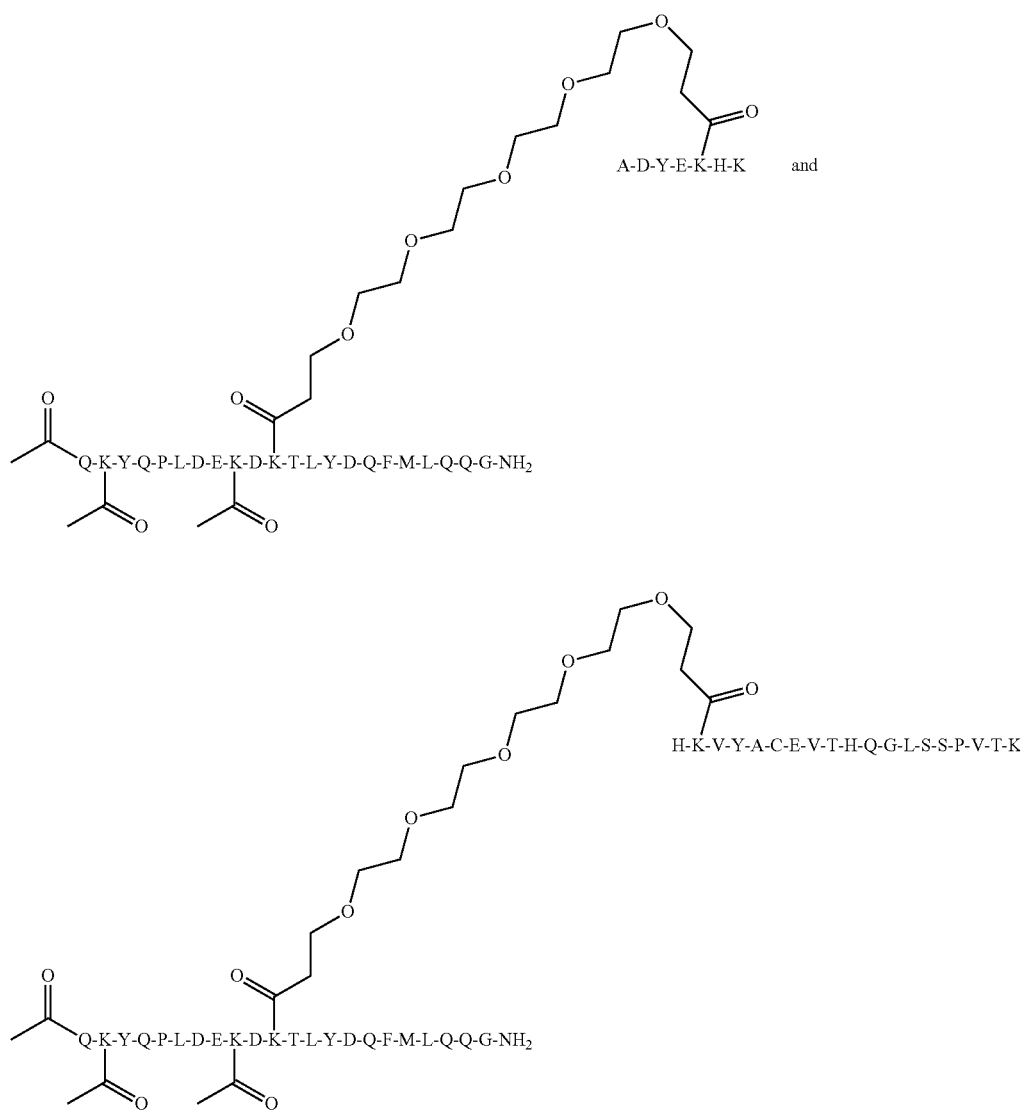

experiment. The results from modification at $K^{190}$ do not provide any data that is unique compared to the negative control.

In contrast to what may be expected, the peptide/linker appears to preferentially decorate $K^{188}$ of the light chain of 2.12.1.fx ($K^{80}$ of SEQ ID NO:15). This has the surprising advantage that the Fc portion of the 2.12.1.fx antibody is unaffected. Tests show that the resulting PK of MAC-2 is approximately equal to the PK of unconjugated 2.12.1.fx. Promiscuous, non-specific conjugation to multiple sites on an antibody can result in a product with lower PK. The directional conjugation of the invention, exemplified by MAC-1 and MAC-2, provide the advantage of minimizing some of the possible deleterious effects that can be caused by promiscuous, non-specific conjugation, including lower PK.

FIG. 6 shows the selected ion LCMS chromatogram data for the trypsin peptide when $K^{188}$ is conjugated to the peptide. FIG. 7 shows the selected ion LCMS chromatogram data for the trypsin fragment when $K^{190}$ is modified with a conjugated peptide. These data suggest that only $K^{188}$ alone is conjugated; this situation results in a significant signal that is detected in MAC-2 but is absent in the 2.12.1.fx control To establish the reproducibility of the process, the experiment was repeated. MAC-2 was diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a conjugated peptide/linker. Relative quantitation of multiple conjugation species is performed by measuring the signal magnitude. FIG. 8 shows a representative spectrum of MAC-2; the calculations used for quantitation are shown in Table 20. The average conjugation additions for the intact MAC-2 is calculated as 2.11 using the following formula: SUMPRODUCT (Number of Conjugation Additions (CA), Percent per CA). This example demonstrates conjugation of peptides occurring as a distribution between 0-4 peptide additions with the largest form being 2 peptide additions and the average number of peptide additions is 2.11. Replicate analysis by multiple individuals demonstrates that the profile of conjugation is consistent and reproducible.

TABLE 20 weighted average of conjugation additions: 2.11

| Conjugation additions | Predicted mass | Intensity | Percent |
|---|---|---|---|
| 0 | 149210 | 1615 | 1% |
| 1 | 152350 | 20533 | 17% |
| 2 | 155490 | 69395 | 56% |
| 3 | 158630 | 27708 | 22% |
| 4 | 161770 | 4818 | 4% |
|  |  | 124069 | 100% |

The extent of peptide conjugation was examined separately on the light and heavy chains of 2.12.1.fx. MAC-2 was denatured and disulfide bonds were reduced using guanidine hydrochloride and dithiothreitol. The resulting free light and heavy chains were analyzed using LCMS to determine the conjugation profile on each. FIG. 9 shows a representative spectrum of each chain; the calculation used for quantitation are shown in Table 21. The average conjugation additions (Avg CA) for the reduced heavy chain MAC-2 is calculated as 0.14 and the Avg CA for the reduced light chain MAC-2 is calculated at 0.86 using the following formula: SUMPRODUCT (Number of Conjugation Additions (CA), Percent per CA). These data demonstrate that the location of conjugation is higher on the light chain; the most abundant form on the light chain contains one peptide addition and the light chain contains an average of 0.86 peptide additions. Conjugation on the heavy chain is observed at a significantly lower level. Replicate analysis of this experiment by multiple individuals demonstrates that the profile of conjugation is consistent and reproducible.

TABLE 21

Peptide mapping characterization of MAC-2 identifying specific location of conjugation

| Mass (Da) | Conj. Additions | Species | Intensity | Percent | Avg CA |
|---|---|---|---|---|---|
| 51020 | 0 | HC | 102093 | 86% |  |
| 54165 | 1 | HC + (1x) ABP-1 | 16204 | 14% |  |
| Total HC |  |  | 118297 | 100% | 0.14 |
| 23584 | 0 | LC | 19752 | 21% |  |
| 26729 | 1 | LC + (1x) ABP-1 | 68757 | 72% |  |
| 29874 | 2 | LC + (2x) ABP-2 | 6561 | 7% |  |
| Total LC |  |  | 95070 | 100% | 0.86 |

MAC-2 was reduced with dithiothreitol and cysteine residues were alkylated by carboxymethylation with iodoacetamide. Chymotrypsin was used for proteolytic digestion. Digested fragments in solution were analyzed using liquid chromatography mass spectrometry (LCMS). Individual fragments were separated over a C18 HPLC column and their accurate mass is measured in a Quadruple Time-of-Flight (Q-ToF) mass spectrometer. The resulting fragment mass was used to identify unmodified fragments or fragments modified with a conjugated peptide. This experiment was interpreted by focusing on chymotryptic fragments that contain a lysine residue, as these were possible sites for peptide conjugation. Table 22 shows a listing of all such fragments. Blank entries are fragments that are not detected using this technique. Detected fragments that are observed with a peptide modifier are considered potential sites of conjugation.

The table entries for Table 16 are explained below:

Fragment number: Chymotrypsin fragment numbering from the N-terminus; joined fragments (i.e. Y1-2) indicate a missed cleavage site.

Start/End: Numbering of the fragment location from the N-terminus.

Peptide Mass (Da): Theoretical mass of the fragment listed in Daltons.

Retention Time (Control/Analyte): Time of chromatographic retention/elution in the LCMS fragment mapping experiment.

MS Signal Intensity (Control/Analyte): Magnitude of observed signal observed by MS.

Mass Error-ppm (Control/Analyte): Comparison of theoretical vs. observed mass of the fragment; values>10, and especially closer to zero (0) demonstrate better mass accuracy.

Modifiers: Potential covalent additions to the fragment; peptide-antibody binding fragment of Lys residue, CAM-carboxymethylation of Cysteine residue., Asterisks indicate the modified (e.g. conjugated) version of the respective fragment.

Pep indicates a conjugated peptide.

Directional conjugation of a peptide to the Y15 fragment is demonstrated by quantitating the conjugation level. The following analysis was performed on each of the peptide fragments that were observed having conjugation during the peptide mapping experiment of the 2.12.1.fx reference product. The ratio of observed signal intensity for the unmodified peptide in the non-conjugated control (2.12.1.fx antibody scaffold—no conjugation) compared to the conjugated reference product (MAC-2) is shown in Table 23. The unmodified signal is used because a direct comparison of the same peptide signal is possible in each sample. For example, an unconjugated peptide would be expected to have the same observed signal intensity in the control vs. product samples resulting in a ratio of one (1). Conjugation would result in a decrease in the observed amount of unmodified peptide in the product sample which would be indicated by a ratio greater than one (1). The data in Table 23 was further normalized to correct for sample and experimental variation between the control and product. Table 23 demonstrates that light chain peptide Y15 is conjugated at a significantly higher level than each of the other conjugated peptides. This suggests that conjugation occurs in a directional manner and is not randomly distributed across K residues.

TABLE 22

| Fragment Number | Start | End | Peptide Mass (Da) | Retention Time Control | Retention Time Analyte | MS Signal Intensity Control | MS Signal Intensity Analyte | Mass Error (ppm) Control | Mass Error (ppm) Analyte | Modifiers |
|---|---|---|---|---|---|---|---|---|---|---|
| Peptide mapping characterization of MAC-2 heavy chain reference product |||||||||||
| Y1 | 1 | 27 | 2617.3533 | | | | | | | |
| Y1-2 | 1 | 29 | 2865.4695 | | | | | | | |
| Y5-6 | 34 | 47 | 1657.8398 | | | | | | | |
| Y6 | 37 | 47 | 1253.688 | 19.2 | 19.2 | 516640 | 583534 | 1.9 | −1.1 | |
| Y6-7 | 37 | 50 | 1602.8518 | 22.1 | 22.1 | 26537 | 37988 | −1.6 | −2.2 | |
| Y6-7* | 37 | 50 | 3295.7017 | | 21.8 | | 6316 | | −19.4 | Pep(1) |
| Y8-9 | 51 | 68 | 1931.9337 | 16.5 | 16.5 | 60894 | 85742 | −2.2 | 0.4 | |
| Y9 | 61 | 68 | 878.461 | 11.3 | 11.3 | 376224 | 412997 | 0 | −1 | |
| Y9-10 | 61 | 80 | 2241.1501 | | | | | | | |
| Y10 | 69 | 80 | 1380.6997 | 13.3 | 13.3 | 261813 | 299847 | −1.1 | 0.7 | |
| Y10* | 69 | 80 | 3073.5498 | | 23.4 | | 6350 | | −8.7 | Pep (1) |
| Y10-011 | 69 | 94 | 2972.4661 | | | | | | | |
| Y19-20 | 111 | 157 | 4748.2773 | | | | | | | |
| Y20 | 116 | 157 | 4160.0405 | | | | | | | |
| Y20-21 | 116 | 166 | 5202.5527 | | | | | | | |
| Y20-21* | 116 | 166 | 5316.5957 | 34.1 | | 6445 | | 0.5 | | CAM(2) |
| Y24-25 | 202 | 245 | 4702.2109 | | | | | | | |
| Y25 | 207 | 245 | 4151.9722 | | | | | | | |
| Y25* | 207 | 245 | 4437.0796 | 20.9 | 20.9 | 1495322 | 1800079 | 1.1 | −3.1 | CAM(5) |
| Y25* | 207 | 245 | 6129.9297 | | 24.4 | | 6652 | | −4.5 | CAM(5) Pep(1) |
| Y25-26 | 207 | 279 | 7985.9092 | | | | | | | |
| Y26 | 246 | 279 | 3851.9478 | | | | | | | |
| Y26-27 | 246 | 281 | 4152.0698 | | | | | | | |
| Y28-29 | 282 | 300 | 2245.1128 | | | | | | | |
| Y29 | 283 | 300 | 2082.0493 | 14.6 | 14.6 | 20665 | 16662 | −0.6 | −3.8 | |
| Y29-30 | 283 | 304 | 2531.2405 | | | | | | | |
| Y31-32 | 305 | 323 | 2241.1907 | | | | | | | |
| Y32 | 318 | 323 | 722.3599 | 7.9 | 7.9 | 93966 | 96639 | 0.1 | 2.6 | |
| Y32 | 318 | 323 | 722.3599 | 17.7 | 18.4 | 37943 | 12802 | 11.4 | 30.6 | |
| Y32 | 318 | 323 | 722.3599 | 18.4 | | 11761 | | 23.8 | | |
| Y32-33 | 318 | 353 | 4028.188 | | | | | | | |
| Y33 | 324 | 353 | 3323.8386 | 20 | | 5422 | | 3.1 | | |
| Y33* | 324 | 353 | 3380.8601 | 19.7 | 19.7 | 2196329 | 2497507 | −2.5 | −3.1 | CAM(1) |
| Y33* | 324 | 353 | 5073.71 | | 24 | | 5973 | | 1.3 | CAM(1) Pep(1) |
| Y33-34 | 324 | 376 | 5883.1577 | | | | | | | |
| Y34 | 354 | 376 | 2577.3293 | | | | | | | |
| Y34-35 | 354 | 385 | 3637.8159 | | | | | | | |
| Y34-35* | 354 | 385 | 3694.8374 | 33 | 32.9 | 10095 | 20682 | 1.9 | −2.4 | CAM(1) |
| Y36-37 | 386 | 408 | 2527.0808 | | | | | | | |
| Y37 | 396 | 408 | 1394.6388 | 19.6 | 19.6 | 62942 | 71902 | −0.9 | −0.4 | |
| Y37-38 | 396 | 409 | 1541.7072 | 25.1 | 25.1 | 827336 | 878570 | 0 | −1.9 | |
| Y37-38* | 396 | 409 | 3234.5571 | | 29.7 | | 7749 | | −5.3 | Pep(1) |
| Y39-40 | 410 | 421 | 1494.8195 | | | | | | | |
| Y40 | 412 | 421 | 1218.672 | 15.8 | 15.8 | 77917 | 88243 | −0.3 | −1.6 | |
| Y40-41 | 412 | 427 | 1891.9905 | 20.3 | 20.3 | 107513 | 149676 | 0.2 | −2 | |
| Y42-43 | 428 | 450 | 2525.1792 | | | | | | | |
| Y43 | 441 | 450 | 1016.5502 | | | | | | | |
| Peptide mapping characterization of MAC-2 light chain reference product |||||||||||
| Y2-3 | 36 | 49 | 1688.9725 | 16.2 | 16.2 | 145374 | 170451 | −1.7 | −2.6 | |
| Y2-3* | 36 | 49 | 3381.8225 | | 24.2 | | 7192 | | −9.2 | Pep(1) |
| Y3 | 37 | 49 | 1525.9093 | 15.5 | 15.5 | 331068 | 393638 | −2.7 | −2.9 | |
| Y3* | 37 | 49 | 3218.7593 | | 24 | | 28193 | | −9 | Pep(1) |
| Y3-4 | 37 | 62 | 2882.6355 | | | | | | | |
| Y9-10 | 88 | 116 | 3244.729 | | | | | | | |
| Y10 | 99 | 116 | 1871.0992 | | | | | | | |
| Y10-11 | 99 | 139 | 4331.335 | | | | | | | |
| Y11 | 117 | 139 | 2478.2463 | | 22.8 | | 47035 | | −5.9 | |
| Y11-12 | 117 | 148 | 3635.8445 | | | | | | | |
| Y12 | 140 | 148 | 1175.6088 | | | | | | | |
| Y12-13 | 140 | 173 | 3886.8245 | | | | | | | |

TABLE 22-continued

| Fragment Number | Start | End | Peptide Mass (Da) | Retention Time Control | Retention Time Analyte | MS Signal Intensity Control | MS Signal Intensity Analyte | Mass Error (ppm) Control | Mass Error (ppm) Analyte | Modifiers |
|---|---|---|---|---|---|---|---|---|---|---|
| Y13 | 149 | 173 | 2729.2263 | 13.1 | 13.1 | 1140556 | 1218022 | −1.1 | 0.1 | |
| Y13* | 149 | 173 | 4422.0762 | | 21.4 | | 8424 | | −6.5 | Pep(1) |
| Y13-14 | 149 | 186 | 4095.9243 | | | | | | | |
| Y14 | 174 | 186 | 1384.7086 | | | | | | | |
| Y14-15 | 174 | 192 | 2169.1318 | | | | | | | |
| Y15 | 187 | 192 | 802.4337 | 7.5 | 7.5 | 275639 | 62720 | −1.9 | −0.2 | |
| Y15* | 187 | 192 | 2495.2837 | | 20.9 | | 936267 | | −9.8 | Pep(1) |
| Y15-16 | 187 | 209 | 2574.29 | | | | | | | |
| Y16 | 193 | 209 | 1789.8668 | 18.7 | | 5400 | | 4.4 | | |
| Y16* | 193 | 209 | 1846.8883 | 18.1 | 18.1 | 169490 | 235914 | −1.7 | −2.5 | CAM(1) |
| Y16-17 | 193 | 214 | 2349.0842 | 17.8 | | 9211 | | 0.1 | | |

TABLE 23

Directional conjugation of peptide to Y15 fragment on the light chain

| Fragment | Unmodified Intensity Ratio: Control/Analyte-normalized |
|---|---|
| Light Y3 | 1.000 |
| Light Y13 | 1.112 |
| Light Y15 | 5.218 |
| Heavy Y6 | 0.831 |
| Heavy Y10 | 1.038 |
| Heavy Y25 | 0.988 |
| Heavy Y33 | 1.045 |
| Heavy Y37 | 1.120 |

Example 13

Ang1-4 Binding ELISA

High-binding half-well plates were coated with recombinant human Ang1, human Ang2, mouse Ang3 or human Ang4 (all reagents from R&D Systems, 250 pg/ml) in 50 ul PBS and incubated at 4° C. overnight. Plates were washed 3 times with washing buffer (0.1% Tween 20, PBS, pH 7.4) and blocked with Superblock, 150 μl/well at RT for 1 hr. Plates were washed 3 times with washing buffer. Following washing, prepared a dosing solution (range: 0.005-50,000 ng/ml) were added to the plate and incubated for 1 hr to allow binding of the compounds to the coated Ang family members on the plates. Positive controls for each angioprotein included either monoclonal or polyclonal antibodies against each family member (supplied by R&D Systems). Plates were washed 3 times, and 50 μl of HRP-conjugated anti-human IgG (0.8 μg/mL) (or respective species for positive controls) was added and incubated at RT for 1 hr. Plates were washed 3 times, and 50 μl (25 ml TMB+25 $H_2O_2$) substrate solution was added and incubated for 1-5 minutes. Color development was stopped with 25 μl of 2 M $H_2SO_4$. OD450 nm with a correction wavelength of 540 nm was measured.

Example 14

Ang2 Reverse Competition Assay

For Ang2 reverse competition ELISA, human Tie2-Fc, angiopoietin-2 protein, biotinylated anti-human Ang2 antibody, and streptavidin HRP (R&D Systems) and TMB substrate from Pierce were used. High-binding half-well plates were coated with Tie2-Fc (50 ng/well) in 50 μl PBS and incubated at 4° C. overnight. Plates were washed 3 times with washing buffer (0.1% Tween 20, PBS, pH 7.4) and blocked with Superblock, 150 μl/well at RT for 1 hr. Plates were washed 3 times. Following washing, 50 μl of an Ang2 binding peptide compound (50 nM, 5× serial dilution) in the presence of 50 ng/ml (0.83 nM) Ang2 in Superblock were added and incubated at RT for 1 hr. Plates were washed 3 times, 50 μl of 1 μg/ml biotinylated anti-Ang2 detection antibody in Superblock was added and incubated at RT for 2 hrs. Plates were washed 3 times, and 50 μl of streptavidin HRP (1:200 dilution in Superblock) was added and incubated at RT for 20 minutes. Plates were washed 3 times, and 50 μl (25 μl TMB+25 μl $H_2O_2$) substrate solution was added and incubated for 20-30 minutes. Color development was stopped with 25 μl of 2 M $H_2SO_4$. OD450 nm with a correction wavelength of 540 nm was measured. IC50 values (50% inhibition of Ang2-Tie2 binding) were calculated using the non-linear Sigmoidal dose-response curve fitting function in the Prism 4 software.

Ang2-h38C2-IgG1 was used as a control in certain examples. The generation and structure of the Ang2-h38C2 is fully described as compound 43 in WO2008056346, whose contents is incorporated herein, with particular reference to aspects referring to the generation of compound 43. Briefly, the structure is as follows:

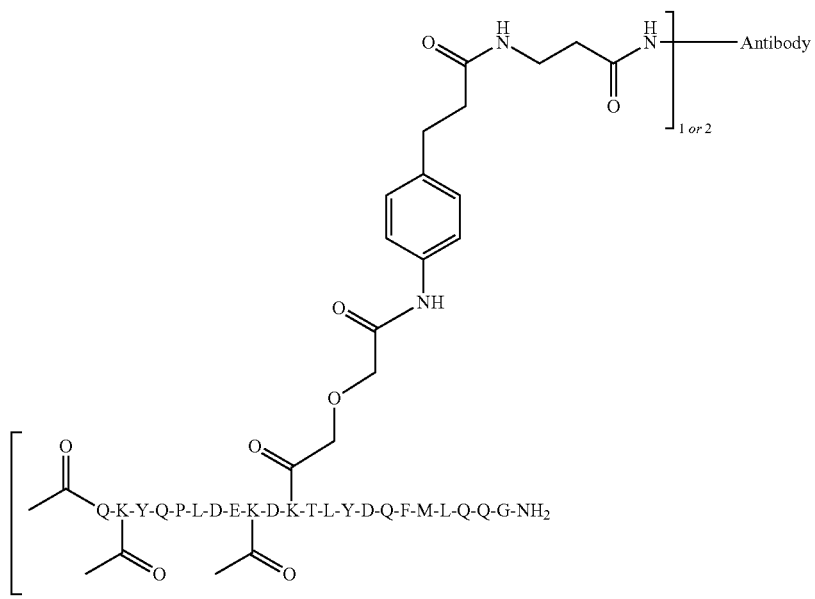

wherein and the linker is covalently attached to the ε-amino group of $K^{99}$ ($K^{93}$ according to Kabat numbering) of the combining site of Antibody and Antibody is h38C2-IgG1 (SEQ ID NO:51 and 52) (SEQ ID NO:189 and SEQ ID NO:190 of WO2008/056346).

Example 15

IGF1R Competition Assay

For the IGF1R competition ELISA, recombinant human IGF1 R (R&D Systems), biotinylated IGF1 (GroPep Ltd.), streptavidin-poly-HRP20 (SDT), Superblock, and TMB substrate (Pierce) were used. High-binding half-well plates were coated with IGF1R (62.5 ng/well) in 50 ul PBS and incubated at 4° C. overnight. Plates were washed 3 times with washing buffer (0.1% Tween 20, PBS, pH 7.4) and blocked with Superblock, 150 µl/well at RT for 1 hour. Plates were washed 3 times with washing buffer. Following washing, 50 µl of an IGF1R binding compound (1 µM, 5× serial dilution) in the presence of 100 ng/mL (13.3 nM) biotinylated IGF1 in Superblock were added and incubated at RT for 1 hr. Plates were washed 0.3 times, and 50 µl of streptavidin-poly-HRP20 (1:5000 dilution in Superblock) was added at RT for 20 minutes. Plates were washed 3 times, and 50 µl (25 µl TMB+25 µl $H_2O_2$) substrate solution was added and incubated for 5-10 minutes. Color development was stopped with 25 µl of 2 M $H_2SO_4$. OD450 nm with a correction wavelength of 540 nm was measured. $IC_{50}$ values (50% inhibition of IGF1 to IGF1R binding) were calculated using non-linear Sigmoidal dose-response curve fitting function in the Prism 4 software.

Example 16

IGF1 Induced IGF1R Autophosphorylation Inhibition Assay

For the IGF1R autophosphorylation inhibition assay, mouse 3T3 cells engineered to express human IGF1R were used, and the phosphorylation determined by Cell Signaling Technologies phospho-IGFI receptor β (Tyr1131) sandwich ELISA kit #7302. Human IGF1R expressing intact cells were seeded ($5.0 \times 10^4$ cells/well) in a 96-well tissue culture treated round-bottom plate and allowed to attach overnight in 50 µL of growth media (37° C., 5% $CO_2$, growth media consisting of DMEM with 10% FBS, 2 mM L-Glutamine, Penicillin-Streptomycin, and 500 µg/mL Geneticin). After 16 hrs, the growth media was removed by aspiration and 50 µL per well of new growth media was added containing an IGF1R binding compound (1 mM, 8× serial dilution) in the presence of 100 ng/mL (13.3 nM) recombinant human IGF1 and incubated for 10 minutes at room temperature. The plate was washed by aspirating liquid away and adding 100 µL per well of ice cold PBS. The cold PBS was immediately aspirated away and 60 pt of lysis buffer (starting with the lysis buffer, all of the following reagents were supplied as part of a commercial kit manufactured by Cell Signaling Technologies designed to quantify the phosphorylation of IGF1R at tyrosine 1131) was added to each well and incubated at room temperature for 10 minutes while shaking. The plates were then centrifuged at 4° C. for 5 minutes. The supernatant (50 µl per well) was then removed and added to a 96 well plate pre-coated with a Phospho-IGF1 Receptor beta (Tyr1131) Rabbit Antibody and containing 50 µL per well of a sample diluent. The plates were incubated overnight for 16 hrs at 4° C. while gently shaking. Following the incubation, the plates were washed 4 times with wash buffer and 100 µL of a human IGF1 Receptor Detection Antibody (mouse origin) was added to each well for 1 hr at 37° C. The plates were washed 4 times with wash buffer and 100 µL of an HRP-linked Mouse IgG Secondary Antibody was added to each well for 30 minutes at 37° C. The plates were washed 4 times, and 100 µL of TMB substrate was added to each well and incubated for 30 minutes. Color development was stopped with 50 µl of 2 M $H_2SO_4$. OD450 nm with a correction wavelength of 540 nm was measured. Internal controls with and without IGF1 treatment confirmed the specificity of the phosphorylation event and determined the % inhibition of transmembrane signaling. $EC_{50}$ values (concentration at which half-maximal signal was achieved) were calculated using non-linear Sigmoidal dose-response curve fitting function in the Prism 4 software.

Example 17

IGF1R Downregulation Assay

For IGF1R downregulation, human colon adenocarcinoma Colo205 cells were used and cell surface expression of IGF1R determined by flow cytometry. Tissue culture 96-well plates plated with $5 \times 10^4$ cells/well in growth media (RPMI, 10% fetal bovine serum, glutamine) were treated with compound titration for 3 hrs at 37° C. Cells were rinsed with PBS, lifted with CellStripper and transferred to fresh 96-well plates. Cells were washed 3 times with PBS with 2.5% fetal bovine serum. Cells were incubated with phycoerythrin-conjugated mouse monoclonal anti-human IGFI R (R&D FAB391P, 10 μl/$5 \times 10^{-5}$ cells) in the dark for one hr. Cells were then washed 3 times with PBS with 2.5% fetal bovine serum. The presence of IGF1R on the cell surface was determined by flow cytometry using a FACSArray and data analyzed with FloJo software. Receptor numbers were calculated by fitting data to standard curves generated using QuantiBRITE PE beads (BD 340495). The data were reported as the percentage of downregulation by test compounds versus negative control hIgG2.

To confirm that the IGF inhibition observed in the competition assay translates into inhibiting IGF induced signaling events, a cell-based functional assay was used to determine the inhibition of IGF1R autophosphorylation following IGF stimulation (FIG. 13 and Table 24). MAC-1 and MAC-2 have similar activity as the parental anti-IGF1R antibody (2.12.2.fx); therefore, conjugation of limited Ang2 peptides does not appear to change the MAC innate binding and inhibition.

In addition to inhibiting IGF1R autophosphorylation, anti-IGF1R antibody also causes IGF1R internalization and degradation resulting in receptor downregulation. This behaviour is observed within 2 hrs of treatment and maintained for 24 hrs. The MACs were tested for the ability to downregulate IGF1R levels on a human colon carcinoma cell line Colo205. Cells were treated for 3 hrs in culture with titration of MAC compounds. Cells were collected and IGF1R surface expression determined by flow cytometry. The percentage of IGF1R downregulated as compared to negative control hIgG2 was determined (Table 24). MAC-1 and MAC-2 have similar IGF1R downregulation activity as the parental IGF1R antibody (2.12.1.fx).

TABLE 24

Ability of MAC-1 and MAC-2 to bind & modulate IGF1R and Ang2

|  | Ang2 $IC_{50}$ (nM) | IGF1R $IC_{50}$ (nM) | IGF1R phosphorylation $IC_{50}$ (nM) | % IGF1R downregulated |
|---|---|---|---|---|
| MAC-1 | 0.092 ± 0.049 | 5.1 ± 1.1 | 150.7 ± 59.6 | 43 ± 5 |
| MAC-2 | 0.057 ± 0.022 | 6.1 ± 1.1 | 91.4 ± 40.2 | 50 ± 5 |
| 2.12.1.fx antibody | nd | 3.8 ± 0.8 | 48.7 ± 14.0 | 48 ± 3 |
| Ang2-h38c2-IgG1 | 0.582 ± 0.242 | nd | nd | nd |

Results and Discussion

The ability of MAC-2 to bind to human Ang2 specifically is shown in FIG. 10. MAC-2 and Ang2-h38c2 were able to bind to human Ang2 but not human Ang1, human Ang4 or mouse Ang3 showing high specificity for Ang2 and not other angioprotein family members.

MAC-1 and MAC-2 were able to bind Ang2 and prevent its binding to Tie2 as shown in the Ang2 competition assay (FIG. 11 and Table 24). Surprisingly, in comparison with Ang2-h38c2, MAC-1 and MAC-2 both showed an increase in ability to competitively bind Ang2. After confirming that the conjugated MACs bound and inhibited Ang2 binding to Tie2, the ability to compete for IGF1 binding to IGF1R was determined by IGF1R competition assay (FIG. 12). MAC-1 and MAC-2 were as efficient as parental anti-IGF1R antibody (2.12.1.fx) for competing with IGF1 for IGF1R binding. MAC-1 and MAC-2 showed $IC_{50}$ values in the low nanomolar range. In contrast, in tests with certain other anti-IGF1R antibodies, conjugation of the peptide was observed to interfere with the ability of the antibody to interact with IGF1R (data not shown).

It was demonstrated that conjugating 2 peptides per antibody was ideal in terms of effecting IGF1R autophosphorylation and downregulation and that conjugating more or less than 2 peptides per antibody lessens the ability of the MAC to effect these functions.

To assess the effect of the number of peptides per antibody on the ability of 2.12.1.fx to modulate IGF1R activity, 2 samples of MAC-1 were prepared where the reaction conditions were set to provide either reduced conjugation (MAC-1 low) or increased conjugation (MAC-1 high) (Table 25). The samples were analysed for the ability to downregulate and phosphorylate IGF1R (Table 25). There is a significant difference in the ability of the MAC-1 high as compared with MAC-1 low to effectively modulate the IGF1R pathway. Conjugation of greater than about 2 peptides per antibody limits the functional activity of the MAC to both inhibit IGF1R autophosphorylation and induce IGF1R downregulation, compared to conjugation of about 2 or less peptides per antibody. Therefore, in order to efficiently modulate 2 different biological pathways in one bifunctional entity, conjugation of about 2 peptides per antibody may be ideal (depending on peptide's and target's pharmacokinetic profile).

TABLE 25 analysis of MAC-1-High and MAC-1 Low

| | Ang2 $IC_{50}$ (nM) | % IGF1R downregulated | Phosphorylation IGF1R $IC_{50}$ (nM) | CA (%) 0 | 1 | 2 | 3 | 4 | 5 | Avg CA |
|---|---|---|---|---|---|---|---|---|---|---|
| MAC-1 Low | 0.103 | 32 ± 1 | 12.8 | 14 | 42 | 32 | 12 | 0 | 0 | 1.42 |
| MAC-1 High | 0.035 | 9 ± 2 | >300 | 0 | 4 | 19 | 41 | 32 | 5 | 3.18 |
| 2.12.1.fx | nd | 36 ± 3 | 3.5 | | | | | | | |
| Ang2-h38c2-IgG1 | 0.252 | nd | nd | | | | | | | |

Example 18

In Vivo Pharmacokinetics

Protocol

A validated direct binding enzyme-linked immunosorbent assay (ELISA) method was used to measure serum MAC levels in mouse and monkey serum. Briefly, the MAC in the sample binds IGF1R or Ang2 that has been passively absorbed onto a microtiter plate, and horseradish peroxidase-conjugated anti-human IgG is used along with a chromogenic substrate to generate a signal that is proportional to the concentration of MAC-2 in the serum sample. The upper and lower limits of quantification of MAC-2 in mouse serum are 26.0 and 1000 ng/ml, and 52.0 and 2000 ng/ml in cynomolgus monkey serum.

Ang2 and IGF1R Reverse ELISA

High-binding half-well plates were coated with IGF1R (62.5 ng/well) or Ang2 (6.25 ng/ml) in 50 ul PBS and incubated at 4° C. overnight. Plates were washed 3 times with washing buffer (0.1% Tween 20, PBS, pH 7.4) and blocked with Superblock, 150 μl/well at RT for 1 hr. Plates were washed 3 times with washing buffer. Following washing, prepared dosing solution standards (range: 3.91-500 ng/ml) and serum samples were added to the plate and incubated for one hr to allow binding of the MAC complexes to the coated Ang2 or IGF1R on the plates. Plates were washed 3 times, and 50 μl of HRP-conjugated goat anti-human IgG (0.8 μg/mL) was added and incubated at RT for one hr. Plates were washed 3 times, and 50 μl (25 μl TMB+25 μl $H_2O_2$) substrate solution was added and incubated for 1-5 minutes. Color development was stopped with 25 μl of 2 M $H_2SO_4$. OD450 nm with a correction wavelength of 540 nm was measured. Serum concentrations of the MAC complexes were calculated using the standard curves. MAC complex concentrations, as determined by ELISA, were plotted as a function of time. Further data analysis was undertaken using WinNonlin version 4.1 (Pharsight Corporation) to determine the β half life (T1/2) and the area under the curve (AUC) for MAC complexes.

Mouse

PK studies were conducted using male Swiss Webster mice (CFW, Charles River, Hollister, Calif.) weighing approximately 20-22 grams at the start of dosing. MAC compounds were intravenously administered. Blood samples were taken from 4 mice per time point at the following time points: 0.08, 0.5, 1, 3, 5, 7 and 24 hrs. Protease inhibitor cocktail was added to all blood tubes prior to sample collection. Blood was allowed to clot on ice for 30 minutes and then centrifuged at 12000 rpm for 5-10 minutes at 4° C. to collect serum and immediately stored at −80° C. until analysis via ELISA. Dosing solutions were used to establish the standard curves for serum sample analysis by Ang2 or IGF1R Reverse ELISA. Aliquots of each serum sample were analyzed by either Ang2 or IGF1R Reverse ELISA.

Monkey

The pharmacokinetic profile of MAC-2 was determined. 2 male Cynomolgus monkeys (*Macaca fascicularis*) were used in the study; MAC-2 was administered via an intravenous (bolus) injection at a dose level of 10 mg/kg. All animals were observed at 5 min, 15 min, 1 h, 4 h and 8 h post dose on Day 1 and twice daily thereafter for any reactions to treatment. Body weights were measured and recorded on Days 1, 2, 3, 4, 5, 7 and 14. Blood samples for toxicokinetic analysis were obtained at the designated time points and serum was separated and stored at −80° C.

There were no adverse clinical signs noted during the study that could be related to treatment with MAC-2. Body weight profiles were satisfactory. Blood samples of approximately 1.0 mL were collected from the femoral vein of each animal and into plain clotting tubes at the time points (0.08-504 hrs). Blood samples were left to stand for one hr at room temperature after collection and then centrifuged at 3000 rpm for 10 minutes at 4° C. The resulting serum samples were stored at approximately −80° C. prior to analysis.

Results

Exploratory non-GLP pharmacokinetic (PK) studies were conducted in male Swiss Webster mice and male cynomolgus monkeys (Table 26 and 27). Both the Ang2 and IGF1R binding activities of the MAC were analyzed. In mouse, MAC-1 and MAC-2 demonstrated similar residence time as the parental anti-IGF1R antibody with beta phase half-lives of 383-397 hrs. The MAC-1 and MAC-2 Ang2 binding capability demonstrated similar residence time as Ang2-h38c2 with beta phase half-lives of 105-120 hrs in mouse in single dose IV studies. In cynomolgus monkey, MAC-2 demonstrated a slightly shorter residence time as the parental anti-IGF1R antibody with beta phase half-lives of 100.4 hrs. The MAC-2 Ang2 binding capability demonstrated similar residence time as Ang2-h38c2 with beta phase half-lives of 97.8 hrs.

TABLE 26

Single-dose PK of IV administered MACs at 10 mg/mk in mouse

| Compound (mg · $Kg^{-1}$) | Beta $t^{1/2}$ (hr) Ang2 portion | Beta $t^{1/2}$ (hr) IGF1R portion |
|---|---|---|
| Ang2-h38c2, (10) | 95.2 | — |
| α-IGF1R antibody, (10) | — | 390 |
| MAC-1, (10) | 105 | 383 |
| MAC-2, (10) | 120 | 397 |

TABLE 27

Single-dose PK of IV administered MACs
at 10 mg/mk in cynomolgus monkey

| Compound (mg · Kg$^{-1}$) | Beta t½ (hr) Ang2 portion | Beta t½ (hr) IGF1R portion |
|---|---|---|
| Ang2-h38c2, (10) mpk | 95.3 | — |
| α-IGF1R antibody, (5) mpk | — | 146.4 |
| MAC-2, (10) mpk | 97.8 | 100.4 |

Example 19

In Vivo Pharmacology

Protocol

The anti-tumour activity of MAC-2 was evaluated in the Colo205 (human colon adenocarcinoma) or MDA-MB-435 (melanoma) xenograft model. Colo205 or MDA-MB-435 cells were cultured with 10% FBS RPMI medium and $3 \times 10^6$ cells in 0.1 ml Hank's balanced salt solution (HBSS) were injected subcutaneously into the upper right flank of 5-7 week old female nu/nu mice and allowed to establish to a volume of 200-400 mm$^3$ prior to initiation of treatment. Once tumours were established, mice were randomized to treatment groups with identical tumour volumes (n=9-10/group), and MAC-2 treatment was administered once weekly by intraperitoneal (IP) injection. In combination studies, additional anti-cancer agents were administered weekly by IP injection, with treatments initiated concomitant with MAC-2. Tumour volumes were measured once or twice weekly, using calipers, and body weights were measured weekly, during the treatment period. In some studies, all mice were euthanized by CO$_2$ asphyxiation and tumours were excised, weighed, and processed for further histological and/or immunochemical evaluation once tumour volume in the vehicle-treated control group reached 2000 mm$^3$. In pseudo-survival studies, mice were euthanized by CO$_2$ asphyxiation and tumours were excised and weighed once the mean tumour volume of each treatment group exceeded 2000 mm$^3$.

Results

An experiment conducted in the Colo205 (human colon adenocarcinoma) xenograft model is illustrated in FIGS. 12A and 13A. Weekly administration of Ang2-h38c2 or anti-IGF1R antibody (2.12.1.fx) inhibited Colo205 tumour growth. Combination of weekly administered Ang2-h38c2 and anti-IGF1R antibody showed an additive benefit on inhibiting Colo205 tumour growth. Weekly administration of MAC-2 alone showed similar benefit as the combination (FIG. 14A). In a separate study, MAC-2 dose-dependently inhibited Colo205 tumour growth and final tumour weights (FIG. 15A, B).

At day 28, compound treated mice were sacrificed, and tumours were excised and snap frozen. To assess the anti-angiogenic effect of MAC-2, tumour microvessel density was assessed immunohistochemically on frozen sections of Colo205 colon adenocarcinoma xenograft tumours treated with Vehicle (PBS) or MAC-2 (dose response ranging from 0.3 mg/kg to 10 mg/kg). Tumours were stained with a mouse-specific monoclonal antibody to CD31, and immunoreactivity was quantified from 5 areas of 3 sections from each tumour (FIG. 13C). Tumour microvessel density was significantly reduced ~42% by MAC-2 (10 mg/kg, once weekly) in comparison with the Vehicle-treated group confirming the anti-angiogenic activity of the MAC-2 treatment.

To investigate whether MAC-2 targets both Ang2 and IGF1R in vivo, the effects of MAC-2 on Ang2 and IGF1R expression levels were assessed in 2 independent Colo205 xenograft tumours treated with Vehicle, Ang2-h38c2, IGF1R antibody (2.12.1.fx) or MAC-2 (dose response ranging from 0.3 mg/kg to 10 mg/kg). Lysates were prepared from frozen excised tumours, and Ang2 and IGF1R immunoreactivity was quantified by ELISA. Ang2 and IGF1R immunoreactivity was significantly reduced by MAC-2 treatment in a dose-dependent manner (1, 3 and 10 mg/kg) in comparison with the Vehicle-treated group (FIGS. 14B, 15D, and 15E). The effect of MAC-2 on IGF1R levels is similar to that observed for an IGF1R antagonizing antibody (2.12.1.fx) (FIG. 14B). In addition, the levels of phosphorylated IGF1R were reduced in tumours from MAC-2 treated animals (data not shown). Immunofluorescense on fixed sections of these tumours also confirmed the reduction in IGF1R and pIGF1R (data not shown). These data demonstrate that MAC-2 treatment affects both Ang2 and IGF1R pathways in Colo205 xenograft model.

In 3 separate studies, MAC-2 treatment led to sustained tumour inhibition compared with the vehicle (PBS), Ang2-h38c2 and IGF1R antibodies (2.12.1.fx and 2.13.2) (FIG. 16A, 16B, 16C). The anti-IGF1R antibody 2.13.1 is described as SEQ ID NO:45 and SEQ ID NO:47 in WO02/053596, less the respective signal sequences. The tumour inhibition by MAC-2 was similar to the combination of Ang2-h38c2 and 2.12.1.fx and more active than Ang2-h38c2 and 2.13.2 (FIG. 16C). MAC-2 treatment did not affect body weight gain (data not shown) and mice appeared to be in good health throughout the study. Tumours in each group of animals were allowed to progress to 2000 mm$^3$ as a pseudo-survival study. Both the Ang2-h38c2 and anti-IGF1R antibody treated groups had to be stopped by day 48; however, the MAC-2 treated tumours (3-10 mpk) were still below 2000 mm$^3$ at day 94 when the study was halted.

The anti-tumour efficacy of MAC-2 was also evaluated in an MDA-MB-435 melanoma xenograft model. Weekly administration of MAC-2 (3 and 20 mg/kg IP) resulted in a significant 40% reduction (day 67) in tumour growth in the MDA-MB-435 model (FIG. 17). Thus, MAC-2 demonstrates significant anti-tumour efficacy in 2 different human xenograft tumour models.

Example 20

Peptide Conjugation Profile of Various Antibodies

The conjugation profiles of several different antibodies with peptides were analyzed, using SEQ ID NO:27 and 5PEG as an exemplary peptide and linker respectively. All antibodies tested were human or fully humanized IgG antibodies with well defined and characterized antigen interactions. hAbλTest comprises a CLλ, whereas 2.12.1.fx, mAbκTest1, h28C2-IgG1 (SEQ ID NO:51 and 52) and h38C2-IgG2 (SEQ ID NO:53 and 54) each comprise CLκ. Each of the antibodies were buffer exchanged into 20 mM HEPES, pH 7.0 and concentrated to 5-20 mg/mL. SEQ ID NO:27/K$^{11}$-5PEG-PFP was resuspended with 50% propylene glycol and mixed with the relevant antibody at a 4.3:1 molar ratio and allowed to react for at least 2 hrs at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a bound peptide. Relative quantitation of multiple peptide conjugation species is performed by measuring the signal magnitude. Table 22 shows the peptide conjugation profile of various antibodies For antibodies containing a CLκ, peptide conjugation occurs at a distribution between 0-4 peptide additions with the largest form being 2 to 3 peptide additions. In contrast, for the CLλ comprising antibody, hAbλTest, conjugation of the peptide occurs at a distribution between 0-4 peptides additions with the largest form being 1 to 2 peptide additions.

The extent of peptide conjugation was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The peptide conjugation profile on the light and heavy chain of various antibodies is shown in Table 28. On 2.12.1.fx and hAbκTest1, the data demonstrates that the location of conjugation is higher on the light chain; the most abundant form on the light chain contains one (1) peptide addition. Conjugation on the heavy chain is observed at a significantly lower level. On h38C2-IgG1 and h38C2-IgG2, comparable levels of conjugation are observed on the light and heavy chain, with a slight conjugation preference on the light chain. On a CLλ containing antibody (hAbλTest), the majority of the conjugation occurs on the heavy chain with a low level of conjugation observed on the light chain.

TABLE 28

Conjugation profile of various antibodies

| Antibody | CA (%) | | | | | Avg | Light Chain % CA | | | Heavy chain % CA | | |
|---|---|---|---|---|---|---|---|---|---|---|---|---|
| | 0 | 1 | 2 | 3 | 4 | CA | 0 | 1 | 2 | 0 | 1 | 2 |
| 2.12.1.fx | 1 | 15 | 53 | 26 | 5 | 2.2 | 20 | 70 | 9 | 84 | 16 | 0 |
| hAbλTest | 10 | 37 | 37 | 11 | 6 | 1.66 | 95 | 5 | 0 | 74 | 22 | 4 |
| hAbκTest1 | 7 | 10 | 35 | 27 | 14 | 2.55 | 11 | 74 | 14 | 87 | 13 | 0 |
| h38C2 IgG1 | 1 | 3 | 28 | 55 | 13 | 2.75 | 49 | 46 | 4 | 70 | 30 | 0 |
| h38C2 IgG2 | 4 | 6 | 31 | 44 | 15 | 2.6 | 61 | 35 | 4 | 73 | 27 | 0 |

Each of the antibodies 2.12.1.fx, hAbλTest and hAbκTest1 was assessed after the conjugation process to determine the effect of the conjugation additions on the ability of the antibody scaffold to retain its receptor binding (compared to native mAb) (Table 29). The results show that the directional conjugation of peptides to the test antibodies did not appear to alter the antibody binding.

TABLE 29

Antibody binding to native antigen before and after conjugation

| | Receptor binding | |
|---|---|---|
| Antibody | Native ($IC_{50}$, nM) | After conjugation ($IC_{50}$, nM) |
| 2.12.1.fx | 3.2 | 5.7 |
| hAbλTest | 0.4 | 1.7 |
| hAbκTest1 | 59 | 53 |

Example 21

Peptide Conjugation Profile of a Representative Antibody of IgG2-κ

The conjugation profile of an IgG2κ antibody (hABκ-Test2) with a 39-mer peptide was analyzed. The antibody was concentrated to 8 mg/mL and buffered exchanged into 40 mM HEPES pH 8.0. The peptide was resuspended with 100% DMSO and mixed with the antibody at a 5.0:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a peptide. Relative quantitation of multiple peptide conjugation species is performed by measuring the signal magnitude. Table 30 shows the peptide conjugation profile of hAbκTest2 with the 39-mer peptide. The conjugation of peptide occurs at a distribution between 0-4 peptide additions with an average of 2.03 peptide additions, and is consistent with directional conjugation on the CLκ-$K^{188}$.

TABLE 30

Conjugation profile of 39-mer peptide and hAbκTest2

| Antibody scaffold | Binding Peptide | % CA | | | | | Avg CA |
|---|---|---|---|---|---|---|---|
| | | 0 | 1 | 2 | 3 | 4 | |
| hAbκTest2 | 39-mer peptide | 1 | 22 | 53 | 18 | 5 | 2.03 |

In a separate experiment, the 39-mer peptide was conjugated to h38C2-IgG2 with MAL-2PEG-PFP as described above, at different molar concentrations. In addition, binding of the cognate receptor for the 39-mer peptide was assayed. The results (Table 31) shown are consistent with directional conjugation at $K^{188}$-CLκ. Moreover, increasing the average number of peptides per antibody did not substantially increase overall binding to the target. This demonstrates that in certain scenarios, increasing the conjugation per antibody may not increase target binding, demonstrating one of the advantages of the invention; control of the number of peptides conjugating per antibody can help achieve the maximum target binding per unit peptide.

TABLE 31

Conjugation profile of 39-mer peptide and H38C2-IgG2

| 39-mer peptide:h38C2-IgG2 mole ratio | CA (%) | | | | Avg # Conjugates | Peptide target: EC50 (nM) |
|---|---|---|---|---|---|---|
| | 0 | 1 | 2 | 3 | | |
| 2:1 | 57 | 32 | 10 | 0 | 0.52 | 0.99 |
| 2.5:1 | 19 | 56 | 25 | 0 | 1.06 | 1.06 |
| 4:1 | 20 | 25 | 35 | 20 | 1.55 | 1.01 |
| 5:1 | 0 | 16 | 45 | 40 | 2.26 | 0.82 |

Example 22

Conjugation of Biotin to 2.12.1.fx Fab

Biotin-2.12.1.fx
The conjugation profile of the Fab region of 2.12.1.fx (SEQ ID NO:50 and 4) with PFP-Biotin was analyzed. The antibody Fab was concentrated to 20 mg/mL and buffered exchanged into 20 mM sodium acetate+200 mM trehalose, pH 5.5 and spiked with 60 mM sodium phosphate pH 7.7. PFP-Biotin was resuspended with 100% DMSO and mixed with the antibody at successive molar ratios and allowed to react overnight at room temperature. All samples were diluted to 2 mg/ml and analyzed as an intact conjugated protein by size exclusion chromatography-mass spectrometry (SEC-MS) to determine the number and quantitation of conjugate forms. This technique measures the molecular weight of each protein form; multiple conjugation sites are observed as distinct signals separated by the mass difference of a conjugated peptide. Relative quantitation of multiple conjugation species is performed by measuring the signal magnitude. Table 32 shows the conjugation profile of 2.12.1.fx Fab with PFP-Biotin at molar ratios. The conjugation of occurs at a distribution between 0-2 additions as the molar ratio increases. The lower number of molecules per antibody was consistent with earlier results, based on the molar ratio used. This is a useful demonstration of the flexibility of the process to control the amount of conjugation by altering one or more of the reaction parameters.

TABLE 32

Conjugation profile of Biotin to 2.12.1.fx Fab

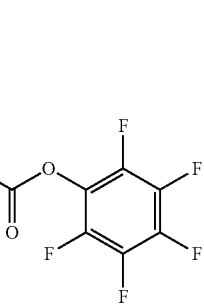

Biotin-PFP

| Antibody scaffold | Binding Peptide | Peptide:Antibody Molar Ratio | % CA 0 | 1 | 2 | 3 | Avg CA |
|---|---|---|---|---|---|---|---|
| 2.12.1.fx Fab | Biotin-PFP | 1:1 | 54 | 46 | — | — | 0.46 |
| 2.12.1.fx Fab | Biotin-PFP | 1.5:1 | 42 | 51 | 7 | — | 0.65 |
| 2.12.1.fx Fab | Biotin-PFP | 2:1 | 34 | 55 | 10 | — | 0.76 |
| 2.12.1.fx Fab | Biotin-PFP | 3:1 | 28 | 55 | 17 | — | 0.88 |
| 2.12.1.fx Fab | Biotin-PFP | 4:1 | 21 | 46 | 26 | 8 | 1.21 |

Example 23

Conjugation of Biotin to h38C2-IgG1

Biotin-h38C2-IgG1

The antibody h38C2-IgG1 was adjusted to 20 mg/mL with HEPES buffer pH 7.5 to a final concentration of 0.02M. Biotin-PFP was reconstituted in water to 10 mg/mL and added to h38C2-IgG1 at a molar ratio of 5:1 and allowed to react at room temperature for 2 hrs. The unreacted PFP-Biotin was removed by size exclusion chromatography and buffer exchanged into a histidine, glycine, and sucrose buffer pH 6.5. The samples were diluted to 2 mg/ml and analyzed as an intact conjugated protein by size exclusion chromatography-mass spectrometry (SEC-MS) to determine the number and quantitation of conjugate forms of the protein. Table 33 shows the conjugation profile of h38C2-IgG1 with Biotin-PFP. Conjugation of h38C2-IgG1 occurs at a distribution between 0-3 CA with an average of 1.1 conjugations. Increased conjugation would be possible following optimization of the reaction conditions. The reactivity of VH-$K^{99}$ ($K^{93}$ according to Kabat numbering) on h38C2-IgG1 was confirmed to be >95% when reacted with the catalytic antibody test compound CATC-1, and analyzed via reversed phase chromatography.

TABLE 33

Conjugation of Biotin and h38C2-IgG1

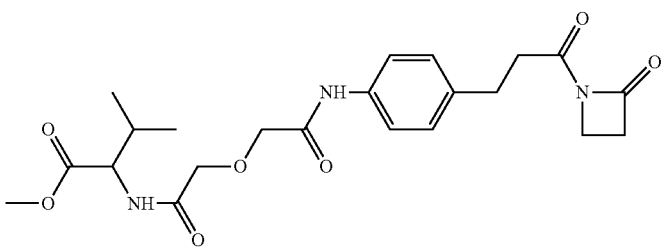 [SMILES: COC(=O)C(NC(=O)COCC(=O)Nc1ccc(CCC(=O)N2CCC2=O)cc1)C(C)C]

CATC-1

| Antibody | 0 | 1 | 2 | 3 | Avg CA |
|---|---|---|---|---|---|
| h38C2-IgG1 | 16 | 61 | 20 | 3 | 1.1 |

Example 24

Conjugation Profile of 2.12.1.fx and $K^{188}$, $K^{190}$ Mutants

Based on peptide mapping, there are 2 Lys in Y15 fragment. In order to distinguish the active conjugation site, $K^{188}$ and $K^{190}$ were mutated to R respectively or in combination. Mutants were generated following protocols described in QuickChange site-directed mutagenesis kit (Stratagene). Mutations were introduced by oligonucleotide primers and confirmed by DNA sequencing. The mutated mAbs were transiently expressed in HEK 293 cells, and purified using protein A affinity column. The purified mAbs were characterized using MS. SEQ ID NOs:33, 34 and 35 show the 2.12.1.fx IGF1r mutant light chain sequences.

The antibody was buffer exchanged to 0.02M HEPES buffer pH 7.5 or 6.5 at 2 mg/mL. If the pH was 6.5, the antibody was then spiked with 60 mM sodium phosphate. The proteins were then spiked with 60 mM sodium phosphate pH 7.7. SEQ ID NO:27-$K^{11}$-5PEG-PFP was resuspended with 50% propylene glycol and mixed with the protein at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a conjugated protein. Relative quantitation of multiple protein conjugation species is performed by measuring the signal magnitude. Table 34 shows the conjugation profile of unmodified 2.12.1.fx, 2.12.1.fx-$K^{188}$R (LC: SEQ ID NO:33), 2.12.1.fx-$K^{190}$R (LC: SEQ ID NO:34), and 2.12.1.fx-$K^{188}$R-$K^{190}$R (LC: SEQ ID NO:35). $K^{188}$R mutant showed reduced conjugation. $K^{190}$R had similar conjugation as the unconjugated 2.12.1.fx. The conjugation of MAC-2 was lower than observed in other assays due using a HEPES/phosphate buffer of about pH 6.5.

TABLE 34

Conjugation profile of 2.12.1.fx, $K^{188}$ and $R^{190}$ mutants

| LC SEQ ID NO: | Mutants | CA (%) 0 | 1 | 2 | 3 | 4 | Avg CA |
|---|---|---|---|---|---|---|---|
| 15 | MAC-2 | 14 | 49 | 31 | 5 | 1 | 1.29 |
| 33 | K188R | 82 | 14 | 4 | 0 | 0 | 0.22 |
| 34 | K190R | 11 | 46 | 36 | 6 | 0 | 1.37 |
| 35 | K188R/K190R | 51 | 37 | 9 | 3 | 0 | 0.63 |

Example 25

2.12.1.fx Mutants to Elucidate Directional Conjugation Mechanism on $K^{188}$ Residues close to $K^{188}$ were examined. $H^{189}$ side chain is very close to the ε-amino group of $K^{188}$. Since His is often involved in proton transfer reactions, $H^{189}$ is very likely required for $K^{188}$ conjugation. In order to study the role of H189 in $K^{188}$ site specific conjugation, we eliminated the imidazole ring by replacing Histidine with Alanine.

$D^{151}$A and $D^{151}$A/$H^{189}$A mutants were made to study the role of $D^{151}$ in site specific conjugation and the combined effect of $D^{151}$ and $H^{189}$.

Mutants were generated following protocols described in QuickChange site-directed mutagenesis kit (Stratagene). Mutations were introduced by oligonucleotide primers and confirmed by DNA sequencing. The mutated mAbs were transiently expressed in HEK 293 cells, and purified using protein A affinity column. The purified mAbs were characterized using MS. The following 2.12.1.fx light chain mutants were generated: $D^{151}$A (SEQ ID NO:36), $K^{188}$A (SEQ ID NO:37), $H^{189}$A (SEQ ID NO:38), $K^{190}$A (SEQ ID NO:39) and $D^{151}$A/$H^{189}$A (SEQ ID NO:40).

Each of the antibodies was buffer exchanged to 20 mM sodium acetate, 200m trehalose pH 5.5 at 20 mg/ml. The proteins were then spiked with 60 mM sodium phosphate pH 7.7. SEQ ID NO:27-$K^{11}$-5PEG-PFP was resuspended with 50% propylene glycol and mixed with the antibody at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple conjugation sites are observed as distinct signals separated by the mass difference of a conjugated peptide. Relative quantitation of multiple conjugation species is performed by measuring the signal magnitude.

Table 35 shows the conjugation profile of 2.12.1.fx, 2.12.1.fx-$D^{151}$A, 2.12.1.fx-$K^{188}$A, 2.12.1.fx-$H^{189}$A 2.12.1.fx-$K^{190}$A, and 2.12.1.fx-$D^{151}$A/$H^{189}$A mutants. All the mutants showed reduced average conjugation level compared to the unmodified 2.12.1.fx antibody, except for $K^{190}$A, which maintained directional conjugation.

The extent of conjugation was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The conjugation profile on the light and heavy chain of 2.12.1.fx and mutants are shown in Table 35. All the mutants listed in the table showed reduced conjugation level on light chain compared to the unmodified 2.12.1.fx except $K^{190}$A. The heavy chain conjugation level of the mutants was at the similar level as the unmodified 2.12.1.fx.

TABLE 35

Conjugation profile of MAC-2 and $K^{188}$A, $D^{151}$ and $H^{189}$ mutants

| LC SEQ ID NO: | Mutants | CA (%) 0 | 1 | 2 | 3 | 4 | Avg CA | LC CA % 0 | 1 | 2 | LC Avg CA - LC | HC CA % 0 | 1 | 2 | HC Avg CA - HC |
|---|---|---|---|---|---|---|---|---|---|---|---|---|---|---|---|
| 15 | MAC-2 | 1 | 15 | 53 | 26 | 5 | 2.2 | 23 | 69 | 8 | 0.85 | 86 | 14 | 0 | 0.14 |
| 36 | $D^{151}$A | 17 | 38 | 31 | 14 | 0 | 1.41 | 68 | 30 | 1 | 0.33 | 79 | 21 | 0 | 0.21 |

TABLE 35-continued

Conjugation profile of MAC-2 and $K^{188}A$, $D^{151}$ and $H^{189}$ mutants

| LC SEQ ID NO: | Mutants | CA (%) 0 | 1 | 2 | 3 | 4 | Avg CA | LC CA % 0 | 1 | 2 | LC Avg CA - LC | HC CA % 0 | 1 | 2 | HC Avg CA - HC |
|---|---|---|---|---|---|---|---|---|---|---|---|---|---|---|---|
| 37 | $K^{188}A$ | 56 | 31 | 10 | 4 | 0 | 0.61 | 89 | 11 | 0 | 0.11 | 91 | 9 | 0 | 0.09 |
| 38 | $H^{189}A$ | 34 | 44 | 17 | 6 | 0 | 0.95 | 89 | 11 | 0 | 0.11 | 78 | 22 | 0 | 0.22 |
| 39 | $K^{190}A$ | 9 | 7 | 31 | 37 | 16 | 2.42 | 8 | 77 | 15 | 1.06 | 83 | 17 | 0 | 0.17 |
| 40 | $D^{151}A/H^{189}A$ | 34 | 39 | 18 | 9 | 0 | 1.02 | 83 | 17 | 0 | 0.17 | 87 | 13 | 0 | 0.13 |

Example 26

Lambda/Kappa Substitution

The LCλ in hAbλTest1 was substituted with LCκ to determine whether this increased the level, directionality and/or control of LC derivatization. The LCλ/LCκ domain substitution hybrid constructs were generated using overlap PCR. The LVλ and LCκ were PCR amplified using hAbλTest and a kappa mAb light chain as templates separately. These 2 PCR products were mixed as templates; hAbλTest1 forward primer and LCκ reverse primer were used in overlap PCR reaction to amplify the full length hAbλTest LV/LCκ DNA. The hybrid antibody constructs were transiently expressed in HEK 293 cells, and purified using protein A affinity column. The purified antibodies were characterized using MS. The hAbλTest LCκ hybrid bound to its cognate receptor similarly to the native mAb (hAbλTest) (Table 36). SEQ ID NOs:41, 42 and 43 are the light chain constant regions from hAbλTest, hAbλTest-λκ (with λJ), and hAbλTest-λκJ (with κJ).

TABLE 36

Antibody: Antigen binding of lambda/Kappa substitution

| hAbλTest1 Mutants | LC SEQ ID NO: | Receptor binding (IC$_{50}$, nM) |
|---|---|---|
| hAbλTest (CONTROL) | 41 | 0.4 |
| hAbλTest-λκ | 42 | 0.3 |
| hAbλTest-λκJ | 43 | 0.3 |

Example 27 hAbλTest1 Mutants: Motif Modification

To establish whether the short motif "KH" was sufficient for MAC formation in the corresponding region of the CLλ, a mutant with simple sequence switch of residues CLλ$^{188/189}$ in hAbλTest to place a histidine beside $K^{187}$ was made, hence "$K_{187}S^{188}H^{189}$" became "$K^{187}H^{188}S^{189}$". Mutants were generated following protocols described in QuickChange site-directed mutagenesis kit (Stratagene). Mutations were introduced by oligonucleotide primers and confirmed by DNA sequencing. The mutated antibody constructs were transiently expressed in HEK 293 cells, and purified using protein A affinity column. The purified antibodies were characterized using MS. The hAbλTest-S$^{188}$H/H$^{189}$S (LC: SEQ ID NO:44) mutant bound to its receptor as well as the parent hAbλTest antibody did (Table 37).

TABLE 37 hAbλTest-S$^{188}$H/H$^{189}$S

| hAbλTest1 Mutants | LC SEQ ID NO: | Receptor binding (IC$_{50}$, nM) |
|---|---|---|
| hAbλTest (CONTROL) | 41 | 0.3 |
| hAbλTest-S$^{188}$H/H$^{189}$S | 44 | 0.4 |

Example 28

Conjugation Profile of hAbλTest1 Mutants

Each antibody (hAbλTest, hAbλTest-λκ, hAbλTest-λκJ and hAbλTest-S$^{188}$H/H$^{189}$S) was buffer exchanged to 20 mM sodium acetate, 200m trehalose pH 5.5 at 20 mg/ml. The proteins were then spiked with 60 mM sodium phosphate pH 7.7. SEQ ID NO:27/K$^{11}$-5PEG-PFP was resuspended with 50% propylene glycol and mixed with the antibody at a 4.3:1 molar ratio and allowed to react overnight at room temperature. All samples were diluted to 2 mg/ml and analyzed as an intact conjugated protein by size exclusion chromatography-mass spectrometry (SEC-MS) to determine the number and quantitation of conjugate forms of the protein. This technique measures the molecular weight of each protein form; multiple peptide conjugation sites are observed as distinct signals separated by the mass difference of a peptide. Relative quantitation of multiple peptide conjugation species is performed by measuring the signal magnitude. Table 38 shows the overall level of conjugation has been increased in the 2 LC-switched hybrids (λκ and λκJ—the former includes a lambda J fragment, the latter includes a kappa J fragment). The conjugation level increases over the hAbλTest control's average CA, going from 1.66 to 2.19 (λκ) and 2.53 (λκJ) respectively. The mutant had little effect compared to the native sequence, suggesting that "KH" motif alone is not sufficient for MAC formation.

The extent of peptide conjugation was examined separately on the light and heavy chains (Table 38). Each sample was denatured and disulfide bonds were reduced using guanidine hydrochloride and dithiothreitol. The resulting free light and heavy chains were analyzed using LCMS to determine the conjugation profile on each. In the reduced analyses, the LC of native hAbλTest has only 5% 1 CA but this jumps dramatically to 58% 1CA for hAbλTest-λκ and 63% 1CA for hAbλTest-λκJ. The LC switch had little effect on the level of HC conjugation, which remained fairly constant (except for λκJ, where HC conjugation increased moderately). Again, the mutant had little effect compared to the native sequence, suggesting that "KH" motif alone is not sufficient for MAC formation.

TABLE 38

Conjugation profile of hAbλTest mutants

| hAbλTest Mutants | LC SEQ ID NO: | CA (%) 0 | 1 | 2 | 3 | 4 | Avg CA | LC CA % 0 | 1 | 2 | Avg CA - LC | HC CA % 0 | 1 | 2 | Avg CA - HC |
|---|---|---|---|---|---|---|---|---|---|---|---|---|---|---|---|
| hAbλTest | 41 | 10 | 37 | 37 | 11 | 6 | 1.66 | 95 | 5 | 0 | 0.05 | 74 | 22 | 4 | 0.3 |
| hAbλTest-λκ | 42 | 3 | 18 | 43 | 29 | 7 | 2.19 | 42 | 58 | 0 | 0.58 | 78 | 22 | 0 | 0.22 |
| hAbλTest-λκJ | 43 | 2 | 11 | 34 | 36 | 17 | 2.53 | 33 | 63 | 4 | 0.71 | 64 | 36 | 0 | 0.36 |
| hAbλTest-$S^{188}H/H^{189}S$ | 44 | 7 | 34 | 37 | 16 | 6 | 1.79 | 82 | 18 | 0 | 0.18 | 79 | 21 | 0 | 0.21 |

The receptor binding attributes of these conjugated forms was also assessed to determine the effect of conjugation with SEQ ID NO:27/$K^{11}$-5PEG-PFP on the ability of the conjugated antibodies to still bind to their receptor (Table 39).

TABLE 39

Antibody: Antigen binding of lambda at antibodies

| SEQ ID NO: 27 conjugated hAbλTest1 Mutants | LC SEQ ID NO: | Receptor binding ($IC_{50}$, nM) |
|---|---|---|
| hAbλTest | 41 | 1.7 |
| hAbλTest-λκ | 42 | 1.5 |
| hAbλTest-λκJ | 43 | 1.6 |
| hAbλTest1-$S^{188}H/H^{189}S$ | 44 | 1.6 |

Example 29

MAC Generation Using Different Leaving Groups

To investigate if the degree of activation and/or structure of the active ester leaving group was important in defining the directional conjugation effect, a series of alternatively activated ester analogs of SEQ ID NO:27-$K^{11}$(SH)MAC-2PEG-PFP were synthesized. The distribution of the conjugate product was examined by MS of the intact conjugates, and the degree of peptide addition to both the light and heavy chains were also determined by MS following reduction of the intact conjugate and separation of the light and heavy chains.

The structure and designations of the alternatively activated esters are shown below.

The alternatively activated peptides were synthesized using the same strategies and methods previously shown in Examples 1-3. Briefly, each activated group was incorporated into a maleimide-2PEG-Z* linker, where Z* represented the new leaving group replacing PFP. To synthesize the above compounds, a sample (30-40 mg) of the purified ABP-thiol peptide (i.e. ABP with K(SH) as linking residue) was dissolved in anhydrous DMF (2 ml). MAL-PEG2-Z* (20 mg) was added along with N-methylmorpholine (5 mL). The reaction was stirred and monitored at RT by HPLC to follow the time-course of product formation. The complete conversion of starting peptide to activate-ester linked ABP product was observed within 2-6 hrs. The solution was filtered and the product peak directly isolated by semi-preparative HPLC. The products were isolated in yields ranging from approximately 30-50%, after lyophilization.

The conjugation reactions were carried out under the standard conditions. Briefly, the 2.12.1.fx antibody solution was prepared by diluting the 2.12.1.fx solution with sodium phosphate, pH 7.7 to a final concentration of 0.06M. Separately, the peptide solution was prepared by dissolving the peptide to 20 mg/ml in propylene glycol, then diluting this solution to 10 mg/ml with water. For the conjugation reaction, the peptide and antibody solutions were mixed at a 4.1:1 molar ratio for the prescribed period. For the time-course studies, samples of the conjugation solution were quenched at various time points by mixing a sample of the conjugation reaction with a solution of 40 mM succinic acid, 200 mM glycine, pH 4.0 (1:1, v/v). Time-course of the conjugation reactions were followed by HPLC. SEQ ID NO:27 was used as an exemplary peptide.

TABLE 40

Reactive esters-intact conjugation at 24 hrs

SEQ ID NO: 27

-K[11]-MAL-2PEG-Z*

| CA | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2, 3 DCI | Z9 2HI 1,3 D | Z10 4NP | Z11 2,6- DFP | Z12 1 NAP |
|---|---|---|---|---|---|---|---|---|---|---|---|---|
| 0 | 3 | 32 | 17 | 100 | 81 | 38 | 73 | 34 | 20 | 41 | 50 | 100 |
| 1 | 34 | 45 | 43 | 0 | 19 | 45 | 25 | 40 | 36 | 42 | 39 | 0 |
| 2 | 51 | 20 | 30 | 0 | 0 | 16 | 2 | 18 | 31 | 15 | 11 | 0 |
| 3 | 12 | 3 | 11 | 0 | 0 | 2 | 0 | 5 | 12 | 3 | 0 | 0 |

Table 40 shows the final product distribution of the intact conjugates 24 hrs after initiation of the conjugation reaction. The results show that some of esters did not react at all (Z4, Z12), others reacted sluggishly (e.g. Z5), while several gave profiles approaching that of PFP (Z1) (e.g. Z3).

Conjugation Kinetics

The rates of addition over time for each of the final conjugates are shown in Tables 41, 42, 43 and 44. 0CA represents underivatized 2.12.1.fx antibody, whereas 1, 2 or 3CA represents additions of 1, 2 or 3 peptides to the 2.12.1.fx antibody at each of the time periods examined.

TABLE 41

Conjugation kinetics of different Z* groups yielding 0 CA

| 0CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6- DFP | Z12 1 nap |
|---|---|---|---|---|---|---|---|---|---|---|---|---|
| 0 | 84 | 97 | 94 | 100 | 100 | 100 | 100 | 95 | 95 | 96 | 100 | 100 |
| 1 | 5 | 83 | 58 | 100 | 100 | 95 | 96 | 43 | 24 | 79 | 93 | 100 |
| 2 | 4 | 75 | 40 | 100 | 100 | 89 | 93 | 42 | 20 | 67 | 88 | 100 |
| 4 | 4 | 62 | 27 | 100 | 96 | 81 | 88 | 40 | 20 | 54 | 79 | 100 |
| 24 | 3 | 32 | 17 | 100 | 81 | 38 | 73 | 34 | 20 | 41 | 50 | 100 |

TABLE 42

Conjugation kinetics of different Z* groups yielding 1 CA

| 1CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6- DFP | Z12 1 nap |
|---|---|---|---|---|---|---|---|---|---|---|---|---|
| 0 | 16 | 3 | 6 | 0 | 0 | 0 | 0 | 5 | 5 | 5 | 0 | 0 |
| 1 | 38 | 17 | 36 | 0 | 0 | 5 | 4 | 39 | 39 | 21 | 8 | 0 |
| 2 | 37 | 25 | 45 | 0 | 0 | 11 | 7 | 39 | 38 | 29 | 12 | 0 |
| 4 | 33 | 34 | 43 | 0 | 4 | 19 | 12 | 42 | 39 | 37 | 21 | 0 |
| 24 | 34 | 45 | 43 | 0 | 19 | 45 | 25 | 40 | 36 | 42 | 39 | 0 |

TABLE 43

Conjugation kinetics of different Z* groups yielding 2 CA

| 2CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6- DFP | Z12 1 nap |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 49 | 0 | 6 | 0 | 0 | 0 | 0 | 15 | 27 | 0 | 0 | 0 |
| 2 | 50 | 0 | 14 | 0 | 0 | 0 | 0 | 16 | 30 | 4 | 0 | 0 |
| 4 | 52 | 4 | 25 | 0 | 0 | 0 | 0 | 15 | 29 | 9 | 0 | 0 |
| 24 | 51 | 20 | 30 | 0 | 0 | 16 | 2 | 18 | 31 | 15 | 11 | 0 |

TABLE 44

Conjugation kinetics of different Z* groups yielding 3 CA

| 3CA time (hr) | Z1 PFP | Z2 2,3,4 TFP | Z3 2,3,6 TFP | Z4 2,3,6 TCP | Z5 2,6 DCP | Z6 2,4 DCN | Z7 5,7 DCQ | Z8 NH5 NB2,3 DCI | Z9 2HI 1,3 D | Z10 4NP | Z11 2,6- DFP | Z12 1 nap |
|---|---|---|---|---|---|---|---|---|---|---|---|---|
| 0 | 0 | 0 | 0 | 0 | 0 | 0 | 0 | 0 | 0 | 0 | 0 | 0 |
| 1 | 8 | 0 | 0 | 0 | 0 | 0 | 0 | 3 | 11 | 0 | 0 | 0 |
| 2 | 10 | 0 | 2 | 0 | 0 | 0 | 0 | 3 | 12 | 0 | 0 | 0 |
| 4 | 12 | 0 | 5 | 0 | 0 | 0 | 0 | 4 | 12 | 0 | 0 | 0 |
| 24 | 12 | 3 | 11 | 0 | 0 | 2 | 0 | 5 | 12 | 3 | 0 | 0 |

Light and Heavy Chain Distribution

The extent of peptide conjugation for each of the alternatively activated esters was examined separately on the light and heavy chains. Each sample was denatured and disulfide bonds were reduced using guanidine hydrochloride and dithiothreitol. The resulting free light and heavy chains were analyzed using LCMS to determine the conjugation profile on each. The peptide conjugation profile on the light and heavy chain of 2.12.1.fx and mutants are shown in Table 45. Almost all of the activated peptides listed in the table showed reduced conjugation level on light chain compared to the compound using PFP (Z1), except 2,3,6-trifluorophenyl (Z3), which showed a similar level of conjugation. Activated esters derived from N-hydroxysuccinimde (NHS), i.e. N-Hydroxyl-5-norbornene-2,3-dicarboxylic acid imide and 2-hydroxyl-isoindoline-1,3-dione (Z8 and Z9) showed a greater propensity for heavy chain derivatization.

TABLE 45

Summary of activated ester results. Some data also presented in Tables 40-44.

| Z# | Z* Name | Z* Structure | CA | Time course of conjugation adducts [separate 24 hr expt in bold] | | | | | Reduced conjugation at 24 hr | | |
|---|---|---|---|---|---|---|---|---|---|---|---|
| | | | | 0 | 1 | 2 | 4 | 24 | | | |
| 1 | Penta Fluoro Phenyl | | 0 | 84 | 5 | 4 | 4 | 3 | LC | LC + 1CA | L + 2CA |
| | | | 1 | 16 | 38 | 37 | 33 | 34 | 30 | 64 | 7 |
| | | | 2 | 0 | 49 | 50 | 52 | 51 | HC | HC + 1CA | HC + 2CA |
| | | | 3 | 0 | 8 | 10 | 12 | 12 | 94 | 6 | — |
| 2 | 2,3,4-trifluoro-phenyl | | 0 | 97 | 83 | 75 | 62 | 32 | LC | LC + 1CA | L + 2CA |
| | | | 1 | 3 | 17 | 25 | 34 | 45 | 59 | 41 | — |
| | | | 2 | 0 | 0 | 0 | 4 | 20 | HC | HC + 1CA | HC + 2CA |
| | | | 3 | 0 | 0 | 0 | 0 | 3 | 94 | 6 | — |
| 3 | 2,3,6-trifluoro-phenyl | | 0 | 94 | 58 | 40 | 27 | 17 | LC | LC + 1CA | L + 2CA |
| | | | 1 | 6 | 36 | 45 | 43 | 43 | 30 | 64 | 7 |
| | | | 2 | 0 | 6 | 14 | 25 | 30 | HC | HC + 1CA | HC + 2CA |
| | | | 3 | 0 | 0 | 2 | 5 | 11 | 90 | 10 | — |

TABLE 45-continued

Summary of activated ester results. Some data also presented in Tables 40-44.

| Z# | Z* Name | Z* Structure | CA | Time course of conjugation adducts [separate 24 hr expt in bold] | | | | | Reduced conjugation at 24 hr | | |
|---|---|---|---|---|---|---|---|---|---|---|---|
| | | | | 0 | 1 | 2 | 4 | 24 | | | |
| 4 | 2,3,6-trichlorophenyl | | 0 | 100 | 100 | 100 | 100 | 100 | LC | LC + 1CA | L + 2CA |
| | | | 1 | 0 | 0 | 0 | 0 | 0 | 95 | 5 | — |
| | | | 2 | 0 | 0 | 0 | 0 | 0 | HC | HC + 1CA | HC + 2CA |
| | | | 3 | 0 | 0 | 0 | 0 | 0 | 100 | — | — |
| 5 | 2,6 dichlorophenyl | | 0 | 100 | 100 | 100 | 96 | 81 | LC | LC + 1CA | L + 2CA |
| | | | 1 | 0 | 0 | 0 | 4 | 19 | 89 | 11 | — |
| | | | 2 | 0 | 0 | 0 | 0 | 0 | HC | HC + 1CA | HC + 2CA |
| | | | 3 | 0 | 0 | 0 | 0 | 0 | 100 | — | — |
| 6 | 2,4 DiCl Napthalene | | 0 | 100 | 95 | 89 | 81 | 38 | LC | LC + 1CA | L + 2CA |
| | | | 1 | 0 | 5 | 11 | 19 | 45 | 66 | 34 | — |
| | | | 2 | 0 | 0 | 0 | 0 | 16 | HC | HC + 1CA | HC + 2CA |
| | | | 3 | 0 | 0 | 0 | 0 | 2 | 95 | 5 | — |
| 7 | 5,7-dichloroquinolin-8-yl | | 0 | 100 | 96 | 93 | 88 | 73 | LC | LC + 1CA | L + 2CA |
| | | | 1 | 0 | 4 | 7 | 12 | 25 | 92 | 8 | — |
| | | | 2 | 0 | 0 | 0 | 0 | 2 | HC | HC + 1CA | HC + 2CA |
| | | | 3 | 0 | 0 | 0 | 0 | 0 | 95 | 5 | — |
| 8 | N-Hydroxyl-5-norbornene-2,3-dicarboxylic acid imide | | 0 | 95 | 43 | 42 | 40 | 38 | LC | LC + 1CA | L + 2CA |
| | | | 1 | 5 | 39 | 39 | 42 | 40 | 77 | 23 | — |
| | | | 2 | 0 | 15 | 16 | 15 | 18 | HC | HC + 1CA | HC + 2CA |
| | | | 3 | 0 | 3 | 3 | 4 | 5 | 82 | 18 | — |

TABLE 45-continued

Summary of activated ester results. Some data also presented in Tables 40-44.

| Z # | Z* Name | Z* Structure | CA | 0 | 1 | 2 | 4 | 24 | Reduced conjugation at 24 hr | | |
|---|---|---|---|---|---|---|---|---|---|---|---|
| 9 | 2-hy-droxyl-isoindo-line-1,3-dione | | 0 | 95 | 24 | 20 | 20 | 20 | LC | LC + 1CA | L + 2CA |
| | | | 1 | 5 | 39 | 38 | 39 | 36 | 70 | 30 | — |
| | | | 2 | 0 | 27 | 30 | 29 | 31 | HC | HC + 1CA | HC + 2CA |
| | | | 3 | 0 | 11 | 12 | 12 | 12 | 50 | 50 | — |
| 10 | 4-nitro-phenyl | | 0 | 96 | 79 | 67 | 54 | 41 | LC | LC + 1CA | L + 2CA |
| | | | 1 | 5 | 21 | 29 | 37 | 42 | 68 | 32 | — |
| | | | 2 | 0 | 0 | 4 | 9 | 15 | HC | HC + 1CA | HC + 2CA |
| | | | 3 | 0 | 0 | 0 | 0 | 3 | 92 | 8 | — |
| 11 | 2,6-difluoro-phenyl | | 0 | 100 | 93 | 88 | 79 | 50 | | | |
| | | | 1 | 0 | 8 | 12 | 29 | 39 | | | |
| | | | 2 | 0 | 0 | 0 | 0 | 11 | | | |
| | | | 3 | 0 | 0 | 0 | 0 | 0 | | | |
| 12 | 1-naphthyl | | 0 | 100 | 100 | 100 | 100 | 100 | | | |
| | | | 1 | 0 | 0 | 0 | 0 | 0 | | | |
| | | | 2 | 0 | 0 | 0 | 0 | 0 | | | |
| | | | 3 | 0 | 0 | 0 | 0 | 0 | | | |

Example 30

Further examples of alternatively activated esters are shown in Table 45. The time-course of conjugation of several analogs of PFP esters were examined. By decreasing the number and position of the fluorine groups in PFP, less reactive active ester forms can be synthesized and investigated. 2,3,5,6-tetrafluorophenyl ester and 2,4,6-trifluorophenyl ester were both tested after conjugation to SEQ ID NO:27-$K^{11}$(SH)MAC-2PEG-PFP. 1-hydroxyl-pyrrolidine-2,5-dione (NHS) was conjugated to SEQ ID NO:27-$K^{11}$-5PEG-PFP.

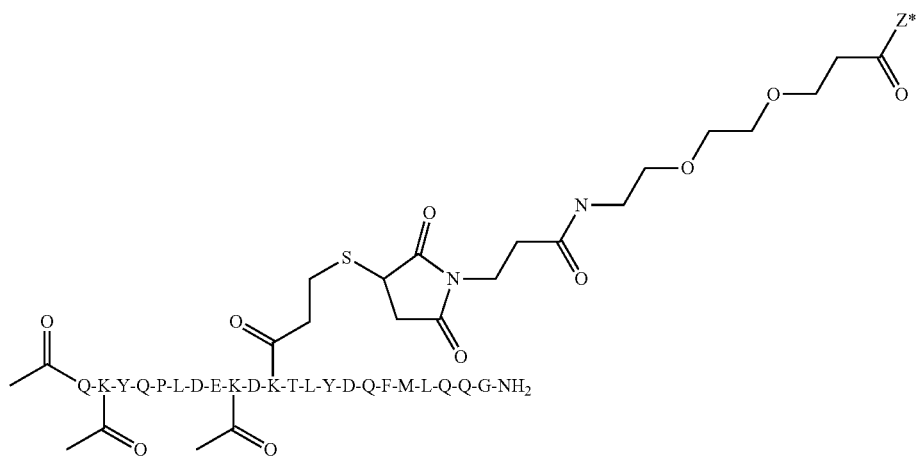

SEQ ID NO: 27-$K^{11}$(SH)MAC-2PEG-PFP

-continued

SEQ ID NO: 27-K[11]-5PEG-PFP

After 2 hrs conjugation, these less activated forms gave lower overall conjugation to 2.12.1.fx than PFP. NHS group also showed lower overall conjugation. NHS and PFP-containing peptides were conjugated to 2.12.1.fx. The reduced forms were analyzed to see the distribution at 2 hrs. PFP showed a much greater propensity for light chain derivatization (77% overall to LC, only 6% to heavy) compared to 1-hydroxyl-pyrrolidine-2,5-dione (NHS) (31% overall to LC, but 34% overall to heavy).

TABLE 46

Alternatively activated esters—further examples

| | Name | Structure | CA | 2 hr | LC | LC + 1CA | LC + 2CA | HC | HC + 1CA | HC + 2CA |
|---|---|---|---|---|---|---|---|---|---|---|
| 1 | Penta Fluoro Phenyl | | 0<br>1<br>2<br>3<br>4 | 3<br>40<br>42<br>14<br>1 | 23 | 72 | 5 | 94 | 6 | 0 |
| 13 | 1-hydroxyl-pyrrolidine-2,5-dione (NHS) | | 0<br>1<br>2<br>3<br>4 | 18<br>44<br>24<br>12<br>3 | 70 | 28 | 3 | 66 | 31 | 3 |
| 14 | 2,3,5,6-tetra-fluoro-phenyl | | 0<br>1<br>2<br>3<br>4 | 21<br>44<br>29<br>5<br>2 | | | | | | |

TABLE 46-continued

Alternatively activated esters—further examples

| | Name | Structure | CA at 2 hr | | Active esters—reduced analysis of conjugation at 2 hr | | | | | | |
|---|---|---|---|---|---|---|---|---|---|---|---|
| | | | CA | 2 hr | LC | LC + 1CA | LC + 2CA | HC | HC + 1CA | HC + 2CA | |
| 15 | 2,4,6-trifluoro-phenyl | | 0 | 80 | | | | | | | |
| | | | 1 | 27 | | | | | | | |
| | | | 2 | 2 | | | | | | | |
| | | | 3 | 0 | | | | | | | |
| | | | 4 | 0 | | | | | | | |

Compounds Z1-Z15 represent a variety of different structural types of active ester. It is enlightening to consider the series of fluorinated aromatic active esters, which have a different number and pattern of substitution of fluorine atoms around the aromatic ring (compounds Z1, Z2, Z3, Z11, Z14 and Z15) and consider how their structure influences their reactivity and propensity for protein derivatization. The kinetics of the antibody-conjugation of these derivatives can be conveniently compared at the 2 hr time-point, when the pentafluorophenyl (Z1) reaction has gone to completion. With an increasing level of fluorine substitution around the ring, there is an increasing level of overall conjugation and a concomitant decrease in unreacted antibody. The rate of reaction is directly related to the pKa of the fluorinated phenol leaving group, with the most acidic phenols giving higher reaction rates. The rates of conjugation are Z1>Z14>Z3>Z15>Z2>Z11. The subtle effects of the fluorine substitution patterns can be seen by comparing compounds Z2, Z3 and Z15.

The structure of the active ester also significantly affected the directionality of the conjugation reaction. In general, the fluorinated aromatic esters showed a marked propensity towards light chain derivatization (principally CLκ-K[188] as previously mentioned). In contrast, several esters based on N-hydroxysuccinimide derivatives (Z8, Z9 and Z13) showed less preference, with often greater levels of heavy chain derivatization observed.

Example 31

The rate of conjugation between MAC-1 (PEG-2-maleimide-mercaptopropionyl linker between the peptide and PFP activating group) and MAC-2 (straight-chained PEG-5 linker between the peptide and PFP activating group) was assessed. Table 47 compares these activated peptides to 2.12.1x. The results show that the activated peptides behave very similarly in terms of the rate and extent of derivatization, despite their slightly different linker structures.

TABLE 47

Comparison of conjugation between MAC-1 and MAC-2

| Intact time | MAC-2 | | | | | MAC-1 | | | | |
|---|---|---|---|---|---|---|---|---|---|---|
| (min) | OCA | 1CA | 2CA | 3CA | 4CA | OCA | 1CA | 2CA | 3CA | 4CA |
| 0 | 72 | 27 | 1 | 0 | 0 | 82 | 18 | 1 | 0 | 0 |
| 10 | 26 | 56 | 17 | 1 | 0 | 29 | 49 | 20 | 2 | 0 |
| 20 | 13 | 53 | 29 | 5 | 0 | 15 | 47 | 33 | 5 | 0 |
| 30 | 9 | 51 | 32 | 8 | 1 | 9 | 43 | 40 | 8 | 0 |
| 40 | 7 | 45 | 39 | 9 | 1 | 8 | 41 | 41 | 8 | 2 |
| 50 | 6 | 43 | 39 | 11 | 1 | 7 | 41 | 42 | 9 | 2 |
| 60 | 5 | 41 | 40 | 11 | 2 | 6 | 36 | 45 | 11 | 2 |
| 70 | 4 | 40 | 40 | 14 | 2 | 6 | 35 | 46 | 11 | 2 |
| 80 | 3 | 38 | 44 | 14 | 2 | 5 | 36 | 47 | 10 | 2 |
| 90 | 4 | 37 | 45 | 13 | 1 | 6 | 35 | 46 | 12 | 2 |
| 100 | 4 | 40 | 41 | 13 | 2 | 6 | 35 | 46 | 11 | 2 |
| 110 | 3 | 40 | 42 | 14 | 1 | 6 | 34 | 46 | 12 | 3 |
| 120 | 4 | 37 | 44 | 13 | 1 | 5 | 35 | 46 | 12 | 2 |

Example 32

Effect of Linker Length

The effect on the final conjugate distribution profile of having different lengths of linker was examined. Compounds were synthesized with different PEG length linkers joining the peptide to the PFP group. The results for the addition to 2.12.1.fx of 0, 1, 2, 3 and 4 peptides are summarized in Table 48. Overall, changing the length of the PEG linker had generally little effect on the distribution of conjugates obtained.

TABLE 48

Effect of linker length

Structure of Example 32 compounds.

Ac-Q-K-Y-Q-P-L-D-E-K-D-K-T-L-Y-D-Q-F-M-L-Q-Q-G-NH₂ with linker containing Y = $-[O-CH_2CH_2]_n-$ attached via acetyl groups to a pentafluorophenyl ester.

| n | CA (%) | | | | |
|---|---|---|---|---|---|
| | 0 | 1 | 2 | 3 | 4 |
| 2 | 8 | 39 | 44 | 8 | 0 |
| 3 | 6 | 34 | 47 | 10 | 2 |
| 5 | 4 | 37 | 44 | 13 | 1 |
| 7 | 4 | 35 | 49 | 11 | 0 |
| 9 | 3 | 28 | 49 | 19 | 2 |
| 13 | 3 | 32 | 54 | 10 | 0 |
| 17 | 6 | 37 | 51 | 7 | 0 |
| 21 | 4 | 43 | 45 | 5 | 2 |
| 25 | 11 | 44 | 38 | 7 | 0 |

Example 33

Conjugation of Alternative Peptide Sequences

To confirm the applicability of the invention across other peptide sequences, SEQ ID NO:60 and SEQ ID NO:61 (Test-peptides-1, and -2) were conjugated. SEQ ID NOs:60 and 61 were subjected to conjugation with 5-PEG-PFP and then the 2.12.1.fx antibody under conditions previously optimized for reaction with SEQ ID NO:27-$K^{11}$-5PEG-PFP. The results of analysis of the conjugation profile and LC/HC conjugation are shown in Table 49. SEQ ID NO:60 and SEQ ID NO:61 both showed directional conjugation to the light chain. On further analysis of the LC/HC distributions, similar profiles to that of MAC-2 were observed, with around 70% LC derivatization and less than 10% on the HC.

TABLE 49

Conjugation profile of SEQ ID NO 60 and SEQ ID NO: 61

| SEQ ID NO: | % CA | | | | | LC % CA | | | HC % CA | | |
|---|---|---|---|---|---|---|---|---|---|---|---|
| | 0 | 1 | 2 | 3 | 4 | LC | LC + 1 | LC + 2 | HC | HC + 1 | HC + 2 |
| 27 | 2 | 24 | 55 | 17 | 3 | 24 | 65 | 11 | 91 | 9 | — |
| 60 | 11 | 39 | 43 | 8 | 0 | 32 | 68 | — | 95 | 5 | — |
| 61 | 8 | 35 | 48 | 10 | 0 | 29 | 71 | — | 94 | 6 | — |

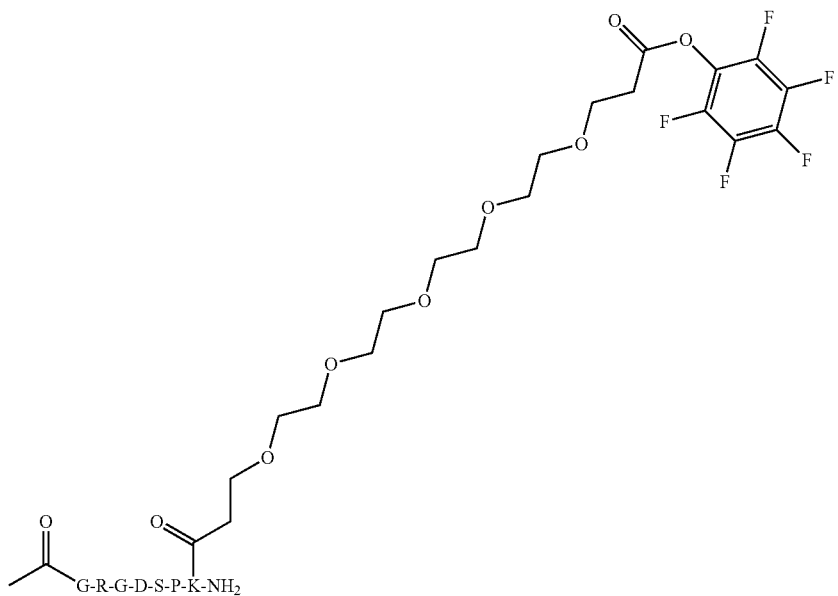

SEQ ID NO: 60/K⁷-5PEG-PFP

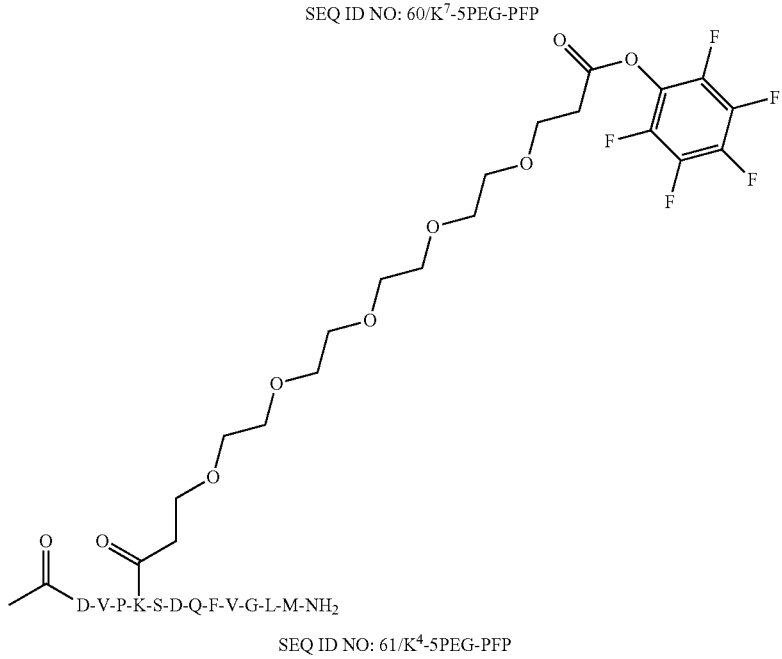

SEQ ID NO: 61/K⁴-5PEG-PFP

Example 34

Peptide mapping experiments were performed on a range of protein/conjugate combinations for the purpose of confirming the important parameters that lead to directional conjugation at $K^{188}$ on antibody light chains. Table 50 lists the results of the peptide mapping experiments performed. For each study parameter, the peptide mapping procedure described earlier was used. "*" indicates a high level of directional conjugation to $K^{188}$-CLκ. "" and to a lesser extent, "*", indicates directional conjugation is still observed, but may show differences, such as slower reaction conditions, less overall conjugation, or averaging at one light chain only, and so may be more suitable to special circumstances, such as generating MACs with between 0.5 and 1.5 peptide per antibody (for example). "-" indicates that these reaction conditions did not appear favorable towards directional conjugation at $K^{188}$-CLκ.

As $K^{188}$-CLκ was observed in MAC-2 to be the location of directional conjugation, peptide mapping studies on alternative parameters focused on this location. Detailed peptide mapping data for each study parameter is not included, but significant conjugation levels at other K residues was not observed, and observations of other MACs were consistent with directional conjugation at $K^{188}$-CLκ.

$K^{188}$R and $K^{188}$A mutations of 2.12.1.fx resulted in the loss of directional conjugation at this site; suggesting an essential role for this specific residue. $K^{190}$R, and $K^{190}$A mutations did not hinder directional conjugation to $K^{188}$, and may even enhance it. Of the other study parameters examined, at least a portion of the sub-type of light chain constant region was observed to have a significant impact on directional conjugation; at least a portion of the light chain sub-type kappa was determined to be necessary. Conjugation onto a lambda light chain sub-type (using an exemplary A containing antibody, hAbλTest1), did not demonstrate directional conjugation. When the LCλ of hAbλTest1 was mutated to a LCκ, directional conjugation at $K^{188}$ was recovered.

TABLE 50

Summary of directional conjugation at $K^{188}CL\kappa$

| Antibody | LC | Mutations/Differences Vs MAC1/2 | SEQ ID NO | Linker | Z* | Directional conjugation |
|---|---|---|---|---|---|---|
| 2.12.1.fx | κ | | 27 | MAL-2PEG | PFP | *** |
| 2.12.1.fx | κ | | 27 | 5PEG | PFP | *** |
| 2.12.1.fx Fab | κ | | 27 | 5PEG | PFP | *** |
| h38C2-IgG1 | κ | | 27 | 5PEG | PFP | *** |
| h38C2-IgG2 | κ | | 27 | 5PEG | PFP | *** |
| hAbλTest | λ | $K^{188}SH$ | 27 | 5PEG | PFP | — |
| hAbκTest1 | κ | | 27 | 5PEG | PFP | *** |
| hAbκTest3 | κ | | 39-mer | 5PEG | PFP | *** |
| hAbλTest | λκ | | 27 | 5PEG | PFP | *** |
| hAbλTest | λκJ | | 27 | 5PEG | PFP | *** |
| 2.12.1.fx | κ | $K^{188}R$ | 27 | 5PEG | PFP | — |
| 2.12.1.fx | κ | $K^{190}R$ | 27 | 5PEG | PFP | *** |
| 2.12.1.fx | κ | $K^{188}R/R^{190}R$ | 27 | 5PEG | PFP | — |
| 2.12.1.fx | κ | $D^{151}A$ | 27 | 5PEG | PFP | ** |
| 2.12.1.fx | κ | $K^{188}A$ | 27 | 5PEG | PFP | — |
| 2.12.1.fx | κ | $H^{189}A$ | 27 | 5PEG | PFP | — |
| 2.12.1.fx | κ | $K^{190}A$ | 27 | 5PEG | PFP | *** |
| 2.12.1.fx | κ | $D^{151}A/H^{189}A$ | 27 | 5PEG | PFP | — |
| hAbλTest1 | λ | $S^{188}H/H^{189}S$ | 27 | 5PEG | PFP | — |
| 2.12.1.fx | κ | | 39-mer | 5PEG | PFP | *** |
| 2.12.1.fx | κ | | 60 | 5PEG | PFP | *** |
| 2.12.1.fx | κ | | 61 | 5PEG | PFP | *** |
| h38C2-IgG2 | κ | | 39-mer | 5PEG | PFP | *** |
| 2.12.1.fx Fab | κ | | biotin | 5PEG | PFP | *** |
| 2.12.1.fx | κ | | 27 | MAL-2PEG | PFP | *** |
| 2.12.1.fx | κ | | 27 | MAL-2PEG | 2,3,4 TFP (2) | ** |
| 2.12.1.fx | κ | | 27 | MAL-2PEG | 2,3,6 TFP (3) | ** |
| 2.12.1.fx | κ | | 27 | MAL-2PEG | 2,3,6 TCP (4) | — |
| 2.12.1.fx | κ | | 27 | MAL-2PEG | 2,6 DCP (5) | — |
| 2.12.1.fx | κ | | 27 | MAL-2PEG | 2,4 DCN (6) | * |
| 2.12.1.fx | κ | | 27 | MAL-2PEG | 5,7 DCQ (7) | — |
| 2.12.1.fx | κ | | 27 | MAL-2PEG | NH-5-N2,3DI (8) | * |
| 2.12.1.fx | κ | | 27 | MAL-2PEG | 2Hi1,3 DIO (9) | * |
| 2.12.1.fx | κ | | 27 | MAL-2PEG | 4NP (10) | ** |
| 2.12.1.fx | κ | | 27 | MAL-2PEG | 2,6 DFP (11) | ** |
| 2.12.1.fx | κ | | 27 | MAL-2PEG | NAP (12) | — |
| 2.12.1.fx | κ | | 27 | MAL-2PEG | 1HP 2,5D (13) | * |
| 2.12.1.fx | κ | | 27 | MAL-2PEG | 2,3,5,6 TFP (14) | ** |
| 2.12.1.fx | κ | | 27 | MAL-2PEG | 2,4,6 TFP (15) | ** |
| 2.12.1.fx | κ | | 27 | MAL-2PEG | Squarate | * |
| 2.12.1.fx | κ | | 27 | MAL-2PEG | AZD | * |

TABLE 50-continued

Summary of directional conjugation at K$^{188}$CLκ

| Antibody | LC | Mutations/ Differences Vs MAC1/2 | SEQ ID NO | Linker | Z* | Directional conjugation |
|---|---|---|---|---|---|---|
| 2.12.1.fx | κ | | 27 | PEG 2-17 | PFP | *** |
| 2.12.1.fx | κ | | 27 | PEG 17-21 | PFP | ** |
| 2.12.1.fx | κ | | 27 | PEG 25 | PFP | ** |

The invention thus has been disclosed broadly and illustrated in reference to representative embodiments described above. Those skilled in the art will recognize that various modifications can be made to the present invention without departing from the spirit and scope thereof. All publications, patent applications, and issued patents, are herein incorporated by reference to the same extent as if each individual publication, patent application or issued patent were specifically and individually indicated to be incorporated by reference in its entirety. Definitions that are contained in text incorporated by reference are excluded to the extent that they contradict definitions in this disclosure.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. In particular, any aspect of the invention described in the claims, alone or in combination with one or more additional claims and/or aspects of the description, is to be understood as being combinable with other aspects of the invention set out elsewhere in the claims and/or description and/or sequence listings and/or drawings In so far as specific examples found herein do not fall within the scope of an invention, said specific example may be explicitly disclaimed.

The use of the term "or" in the claims is used to mean "and/or" unless explicitly indicated to refer to alternatives only or the alternative are mutually exclusive, although the disclosure supports a definition that refers to only alternatives and "and/or." As used herein the specification, "a" or "an" may mean one or more, unless clearly indicated otherwise. As used herein in the claim(s), when used in conjunction with the word "comprising," the words "a" or "an" may mean one or more than one. As used herein "another" may mean at least a second or more. Unless otherwise defined herein, scientific and technical terms used in connection with the present invention shall have the meanings that are commonly understood by those of ordinary skill in the art. Further, unless otherwise required by context, singular terms shall include pluralities and plural terms shall include the singular. The words "comprises/comprising" and the words "having/including" when used herein with reference to the present invention are used to specify the presence of stated features, integers, steps or components but does not preclude the presence or addition of one or more other features, integers, steps, components or groups thereof.

SEQUENCE LIST

| SEQ ID: | Description | Sequence |
|---|---|---|
| 1 | Heavy Chain 2.12.1 | QAQLVESGGG LVKPGGSLRL SCAASGFTFS DYYMSWIRQA PGKGLEWVSY ISSSGSTRDY ADSVKGRFTI SRDNAKNSLY LQMNSLRAED TAVYYCVRDG VETTFYYYYY GMDVWGQGTT VTVSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE CPPCPAPPVA GPSVFLFPPK PKDTLMISRT PEVTCVVVDV SHEDPEVQFN WYVDGVEVHN AKTKPREEQF NSTFRVVSVL TVVHQDWLNG KEYKCKVSNK GLPAPIEKTI SKTKGQPREP QVYTLPPSRE EMTKNQVSLT CLVKGFYPSD IAVEWESNGQ PENNYKTTPP MLDSDGSFFL YSKLTVDKSR WQQGNVFSCS VMHEALHNHY TQKSLSLSPG K |
| 2 | Light Chain 2.12.1 | DIQMTQSPSS LSASVGDRVT FTCRASQDIR RDLGWYQQKP GKAPKRLIYA ASRLQSGVPS RFSGSGSGTE FTLTISSLQP EDFATYYCLQ HNNYPRTFGQ GTEVEIIRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |

-continued

SEQUENCE LIST

| SEQ ID: | Description | Sequence |
|---|---|---|
| 3 | Heavy Chain 2.12.1.fx | QVQLVESGGG LVKPGGSLRL SCAAS*GFTFS DYYMS*WIRQA PGKGLEWVS*Y ISSSGSTRDY ADSVKGRFTI* SRDNAKNSLY LQMNSLRAED TAVYYCVRD*G VETTFYYYY GMDVWGQGTT* VT*VSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE CPPCPAPPVA GPSVFLFPPK PKDTLMISRT PEVTCVVVDV SHEDPEVQFN WYVDGVEVHN AKTKPREEQF NSTFRVVSVL TVVHQDWLNG KEYKCKVSNK GLPAPIEKTI SKTKGQPREP QVYTLPPSRE EMTKNQVSLT CLVKGFYPSD IAVEWESNGQ PENNYKTTPP MLDSDGSFFL YSKLTVDKSR WQQGNVFSCS VMHEALHNHY TQKSLSLSPG K* |
| 4 | Light Chain 2.12.1.fx | DIQMTQSPSS LSASVGDRVT ITCRASQDIR RDLGWYQQKP GKAPKRLIYA ASRLQSGVPS RFSGSGSGTE FTLTISSLQP EDFATYYCLQ HNNYPRTFGQ GTKLVIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC |
| 5 | Constant heavy (CH) 2.12.1 & 2.12.1.fx. | VSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE CPPCPAPPVA GPSVFLFPPK PKDTLMISRT PEVTCVVVDV SHEDPEVQFN WYVDGVEVHN AKTKPREEQF NSTFRVVSVL TVVHQDWLNG KEYKCKVSNK GLPAPIEKTI SKTKGQPREP QVYTLPPSRE EMTKNQVSLT CLVKGFYPSD IAVEWESNGQ PENNYKTTPP MLDSDGSFFL YSKLTVDKSR WQQGNVFSCS VMHEALHNHY TQKSLSLSPG K |
| 6 | Consensus VH 2.12.1 & 2.12.1.fx. $x^2$ = V/A | QxQLVESGGG LVKPGGSLRL SCAASGFTFS DYYMSWIRQA PGKGLEWVSY ISSSGSTRDY ADSVKGRFTI SRDNAKNSLY LQMNSLRAED TAVYYCVRDG VETTFYYYY GMDVWGQGTT VT |
| 7 | VHCDR1 2.12.1/2.12.1.fx | GFTFSDYYMS |
| 8 | VHCDR2 2.12.1/2.12.1.fx | YISSSGSTRD YADSV |
| 9 | VHCDR3 2.12.1/2.12.1.fx | DGVETTFYYY YYGMDV |
| 10 | VHFR1 2.12.1/2.12.1.fx | QxQLVESGGG LVKPGGSLRL SCAAS [$x^2$ = V/A] |
| 11 | VHFR1 2.12.1.fx | QVQLVESGGG LVKPGGSLRL SCAAS |
| 12 | VHFR2 2.12.1/2.12.1.fx | WIRQAPGKGL EWVS |
| 13 | VHFR3 2.12.1/2.12.1.fx | KGRFTISRDN AKNSLYLQMN SLRAEDTAVY YCVR |
| 14 | VHFR4 2.12.1/2.12.1.fx | WGQGTTVT |
| 15 | Human CLK 1-106 K$^{80}$ is bold and underlined. | TVAAPSVFIF PPSDEQLKSG TASVVCLLNN FYPREAKVQW KVDNALQSGN SQESVTEQDS KDSTYSLSST LTLSKADYEK HKVYACEVTH QGLSSPVTKS FNRGEC |
| 16 | Consensus CL 2.12.1 and | DIQMTQSPSS LSASVGDRVT xTCRASQDIR RDLGWYQQKP GKAPKRLIYA |

SEQUENCE LIST

| SEQ ID: | Description | Sequence |
|---|---|---|
| | 2.12.1.fx $x^{21}$ = I/F, $x^{107}$ = K/I | ASRLQSGVPS RFSGSGSGTE FTLTISSLQP EDFATYYCLQ HNNYPRTFGQ GTKLVIxR |
| 17 | VLCDR1 2.12.1/2.12.1.fx | CRASQDIRRD LGW |
| 18 | VLCDR2 2.12.1/2.12.1.fx | IYAASRL |
| 19 | VLCDR3 2.12.1/2.12.1.fx | LQHNNYPRT |
| 20 | VLFR1 2.12.1/2.12.1.fx | DIQMTQSPSS LSASVGDRVT xT [$X^{21}$ = I/F] |
| 21 | VLFRR1 2.12.1.fx | DIQMTQSPSS LSASVGDRVT IT |
| 22 | VLFR2 2.12.1/2.12.1.fx | YQQKPGKAPK RL |
| 23 | VLFR3 2.12.1/2.12.1.fx | QSGVPSRFSG SGSGTEFTLT ISSLQPEDFA TYYC [x10 = K/I] |
| 24 | VLFR4 2.12.1/2.12.1.fx | FGQGTKLVIxR |
| 25 | 2.12.1.fx | VLFR4FGQGTKLVIK R |
| 26 | ABP X2 = AcK X9 = AcK/L | QxYQPLDExD KTLYDQFMLQ QG |
| 27 | ABP X2 = AcK X9 = AcK | QxYQPLDExD KTLYDQFMLQ QG |
| 28 | ABP X2 = AcK | QxYQPLDELD KTLYDQFMLQ QG |
| 29 | ABP X2 = AcK X11 = AcK | QxYQPLDEKD xTLYDQFMLQ QG |
| 30 | ABP X2 = AcK X11 = AcK | QxYQPLDELD xTLYDKFMLQ QG |
| 31 | ABP X2 = AcK X11 = AcK | QxYQPLDELD xTLYDQFKLQ QG |
| 32 | ABP X2 = AcK X11 = AcK | QxYQPLDELD xTLYDQFMKQ QG |
| 33 | 2.12.1.fx $K^{188}R$ light chain sequence | DIQMTQSPSS LSASVGDRVT ITCRASQDIR RDLGWYQQKP GKAPKRLIYA ASRLQSGVPS RFSGSGSGTE FTLTISSLQP EDFATYYCLQ HNNYPRTFGQ GTKVEIKRTV AAPSVFIFPP SDEQLKSGTA SVVCLLNNFY PREAKVQWKV DNALQSGNSQ ESVTEQDSKD STYSLSSTLT LSKADYERHK VYACEVTHQG LSSPVTKSFN RGEC |
| 34 | 2.12.1.fx $K^{190}R$ light chain sequence | DIQMTQSPSS LSASVGDRVT ITCRASQDIR RDLGWYQQKP GKAPKRLIYA ASRLQSGVPS RFSGSGSGTE FTLTISSLQP EDFATYYCLQ HNNYPRTFGQ GTKVEIKRTV AAPSVFIFPP SDEQLKSGTA SVVCLLNNFY PREAKVQWKV DNALQSGNSQ ESVTEQDSKD STYSLSSTLT LSKADYEKHR VYACEVTHQG LSSPVTKSFN RGEC |
| 35 | 2.12.1.fx $K^{188}R/K^{190}R$ light chain sequence | DIQMTQSPSS LSASVGDRVT ITCRASQDIR RDLGWYQQKP GKAPKRLIYA ASRLQSGVPS RFSGSGSGTE FTLTISSLQP EDFATYYCLQ HNNYPRTFGQ GTKVEIKRTV AAPSVFIFPP SDEQLKSGTA SVVCLLNNFY PREAKVQWKV DNALQSGNSQ ESVTEQDSKD STYSLSSTLT LSKADYERHR VYACEVTHQG LSSPVTKSFN RGEC |

SEQUENCE LIST

| SEQ ID: | Description | Sequence |
|---|---|---|
| 36 | 2.12.1.fx D$^{151}$A light chain sequence | DIQMTQSPSS LSASVGDRVT ITCRASQDIR<br>RDLGWYQQKP GKAPKRLIYA ASRLQSGVPS<br>RFSGSGSGTE FTLTISSLQP EDFATYYCLQ<br>HNNYPRTFGQ GTKVEIKRTV AAPSVFIFPP<br>SDEQLKSGTA SVVCLLNNFY PREAKVQWKV<br><u>A</u>NALQSGNSQ ESVTEQDSKD STYSLSSTLT<br>LSKADYEKHK VYACEVTHQG LSSPVTKSFN RGEC |
| 37 | 2.12.1.fx K$^{188}$A light chain sequence | DIQMTQSPSS LSASVGDRVT ITCRASQDIR<br>RDLGWYQQKP GKAPKRLIYA ASRLQSGVPS<br>RFSGSGSGTE FTLTISSLQP EDFATYYCLQ<br>HNNYPRTFGQ GTKVEIKRTV AAPSVFIFPP<br>SDEQLKSGTA SVVCLLNNFY PREAKVQWKV<br>DNALQSGNSQ ESVTEQDSKD STYSLSSTLT<br>LSKADYE<u>A</u>HK VYACEVTHQG LSSPVTKSFN RGEC |
| 38 | 2.12.1.fx H$^{189}$A light chain sequence | DIQMTQSPSS LSASVGDRVT ITCRASQDIR<br>RDLGWYQQKP GKAPKRLIYA ASRLQSGVPS<br>RFSGSGSGTE FTLTISSLQP EDFATYYCLQ<br>HNNYPRTFGQ GTKVEIKRTV AAPSVFIFPP<br>SDEQLKSGTA SVVCLLNNFY PREAKVQWKV<br>DNALQSGNSQ ESVTEQDSKD STYSLSSTLT<br>LSKADYEK<u>A</u>K VYACEVTHQG LSSPVTKSFN RGEC |
| 39 | 2.12.1.fx K$^{190}$A light chain sequence | DIQMTQSPSS LSASVGDRVT ITCRASQDIR<br>RDLGWYQQKP GKAPKRLIYA ASRLQSGVPS<br>RFSGSGSGTE FTLTISSLQP EDFATYYCLQ<br>HNNYPRTFGQ GTKVEIKRTV AAPSVFIFPP<br>SDEQLKSGTA SVVCLLNNFY PREAKVQWKV<br>DNALQSGNSQ ESVTEQDSKD STYSLSSTLT<br>LSKADYEKH<u>A</u> VYACEVTHQG LSSPVTKSFN RGEC |
| 40 | 2.12.1.fx D$^{151}$A/H$^{189}$A light chain sequence | DIQMTQSPSS LSASVGDRVT ITCRASQDIR<br>RDLGWYQQKP GKAPKRLIYA ASRLQSGVPS<br>RFSGSGSGTE FTLTISSLQP EDFATYYCLQ<br>HNNYPRTFGQ GTKVEIKRTV AAPSVFIFPP<br>SDEQLKSGTA SVVCLLNNFY PREAKVQWKV<br><u>A</u>NALQSGNSQ ESVTEQDSKD STYSLSSTLT<br>LSKADYEK<u>A</u>K VYACEVTHQG LSSPVTKSFN RGEC |
| 41 | hAbλTest LC Light chain constant region (lambda) | FGGGTQLTVL GQPKAAPSVT LFPPSSEELQ<br>ANKATLVCLI SDFYPGAVTV AWKADSSPVK<br>AGVETTTPSK QSNNKYAASS YLSLTPEQWK<br>SHRSYSCQVT HEGSTVEKTV APTECS |
| 42 | hAbλTest-λκ Light chain constant region (kappa swap) | FGGGTQLTVL *RTVAAPSVFI FPPSDEQLKS*<br>*GTASVVCLLN NFYPREAKVQ WKVDNALQSG*<br>*NSQESVTEQD SKDSTYSLSS TLTLSKADYE*<br>*KHKVYACEVT HQGLSSPVTK SFNRGEC* |
| 43 | hAbλTest-λκJ Light chain constant region (lkappa & J) | FGGGT*KVEIK RTVAAPSVFI FPPSDEQLKS*<br>*GTASVVCLLN NFYPREAKVQ WKVDNALQSG*<br>*NSQESVTEQD SKDSTYSLSS TLTLSKADYE*<br>*KHKVYACEVT HQGLSSPVTK SFNRGEC* |
| 44 | hAbλTest light chain constant region S$^{188}$H/H$^{189}$S | FGGGTQLTVL GQPKAAPSVT LFPPSSEELQ<br>ANKATLVCLI SDFYPGAVTV AWKADSSPVK<br>AGVETTTPSK QSNNKYAASS YLSLTPEQWK<br><u>HS</u>RSYSCQVT HEGSTVEKTV APTECS |
| 45 | Human CLK 1-106 X$^{82}$ = any aa except p X45 = V/A  X83 = L/V | TVAAPSVFIF PPSDEQLKSG TASVVCLLNN<br>FYPREAKVQW KVDNxLQSGN SQESVTEQDS<br>KDSTYSLSST LTLSKADYEK HxxYACEVTH<br>QGLSSPVTKS FNRGEC |
| 46 | Human CLK 1-106 X45 = V/A  X83 = L/V | TVAAPSVFIF PPSDEQLKSG TASVVCLLNN<br>FYPREAKVQW KVDNxLQSGN SQESVTEQDS<br>KDSTYSLSST LTLSKADYEK HKxYACEVTH<br>QGLSSPVTKS FNRGEC |
| 47 | Human CLK 1-106 X$^{82}$ = any aa except p | TVAAPSVFIF PPSDEQLKSG TASVVCLLNN<br>FYPREAKVQW KVDNALQSGN SQESVTEQDS<br>KDSTYSLSST LTLSKADYEK HxVYACEVTH<br>QGLSSPVTKS FNRGEC |

-continued

| SEQ ID: | Description | Sequence |
|---|---|---|
| 48 | Human CLλ | GQPKAAPSVT LFPPSSEELQ ANKATLVCLI SDFYPGAVTV AWKADSSPVK AGVETTTPSK QSNNKYAASS YLSLTPEQWK SHRSYSCQVT HEGSTVEKTV APTECS |
| 49 | Murine Light chain Kappa constant region mCLκ | ADAAPTVSIF PPSSEQLTSG GASVVCFLNN FYPRDINVKW KIDGSERQNG VLNSWTDQDS KDSTYSMSST LTLTKDEYER HNSYTCEATH KTSTSPIVKS FNRNEC |
| 50 | 2.12.1.fx Fab Heavy chain | QVQLVESGGG LVKPGGSLRL SCAASGFTFS DYYMSWIRQA PGKGLEWVSY ISSSGSTRDY ADSVKGRFTI SRDNAKNSLY LQMNSLRAED TAVYYCVRDG VETTFYYYYY GMDVWGQGTT VTVSSASTKG PSVFPLAPCS RSTSESTAAL GCLVKDYFPE PVTVSWNSGA LTSGVHTFPA VLQSSGLYSL SSVVTVPSSN FGTQTYTCNV DHKPSNTKVD KTVERKCCVE |
| 51 | h38C2-IgG1 light chain | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 52 | h38C2-IgG1 heavy chain | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS TKGPSVFPLA PSSKSTSGGT AALGCLVKDY FPEPVTVSWN SGALTSGVHT FPAVLQSSGL YSLSSVVTVP SSSLGTQTYI CNVNHKPSNT KVDKRVEPKS CDKTHTCPPC PAPELLGGPS VFLFPPKPKD TLMISRTPEV TCVVVDVSHE DPEVKFNWYV DGVEVHNAKT KPREEQYNST YRVVSVLTVL HQDWLNGKEY KCKVSNKALP APIEKTISKA KGQPREPQVY TLPPSREEMT KNQVSLTCLV KGFYPSDIAV EWESNGQPEN NYKTTPPVLD SDGSFFLYSK LTVDKSRWQQ GNVFSCSVMH EALHNHYTQK SLSLSPGK |
| 53 | h38C2-IgG2 light chain | ELQMTQSPSS LSASVGDRVT ITCRSSQSLL HTYGSPYLNW YLQKPGQSPK LLIYKVSNRF SGVPSRFSGS GSGTDFTLTI SSLQPEDFAV YFCSQGTHLP YTFGGGTKVE IKRTVAAPSV FIFPPSDEQL KSGTASVVCL LNNFYPREAK VQWKVDNALQ SGNSQESVTE QDSKDSTYSL SSTLTLSKAD YEKHKVYACE VTHQGLSSPV TKSFNRGEC |
| 54 | h38C2-IgG2 heavy chain | EVQLVESGGG LVQPGGSLRL SCAASGFTFS NYWMSWVRQS PEKGLEWVSE IRLRSDNYAT HYAESVKGRF TISRDNSKNT LYLQMNSLRA EDTGIYYCKT YFYSFSYWGQ GTLVTVSSAS TKGPSVFPLA PCSRSTSEST AALGCLVKDY FPEPVTVSWN SGALTSGVHT FPAVLQSSGL YSLSSVVTVP SSNFGTQTYT CNVDHKPSNT KVDKTVERKC CVECPPCPAP PVAGPSVFLF PPKPKDTLMI SRTPEVTCVV VDVSHEDPEV QFNWYVDGVE VHNAKTKPRE EQFNSTFRVV SVLTVVHQDW LNGKEYKCKV SNKGLPSSIE KTISKTKGQP REPQVYTLPP SREEMTKNQV SLTCLVKGFY PSDIAVEWES NGQPENNYKT TPPMLDSDGS FFLYSKLTVD KSRWQQGNVF SCSVMHEALH NHYTQKSLSL SPGK |
| 55 | VL h38C2 | ELQMTQSPSS LSASVGDRVT ITC*RSSQSLL HTYGSPYLNW* YLQKPGQSPK LLIYKVSNRF SGVPSRFSGS GSGTDFTLTI SSLQPEDFAV YFCSQGTHLP YTFGGGTKVE IK |
| 56 | VH h38C2 | EVQLVESGGG LVQPGGSLRL SCAASGFTFS NYWMSWVRQS PEKGLEWVSE IRLRSDNYAT |

SEQUENCE LIST

| SEQ ID: | Description | Sequence |
|---|---|---|
| | | HYAESVKGRF TISRDNSKNT LYLQMNSLRA |
| | | EDTGIYYCKT YFYSFSYWGQ GTLVTVSS |
| 57 | VL m38C2 | DVVMTQTPLS LPVRLGDQAS ISCRSSQSLL |
| | | HTYGSPYLNW YLQKPGQSPK LLIYKVSNRF |
| | | SGVPDRFSGS GSGTDFTLRI SRVEAEDLGV |
| | | YFCSQGTHLP YTFGGGTKLE IK |
| 58 | VH m38C2 | EVKLVESGGG LVQPGGTMKL SCEISGLTFR |
| | | NYWMSWVRQS PEKGLEWVAE IRLRSDNYAT |
| | | HYAESVKGKF TISRDDSKSR LYLQMNSLRT |
| | | EDTGIYYCKY YFYSFSYWGQ GTLVTVSA |
| 59 | (Gly$_4$ Ser)$_3$ | GGGGSGGGG SGGGGS |
| 60 | Test peptide-1 | GRGDSPK |
| 61 | Test peptide-2 | DVPKSDQFVG LM |

The invention claimed is:

1. A composition comprising a multifunctional antibody conjugate (MAC), the MAC comprising
   (i) an antibody or antigen binding portion thereof, comprising at least a fragment of a light chain constant kappa region (CLκ) comprising $K^{188}$ according to Kabat numbering;
   (ii) a linker comprising the formula X-Y-Z, wherein Z is a group of formula

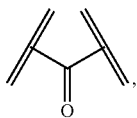

and is covalently connected to the antibody through the ε-amino group of the side chain of $K^{188}$, Y is a linear or branched biologically compatible connecting chain, and X is a group covalently connected to at least one Effector Moiety,
and pharmaceutically acceptable salts, stereoisomers, tautomers, solvates, and prodrugs thereof,
wherein the MAC is prepared by covalently attaching the Effector Moiety to a linker terminating in an activated ester with a leaving group Z* of the formula:

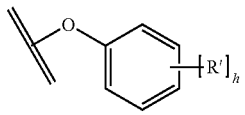

where $R^1$ is F, and h=3, 4 or 5,
and reacting the Effector Moiety-Linker-Z* complex so formed with the antibody, wherein at least about 50% of the Effector Moiety in the composition or sample is conjugated to K188-CLK.

2. The composition as claimed in claim 1, further comprising $H^{18[9]}$-CLκ.

3. The composition as claimed in claim 1, further comprising $D^{151}$-CLκ.

4. The composition as claimed in claim 1, wherein the CLκ region comprises at least residues 62-103 of SEQ ID NO:15, SEQ ID NO:45, SEQ ID NO:46, or SEQ ID NO:47.

5. The composition as claimed in claim 1, wherein the CLκ region comprises at least residues 1-106 of SEQ ID NO: 15, SEQ ID NO:45, SEQ ID NO:46, or SEQ ID NO:47.

6. The composition as claimed in claim 1, wherein the Effector Moiety is only conjugated to the MAC at $K^{188}$ CLκ.

7. The composition as claimed in claim 1, wherein the Effector Moiety is conjugated to the MAC at $K^{188}$ CLκ on at least one light chain, and at one other location on the antibody.

8. The composition as claimed in claim 1, wherein the Effector Moiety is conjugated to CLκ $K^{188}$ on both light chains.

9. The composition as claimed in claim 1, wherein the Effector Moiety is conjugated to CLκ $K^{188}$ on one light chain only.

10. The composition as claimed in claim 1, wherein the Effector Moiety is a therapeutic agent, protein, peptide, nucleic acid, aptamer, small molecule, protein agonist, protein antagonist, metabolic regulator, hormone, toxin, growth factor, or diagnostic agent, such that when the at least one Effector Moiety is a protein or peptide, the X group of the linker is covalently attached to the amino terminus, carboxyl terminus, or side chain of a peptide-linking residue in the protein or peptide, and wherein said peptide-linking residue may be selected from the group consisting of K, R, C, T, Y, S, Dap, Dab, K(SH), and homologs of K and C.

11. The composition as claimed in claim 1, wherein Y, X-Y, Y-Z, or X-Y-Z is selected from the group consisting of:

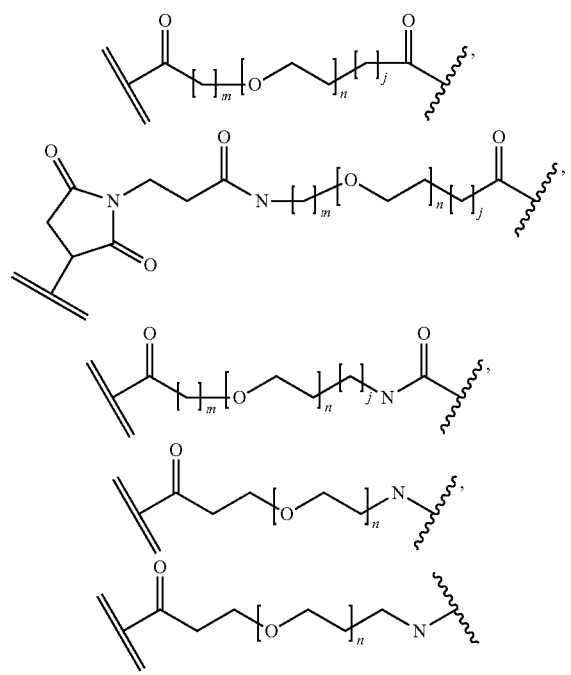

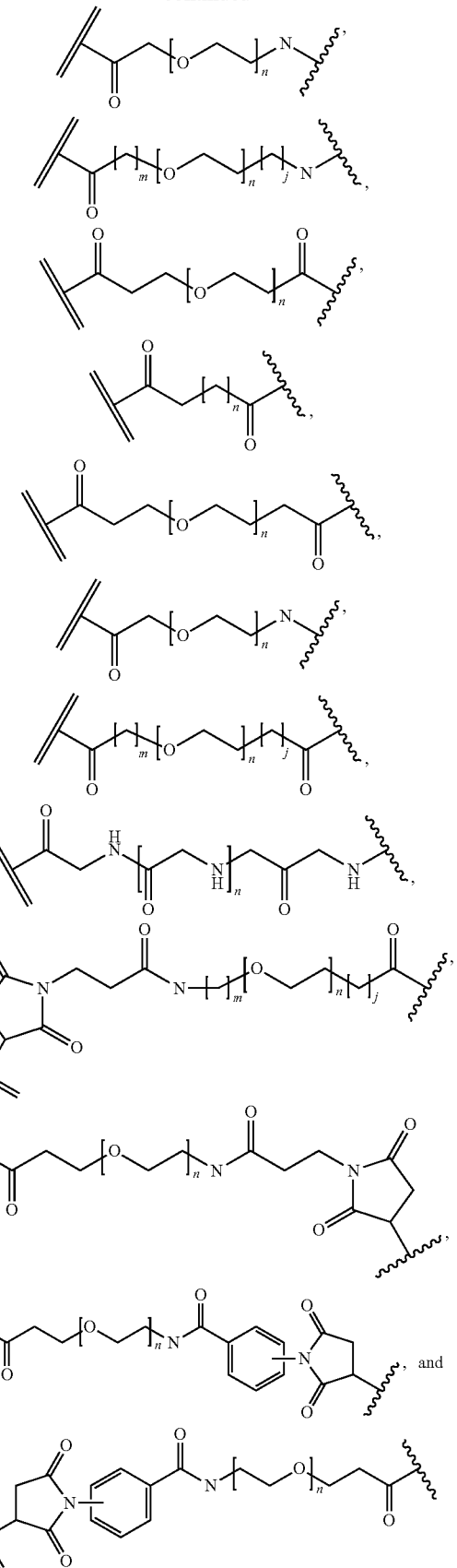

wherein m, n and j are each independently a range whose lower limits are selected from the group consisting of 0, 1, 2, 3, 4, 5, 6, 7, 8, 9, 10, 11, 12, 13, 14, 15, 16, 17, 18, 19, and 20, and whose upper limit is selected from the group consisting of 2, 3, 4, 5, 6, 7, 8, 9, 10, 11, 12, 13, 14, 15, 16, 17, 18, 19, 20, 21, 22, 23, 24, 25, 26, 27, 28, 29, and 30, and wherein the overall length of the linker does not exceed 200 atoms.

12. The composition as claimed in claim 11, wherein the overall length of the linker does not exceed 60 atoms.

13. The composition as claimed in claim 1, wherein the antibody is selected from the group consisting of, Rituximab, Cetuximab, Infliximab, Adalimumab, Natalizumab, Omalizumab, Ranibizumab, Palivizumab, aldolase catalytic antibodies, and full length Fab, Fab', F(ab')2, Fv, dsFv, scFv, VH, diabody, or minibody versions thereof.

14. The MAC as claimed in claim 1, wherein the antibody comprises or SEQ ID NO:3 & SEQ ID NO:4, or SEQ ID NO:51 & SEQ ID NO:52, or SEQ ID NO:53 & SEQ ID NO:54, or a HC region comprising SEQ ID NO:5, a VH region comprising SEQ ID NO:6, a VL region comprising SEQ ID NO:16, and a CL region comprising one of SEQ ID NO:15, SEQ ID NO:45, SEQ ID NO:46 or SEQ ID NO:47.

15. The MAC as claimed in claim 1, wherein the Effector Moiety is an Ang2 binding peptide, and may be selected from the group consisting of SEQ ID NO:26, SEQ ID NO:27, SEQ ID NO:28, SEQ ID NO:29, SEQ ID NO:30, SEQ ID NO:31, and SEQ ID NO:32.

16. The MAC as claimed in claim 15, comprising the structure:

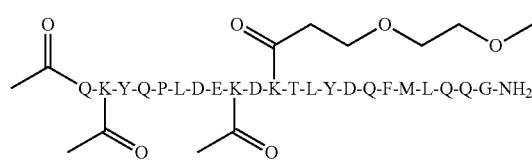

wherein $K^{188}$-CLκ is a covalent link to the side chain of the said $K^{188}$-CLκ, and the antibody comprises SEQ ID NO:3 and SEQ ID NO:4.

17. The composition as claimed in claim 1, wherein at least about 80% of the Effector Moiety in the composition or sample is conjugated to $K^{188}$-CLκ.

18. A composition comprising the MAC as claimed in claim 1, wherein at least about 50% of the antibody comprises an Effector Moiety covalently attached to $K^{188}$-CLκ.

19. The composition as claimed in claim 18, wherein at least about 80% of the antibody comprises an Effector Moiety covalently attached to $K^{188}$-CLκ.

20. The composition comprising the MAC as claimed in claim 1, wherein at least about 70% of the heavy chain molecules are unconjugated with the Effector Moiety.

21. The composition comprising the MAC as claimed in claim 1, wherein the average number of conjugations per antibody is between about 0.5 and about 1.5.

22. The composition comprising the MAC as claimed in claim 1, wherein the average number of conjugations per antibody is between about 1.5 and about 2.5.

23. A method for preparing a Multifunctional Antibody Conjugate (MAC), said MAC comprising (i) an antibody or antigen binding portion thereof, comprising at least a fragment of a light chain constant kappa region (CLκ) comprising $K^{188}$ according to Kabat numbering; and (ii) a linker comprising the formula X-Y-Z, wherein Z is a group of formula

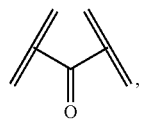

and is covalently connected to the antibody through the ε-amino group of the side chain of $K^{188}$, Y is a linear or branched biologically compatible connecting chain, and X is a group covalently connected to at least one Effector Moiety, and pharmaceutically acceptable salts, stereoisomers, tautomers, solvates, and prodrugs thereof, said method comprising a conjugation reaction comprising covalently attaching the Effector Moiety to a linker terminating in a leaving group Z* of the formula:

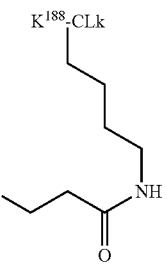

where R1 is F or Cl, h=2, 3, 4 or 5 and reacting the Effector Moiety-Linker-Z* complex so formed with the antibody.

24. The method as claimed in claim 23, wherein Z* is selected from the group consisting of:

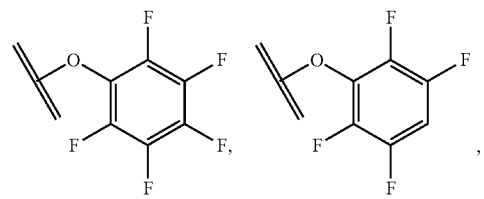

-continued

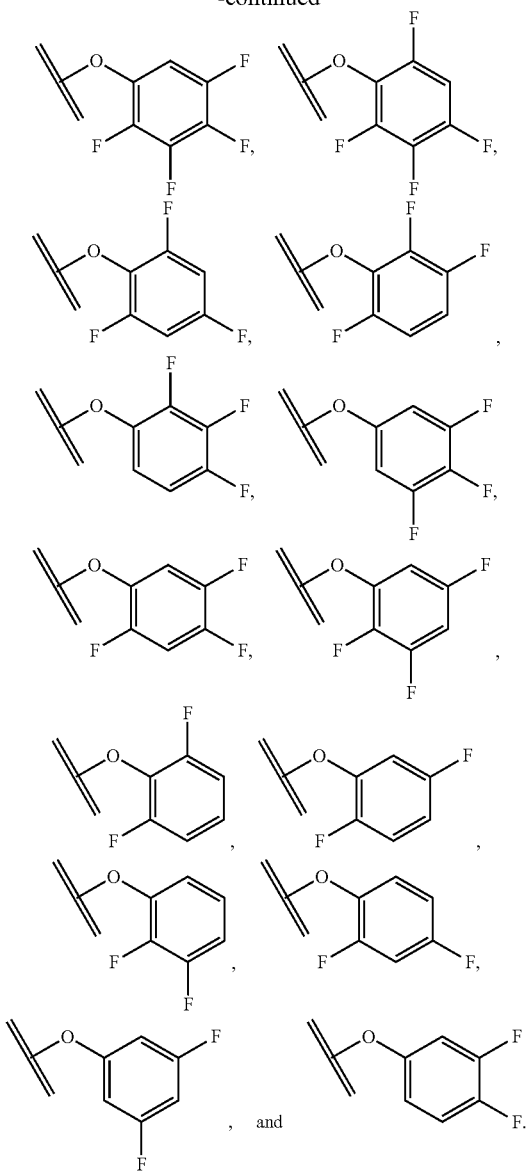

, and

25. The method as claimed in claim 24, wherein h=4 or 5.
26. The method as claimed in claim 25, wherein Z* is of the formula:

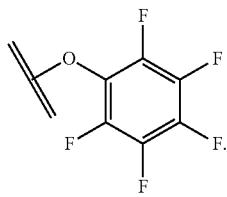

27. The method as claimed in claim 23, wherein the ratio of Effector Moiety:antibody is between about 1:1 to about 15:1.
28. The method as claimed in claim 23, wherein the ratio is between about 3:1 to about 6:1.
29. The method as claimed in claim 23, wherein the antibody concentration during the conjugation reaction is between about 1 and about 100 mg/ml.

30. The method as claimed in claim 23, wherein the reaction takes place at a pH of between about 6.5 and about 8.
31. A pharmaceutical composition comprising the MAC as claimed in claim 1, and further comprising an acceptable carrier.
32. The pharmaceutical composition as claimed in claim 31, further comprising one or more compounds selected from the group consisting of 5-fluorouracil, irinotecan, oxilaplatin, cetuximab, sunitinib, and rituximab.
33. A method of inhibiting or reducing angiogenesis or treating or preventing a disease or symptom associated with an angiogenic disorder comprising administering to a patient a therapeutically effective dose of a pharmaceutical composition as claimed in claim 32, wherein said angiogenic disorder may be selected from the group consisting of cancers of the lung (NSCLC and SCLC), the head or neck, the ovary, the colon, the rectum, the prostate, the anal region, the stomach, the breast, the kidney or ureter, the renal pelvis, the thyroid gland, the bladder, the brain, renal cell carcinoma, carcinoma of, neoplasms of the central nervous system (CNS), primary CNS lymphoma, non-Hodgkins's lymphoma, spinal axis tumours, carcinomas of the, oropharynx, hypopharynx, esophagus, pancreas, liver, gallbladder and bile ducts, small intestine, urinary tract; or lymphoma, lung cancer (NSCLC and SCLC), breast cancer, ovarian cancer, colon cancer, rectal cancer, prostate cancer, cancer of the anal region or a combination of one or more of the foregoing cancers.
34. The composition as claimed in claim 1, wherein at least about 60% of the Effector Moiety in the composition or sample is conjugated to $K^{188}$-CLκ.
35. The composition as claimed in claim 1, wherein at least about 70% of the Effector Moiety in the composition or sample is conjugated to $K^{188}$-CLκ.
36. A composition comprising a multifunctional antibody conjugate (MAC), the MAC comprising
   (i) an antibody or antigen binding portion thereof, comprising at least a fragment of a light chain constant kappa region (CLκ) comprising $K^{188}$ according to Kabat numbering;
   (ii) a linker comprising the formula X-Y-Z, wherein Z is a group of formula

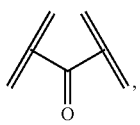

and is covalently connected to the antibody through the ε-amino group of the side chain of $K^{188}$, Y is a linear or branched biologically compatible connecting chain, and X is a group covalently connected to at least one Effector Moiety,
and pharmaceutically acceptable salts, stereoisomers, tautomers, solvates, and prodrugs thereof
and wherein at least about 50% of the Effector Moiety in the composition or sample is conjugated to $K^{188}$-CLκ.
37. The composition comprising the MAC as claimed in claim 36, wherein at least about 60% of the antibody comprises an Effector Moiety covalently attached to $K^{188}$-CLκ.
38. The composition comprising the MAC as claimed in claim 36, wherein at least about 70% of the antibody comprises an Effector Moiety covalently attached to $K^{188}$-CLκ.
39. The composition comprising the MAC as claimed in claim 36, wherein at least about 80% of the antibody comprises an Effector Moiety covalently attached to $K^{188}$-CLκ.

40. A composition comprising a multifunctional antibody conjugate (MAC), the MAC comprising
   (i) an antibody or antigen binding portion thereof, comprising at least a fragment of a light chain constant kappa region (CLκ) comprising $K^{188}$ according to Kabat numbering;
   (ii) a linker comprising the formula X-Y-Z, wherein Z is a group of formula

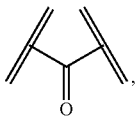

and is covalently connected to the antibody through the ε-amino group of the side chain of $K^{188}$, Y is a linear or branched biologically compatible connecting chain, and X is a group covalently connected to at least one Effector Moiety,
   and pharmaceutically acceptable salts, stereoisomers, tautomers, solvates, and prodrugs thereof,
and wherein at least about 70% of the heavy chain molecules are unconjugated with the Effector Moiety.

41. A composition comprising a multifunctional antibody conjugate (MAC), the MAC comprising
   (i) an antibody or antigen binding portion thereof, comprising at least a fragment of a light chain constant kappa region (CLκ) comprising $K^{188}$ according to Kabat numbering;
   (ii) a linker comprising the formula X-Y-Z, wherein Z is a group of formula

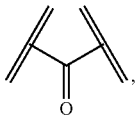

and is covalently connected to the antibody through the ε-amino group of the side chain of $K^{188}$, Y is a linear or branched biologically compatible connecting chain, and X is a group covalently connected to at least one Effector Moiety,
   and pharmaceutically acceptable salts, stereoisomers, tautomers, solvates, and prodrugs thereof,
wherein the average number of conjugations per antibody is between about 0.5 and about 1.5, wherein at least about 50% of the Effector Moiety in the composition or sample is conjugated to K188-CLK.

42. A composition comprising a multifunctional antibody conjugate (MAC), the MAC comprising
   (i) an antibody or antigen binding portion thereof, comprising at least a fragment of a light chain constant kappa region (CLκ) comprising $K^{188}$ according to Kabat numbering;
   (ii) a linker comprising the formula X-Y-Z, wherein Z is a group of formula

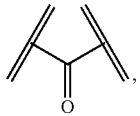

and is covalently connected to the antibody through the ε-amino group of the side chain of $K^{188}$, Y is a linear or branched biologically compatible connecting chain, and X is a group covalently connected to at least one Effector Moiety,
   and pharmaceutically acceptable salts, stereoisomers, tautomers, solvates, and prodrugs thereof,
wherein the average number of conjugations per antibody is between about 1.5 and about 2.5, wherein at least about 50% of the Effector Moiety in the composition or sample is conjugated to K188-CLK.

* * * * *

SEQUENCE LISTING

<160> NUMBER OF SEQ ID NOS: 61

<210> SEQ ID NO 1
<211> LENGTH: 451
<212> TYPE: PRT
<213> ORGANISM: Homo sapiens

<400> SEQUENCE: 1

```
Gln Ala Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Arg Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Gly Val Glu Thr Thr Phe Tyr Tyr Tyr Tyr Gly Met
            100                 105                 110

Asp Val Trp Gly Gln Gly Thr Thr Val Thr Val Ser Ser Ala Ser Thr
        115                 120                 125

Lys Gly Pro Ser Val Phe Pro Leu Ala Pro Cys Ser Arg Ser Thr Ser
    130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205
```

```
Asn Val Asp His Lys Pro Ser Asn Thr Lys Val Asp Lys Thr Val Glu
            210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285

His Asn Ala Lys Thr Lys Pro Arg Glu Glu Gln Phe Asn Ser Thr Phe
    290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
                325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 2
<211> LENGTH: 214
<212> TYPE: PRT
<213> ORGANISM: Homo sapiens

<400> SEQUENCE: 2

Asp Ile Gln Met Thr Gln Ser Pro Ser Ser Leu Ser Ala Ser Val Gly
1               5                   10                  15

Asp Arg Val Thr Phe Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Glu Val Glu Ile Ile Arg Thr Val Ala Ala
            100                 105                 110

Pro Ser Val Phe Ile Phe Pro Pro Ser Asp Glu Gln Leu Lys Ser Gly
        115                 120                 125
```

```
Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
    210

<210> SEQ ID NO 3
<211> LENGTH: 451
<212> TYPE: PRT
<213> ORGANISM: Homo sapiens

<400> SEQUENCE: 3

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
                20                  25                  30

Tyr Met Ser Trp Ile Arg Gln Ala Pro Gly Lys Gly Leu Glu Trp Val
            35                  40                  45

Ser Tyr Ile Ser Ser Ser Gly Ser Thr Arg Asp Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Arg Asp Gly Val Glu Thr Thr Phe Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
130                 135                 140

Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu Cys Pro Pro Cys Pro Ala Pro Pro Val Ala
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Gln Phe Asn Trp Tyr Val Asp Gly Val Glu Val
        275                 280                 285
```

His Asn Ala Lys Thr Lys Pro Arg Glu Glu Gln Phe Asn Ser Thr Phe
290                 295                 300

Arg Val Val Ser Val Leu Thr Val Val His Gln Asp Trp Leu Asn Gly
305                 310                 315                 320

Lys Glu Tyr Lys Cys Lys Val Ser Asn Lys Gly Leu Pro Ala Pro Ile
            325                 330                 335

Glu Lys Thr Ile Ser Lys Thr Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Met Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
            435                 440                 445

Pro Gly Lys
    450

<210> SEQ ID NO 4
<211> LENGTH: 214
<212> TYPE: PRT
<213> ORGANISM: Homo sapiens

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Leu Val Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 5
<211> LENGTH: 329
<212> TYPE: PRT
<213> ORGANISM: Homo sapiens

<400> SEQUENCE: 5

Val Ser Ser Ala Ser Thr Lys Gly Pro Ser Val Phe Pro Leu Ala Pro
1               5                   10                  15

Cys Ser Arg Ser Thr Ser Glu Ser Thr Ala Ala Leu Gly Cys Leu Val
            20                  25                  30

Lys Asp Tyr Phe Pro Glu Pro Val Thr Val Ser Trp Asn Ser Gly Ala
        35                  40                  45

Leu Thr Ser Gly Val His Thr Phe Pro Ala Val Leu Gln Ser Ser Gly
    50                  55                  60

Leu Tyr Ser Leu Ser Ser Val Val Thr Val Pro Ser Ser Asn Phe Gly
65                  70                  75                  80

Thr Gln Thr Tyr Thr Cys Asn Val Asp His Lys Pro Ser Asn Thr Lys
                85                  90                  95

Val Asp Lys Thr Val Glu Arg Lys Cys Cys Val Glu Cys Pro Pro Cys
            100                 105                 110

Pro Ala Pro Pro Val Ala Gly Pro Ser Val Phe Leu Phe Pro Pro Lys
        115                 120                 125

Pro Lys Asp Thr Leu Met Ile Ser Arg Thr Pro Glu Val Thr Cys Val
130                 135                 140

Val Val Asp Val Ser His Glu Asp Pro Glu Val Gln Phe Asn Trp Tyr
145                 150                 155                 160

Val Asp Gly Val Glu Val His Asn Ala Lys Thr Lys Pro Arg Glu Glu
                165                 170                 175

Gln Phe Asn Ser Thr Phe Arg Val Val Ser Val Leu Thr Val Val His
            180                 185                 190

Gln Asp Trp Leu Asn Gly Lys Glu Tyr Lys Cys Lys Val Ser Asn Lys
        195                 200                 205

Gly Leu Pro Ala Pro Ile Glu Lys Thr Ile Ser Lys Thr Lys Gly Gln
    210                 215                 220

Pro Arg Glu Pro Gln Val Tyr Thr Leu Pro Pro Ser Arg Glu Glu Met
225                 230                 235                 240

Thr Lys Asn Gln Val Ser Leu Thr Cys Leu Val Lys Gly Phe Tyr Pro
                245                 250                 255

Ser Asp Ile Ala Val Glu Trp Glu Ser Asn Gly Gln Pro Glu Asn Asn
            260                 265                 270

Tyr Lys Thr Thr Pro Pro Met Leu Asp Ser Asp Gly Ser Phe Phe Leu
        275                 280                 285

Tyr Ser Lys Leu Thr Val Asp Lys Ser Arg Trp Gln Gln Gly Asn Val
    290                 295                 300

Phe Ser Cys Ser Val Met His Glu Ala Leu His Asn His Tyr Thr Gln
305                 310                 315                 320

Lys Ser Leu Ser Leu Ser Pro Gly Lys
                325

<210> SEQ ID NO 6
<211> LENGTH: 122
<212> TYPE: PRT
<213> ORGANISM: Homo sapiens
<220> FEATURE:

```
<221> NAME/KEY: MISC_FEATURE
<222> LOCATION: (2)..(2)
<223> OTHER INFORMATION: Xaa = V or A

<400> SEQUENCE: 6

Gln Xaa Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
             20                  25                  30

Tyr Met Ser Trp Ile Arg Gln Ala Pro Gly Lys Gly Leu Glu Trp Val
         35                  40                  45

Ser Tyr Ile Ser Ser Ser Gly Ser Thr Arg Asp Tyr Ala Asp Ser Val
     50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                 85                  90                  95

Val Arg Asp Gly Val Glu Thr Thr Phe Tyr Tyr Tyr Tyr Gly Met
            100                 105                 110

Asp Val Trp Gly Gln Gly Thr Thr Val Thr
        115                 120

<210> SEQ ID NO 7
<211> LENGTH: 10
<212> TYPE: PRT
<213> ORGANISM: Homo sapiens

<400> SEQUENCE: 7

Gly Phe Thr Phe Ser Asp Tyr Tyr Met Ser
 1               5                  10

<210> SEQ ID NO 8
<211> LENGTH: 15
<212> TYPE: PRT
<213> ORGANISM: Homo sapiens

<400> SEQUENCE: 8

Tyr Ile Ser Ser Ser Gly Ser Thr Arg Asp Tyr Ala Asp Ser Val
 1               5                  10                  15

<210> SEQ ID NO 9
<211> LENGTH: 16
<212> TYPE: PRT
<213> ORGANISM: Homo sapiens

<400> SEQUENCE: 9

Asp Gly Val Glu Thr Thr Phe Tyr Tyr Tyr Tyr Gly Met Asp Val
 1               5                  10                  15

<210> SEQ ID NO 10
<211> LENGTH: 25
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = V or A

<400> SEQUENCE: 10

Gln Xaa Gln Leu Val Glu Ser Gly Gly Gly Leu Val Lys Pro Gly Gly
 1               5                  10                  15

Ser Leu Arg Leu Ser Cys Ala Ala Ser
             20                  25
```

<210> SEQ ID NO 11
<211> LENGTH: 25
<212> TYPE: PRT
<213> ORGANISM: Homo sapiens

<400> SEQUENCE: 11

Gln Val Gln Leu Val Glu Ser Gly Gly Gly Leu Val Lys Pro Gly Gly
1               5                   10                  15

Ser Leu Arg Leu Ser Cys Ala Ala Ser
            20                  25

<210> SEQ ID NO 12
<211> LENGTH: 14
<212> TYPE: PRT
<213> ORGANISM: Homo sapiens

<400> SEQUENCE: 12

Trp Ile Arg Gln Ala Pro Gly Lys Gly Leu Glu Trp Val Ser
1               5                   10

<210> SEQ ID NO 13
<211> LENGTH: 34
<212> TYPE: PRT
<213> ORGANISM: Homo sapiens

<400> SEQUENCE: 13

Lys Gly Arg Phe Thr Ile Ser Arg Asp Asn Ala Lys Asn Ser Leu Tyr
1               5                   10                  15

Leu Gln Met Asn Ser Leu Arg Ala Glu Asp Thr Ala Val Tyr Tyr Cys
            20                  25                  30

Val Arg

<210> SEQ ID NO 14
<211> LENGTH: 8
<212> TYPE: PRT
<213> ORGANISM: Homo sapiens

<400> SEQUENCE: 14

Trp Gly Gln Gly Thr Thr Val Thr
1               5

<210> SEQ ID NO 15
<211> LENGTH: 106
<212> TYPE: PRT
<213> ORGANISM: Homo sapiens

<400> SEQUENCE: 15

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys

<210> SEQ ID NO 16
<211> LENGTH: 108
<212> TYPE: PRT
<213> ORGANISM: Homo sapiens
<220> FEATURE:
<221> NAME/KEY: MISC_FEATURE
<222> LOCATION: (21)..(21)
<223> OTHER INFORMATION: Xaa = I or F
<220> FEATURE:
<221> NAME/KEY: MISC_FEATURE
<222> LOCATION: (107)..(107)
<223> OTHER INFORMATION: Xaa = K or I

<400> SEQUENCE: 16

Asp Ile Gln Met Thr Gln Ser Pro Ser Ser Leu Ser Ala Ser Val Gly
1               5                   10                  15

Asp Arg Val Thr Xaa Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Leu Val Ile Xaa Arg
            100                 105

<210> SEQ ID NO 17
<211> LENGTH: 13
<212> TYPE: PRT
<213> ORGANISM: Homo sapiens

<400> SEQUENCE: 17

Cys Arg Ala Ser Gln Asp Ile Arg Arg Asp Leu Gly Trp
1               5                   10

<210> SEQ ID NO 18
<211> LENGTH: 7
<212> TYPE: PRT
<213> ORGANISM: Homo sapiens

<400> SEQUENCE: 18

Ile Tyr Ala Ala Ser Arg Leu
1               5

<210> SEQ ID NO 19
<211> LENGTH: 9
<212> TYPE: PRT
<213> ORGANISM: Homo sapiens

<400> SEQUENCE: 19

Leu Gln His Asn Asn Tyr Pro Arg Thr
1               5

<210> SEQ ID NO 20
<211> LENGTH: 22
<212> TYPE: PRT
<213> ORGANISM: Homo sapiens
<220> FEATURE:
<221> NAME/KEY: MISC_FEATURE
<222> LOCATION: (21)..(21)

<223> OTHER INFORMATION: Xaa = I or F

<400> SEQUENCE: 20

Asp Ile Gln Met Thr Gln Ser Pro Ser Ser Leu Ser Ala Ser Val Gly
1               5                   10                  15

Asp Arg Val Thr Xaa Thr
            20

<210> SEQ ID NO 21
<211> LENGTH: 22
<212> TYPE: PRT
<213> ORGANISM: Homo sapiens

<400> SEQUENCE: 21

Asp Ile Gln Met Thr Gln Ser Pro Ser Ser Leu Ser Ala Ser Val Gly
1               5                   10                  15

Asp Arg Val Thr Ile Thr
            20

<210> SEQ ID NO 22
<211> LENGTH: 12
<212> TYPE: PRT
<213> ORGANISM: Homo sapiens

<400> SEQUENCE: 22

Tyr Gln Gln Lys Pro Gly Lys Ala Pro Lys Arg Leu
1               5                   10

<210> SEQ ID NO 23
<211> LENGTH: 34
<212> TYPE: PRT
<213> ORGANISM: Homo sapiens

<400> SEQUENCE: 23

Gln Ser Gly Val Pro Ser Arg Phe Ser Gly Ser Gly Ser Gly Thr Glu
1               5                   10                  15

Phe Thr Leu Thr Ile Ser Ser Leu Gln Pro Glu Asp Phe Ala Thr Tyr
            20                  25                  30

Tyr Cys

<210> SEQ ID NO 24
<211> LENGTH: 11
<212> TYPE: PRT
<213> ORGANISM: Homo sapiens
<220> FEATURE:
<221> NAME/KEY: MISC_FEATURE
<222> LOCATION: (10)..(10)
<223> OTHER INFORMATION: Xaa= K or I

<400> SEQUENCE: 24

Phe Gly Gln Gly Thr Lys Leu Val Ile Xaa Arg
1               5                   10

<210> SEQ ID NO 25
<211> LENGTH: 11
<212> TYPE: PRT
<213> ORGANISM: Homo sapiens

<400> SEQUENCE: 25

Phe Gly Gln Gly Thr Lys Leu Val Ile Lys Arg
1               5                   10

<210> SEQ ID NO 26
<211> LENGTH: 22

```
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (9)..(9)
<223> OTHER INFORMATION: Xaa= AcK  or Leu

<400> SEQUENCE: 26

Gln Xaa Tyr Gln Pro Leu Asp Glu Xaa Asp Lys Thr Leu Tyr Asp Gln
1               5                   10                  15

Phe Met Leu Gln Gln Gly
            20

<210> SEQ ID NO 27
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (9)..(9)
<223> OTHER INFORMATION: Xaa= AcK

<400> SEQUENCE: 27

Gln Xaa Tyr Gln Pro Leu Asp Glu Xaa Asp Lys Thr Leu Tyr Asp Gln
1               5                   10                  15

Phe Met Leu Gln Gln Gly
            20

<210> SEQ ID NO 28
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK

<400> SEQUENCE: 28

Gln Xaa Tyr Gln Pro Leu Asp Glu Leu Asp Lys Thr Leu Tyr Asp Gln
1               5                   10                  15

Phe Met Leu Gln Gln Gly
            20

<210> SEQ ID NO 29
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (11)..(11)
<223> OTHER INFORMATION: Xaa = AcK

<400> SEQUENCE: 29

Gln Xaa Tyr Gln Pro Leu Asp Glu Lys Asp Xaa Thr Leu Tyr Asp Gln
1               5                   10                  15

Phe Met Leu Gln Gln Gly
            20
```

```
<210> SEQ ID NO 30
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (11)..(11)
<223> OTHER INFORMATION: Xaa = AcK

<400> SEQUENCE: 30

Gln Xaa Tyr Gln Pro Leu Asp Glu Leu Asp Xaa Thr Leu Tyr Asp Lys
1               5                   10                  15

Phe Met Leu Gln Gln Gly
            20

<210> SEQ ID NO 31
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (11)..(11)
<223> OTHER INFORMATION: Xaa= AcK

<400> SEQUENCE: 31

Gln Xaa Tyr Gln Pro Leu Asp Glu Leu Asp Xaa Thr Leu Tyr Asp Gln
1               5                   10                  15

Phe Lys Leu Gln Gln Gly
            20

<210> SEQ ID NO 32
<211> LENGTH: 22
<212> TYPE: PRT
<213> ORGANISM: Homo sapiens
<220> FEATURE:
<221> NAME/KEY: MISC_FEATURE
<222> LOCATION: (2)..(2)
<223> OTHER INFORMATION: Xaa = AcK
<220> FEATURE:
<221> NAME/KEY: MISC_FEATURE
<222> LOCATION: (11)..(11)
<223> OTHER INFORMATION: Xaa = AcK

<400> SEQUENCE: 32

Gln Xaa Tyr Gln Pro Leu Asp Glu Leu Asp Xaa Thr Leu Tyr Asp Gln
1               5                   10                  15

Phe Met Lys Gln Gln Gly
            20

<210> SEQ ID NO 33
<211> LENGTH: 214
<212> TYPE: PRT
<213> ORGANISM: Homo sapiens

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30
```

Leu Gly Trp Tyr Gln Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Arg His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 34
<211> LENGTH: 214
<212> TYPE: PRT
<213> ORGANISM: Homo sapiens

<400> SEQUENCE: 34

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Arg Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 35
<211> LENGTH: 214
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Arg His Arg Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 36
<211> LENGTH: 214
        <212> TYPE: PRT
<213> ORGANISM: Homo sapiens

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

```
Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Ala Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 37
<211> LENGTH: 214
<212> TYPE: PRT
<213> ORGANISM: Homo sapiens

<400> SEQUENCE: 37

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Ala His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210
```

<210> SEQ ID NO 38
<211> LENGTH: 214

```
<212> TYPE: PRT
<213> ORGANISM: Homo sapiens

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys Ala Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 39
<211> LENGTH: 214
<212> TYPE: PRT
<213> ORGANISM: Homo sapiens

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
            20                  25                  30

Leu Gly Trp Tyr Gln Gln Lys Pro Gly Lys Ala Pro Lys Arg Leu Ile
        35                  40                  45

Tyr Ala Ala Ser Arg Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
```

```
                130                 135                 140
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Ala Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 40
<211> LENGTH: 214
<212> TYPE: PRT
<213> ORGANISM: Homo sapiens

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Arg Asp
                20                  25                  30

Leu Gly Trp Tyr Gln Gln Lys Pro Gly Lys Ala Pro Lys Arg Leu Ile
            35                  40                  45

Tyr Ala Ala Ser Arg Leu Gln Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Asn Tyr Pro Arg
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Ala Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys Ala Lys Val Tyr
                180                 185                 190

Ala Cys Glu Val Thr His Gln Gly Leu Ser Ser Pro Val Thr Lys Ser
                195                 200                 205

Phe Asn Arg Gly Glu Cys
            210

<210> SEQ ID NO 41
<211> LENGTH: 116
<212> TYPE: PRT
<213> ORGANISM: Homo sapiens

<400> SEQUENCE: 41

Phe Gly Gly Gly Thr Gln Leu Thr Val Leu Gly Gln Pro Lys Ala Ala
1               5                   10                  15

Pro Ser Val Thr Leu Phe Pro Pro Ser Ser Glu Glu Leu Gln Ala Asn
                20                  25                  30
```

```
Lys Ala Thr Leu Val Cys Leu Ile Ser Asp Phe Tyr Pro Gly Ala Val
            35                  40                  45

Thr Val Ala Trp Lys Ala Asp Ser Ser Pro Val Lys Ala Gly Val Glu
 50                  55                  60

Thr Thr Thr Pro Ser Lys Gln Ser Asn Asn Lys Tyr Ala Ala Ser Ser
 65                  70                  75                  80

Tyr Leu Ser Leu Thr Pro Glu Gln Trp Lys Ser His Arg Ser Tyr Ser
                 85                  90                  95

Cys Gln Val Thr His Glu Gly Ser Thr Val Glu Lys Thr Val Ala Pro
                100                 105                 110

Thr Glu Cys Ser
            115

<210> SEQ ID NO 42
<211> LENGTH: 117
<212> TYPE: PRT
<213> ORGANISM: Homo sapiens

<400> SEQUENCE: 42

Phe Gly Gly Gly Thr Gln Leu Thr Val Leu Arg Thr Val Ala Ala Pro
 1               5                  10                  15

Ser Val Phe Ile Phe Pro Pro Ser Asp Glu Gln Leu Lys Ser Gly Thr
                 20                  25                  30

Ala Ser Val Val Cys Leu Leu Asn Asn Phe Tyr Pro Arg Glu Ala Lys
            35                  40                  45

Val Gln Trp Lys Val Asp Asn Ala Leu Gln Ser Gly Asn Ser Gln Glu
 50                  55                  60

Ser Val Thr Glu Gln Asp Ser Lys Asp Ser Thr Tyr Ser Leu Ser Ser
 65                  70                  75                  80

Thr Leu Thr Leu Ser Lys Ala Asp Tyr Glu Lys His Lys Val Tyr Ala
                 85                  90                  95

Cys Glu Val Thr His Gln Gly Leu Ser Ser Pro Val Thr Lys Ser Phe
                100                 105                 110

Asn Arg Gly Glu Cys
            115

<210> SEQ ID NO 43
<211> LENGTH: 117
<212> TYPE: PRT
<213> ORGANISM: Homo sapiens

<400> SEQUENCE: 43

Phe Gly Gly Gly Thr Lys Val Glu Ile Lys Arg Thr Val Ala Ala Pro
 1               5                  10                  15

Ser Val Phe Ile Phe Pro Pro Ser Asp Glu Gln Leu Lys Ser Gly Thr
                 20                  25                  30

Ala Ser Val Val Cys Leu Leu Asn Asn Phe Tyr Pro Arg Glu Ala Lys
            35                  40                  45

Val Gln Trp Lys Val Asp Asn Ala Leu Gln Ser Gly Asn Ser Gln Glu
 50                  55                  60

Ser Val Thr Glu Gln Asp Ser Lys Asp Ser Thr Tyr Ser Leu Ser Ser
 65                  70                  75                  80

Thr Leu Thr Leu Ser Lys Ala Asp Tyr Glu Lys His Lys Val Tyr Ala
                 85                  90                  95

Cys Glu Val Thr His Gln Gly Leu Ser Ser Pro Val Thr Lys Ser Phe
                100                 105                 110
```

```
Asn Arg Gly Glu Cys
         115

<210> SEQ ID NO 44
<211> LENGTH: 116
<212> TYPE: PRT
<213> ORGANISM: Homo sapiens

<400> SEQUENCE: 44

Phe Gly Gly Gly Thr Gln Leu Thr Val Leu Gly Gln Pro Lys Ala Ala
1               5                   10                  15

Pro Ser Val Thr Leu Phe Pro Pro Ser Ser Glu Glu Leu Gln Ala Asn
                20                  25                  30

Lys Ala Thr Leu Val Cys Leu Ile Ser Asp Phe Tyr Pro Gly Ala Val
                35                  40                  45

Thr Val Ala Trp Lys Ala Asp Ser Ser Pro Val Lys Ala Gly Val Glu
            50                  55                  60

Thr Thr Thr Pro Ser Lys Gln Ser Asn Asn Lys Tyr Ala Ala Ser Ser
65                  70                  75                  80

Tyr Leu Ser Leu Thr Pro Glu Gln Trp Lys His Ser Arg Ser Tyr Ser
                85                  90                  95

Cys Gln Val Thr His Glu Gly Ser Thr Val Glu Lys Thr Val Ala Pro
                100                 105                 110

Thr Glu Cys Ser
         115

<210> SEQ ID NO 45
<211> LENGTH: 106
<212> TYPE: PRT
<213> ORGANISM: Homo sapiens
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (82)..(82)
<223> OTHER INFORMATION: Xaa = G, A, V, L, I, S, T, C, M, N, Q, F, Y, W,
      K, R, H, D or E
<220> FEATURE:
<221> NAME/KEY: MISC_FEATURE
<222> LOCATION: (83)..(83)
<223> OTHER INFORMATION: Xaa = L or V

<400> SEQUENCE: 45

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
                20                  25                  30

Pro Arg Glu Ala Lys Val Gln Trp Lys Val Asp Asn Xaa Leu Gln Ser
                35                  40                  45

Gly Asn Ser Gln Glu Ser Val Thr Glu Gln Asp Ser Lys Asp Ser Thr
            50                  55                  60

Tyr Ser Leu Ser Ser Thr Leu Thr Leu Ser Lys Ala Asp Tyr Glu Lys
65                  70                  75                  80

His Xaa Xaa Tyr Ala Cys Glu Val Thr His Gln Gly Leu Ser Ser Pro
                85                  90                  95

Val Thr Lys Ser Phe Asn Arg Gly Glu Cys
                100                 105

<210> SEQ ID NO 46
<211> LENGTH: 106
```

```
<212> TYPE: PRT
<213> ORGANISM: Homo sapiens
<220> FEATURE:
<221> NAME/KEY: MISC_FEATURE
<222> LOCATION: (45)..(45)
<223> OTHER INFORMATION: Xaa = V or A
<220> FEATURE:
<221> NAME/KEY: MISC_FEATURE
<222> LOCATION: (83)..(83)
<223> OTHER INFORMATION: Xaa = L or V

<400> SEQUENCE: 46

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Xaa Leu Gln Ser
        35                  40                  45

Gly Asn Ser Gln Glu Ser Val Thr Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Xaa Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 47
<211> LENGTH: 106
<212> TYPE: PRT
<213> ORGANISM: Homo sapiens
<220> FEATURE:
<221> NAME/KEY: MISC_FEATURE
<222> LOCATION: (82)..(82)
<223> OTHER INFORMATION: Xaa = G, A, V, L, I, S, T, C, M, N, Q, F, Y, W,
      K, R, H, D or E

<400> SEQUENCE: 47

Thr Val Ala Ala Pro Ser Val Phe Ile Phe Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Xaa Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 48
<211> LENGTH: 106
<212> TYPE: PRT
<213> ORGANISM: Homo sapiens

<400> SEQUENCE: 48

Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
```

```
                        20                  25                  30
Phe Tyr Pro Gly Ala Val Thr Val Ala Trp Lys Ala Asp Ser Ser Pro
            35                  40                  45

Val Lys Ala Gly Val Glu Thr Thr Thr Pro Ser Lys Gln Ser Asn Asn
 50                  55                  60

Lys Tyr Ala Ala Ser Ser Tyr Leu Ser Leu Thr Pro Glu Gln Trp Lys
 65                  70                  75                  80

Ser His Arg Ser Tyr Ser Cys Gln Val Thr His Glu Gly Ser Thr Val
                    85                  90                  95

Glu Lys Thr Val Ala Pro Thr Glu Cys Ser
                100                 105

<210> SEQ ID NO 49
<211> LENGTH: 106
<212> TYPE: PRT
<213> ORGANISM: Mus musculus

<400> SEQUENCE: 49

Ala Asp Ala Ala Pro Thr Val Ser Ile Phe Pro Pro Ser Ser Glu Gln
 1               5                  10                  15

Leu Thr Ser Gly Gly Ala Ser Val Val Cys Phe Leu Asn Asn Phe Tyr
            20                  25                  30

Pro Arg Asp Ile Asn Val Lys Trp Lys Ile Asp Gly Ser Glu Arg Gln
        35                  40                  45

Asn Gly Val Leu Asn Ser Trp Thr Asp Gln Asp Ser Lys Asp Ser Thr
 50                  55                  60

Tyr Ser Met Ser Ser Thr Leu Thr Leu Thr Lys Asp Glu Tyr Glu Arg
 65                  70                  75                  80

His Asn Ser Tyr Thr Cys Glu Ala Thr His Lys Thr Ser Thr Ser Pro
                    85                  90                  95

Ile Val Lys Ser Phe Asn Arg Asn Glu Cys
                100                 105

<210> SEQ ID NO 50
<211> LENGTH: 230
<212> TYPE: PRT
<213> ORGANISM: Homo sapiens

<400> SEQUENCE: 50

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Arg Asp Tyr Ala Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
                    85                  90                  95

Val Arg Asp Gly Val Glu Thr Thr Phe Tyr Tyr Tyr Tyr Gly Met
                100                 105                 110

Asp Val Trp Gly Gln Gly Thr Thr Val Thr Val Ser Ser Ala Ser Thr
            115                 120                 125

Lys Gly Pro Ser Val Phe Pro Leu Ala Pro Cys Ser Arg Ser Thr Ser
        130                 135                 140
```

```
Glu Ser Thr Ala Ala Leu Gly Cys Leu Val Lys Asp Tyr Phe Pro Glu
145                 150                 155                 160

Pro Val Thr Val Ser Trp Asn Ser Gly Ala Leu Thr Ser Gly Val His
                165                 170                 175

Thr Phe Pro Ala Val Leu Gln Ser Ser Gly Leu Tyr Ser Leu Ser Ser
            180                 185                 190

Val Val Thr Val Pro Ser Ser Asn Phe Gly Thr Gln Thr Tyr Thr Cys
        195                 200                 205

Asn Val Asp His Lys Pro Ser Asn Thr Lys Val Asp Lys Thr Val Glu
    210                 215                 220

Arg Lys Cys Cys Val Glu
225                 230

<210> SEQ ID NO 51
<211> LENGTH: 219
<212> TYPE: PRT
<213> ORGANISM: Homo sapiens

<400> SEQUENCE: 51

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 52
<211> LENGTH: 448
<212> TYPE: PRT
<213> ORGANISM: Homo sapiens

<400> SEQUENCE: 52

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
 50                  55                  60

Ser Val Lys Gly Arg Phe Thr Ile Ser Arg Asp Asn Ser Lys Asn Thr
 65                  70                  75                  80

Leu Tyr Leu Gln Met Asn Ser Leu Arg Ala Glu Asp Thr Gly Ile Tyr
                 85                  90                  95

Tyr Cys Lys Thr Tyr Phe Tyr Ser Phe Ser Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445
```

<210> SEQ ID NO 53
<211> LENGTH: 219
<212> TYPE: PRT
<213> ORGANISM: Homo sapiens

<400> SEQUENCE: 53

```
Glu Leu Gln Met Thr Gln Ser Pro Ser Ser Leu Ser Ala Ser Val Gly
1               5                   10                  15

Asp Arg Val Thr Ile Thr Cys Arg Ser Gln Ser Leu Leu His Ser
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215
```

<210> SEQ ID NO 54
<211> LENGTH: 444
<212> TYPE: PRT
<213> ORGANISM: Homo sapiens

<400> SEQUENCE: 54

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110
```

```
Leu Val Thr Val Ser Ser Ala Ser Thr Lys Gly Pro Ser Val Phe Pro
            115                 120                 125

Leu Ala Pro Cys Ser Arg Ser Thr Ser Glu Ser Thr Ala Ala Leu Gly
            130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Asn Phe Gly Thr Gln Thr Tyr Thr Cys Asn Val Asp His Lys Pro Ser
                195                 200                 205

Asn Thr Lys Val Asp Lys Thr Val Glu Arg Lys Cys Cys Val Glu Cys
            210                 215                 220

Pro Pro Cys Pro Ala Pro Pro Val Ala Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Gln Phe
                260                 265                 270

Asn Trp Tyr Val Asp Gly Val Glu Val His Asn Ala Lys Thr Lys Pro
            275                 280                 285

Arg Glu Glu Gln Phe Asn Ser Thr Phe Arg Val Val Ser Val Leu Thr
            290                 295                 300

Val Val His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Thr
                325                 330                 335

Lys Gly Gln Pro Arg Glu Pro Gln Val Tyr Thr Leu Pro Pro Ser Arg
                340                 345                 350

Glu Glu Met Thr Lys Asn Gln Val Ser Leu Thr Cys Leu Val Lys Gly
            355                 360                 365

Phe Tyr Pro Ser Asp Ile Ala Val Glu Trp Glu Ser Asn Gly Gln Pro
            370                 375                 380

Glu Asn Asn Tyr Lys Thr Thr Pro Pro Met Leu Asp Ser Asp Gly Ser
385                 390                 395                 400

Phe Phe Leu Tyr Ser Lys Leu Thr Val Asp Lys Ser Arg Trp Gln Gln
                405                 410                 415

Gly Asn Val Phe Ser Cys Ser Val Met His Glu Ala Leu His Asn His
                420                 425                 430

Tyr Thr Gln Lys Ser Leu Ser Leu Ser Pro Gly Lys
            435                 440

<210> SEQ ID NO 55
<211> LENGTH: 112
<212> TYPE: PRT
<213> ORGANISM: Homo sapiens

<400> SEQUENCE: 55

Glu Leu Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45
```

```
Pro Lys Leu Leu Ile Tyr Lys Val Ser Asn Arg Phe Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Val Tyr Phe Cys Ser Gln Gly
                85                  90                  95

Thr His Leu Pro Tyr Thr Phe Gly Gly Gly Thr Lys Val Glu Ile Lys
            100                 105                 110
```

<210> SEQ ID NO 56
<211> LENGTH: 118
<212> TYPE: PRT
<213> ORGANISM: Homo sapiens

<400> SEQUENCE: 56

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Trp Met Ser Trp Val Arg Gln Ser Pro Glu Lys Gly Leu Glu Trp Val
        35                  40                  45

Ser Glu Ile Arg Leu Arg Ser Asp Asn Tyr Ala Thr His Tyr Ala Glu
    50                  55                  60

Ser Val Lys Gly Arg Phe Thr Ile Ser Arg Asp Asn Ser Lys Asn Thr
65                  70                  75                  80

Leu Tyr Leu Gln Met Asn Ser Leu Arg Ala Glu Asp Thr Gly Ile Tyr
                85                  90                  95

Tyr Cys Lys Thr Tyr Phe Tyr Ser Phe Ser Tyr Trp Gly Gln Gly Thr
            100                 105                 110

Leu Val Thr Val Ser Ser
        115
```

<210> SEQ ID NO 57
<211> LENGTH: 112
<212> TYPE: PRT
<213> ORGANISM: Mus musculus

<400> SEQUENCE: 57

```
Asp Val Val Met Thr Gln Thr Pro Leu Ser Leu Pro Val Arg Leu Gly
1               5                   10                  15

Asp Gln Ala Ser Ile Ser Cys Arg Ser Ser Gln Ser Leu Leu His Thr
            20                  25                  30

Tyr Gly Ser Pro Tyr Leu Asn Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Arg Ile
65                  70                  75                  80

Ser Arg Val Glu Ala Glu Asp Leu Gly Val Tyr Phe Cys Ser Gln Gly
                85                  90                  95

Thr His Leu Pro Tyr Thr Phe Gly Gly Gly Thr Lys Leu Glu Ile Lys
            100                 105                 110
```

<210> SEQ ID NO 58
<211> LENGTH: 118
<212> TYPE: PRT
<213> ORGANISM: Mus musculus

<400> SEQUENCE: 58

```
Glu Val Lys Leu Val Glu Ser Gly Gly Gly Leu Val Gln Pro Gly Gly
1               5                   10                  15

Thr Met Lys Leu Ser Cys Glu Ile Ser Gly Leu Thr Phe Arg Asn Tyr
            20                  25                  30

Trp Met Ser Trp Val Arg Gln Ser Pro Glu Lys Gly Leu Glu Trp Val
        35                  40                  45

Ala Glu Ile Arg Leu Arg Ser Asp Asn Tyr Ala Thr His Tyr Ala Glu
    50                  55                  60

Ser Val Lys Gly Lys Phe Thr Ile Ser Arg Asp Asp Ser Lys Ser Arg
65                  70                  75                  80

Leu Tyr Leu Gln Met Asn Ser Leu Arg Thr Glu Asp Thr Gly Ile Tyr
                85                  90                  95

Tyr Cys Lys Tyr Tyr Phe Tyr Ser Phe Ser Tyr Trp Gly Gln Gly Thr
            100                 105                 110

Leu Val Thr Val Ser Ala
        115

<210> SEQ ID NO 59
<211> LENGTH: 15
<212> TYPE: PRT
<213> ORGANISM: Homo sapiens

<400> SEQUENCE: 59

Gly Gly Gly Gly Ser Gly Gly Gly Gly Ser Gly Gly Gly Gly Ser
1               5                   10                  15

<210> SEQ ID NO 60
<211> LENGTH: 7
<212> TYPE: PRT
<213> ORGANISM: Homo sapiens

<400> SEQUENCE: 60

Gly Arg Gly Asp Ser Pro Lys
1               5

<210> SEQ ID NO 61
<211> LENGTH: 12
<212> TYPE: PRT
<213> ORGANISM: Homo sapiens

<400> SEQUENCE: 61

Asp Val Pro Lys Ser Asp Gln Phe Val Gly Leu Met
1               5                   10
```